US012582725B2

(12) United States Patent
Kleopa et al.

(10) Patent No.: US 12,582,725 B2
(45) Date of Patent: Mar. 24, 2026

(54) AAV VECTORS WITH MYELIN PROTEIN ZERO PROMOTER AND USES THEREOF FOR TREATING SCHWANN CELL-ASSOCIATED DISEASES LIKE CHARCOT-MARIE-TOOTH DISEASE

(71) Applicant: THE CYPRUS FOUNDATION FOR MUSCULAR DYSTROPHY RESEARCH, Nicosia (CY)

(72) Inventors: Kleopas Kleopa, Nicosia (CY); Alexia Kagiava, Nicosia (CY); Natasa Schiza, Nicosia (CY); Irene Sargiannidou, Nicosia (CY)

(73) Assignee: THE CYPRUS FOUNDATION FOR MUSCULAR DYSTROPHY RESEARCH, Nicosia (CY)

( * ) Notice: Subject to any disclaimer, the term of this patent is extended or adjusted under 35 U.S.C. 154(b) by 1017 days.

(21) Appl. No.: 17/616,006

(22) PCT Filed: Jun. 3, 2020

(86) PCT No.: PCT/EP2020/065312

§ 371 (c)(1),
(2) Date: Dec. 2, 2021

(87) PCT Pub. No.: WO2020/245169

PCT Pub. Date: Dec. 10, 2020

(65) Prior Publication Data

US 2022/0323611 A1 Oct. 13, 2022

(30) Foreign Application Priority Data

Jun. 3, 2019 (GB) ..................................... 1907882

(51) Int. Cl.

| | |
|---|---|
| ***C07K 14/47*** | (2006.01) |
| ***A61K 48/00*** | (2006.01) |
| ***A61P 25/02*** | (2006.01) |
| ***C07K 14/705*** | (2006.01) |
| ***C12N 15/86*** | (2006.01) |

(52) U.S. Cl.

CPC ...... *A61K 48/0058* (2013.01); *A61K 48/0075* (2013.01); *A61P 25/02* (2018.01); *C07K 14/47* (2013.01); *C07K 14/70503* (2013.01); *C12N 15/86* (2013.01); *C12N 2750/14143* (2013.01); *C12N 2830/008* (2013.01)

(58) Field of Classification Search

CPC .............. C12N 15/86; C12N 2830/008; C12N 2330/51; C12N 2750/14143; A61P 25/00; A61P 21/00; A61P 25/02; A01K 2267/0318; C07K 14/705

See application file for complete search history.

(56) References Cited

U.S. PATENT DOCUMENTS

| | | | | |
|---|---|---|---|---|
| 9,644,215 | B2 * | 5/2017 | Brenner | A61K 48/005 |
| 12,178,845 | B2 * | 12/2024 | Brenner | C12N 15/86 |
| 2009/0018031 | A1 | 1/2009 | Trinklein et al. | |
| 2009/0215178 | A1 | 8/2009 | Tang | |
| 2010/0086539 | A1 | 4/2010 | Jurewics et al. | |
| 2011/0179502 | A1 | 7/2011 | Emery et al. | |
| 2012/0233713 | A1 | 9/2012 | Popko et al. | |
| 2013/0195801 | A1 | 8/2013 | Gao et al. | |
| 2013/0224150 | A1 | 8/2013 | Kury et al. | |
| 2014/0147432 | A1 | 5/2014 | Bancel et al. | |
| 2014/0309288 | A1 | 10/2014 | Brenner et al. | |
| 2015/0044277 | A1 | 2/2015 | Bancel et al. | |
| 2017/0095531 | A1 | 4/2017 | Schreiber et al. | |
| 2017/0252484 | A1 | 9/2017 | Sowa et al. | |
| 2018/0305689 | A1 | 10/2018 | Sætrom et al. | |

FOREIGN PATENT DOCUMENTS

| | | | | |
|---|---|---|---|---|
| WO | 2012162669 | A1 | 11/2012 | |
| WO | 2015140351 | A1 | 9/2015 | |
| WO | 2015/158924 | A1 | 10/2015 | |
| WO | 2018056412 | A1 | 3/2018 | |
| WO | 2018071868 | A1 | 4/2018 | |
| WO | 2018088694 | A2 | 5/2018 | |
| WO | 2018/106753 | | 6/2018 | |
| WO | WO-2018106753 | A1 * | 6/2018 | C12N 7/00 |
| WO | 2018220211 | A1 | 12/2018 | |
| WO | 2019/070741 | A1 | 4/2019 | |
| WO | 2019/079755 | | 4/2019 | |
| WO | 2022015715 | A1 | 1/2022 | |

OTHER PUBLICATIONS

International Search Report and Written Opinion issued in PCT/EP2020/065312, dated Aug. 4, 2020, 18 pages.
Ahmed Sherif et al., 2019, "Schwannoma gene therapy by adeno-associated virus delivery of the pore-forming protein Gasdermin-D", Cancer Gene Therapy, 26(9-10):259-267.
Manisha Juneja et al., 2018, "Challenges in modelling the Charcot-Marie-Tooth neuropathies for therapy development", J. Neurol. Neurosurg. & Psychiatry.
Sargiannidou I, Kagiava A, Bashiardes S, Richter J, Christodoulou C, Scherer SS, et al. Intraneural GJB1 gene delivery improves nerve pathology in a model of CMT1X. Ann Neurol. 2015;78:303-16.
Thompson, Julie D., Desmond G. Higgins, and Toby J. Gibson. "Clustal W: improving the sensitivity of progressive multiple sequence alignment through sequence weighting, position-specific gap penalties and weight matrix choice." Nucleic acids research 22.22 (1994): 4673-4680.

(Continued)

*Primary Examiner* — Bao Q Li
(74) *Attorney, Agent, or Firm* — Meunier Carlin & Curfman LLC

(57) ABSTRACT

The present invention provides viral vectors for use in the treatment and prevention of diseases associated with Schwann cells by delivering polynucleotides specifically to Schwann cells and achieving Schwann cell specific expression. The present invention has particular application in treatment and prevention of Charcot-Marie-Tooth disease and other demyelinating neuropathies. The preferred vectors are adeno-associated vectors (AAV) having a Schwann cell-specific promoter from the Myelin Protein Zero (Mpz, P0) or a minimal Mpz promoter.

10 Claims, 26 Drawing Sheets

Specification includes a Sequence Listing.

(56) References Cited

OTHER PUBLICATIONS

Inherited Neuropathy Variant Browser, available at: http://hihg.med.miami.edu/code/http/cmt/public_html/index.html#/.
GenBank website, available at: https://www.ncbi.nlm.nih.gov/genbank/.
Home—Protein—NCBI—https://www.ncbi.nlm.nih.gov/protein#.
NCT02362438—Intrathecal Administration of scAAV9/JeT-GAN for the Treatment of Giant Axonal Neuropathy, accessible at https://clinicaltrials.gov/ct2/show/NCT02362438.
Baets J, De Jonghe P, Timmerman V. Recent advances in Charcot-Marie-Tooth disease. Curr Opin Neurol. 2014;27(5):532-40.
Kleopa KA, Scherer SS. Inherited Neuropathies. Neurol Clinics North America. 2002;20:679-709.
Kleopa KA, Kagiava A, Sargiannidou I. Gene Therapy for CMT Inherited Neuropathy. In: Duan D, Mendell J (eds): Muscle Gene Therapy. 2019; https://doi.org/10.1007/978-3-030-03095-7_35 (Springer, Cham ).
Bergoffen J, Scherer SS, Wang S, Oronzi-Scott M, Bone L, Paul DL, et al. Connexin mutations in X-linked Charcot-Marie-Tooth disease. Science. 1993;262:2039-42.
Kleopa KA, Scherer SS. Molecular genetics of X-linked Charcot-Marie-Tooth disease. Neuromolecular Med. 2006;8:107-22.
Hahn AF, Brown WF, Koopman WJ, Feasby TE. X-linked dominant hereditary motor and sensory neuropathy. Brain. 1990;113:1511-25.
Birouk N, Le Guern E, Maisonobe T, Rouger H, Gouider R, Gugenheim M, et al. X- linked Charcot-Marie-Tooth disease with connexin 32 mutations—clinical and electrophysiological study. Neurology. 1998;50:1074-82.
Shy ME, Siskind C, Swan ER, Krajewski KM, Doherty T, Fuerst DR, et al. CMT1X phenotypes represent loss of GJB1 gene function. Neurology. 2007;68:849-55.
Dubourg O, Tardieu S, Birouk N, Gouider R, Léger JM, Maisonobe T, et al. Clinical, electrophysiological and molecular genetic characteristics of 93 patients with X-linked Charcot-Marie-Tooth disease. Brain. 2001; 124:1958-67.
Liang GSL, de Miguel M, Gomez-Hernandez JM, Glass JD, Scherer SS, Mintz M, et al. Severe neuropathy with leaky connexin32 hemichannels. Ann Neurol. 2005;57:749-54.
Al-Mateen M, Craig AK, Chance PF. The Central Nervous System Phenotype of X- Linked Charcot-Marie-Tooth Disease: A Transient Disorder of Children and Young Adults. J Child Neurol. 2014;29:342-8.
Hahn AF, Ainsworth PJ, Bolton CF, Bilbao JM, Vallat J-M. Pathological findings in the X-linked form of Charcot-Marie-Tooth disease: a morphometric and ultrastructural analysis. Acta Neuropathol. 2001;101:129-39.
Hattori N, Yamamoto M, Yoshihara T, Koike H, Nakagawa M, Yoshikawa H, et al. Demyelinating and axonal features of Charcot-Marie-Tooth disease with mutations of myelin-related proteins (PMP22, MPZ and Cx32): a clinicopathological study of 205 Japanese patients. Brain. 2003; 126:134-51.
Kleopa KA, Zamba-Papanicolaou E, Alevra X, Nicolaou P, Georgiou D-M, Hadjisavvas A, et al. Phenotypic and cellular expression of two novel connexin32 mutations causing CMT1X. Neurology. 2006;66:396-402.
Omori Y, Mesnil M, Yamasaki H. Connexin 32 mutations from X-linked Charcot- Marie-Tooth disease patients: functional defects and dominant negative effects. Mol Biol Cell. 1996;7(6):907-16.
Yoshimura T, Satake M, Ohnishi A, Tsutsumi Y, Fujikura Y. Mutations of connexin32 in Charcot-Marie-Tooth disease type X interfere with cell-to-cell communication but not cell proliferation and myelin-specific gene expression. J Neurosci Res. 1998;51(2):154-61.
Yum SW, Kleopa KA, Shumas S, Scherer SS. Diverse trafficking abnormalities of Connexin32 mutants causing CMTX. Neurobiol Dis. 2002; 11:43-52.
Deschênes SM, Walcott JL, Wexler TL, Scherer SS, Fischbeck KH. Altered trafficking of mutant connexin32. J Neurosci. 1997; 17:9077-84.
Oh S, Ri Y, Bennett MVL, Trexler EB, Verselis VK, Bargiello TA. Changes in permeability caused by connexin 32 mutations underlie X-linked Charcot-Marie-Tooth disease. Neuron. 1997; 19(4):927-38.
Martin PEM, Mambetisaeva ET, Archer DA, George CH, Evans WH. Analysis of gap junctions assembly using mutated connexins detected in Charcot-Marie-Tooth X-linked disease. J Neurochem. 2000;74:711-20.
Kleopa KA, Yum SW, Scherer SS. Cellular mechanisms of connexin32 mutations associated with CNS manifestations. J Neurosci Res. 2002;68:522-34.
Sargiannidou I, Vavlitou N, Aristodemou S, Hadjisavvas A, Kyriacou K, Scherer SS, et al. Connexin32 mutations cause loss of function in Schwann cells and oligodendrocytes leading to PNS and CNS myelination defects. J Neurosci. 2009;29:4736-49.
Sargiannidou I, Kim GH, Kyriakoudi S, Eun BL, Kleopa Ka. A start codon CMT1X mutation associated with transient encephalomyelitis causes complete loss of Cx32. Neurogenetics. 2015;16(3):193-200.
Anzini P, Neuberg DH-H, Schachner M, Nelles E, Willecke K, Zielasek J, et al. Structural abnormalities and deficient maintenance of peripheral nerve myelin in mice lacking the gap junction protein connexin32. J Neurosci. 1997;17:4545-51.
Scherer SS, Xu Y-T, Nelles E, Fischbeck K, Willecke K, Bone LJ. Connexin32-null mice develop a demyelinating peripheral neuropathy. Glia. 1998; 24:8-20.
Scherer SS, Xu YT, Messing A, Willecke K, Fischbeck KH, Jeng LJ. Transgenic expression of human connexin32 in myelinating Schwann cells prevents demyelination in connexin32-null mice. J Neurosci. 2005;25:1550-9.
Abel A, Bone LJ, Messing A, Scherer SS, Fischbeck KF. Studies in transgenic mice indicate a loss of connexin32 function in X-linked Charcot-Marie-Tooth disease. J Neuropathol Exp Neurol. 1999;58:702-10.
Jeng LJ, Balice-Gordon RJ, Messing A, Fischbeck KH, Scherer SS. The effects of a dominant connexin32 mutant in myelinating Schwann cells. Mol Cell Neurosci. 2006;32:283-98.
Kagiava A, Karaiskos C, Richter J, Tryfonos C, Lapathitis G, Sargiannidou I, et al. Intrathecal gene therapy in mouse models expressing CMT1X mutations. Hum Mol Genet. 2018;27(8):1460-73.
Huang Y, Sirkowski EE, Stickney JT, Scherer SS. Prenylation-defective human connexin32 mutants are normally localized and function equivalently to wild-type connexin32 in myelinating Schwann cells. J Neurosci. 2005;25:7111-20.
Hahn AF, Ainsworth PJ, Naus CCG, Mao J, Bolton CF. Clinical and pathological observations in men lacking the gap junction protein connexin 32. Muscle Nerve. 2000:S39-S48.
Kagiava A, Sargiannidou I, Theophilidis G, Karaiskos C, Richter J, Bashiardes S, et al. Intrathecal gene therapy rescues a model of demyelinating peripheral neuropathy. PNAS USA. 2016;113(17):E2421-9. doi: 10.1073/pnas.1522202113.
Kyriakoudi S, Sargiannidou I, Kagiava A, Olympiou M, Kleopa KA. Golgi-retained Cx32 mutants interfere with gene addition therapy for CMT1X. Hum Mol Genet. 2017;26(9):1622-33.
Fridman V, Bundy B, Reilly MM, Pareyson D, Bacon C, Burns J, et al. CMT subtypes and disease burden in patients enrolled in the Inherited Neuropathies Consortium natural history study: a cross-sectional analysis. J Neurol Neurosurg Psychiatry. 2015;86(8):873-8.
Kessali M, Zemmouri R, Guilbot A, Maisonobe T, Brice A, LeGuern E, et al. A clinical, electrophysiologic, neuropathologic, and genetic study of two large Algerian families with an autosomal recessive demyelinating form of Charcot-Marie-Tooth disease. Neurology. 1997;48(4):867-73.
Gabreels-Festen A, van Beersum S, Eshuis L, LeGuern E, Gabreels F, van Engelen B, et al. Study on the gene and phenotypic characterisation of autosomal recessive demyelinating motor and sensory neuropathy (Charcot-Marie-Tooth disease) with a gene locus on chromosome 5q23-q33. J Neurol Neurosurg Psychiatry. 1999;66(5):569-74.

(56) References Cited

OTHER PUBLICATIONS

Azzedine H, Ravise N, Verny C, Gabreels-Festen A, Lammens M, Grid D, et al. Spine deformities in Charcot-Marie-Tooth 4C caused by SH3TC2 gene mutations. Neurology. 2006;67(4):602-6.
Gooding R, Colomer J, King R, Angelicheva D, Marns L, Parman Y, et al. A novel Gypsy founder mutation, p.Arg1109X in the CMT4C gene, causes variable peripheral neuropathy phenotypes. J Med Genet. 2005;42(12):e69.
Colomer J, Gooding R, Angelicheva D, King RH, Guillen-Navarro E, Parman Y, et al. Clinical spectrum of CMT4C disease in patients homozygous for the p.Arg1109X mutation in SH3TC2. Neuromuscul Disord. 2006; 16(7):449-53.
Varley TL, Bourque PR, Baker SK. Phenotypic variability of CMT4C in a French-Canadian kindred. Muscle Nerve. 2015.
Senderek J, Bergmann C, Stendel C, Kirfel J, Verpoorten N, De Jonghe P, et al. Mutations in a Gene Encoding a Novel SH3/TPR Domain Protein Cause Autosomal Recessive Charcot-Marie-Tooth Type 4C Neuropathy. Am J Hum Genet. 2003;73:1106-19.
LeGuern E, Guilbot A, Kessali M, Ravise N, Tassin J, Maisonobe T, et al. Homozygosity mapping of an autosomal recessive form of demyelinating Charcot- Marie-Tooth disease to chromosome 5q23-q33. Hum Mol Genet. 1996;5(10):1685-8.
Lassuthova P, Mazanec R, Vondracek P, Siskova D, Haberlova J, Sabova J, et al. High frequency of SH3TC2 mutations in Czech Hmsn I patients. Clin Genet. 2011;80(4):334-45.
Lupo V, Galindo MI, Martinez-Rubio D, Sevilla T, Vilchez JJ, Palau F, et al. Missense mutations in the SH3TC2 protein causing Charcot-Marie-Tooth disease type 4C affect its localization in the plasma membrane and endocytic pathway. Hum Mol Genet. 2009;18(23):4603-14.
Arnaud E, Zenker J, de Preux Charles AS, Stendel C, Roos A, Medard JJ, et al. SH3TC2/KIAA1985 protein is required for proper myelination and the integrity of the node of Ranvier in the peripheral nervous system. Proc Natl Acad Sci U S A. 2009;106(41):17528-33.
Gouttenoire EA, Lupo V, Calpena E, Bartesaghi L, Schupfer F, Medard JJ, et al. Sh3tc2 deficiency affects neuregulin-1/ErbB signaling. Glia. 2013;61(7):1041-51.
Zoupi L, Savvaki M, Karagogeos D. Axons and myelinating glia: An intimate contact. IUBMB Life. 2011;63(9):730-5.
Schiza N, Georgiou E, Kagiava A, Médard J-J, Richter J, Tryfonos C, et al. Gene replacement therapy in a model of Charcot-Marie-Tooth 4C neuropathy. Brain. 2019; 142(5):1227-1241.
Tanguy Y, Biferi MG, Besse A, Astord S, Cohen-Tannoudji M, Marais T, et al. Systemic AAVrh10 provides higher transgene expression than AAV9 in the brain and the spinal cord of neonatal mice. Front Mol Neurosci. 2015;8:36.
Foust KD, Nurre E, Montgomery CL, Hernandez A, Chan CM, Kaspar BK. Intravascular AAV9 preferentially targets neonatal neurons and adult astrocytes. Nat Biotechnol. 2009;27(1):59-65.
Gurda BL, De Guilhem De Lataillade A, Bell P, Zhu Y, Yu H, Wang P, et al. Evaluation of AAV-mediated Gene Therapy for Central Nervous System Disease in Canine Mucopolysaccharidosis VII. Mol Ther. 2016;24(2):206-16.
Calcedo R, Wilson JM. Humoral Immune Response to AAV. Front Immunol. 2013;4:341.
Jackson KL, Dayton RD, Klein RL. AAV9 supports wide-scale transduction of the CNS and TDP-43 disease modeling in adult rats. Mol Ther Methods Clin Dev. 2015;2:15036.
Meyer K, Ferraiuolo L, Schmelzer L, Braun L, McGovern V, Likhite S, et al. Improving single injection CSF delivery of AAV9-mediated gene therapy for SMA: a dose-response study in mice and nonhuman primates. Mol Ther. 2015;23(3):477-87.
Jang SW, Svaren J. Induction of myelin protein zero by early growth response 2 through upstream and intragenic elements. J Biol Chem. 2009;284(30):20111-20.
Von Jonquieres G, Mersmann N, Klugmann CB, Harasta AE, Lutz B, Teahan O, et al. Glial promoter selectivity following AAV-delivery to the immature brain. PLoS One. 2013;8(6):e65646.
Georgiou E, Sidiropoulou K, Richter J, Papaneophytou C, Sargiannidou I, Kagiava A, et al. Gene therapy targeting oligodendrocytes provides therapeutic benefit in a leukodystrophy model. Brain. 2017;140(3):599-616.
Zolotukhin S, Byrne BJ, Mason E, Zolotukhin I, Potter M, Chesnut K, et al. Recombinant adeno-associated virus purification using novel methods improves infectious titer and yield. Gene Ther. 1999;6(6):973-85.
Piedra J, Ontiveros M, Miravet S, Penalva C, Monfar M, Chillon M. Development of a rapid, robust, and universal picogreen-based method to titer adeno-associated vectors. Hum Gene Ther Methods. 2015;26(1):35-42.
Savvaki M, Panagiotaropoulos T, Stamatakis A, Sargiannidou I, Karatzioula P, Watanabe K, et al. Impairment of learning and memory in TAG-1 deficient mice associated with shorter CNS internodes and disrupted juxtaparanodes. Mol Cell Neurosci. 2008;39:478-90.
Zielasek J, Martini R, Toyka KV. Functional abnormalities in PO-deficient mice resemble human hereditary neuropathies linked to PO gene mutations. Muscle Nerve. 1996;19(8):946-52.
Vavlitou N, Sargiannidou I, Markoullis K, Kyriacou K, Scherer SS, Kleopa KA. Axonal pathology precedes demyelination in a mouse model of X-linked demyelinating/type I Charcot-Marie Tooth neuropathy. J Neuropathol Exp Neurol. 2010;69:945-58.
Kobsar I, Berghoff M, Samsam M, Wessig C, Maurer M, Toyka KV, et al. Preserved myelin integrity and reduced axonopathy in connexin32-deficient mice lacking the recombination activating gene-1. Brain. 2003;126:804-13.
Groh J, Heinl K, Kohl B, Wessig C, Greeske J, Fischer S, et al. Attenuation of MCP-1/CCL2 expression ameliorates neuropathy in a mouse model for Charcot-Marie-Tooth 1X. Hum Mol Genet. 2010;19:3530-43.
Shevtsova, Z., et al. (2005). "Promoters and serotypes: targeting of adeno-associated virus vectors for gene transfer in the rat central nervous system in vitro and in vivo." Exp Physiol; 90(1): 53-59.
Von Jonquieres, G., et al. (2016). "Recombinant Human Myelin-Associated Glycoprotein Promoter Drives Selective AAV-Mediated Transgene Expression in Oligodendrocytes." Front Mol Neurosci; 9: 13.
Levitt, N., Briggs, D., Gil, A., and Proudfoot, N.J. (1989). Definition of an efficient synthetic poly(A) site. Genes Dev. 3, 1019-1025.
Bailey RM, Armao D, Nagabhushan Kalburgi S, Gray SJ. Development of Intrathecal AAV9 Gene Therapy for Giant Axonal Neuropathy. Mol Ther Methods Clin Dev. Feb. 15, 2018;9:160-171.
Kagiava A., Karaiskos C., Richter J., Tryfonos C., Rossor A., Reilly M.M., Sargiannidou I., Christodoulou C., Kleopa K.A "Gene replacement therapy for CMT1X neuropathy"; 2019 PNS Annual Meeting (Jun. 22-26, 2019, Genova—Italy).
Marina Stavrou, Irene Sargiannidou, Alexia Kagiava, Jan Richter, Christina Tryfonos, Christina Christodoulou, Christos Karaiskos, George Lapathitis and Kleopas A. Kleopa. Testing an shRNA Gene Silencing Approach in a Mouse Model of Charcot-Marie-Tooth Disease Type 1A. 2019 Peripheral Nerve Society Annual Meeting annual meeting, (Jun. 22-26, 2019, Genova—Italy).
Schiza N, Sargiannidou I, Richter J, Tryfonos, C, Christodoulou C, Svaren J, Kleopa, KA. Gene delivery targeted to Schwann cell using a minimal myelin promoter. 2019 Peripheral Nerve Society Annual Meeting annual meeting held in Genoa, Italy (Jun. 22-26, 2019, Genova—Italy).
Sargiannidou et al., 2020, "Gene therapy approaches targeting Schwann cells for demyelinating neuropathies", Brain Res., 1728:146572.
Hinderer et al., 2018 "Evaluation of intrathecal routes of administration for adeno-associated viral vectors in large animals", Human Gene Therapy, vol. 29, No. 1, p. 15-24.
Bai RY, Esposito D, Tam AJ, McCormick F, Riggins GJ, Wade Clapp D, Staedtke V. Feasibility of using NF1-GRD and AAV for gene replacement therapy in NF1-associated tumors. Gene Ther. Jun. 2019;26(6):277-286. Doi: 10.1038/ s41434-019-0080-9. Epub May 24, 2019. PMID: 31127187; PMCID: PMC6588423.
Helbing, DL., Schulz, A. & Morrison, H. Pathomechanisms in schwannoma development and progression. Oncogene 39, 5421-5429 (2020). Doi: 10.1038/s41388-020-1374-5.

(56) References Cited

OTHER PUBLICATIONS

Hoyng SA, de Winter F, Tannemaat MR, Blits B, Malessy MJ, Verhaagen J. Gene therapy and peripheral nerve repair: a perspective. Front Mol Neurosci. Jul. 15, 2015;8:32. Doi: 10.3389/fnmol.2015.00032. PMID: 26236188; PMCID: PMC4502351.
Brown et al., 1997, The Journal of Biological Chemistry, 272(46):28939-28947. Doi: 10.1074/jbc.272.46.28939.
Vijay, S., et al (2016). Exclusive expression of the Rab11 effector SH3TC2 in Schwann cells links integrin-a6 and myelin maintenance to Charcot-Marie-Tooth disease type 4C. Biochimica et Biophysica Acta, 1862(7), 1279-1290.
Kleopa, K. A., et al (2012). How do mutations in GJB1 cause X-linked Charcot-Marie-Tooth disease? Brain Research, 1487, 198-205. https://doi.org/10.1016/j.brainres.2012.03.068.
Ahmed, S. G., et al (2022). Schwannoma Gene Therapy via Adeno-Associated Viral Vector Delivery of Apoptosis-Associated Speck-like Protein Containing Card (ASC): Preclinical Efficacy and Safety. International Journal of Molecular Sciences, 23(2), 819.
Bort, S., et al (1997). Mutational analysis of the MPZ, PMP22 and Cx32 genes in patients of Spanish ancestry with Charcot-Marie-Tooth disease and hereditary neuropathy with liability to pressure palsies. Human Genetics, 99(6), 746-754.
Sahenk, Z., et al (2014). AAV1.NT-3 gene therapy for Charcot-Marie-Tooth neuropathy. Molecular Therapy: The Journal of the American Society of Gene Therapy, 22(3), 511-521.
Terzano et al.; “The Minimal Promoter of the Human a3 Nicotinic Receptor Subunit Gene”; The Journal of Biological Chemistry vol. 275, No. 52; dated Dec. 29, 2000; 9 pages.
Butcher et al.; “Identifification of a minimal promoter sequence for the human Nacetyltransferase Type I gene that binds AP-1 (activator protein 1) and YY-1 (Yin and Yang 1)”; Biochem. J.; dated 2003; 9 pages.
Sánchez-García et al.; “Modular organization of a hypocretin gene minimal promoter”; Molecular Medicine Reports; dated Jun. 14, 2017; 8 pages.
Preston, M. A., et al.(2019). A novel myelin protein zero transgenic zebrafish designed for rapid readout of in vivo myelination. Glia, 67(4), 650-667 (34 pages).

* cited by examiner

AAV VECTORS WITH MYELIN PROTEIN ZERO PROMOTER AND USES THEREOF FOR TREATING SCHWANN CELL-ASSOCIATED DISEASES LIKE CHARCOT-MARIE-TOOTH DISEASE

FIELD OF THE INVENTION

The present invention relates to viral vectors targeting diseases associated with Schwann cells.

BACKGROUND

Charcot-Marie-Tooth (CMT) disease encompasses numerous types of non-syndromic inherited neuropathies, which together are considered to be one of the most common neurogenetic disorders, with a frequency of affected individuals reaching 1:2500 of the general population (1, 2). CMT neuropathies are characterized by the involvement of an ever-increasing number of causative genes and overlapping phenotypes caused by different genes. Moreover, several different genes may cause identical phenotypes. Despite the increasing understanding of the complex genetic basis and diverse disease mechanisms underpinning CMT neuropathies, there is currently no effective treatment for any of the CMT forms and only symptomatic and supportive therapy can be offered to patients. Thus, there is a great need for new treatment strategies for CMT. In the last two decades there has been an effort to develop gene therapies for the treatment of CMT. While different gene therapy approaches hold promise for the future to treat diseases of the central and peripheral nervous system (PNS), multiple challenges remain to be overcome (3).

For example, (49) shows how it is possible to achieve a therapeutic effect in the treatment of CMT4C using a lentiviral vector. However, this effect was partial and the lentiviral vector has safety limitations for in vivo human therapies. Previously, other vectors such as adeno-associated viral vectors (AAVs) were not considered as useful, as despite being more stable and not integrating into the host genome, due to their maximum packaging capacity of inserts of approximately 4.4 kb in length, the utility of AAVs in gene therapy strategies was limited, especially in cases where the gene to be replaced is relatively long.

Gene therapy techniques targeting Schwann cells can be applied to many other diseases associated with Schwann cells aside from CMT, for example motor neuron disease (MND), and include those not exclusively caused by genetic factors. Many of these diseases have multiple causes and are not well understood, and therefore targeting these diseases using viral vectors may be particularly advantageous.

Overall, there remains a need for improved methods of targeting diseases associated with Schwann cells, including demyelinating neuropathies such as CMT, to achieve better therapeutic effects.

SUMMARY OF THE INVENTION

The inventors have developed for the first time a useful means of delivering polynucleotides, for example therapeutic polynucleotides to the Schwann cells of the peripheral nervous system (PNS) and driving expression of said polynucleotides specifically in Schwann cells. The present invention can be applied to the treatment of diseases associated with Schwann cells, and is considered to be particularly beneficial when applied to the treatment of demyelinating neuropathies such as Charcot-Marie-Tooth disease (CMT). However, the underlying mechanism of the invention is considered to be applicable to many other diseases that affect Schwann cells and is also considered to have general utility in any situation where delivery of a polynucleotide to a Schwann cell is considered to be advantageous, for example in imaging of Schwann cells.

A feature of one aspect of the present invention is the use of an AAV vector to achieve transcription of a first nucleic acid resulting in the production of first polynucleotide of interest specifically in Schwann cells of the PNS. In some embodiments, this cell-type specific expression is achieved using a myelin specific promoter, and in some embodiments this is achieved using a minimal version of a myelin specific promoter.

Another feature of the present invention is the provision of a minimal myelin specific promoter, which in some embodiments is based on the sequence of the full length myelin protein zero (Mpz) promoter. In some embodiments, viral vectors that comprise a shorter minimal promoter allow larger nucleic acid sequences, for example therapeutic nucleic acid sequences, to be included in the vector and delivered to Schwann cells. This is considered to have the advantageous property of providing a universal vector for delivery of nucleic acids to the Schwann cells, and can be used to treat a large range of diseases, since current approaches are limited in, for example, the genes that can be expressed from the viral vector due to their size.

DETAILED DESCRIPTION OF THE INVENTION

The invention is as defined by the claims.

The invention generally provides a viral vector as described herein for use in medicine and also a provides a method of therapy that comprises administering a vector according to the invention, for example administering by any of the means described herein.

A first aspect of the invention provides a viral vector for use in treating or preventing a disease associated with Schwann cells. In some embodiments, the viral vector comprises a first nucleic acid sequence that can be transcribed into a first polynucleotide.

The viral vector may be any viral vector.

Viral vectors are well known in the art and examples include but are not limited to: adeno-associated viral vectors (AAV vectors); lentiviral vectors (e.g. those derived from Human Immunodeficiency Virus (HIV)); retroviral vectors (e.g. MMLV).

In some embodiments, the viral vector is an adeno-associated viral vector (AAV vector). In a preferred embodiment, the invention provides an AAV vector for use in treating or preventing a disease associated with Schwann cells, wherein the AAV vector comprises a first nucleic acid sequence that can be transcribed into a first polynucleotide.

It is preferred if the first nucleic acid sequence is transcribed, for example is transcribed in a target cell or target organism. Accordingly, a further embodiment provides a viral vector for use in treating or preventing a disease associated with Schwann cell wherein the viral vector comprises a first nucleic acid sequence that is transcribed into a first polynucleotide.

A further embodiment provides an AAV for use in treating or preventing a disease associated with Schwann cells wherein the viral vector comprises a first nucleic acid sequence that is transcribed into a first polynucleotide.

The first nucleic acid sequence may be transcribed into a first polynucleotide in a target cell or target organism, for example is transcribed in a Schwann cell. The Schwann cell may be in vivo, for example may be in a mammalian organism, which for example may be a human, cat, dog, mouse, rabbit, horse, for example.

Schwann cells are glial cells of the peripheral nervous system (PNS) that wrap around the axons of sensory and motor neurons and produce the surrounding myelin sheath. The myelin sheath is made up of several protein components (e.g. myelin protein zero) and is an essential insulating component of neurons that allows fast conduction of nervous impulses (action potentials) along nerves.

Some current viral-vector based therapeutic strategies utilize vectors that have undesirable characteristics. For example, some viral vectors integrate into the host genome with clear potential deleterious consequences. Accordingly, in one embodiment the viral vector is not a viral vector that integrates into the genome of the host cell, for example will not integrate into the nucleic acid of a Schwann cell. Viral vectors that are not considered to integrate into the host genome, in some embodiments are particularly preferred, and include AAVs and adenoviral vectors. AAV vectors infect target cells and the delivered genetic material does not integrate into the genome of the host cell. Instead, the delivered genetic material remains episomal.

Viral vectors that are considered to integrate into the host genome include the retroviral vectors, for example lentiviral vectors. Accordingly, in one embodiment the viral vector is not a vector that integrates into the host genome, for example is not a retroviral vector, for example is not a lentiviral vector.

Some vectors are also not able to transduce Schwann cells. The skilled person will understand the types of vectors that can and cannot transduce Schwann cells. Accordingly, in one embodiment the viral vector of the invention is not a viral vector that is unable to transduce Schwann cells. In some embodiments, the viral vector has the ability to transduce Schwann cells. By "transduce" we mean that the viral vector is capable of infecting the target cells and delivering the polynucleotide construct found within it into the target cell. Examples of such vectors include AAVs and lentiviral vectors.

In one embodiment the vector is a vector in which only an insert of limited size can be incorporated before becoming unstable. For example, such vectors include AAV vectors.

Preferably, the viral vector is an AAV vector and in some embodiments, the AAV vector is selected from the group comprising or consisting of: AAV9 and AAVrh10. In a particularly preferred embodiment, the AAV is an AAV9.

It is preferred that transcription of the first nucleic acid only occurs, or substantially only occurs in Schwann cells. Accordingly, in some embodiments, the viral vector also contains a Schwann cell specific promoter operably linked to the first nucleic acid.

By "Schwann cell specific promoter" we include the meaning of a promoter that results in significant expression in Schwann cells and no or low expression in non-Schwann cells. For example, a Schwann cell specific promoter may drive high levels of transcription from the first nucleic acid in Schwann cells (e.g. 95% or more total expression occurs in Schwann cells) whereas expression of the first polynucleotide is low in other cell types, for example those of the central nervous system (e.g. less than 5% of total expression occurs in cells other than Schwann cells). For example, in one embodiment, the ratio of transcription in Schwann cells to non-Schwann cell is at least 100:0; 95:5; 90:10; 85:15; 80:20; 75:25; 70:30; 65:35; 60:40; or 55:45.

In one embodiment the level of transcription in a Schwann cell is at least 1.5, 2, 3, 4, 5, 6, 7, 8, 9, 10, 20, 30, 40, 50, 60, 70, 80, 90, 100, 250, 500, 750, 1000, 2500, 5000, 7500, 10000 times higher than in any other non-Schwann cell.

In one embodiment a Schwann cell specific promoter results in the majority of expression occurring in Schwann cells rather than non-Schwann cells.

The skilled person will understand that even very specific promoters may result in some expression in other cells or tissues. The skilled person is well aware of the differential expression level between a target cell or tissue and a non-target cell or tissue that is required to classify a promoter as cell or tissue specific, for example Schwann cell specific. For example, (66) and (67) demonstrate the identification of cell-specific promoters in the central nervous system (CNS). The skilled person would be aware that for a promoter to be cell-specific it must contain regulatory elements that activate the promoter in certain cell types only (e.g. binding sites for transcription factors), and the promoter must be able to drive demonstrable expression of reporter genes or other genes in vitro and in vivo.

Preferably the Schwann cell specific promoter results in transcription of the first nucleic acid at a detectable level only in Schwann cells. The skilled person is well aware of routine methods to detect transcription, for example northern blot, PCR based techniques and immunofluorescence labelling. In one embodiment the Schwann cell specific promoter results in detectable transcription of the first nucleic acid in Schwann cells but does not result in detectable levels of transcription of the first nucleic acid in non-Schwann cells, for example in other cells of the peripheral nervous system or brain when the detection is performed using a northern blot analysis. In another embodiment the Schwann cell specific promoter results in detectable transcription of the first nucleic acid in Schwann cells but does not result in detectable levels of transcription of the first nucleic acid in non-Schwann cells, for example in other cells of the peripheral nervous system or brain when the detection is performed using an immunofluorescence labelling analysis with cell markers.

For example (32) and (33) demonstrate that Schwann cell specific expression can be achieved both in vitro and in vivo using constructs driven by the full-length Mpz promoter using lentiviral vectors.

Schwann cell specific promoters include, in some embodiments, myelin specific promoters. By "myelin specific promoter" we mean a promoter that typically drives the expression of genes encoding proteins making up the myelin sheath. Examples of myelin specific promoters include but are not limited to: the myelin protein zero (Mpz) promoter; the peripheral myelin protein 22 (PMP22) promoter; myelin associated glycoprotein (Mag) promoter.

In some embodiments, the expression of the first polynucleotide is under the control of a full-length myelin protein zero (Mpz) promoter, such as the full-length rat myelin protein zero (Mpz) promoter, the sequence of which is defined in SEQ ID NO. 4. In some embodiments, the sequence of the Mpz promoter has a sequence with at least 75% sequence homology or sequence identity with SEQ ID NO. 4, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 4.

In some embodiments, it will be clear to the skilled person that it is preferable for the promoter sequence to be derived from a human or humanised promoter sequence. In some embodiments the expression of the first polynucleotide is under the control of the full-length human myelin protein zero (hP0) promoter, the sequence of which is defined in SEQ ID NO. 18. In some embodiments, the sequence of the hP0 promoter has a sequence with at least 75% sequence homology or sequence identity with SEQ ID NO. 18, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 18.

As discussed above, it is considered advantageous if the promoter is as short as possible, particular where the vector is a vector that can only handle a limited insert size before becoming unstable. Therefore, in some embodiments, the expression of the first polynucleotide is under the control of a promoter that is between 100 bp and 1100 bp in length, optionally wherein the promoter ranges from 200 bp to 900 bp in length, 300 bp to 800 bp in length, 400 bp to 700 bp in length, optionally wherein the promoter is between 500 bp and 600 bp in length, for example is 410 bp in length. In the same or other embodiments, the promoter is less than 1100 bp in length, for example is less than 1000 bp, 900 bp, 800 bp, 700 bp, 600 bp, 500 bp, 400 bp, 300 bp, 200 bp or less than 100 bp in length.

In some embodiments the promoter is a naturally occurring Mpz promoter of a length as defined herein. In an alternative embodiment, the promoter is an engineered Mpz promoter of a length as defined herein. By "naturally occurring promoter" we mean a promoter that has not been modified, shortened or lengthened compared to the corresponding promoter sequence that is found in wild-type Schwann cells. By "engineered promoter", we mean a wild-type promoter that has been altered in some way. For example, the sequence may have been modified to have for example at least 75% sequence homology or sequence identity with the naturally occurring promoter sequence, optionally at least 80%, or 82%, or 84%, or 86%, or 88%, or 90%, or 92%, or 94%, or 96%, or 97%, or 98%, or 99%, or 100% sequence identity or sequence homology to the naturally occurring promoter sequence. In another or the same embodiment, the promoter may also have been modified in length, for example the length of the wild-type promoter may have been reduced from a longer sequence to, for example between 100 bp and 1100 bp in length, optionally from 200 bp to 900 bp in length, 300 bp to 800 bp in length, 400 bp to 700 bp in length, optionally between 500 bp and 600 bp in length, for example is 410 bp in length, or is less than 1100 bp in length, for example is less than 1000 bp, 900 bp, 800 bp, 700 bp, 600 bp, 500 bp, 400 bp, 300 bp, 200 bp or less than 100 bp in length.

In another embodiment, the promoter length may have been increased relative to a wildtype promoter.

The skilled person will understand that it is possible that only portions of a particular nucleic acid region considered to be a promoter are actually required for promoter activity. In another example, the engineered promoter includes part of the sequence of the wild type promoter, or includes the whole sequence of the wild type promoter as part of a longer promoter sequence. As discussed, preferably the promoter is specifically active in Schwann cells. The skilled person would be able to test whether a particular fragment of a full-length promoter results in Schwann cell specific expression of a protein under control of said promoter fragment, for example by screening for expression of a reporter gene in Schwann cells. In some examples the reporter gene is EGFP.

In another embodiment, the engineered promoter is a truncated version of the wild type promoter and may have, for example, at least 75% sequence homology or sequence identity with the naturally occurring promoter sequence, optionally at least 80%, or 82%, or 84%, or 86%, or 88%, or 90%, or 92%, or 94%, or 96%, or 97%, or 98%, or 99%, or 100% sequence identity or sequence homology to the naturally occurring promoter sequence.

In addition to being a truncated version of a native promoter, the engineered promoter may additionally or alternatively comprise mutations, substitutions, deletions and insertions relative to the native promoter sequences. For example, an engineered promoter may comprise various different regions of the native promoter in one consecutive sequence.

An engineered promoter that is shorter in length than the corresponding native or wildtype promoter may be termed a minimal promoter.

In some embodiments, an engineered promoter retains the same function as the corresponding naturally occurring promoter that it is derived from i.e. it can still effectively drive transcription of polynucleotide sequences from nucleic acid sequences to which the promoter is operably linked and can in preferable instances effectively drive transcription in a cell-specific manner, i.e. in a Schwann cell specific manner.

In some embodiments the expression of the first polynucleotide may be under the control of, for example, a shortened naturally occurring myelin specific promoter, which is termed herein a minimal myelin specific promoter, optionally this is a minimal myelin protein zero (Mpz) promoter. In some embodiments the sequence of the minimal myelin specific promoter comprises or consists of the 410 bp sequence as defined in SEQ ID NO. 5, which is derived from the full length rat Mpz promoter sequence. In some embodiments, the minimal myelin specific promoter comprises or consists of a sequence with at least 75% sequence homology or sequence identity with SEQ ID NO. 5, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 5.

In some embodiments it is prefereable for the minimal promoter to be derived from a human or humanised promoter sequence. In some embodiments the sequence of the minimal myelin specific promoter comprises or consists of the 429 bp sequence as defined in SEQ ID NO. 22, which is derived from the full length human hP0 promoter sequence. In some embodiments, the minimal myelin specific promoter comprises or consists of a sequence with at least 75% sequence homology or sequence identity with SEQ ID NO. 22, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 22. The minimal myelin specific promoters derived from rat Mpz or human hP0 are termed miniMpz herein.

By "sequence identity" or "sequence homology" we mean the identical sequence of base pairs in the specific DNA region. For example, in a sequence that has 75% sequence homology or sequence identity to a reference sequence, 75% of the base pairs are identical.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., (1994) *Nucleic Acids Res* 22, 4673-80). The parameters used may be as follows: Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05. Scoring matrix: BLOSUM.

In one embodiment, the minimal Mpz promoter described herein may be produced as described in Example 9, for example by taking the 410 base pair region upstream of the start codon of the full length promoter, for example the full length myelin protein zero (Mpz) promoter. In another embodiment a minimal Mpz promoter described herein may be produced as described in Example 13. AAV vectors have a maximum capacity to carry polynucleotides of around 4.4 kb, therefore the use of a shorter Mpz promoter as described herein, rather than the full length Mpz promoter which is approximately 1.1 kb in length, has the advantage of allowing longer first nucleic acid sequences to be operably linked to the promoter region for packaging into the AAV. In some embodiments where the promoter is a shorter promoter, for example with a length of between 100 bp and 1100 bp in length, 200 bp to 900 bp, 300 bp to 800 bp, 400 bp to 700 bp, 500 bp to 600 bp, or 410 bp in length, or with a length of less than 1100 bp in length, for example is less than 1000 bp, 900 bp, 800 bp, 700 bp, 600 bp, 500 bp, 400 bp, 300 bp, 200 bp or less than 100 bp, for example an engineered promoter or a minimal promoter, this allows the present invention to be applied to a wider range of genes of greater lengths than AAV vectors utilizing the full length promoter. For example, currently there are some situations where it is not possible to insert a nucleic acid sequence, for example a gene, of a particular length into an AAV since the length of the nucleic acid can exceed the maximum capacity of the AAV when longer promoters, for example the full length Mpz promoter is used. For example, if the first nucleic acid, for example the therapeutic gene, is longer than 3.0-3.3 kb in length (4.4 kb-1.1 kb=3.3 kb). In this case, use of the advantageous shorter promoters described herein, for example the minimal myelin specific promoter, allows the present invention to be applied to, for example, replacement of larger genes, such as the SH3TC2 gene which causes CMT type 4C (CMT4C), which is approximately 3.9 kb in length. Other Schwann cell-related genes that may be close to the stability limit of the AAV, and will therefore be optimally delivered under a minimal Mpz promoter, include EGR2 (2.98 kb) which is associated with CMT4E, and FGD4 (2.3 kb) which is associated with CMT4H.

In further additional embodiments, the vectors described herein can be modified in the inverted terminal repeat segment to further reduce their size. For example, the woodchuck hepatitis virus post-transcriptional regulatory element (WPRE), as described in Example 1, can be removed and/or the polyA sequence can be replaced with a minimal synthetic polyA (68, 69). Such modifications can further reduce the size of the vector to allow it to remail within the maximum capacity of the AAV and to allow efficient packaging when delivering larger genes. In further additional embodiments, the size of the vector can be further reduced by, for example, also using minimal versions of the protein coding gene to be delivered, wherein the minimal version of the protein coding gene is still able to produce functional protein.

In some embodiments, the viral vector described herein may be produced as described in Example 12. In some embodiments the viral vector has the sequence shown in SEQ ID NO: 20, which has the WPRE removed and has a synthetic polyA sequence. In some embodiments the synthetic polyA sequence comprises or consists of a minimum sequence required for efficient poyadenylation of mRNA constructs (68, 69). In some embodiments the synthetic polyA sequence comprises or consists of the sequence of SEQ ID NO: 24, which is included in the sequences of SEQ ID NO: 20 and 21. In other embodiments the synthetic polyA sequence has at least 80%, or 82%, or 84%, or 86%, or 88%, or 90%, or 92%, or 94%, or 96%, or 97%, or 98%, or 99%, or 100% sequence identity or sequence homology to SEQ ID NO. 24.

In some embodiments, the viral vector also contains binding sites for Egr2 and Sox10 transcription factors. For example, the viral vector may also contain enhancer elements to which transcription factors such as Egr2 and Sox10 can bind.

In some embodiments, the first nucleic acid of the viral vector is transcribed into a first polynucleotide that in some embodiments encodes and is translated into a first polypeptide or protein. In some embodiments, the first nucleic acid is the open reading frame (ORF) of a gene sequence or the cDNA corresponding to a gene sequence. In some embodiments, the first nucleic acid is the ORF or cDNA of a wild-type or other therapeutically beneficial gene sequence. In a preferred embodiment, the first nucleic acid is the ORF or cDNA of a wild-type or therapeutically beneficial sequence of a neuropathy-associated gene, optionally wherein the neuropathy is a demyelinating neuropathy.

By "wild type or therapeutically beneficial form" we include any form of the gene sequence that encodes a polypeptide or protein that can be used to effectively treat the disease associated with Schwann cells. The skilled person would understand that this would typically be the wild type form of the protein (i.e. that which is naturally occurring in Schwann cells) in situations where the disease arises through underproduction of the wildtype form of the polypeptide by the Schwann cells, but can also include forms of the protein that have mutations or insertions or are truncated compared to the wild type sequence to provide a therapeutic advantage, for example increased expression levels, resistance to degradation, increased stability, increased activity, or an advantageous gain of function, or to suppress a toxic gain of function. For example, in the latter case, the polypeptide may be an antibody capable of binding to the toxic gain of function mutant and supress the toxicity.

The skilled person will be aware that protein expression is routinely carried out by introducing the ORF of the relevant gene, or the cDNA into the viral vector. In one embodiment the first nucleic acid is a cDNA sequence that when transcribed produces a first polynucleotide that is translated into a first polypeptide or protein. For example, the cDNA may be a cDNA sequence that is transcribed into GJB1 mRNA which is subsequently translated into Cx32 protein.

The skilled person will understand that the use of ORF sequences rather than cDNA sequences may be preferable in some instances, since the ORF sequence lacks additional non-coding elements found in cDNA and is smaller in size, which is particularly advantageous in the present invention when the viral vector is a vector that becomes unstable when the size increases above a particular threshold.

In some additional embodiments, the first nucleic acid sequence as described herein also optionally contains other regulatory elements in addition to the cDNA or ORF of the gene. These additional elements may be downstream of the ORF.

As discussed above, the invention has utility in the prevention or treatment of a disease associated with Schwann cells. By a "disease associated with Schwann cells" we include the meaning of all diseases that are associated with abnormal functioning of Schwann cells. This includes diseases associated with destruction of the myelin sheath formed by Schwann cells and/or diseases associated with reduced expression of myelin sheath formed by Schwann cells. In some embodiments, diseases associated with Schwann cells are demyelinating neuropathies. Examples of demyelinating neuropathies include but are not limited to Charcot-Marie-Tooth disease (CMT).

A "disease associated with Schwann cells" also includes in its meaning diseases that are associated with Schwann cells, but which are also associated with other cell types or tissues for example. It is considered that the invention is useful in such situations since an improvement in the function of Schwann cells can alleviate some symptoms, even if the invention does not target any other cell types that are associated with the disease.

Therefore, in one embodiment, the viral vectors described herein can be for use in treatment or prevention of a disease selected from the group consisting of: Charcot-Marie-Tooth disease (CMT); hereditary neuropathy with liability to pressure palsies (HNPP); diabetic and other toxic peripheral neuropathies; motor neuron disease (MND).

In some specific embodiments, the viral vectors described herein can be for use in treatment or prevention of Charcot-Marie-Tooth type 1X (CMT1X); Charcot-Marie-Tooth types 1A-1F (i.e. CMT1A, CMT1B, CMT1C, CMT1D, CMT1E and CMT1F); Charcot-Marie-Tooth types 4A-4H (i.e. CMT4A, CMT4B, CMT4C, CMT4D, CMT4E, CMT4F, CMT4G and CMT4H). In a more specific embodiment the viral vectors described herein can be used to treat or prevent Charcot-Marie-Tooth type 1X. In an alternative more specific embodiment, the viral vectors described herein can be used to treat or prevent Charcot-Marie-Tooth disease type 4C.

Charcot-Marie Tooth disease (CMT) is a group of demyelinating neuropathies caused by mutations in numerous different genes resulting in overlapping phenotypes. Charcot-Marie-Tooth type 1X (CMT1X) neuropathy is the second most common CMT form (4, 5) and presents with characteristic CMT1 symptoms, including progressive weakness and atrophy starting in distal leg muscles, difficulty running and frequently sprained ankles, with onset by 10 years of age or earlier in most affected males (6-8). The disease is slowly progressive causing weakness of foreleg muscles, foot drop, foot deformities, hand muscle weakness, and distal sensory loss with sometimes painful paresthesias by late adolescence or early adulthood and slow progression over the lifespan. Heterozygous females with CMT1X may be asymptomatic or develop milder clinical manifestations at an older age, but exceptionally severe neuropathy has been reported (9, 10). Transient CNS manifestations may occur in some, mostly younger CMT1X patients (11). Intermediate slowing (30-40 m/s) of motor nerve conduction velocities (MNCV) and progressive loss of motor units due to length-dependent axonal degeneration are typical electrophysiological features (6, 7). Nerve biopsies show mixed axonal and demyelinating abnormalities (12, 13) with thin myelin sheaths and loss of large myelinated fibers replaced by regenerating axon clusters (6, 14).

Cx32 is a transmembrane protein forming gap junction (GJ) channels through the non-compact myelin layers specifically expressed by myelinating Schwann cells in the peripheral nervous system (PNS), as well as by a subset of oligodendrocytes in the CNS. GJ channels formed by Cx32 serve important homeostatic and signaling functions that are essential for the function and survival of myelin and axons (4, 5). The corresponding gene that encodes Cx32 is GJB1.

More than 400 GJB1 mutations have been reported to date occurring throughout the open reading frame (ORF) and many in more than one family, including: 498 missense (71%); 3 stop-lost; 49 Inframe INDELs (7%); 25 Stop-Gained (4%); and 122 Frameshift INDELs (17%) (http://hihg.med.miami.edu/code/http/cmt/public_html/index-.html#/). Several mutations have been reported also in non-coding GJB1 regions. Frameshift, premature stop and non-coding mutations are likely to cause complete loss of protein synthesis or rapid degradation, and are not expected to result in any dominant-negative effects. Several missense and in-frame mutations expressed in vitro showed intracellular retention (15-17) in the ER and/or Golgi (17-21) with failure to form functional channels. Some also exerted dominant-negative effects on co-expressed WT Cx32 (15). Other mutants formed functional channels with altered biophysical characteristics (19). Cx32 knockout (KO) mice with complete deletion of the Gjb1/Cx32 gene develop a progressive, predominantly motor demyelinating peripheral neuropathy beginning at about three months of age with reduced sciatic MNCV and motor amplitude (24, 25). Expression of WT human Cx32 protein driven by the rat Mpz/P0 promoter prevented demyelination in Cx32 KO mice (26), confirming that loss of Schwann cell autonomous expression of Cx32 is sufficient to cause CMT1X pathology.

Thus, several in vitro and in vivo studies of CMT1X mutants support the overall conclusion that loss of Cx32 function mainly leads to the neuropathy in CMT1X (8, 17-19, 21-23). Accordingly, in one embodiment, gene replacement therapy using the viral vector and therapeutic methods as described herein is used to treat or prevent CMT1X, for example when the viral vector comprises a first nucleic acid sequences that encodes the wild type or therapeutically beneficial Cx32 protein.

Transgenic mice with mutations causing CMT1X on a KO background showed no detectable Cx32 protein in the 175fs mutant line (27), while R142W, T55I, R75W and N175D transgenic mice showed retention of the mutant protein in the perinuclear region, similar to in vitro pattern (above) and developed a demyelinating neuropathy similar to Cx32 KO mice (22, 28, 29). In the presence of the Golgi-retained R142W, R75W and N175D mutants (but not of the ER-retained T55I mutant), there was reduced expression of the endogenous mouse WT Cx32, indicating that Golgi-retained mutants may have dominant-negative effects on WT Cx32. This is not clinically relevant for CMT1X patients expressing only one GJB1 allele in each cell, but must be considered when planning a gene addition therapy. None of the mutants expressed in vivo had any other toxic or dominant effects on other co-expressed connexins (22, 28). The C-terminus mutants C280G and S281X were properly localized and prevented demyelination in Cx32 KO mice, leaving unclear how they cause neuropathy in humans (30).

Accordingly, CMT1X may also be caused by dominant negative mutations in the Cx32 protein. In this instance the skilled person will understand that it is beneficial if the viral vector of the invention comprises a first nucleic acid that is transcribed into a non-coding RNA that itself is directed towards the mutant Cx32 mRNA to prevent translation of the mutant protein. The skilled person will understand how to arrive at suitable nucleic acid sequences that, for example, target the mutant Cx32 mRNA but not a wild-type or therapeutically advantageous Cx32 mRNA. In this way, in one embodiment, the subject may be treated with a viral vector that comprises a first nucleic acid that is transcribed into a non-coding RNA that targets the mutant Cx32, and the subject may also be treated with a second viral vector according to the invention wherein the second viral vector comprises a second nucleic acid that encodes the wild type or therapeutically advantageous Cx32 protein. In some embodiments, the first and second nucleic acid may be on the same viral vector according to the invention. A similar approach may be taken in the treatment or prevention of any Schwann cell associated disease as described herein.

In some embodiments, the first nucleic acid may be the ORF or cDNA of a wild-type gene sequence of a neuropathy associated gene. In some embodiments, the first nucleic acid may be the cDNA of a wild-type sequence of the gap junction beta 1 (GJB1) gene, which is considered to have a sequence as defined in SEQ ID NO. 6. In some embodiments, the first nucleic acid has at least 75% sequence homology or sequence identity with SEQ ID NO. 6, optionally at least 80%, or 82%, or 84%, or 86%, or 88%, or 90%, or 92%, or 94%, or 96%, or 97%, or 98%, or 99%, or 100% sequence identity or sequence homology with SEQ ID NO. 6. In other embodiments the first nucleic acid has at least 75% sequence homology or sequence identity with the ORF sequence of GJB1, optionally at least 80%, or 82%, or 84%, or 86%, or 88%, or 90%, or 92%, or 94%, or 96%, or 97%, or 98%, or 99%, or 100% sequence identity or sequence homology with the ORF sequence of GJB1.

CMT1X is caused by mutations in the GJB1 gene, causing under-expression of wild-type functional Cx32 protein. It follows that in some embodiments the viral vectors described herein may be for use in treatment or prevention of CMT1X by delivery of a wild-type copy or other therapeutically beneficial copy of the open reading frame or cDNA of the GJB1 gene.

Charcot-Marie-Tooth type 4C (CMT4C) disease is an autosomal recessive inherited neuropathy that appears to be the most prevalent among the overall rare recessive demyelinating CMT4 forms of neuropathies, being responsible for almost half of all CMT4 cases (35). Patients with CMT4C usually present in the first decade of life with foot deformities and scoliosis, weakness, areflexia and sensory loss (36-38). Cranial nerve involvement with hearing impairment, slow pupillary light reflexes, and lingual fasciculation are common and phenotypic variations in patients with identical mutations have been described (39-41). Electrophysiological studies in CMT4C patients confirm the demyelinating process with mean median motor nerve conduction velocity (NCV) at 22.6 m/s. Nerve biopsy findings are characterized by an increase of basal membranes around myelinated, demyelinated, and unmyelinated axons, relatively few onion bulbs, and, most typically, large cytoplasmic extensions of Schwann cells (36, 37, 42).

Molecular genetics of CMT4C: Linkage analysis studies and homozygosity mapping (43) led to the discovery of the disease locus on chromosome 5q32 and subsequently to the initial discovery of 11 different mutations in the SH3TC2 gene, mostly truncating but also missense (42). At least 28 different SH3TC2 mutations have been described to date, and they may be more common among certain ethnic groups (44) with likely founder effects (39). The full transcript cDNA length measures 3864 bp. SH3TC2 encodes a protein of 1,288 aa containing two Src homology 3 (SH3) and 10 tetratricopeptide repeat (TPR) domains sharing no overall significant similarity to any other human protein with known function. The presence of SH3 and TPR domains suggests that SH3TC2 could act as a scaffold protein (42). SH3TC2 is well conserved among vertebrate species, whereas no non-vertebrate orthologs were identified. SH3TC2 is present in several components of the endocytic pathway including early and late endosomes, and clathrin-coated vesicles close to the trans-Golgi network and in the plasma membrane. This localization is altered in CMT4C (45).

The Sh3tc2−/− KO mouse model of CMT4C develops an early onset but progressive peripheral neuropathy with slowing of motor and sensory nerve conduction velocities and early onset hypomyelination (46, 47). This phenotype is progressive with increasing myelin pathology at 2 and 12 months of age. Murine Sh3tc2 is specifically expressed in Schwann cells and is localized to the plasma membrane and to the perinuclear endocytic recycling compartment, suggesting a possible function in myelination and/or in regions of axoglial interactions (48). Ultrastructural analysis of myelin in the peripheral nerve of mutant mice showed abnormal organization of the node of Ranvier, a phenotype that was confirmed in nerve biopsies from CMT4C patients. These findings suggested a role for the SH3TC2 gene product in myelination and in the integrity of the node of Ranvier (46). Thus, the Sh3tc2−/− mouse recapitulates all major features of CMT4C disease and provides a relevant model to test therapies.

Therefore, in some embodiments, the first nucleic acid may be the ORF or cDNA of the wild-type sequence of the gene SH3 domain and tetratricopeptide repeats 2 (SH3TC2) gene. The ORF of SH3TC2 is considered to have a sequence as defined in SEQ ID NO. 7. In some embodiments, the first nucleic acid has at least 75% sequence homology or sequence identity with SEQ ID NO. 7, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 7. In other embodiments the first nucleic acid has at least 75% sequence homology or sequence identity with the cDNA sequence of SH3TC2, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of SH3TC2.

As discussed above, CMT4C is caused by mutations in the SH3TC2 gene, causing under-expression of wild-type functional SH3TC2 protein. It follows that in some embodiments the viral vectors described herein may be for use in treatment or prevention of CMT4C by delivery of a wild-type copy or other therapeutically beneficial copy of the open reading frame or cDNA of SH3TC2, to, for example, increase expression of the wildtype SH3TC2.

In another embodiment, the viral vectors described herein can be used in methods of treatment or prevention of other types of autosomal dominant demyelinating CMT.

CMT1B is caused by mutations in the myelin protein zero (Mpz) gene, causing under-expression of wild-type functional Mpz protein.

Therefore, in some embodiments, the first nucleic acid may be the ORF or cDNA of the wild-type sequence of the myelin protein zero (MPZ) gene. The ORF of MPZ is considered to have a sequence as defined in SEQ ID NO. 9. In some embodiments, the first nucleic acid has at least 75% sequence homology or sequence identity with SEQ ID NO. 9, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 9. In other embodiments the first nucleic acid has at least 75% sequence homology or sequence identity with the cDNA sequence of MPZ, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of MPZ.

It follows that in some embodiments the viral vectors described herein may be for use in treatment or prevention of CMT1B by delivery of non-coding RNAs as described herein targeting and knocking down toxic mutant alleles of the MPZ gene in addition to delivering a wild-type copy or other therapeutically beneficial copy of the open reading frame or cDNA of the MPZ gene.

CMT1D is caused by mutations in the EGR2 gene, causing under-expression of wild-type functional EGR2 protein.

Therefore, in some embodiments, the first nucleic acid may be the ORF or cDNA of the wild-type sequence of the early growth response 2 (EGR2) gene. The ORF of EGR2 is considered to have a sequence as defined in SEQ ID NO. 10. In some embodiments, the first nucleic acid has at least 75% sequence homology or sequence identity with SEQ ID NO. 10, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 10. In other embodiments the first nucleic acid has at least 75% sequence homology or sequence identity with the cDNA sequence of EGR2, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of EGR2.

It follows that in some embodiments the viral vectors described herein may be for use in treatment or prevention of CMT1D by delivery of a wild-type copy or other therapeutically beneficial copy of the open reading frame or cDNA of the EGR2 gene.

In another embodiment, the viral vectors described herein can be used in methods of treatment or prevention of other types of autosomal recessive demyelinating CMT. CMT4A is caused by mutations in the GDAP1 gene, causing under-expression of wild-type functional GDAP1 protein.

Therefore, in some embodiments, the first nucleic acid may be the ORF of the wild-type sequence of the ganglioside induced differentiation associated protein 1 (GDAP1) gene. The ORF of GDAP1 is considered to have a sequence as defined in SEQ ID NO. 11. In some embodiments, the first nucleic acid has at least 75% sequence homology or sequence identity with SEQ ID NO. 11, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 11. In other embodiments the first nucleic acid has at least 75% sequence homology or sequence identity with the cDNA sequence of GDAP1, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of GDAP1.

It follows that in some embodiments, the viral vectors described herein may be for use in treatment or prevention of CMT4A by delivery of a wild-type copy or other therapeutically beneficial copy of the open reading frame or cDNA of the GDAP1 gene.

CMT4D is caused by mutations in the NDRG1 gene, causing under-expression of wild-type functional NDRG1 protein.

Therefore, in some embodiments, the first nucleic acid may be the ORF or cDNA of the wild-type sequence of the N-Myc downstream regulated 1 (NDRG1) gene. The ORF of NDRG1 is considered to have a sequence as defined in SEQ ID NO. 12. In some embodiments, the first nucleic acid has at least 75% sequence homology or sequence identity with SEQ ID NO. 12, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 12. In other embodiments the first nucleic acid has at least 75% sequence homology or sequence identity with the cDNA sequence of NDRG1, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of NDRG1.

It follows that in some embodiments the viral vectors described herein may be for use in treatment or prevention of CMT4D by delivery of a wild-type copy or other therapeutically beneficial copy of the open reading frame or cDNA of the NDRG1 gene.

CMT4E is caused by mutations in the EGR2 gene, causing under-expression of wild-type functional EGR2 protein.

Therefore, in some embodiments, the first nucleic acid may be the ORF or cDNA of the wild-type sequence of the early growth response 2 (EGR2) gene. The ORF of EGR2 is considered to have a sequence as defined in SEQ ID NO. 10. In some embodiments, the first nucleic acid has at least 75% sequence homology or sequence identity with SEQ ID NO. 10, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 10. In other embodiments the first nucleic acid has at least 75% sequence homology or sequence identity with the cDNA sequence of EGR2, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of EGR2.

It follows that in some embodiments the viral vectors described herein may be for use in treatment or prevention of CMT4E by delivery of a wild-type copy or other therapeutically beneficial copy of the open reading frame or cDNA of the EGR2 gene.

Hereditary neuropathy with liability to pressure palsies (HNPP) is associated with a mutation in the PMP22 gene, causing under-expression of wild-type functional PMP22 protein.

Therefore, in some embodiments, the first nucleic acid may be the ORF or cDNA of the wild-type sequence of the peripheral myelin protein 22 (PMP22) gene. The ORF of PMP22 is considered to have a sequence as defined in SEQ ID NO. 8. In some embodiments, the first nucleic acid has at least 75% sequence homology or sequence identity with SEQ ID NO. 8, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 8. In other embodiments the first nucleic acid has at least 75% sequence homology or sequence identity with the cDNA sequence of PMP22, optionally at least 80%, or 82%, or 84%, or 86%, or 88%, or 90%, or 92%, or 94%, or 96%, or 97%, or 98%, or 99%, or 100% sequence identity or sequence homology with the cDNA sequence of PMP22.

It follows that in some embodiments, the viral vectors described herein may be for use in treatment or prevention of HNPP by delivery of a wild-type copy or other therapeutically beneficial copy of the open reading frame or cDNA of the PMP22 gene.

In another embodiment, the first nucleic acid may be the ORF or cDNA of another gene associated with a demyelinating neuropathy and/or Schwann cell dysfunction. It follows that, in some embodiments, the viral vectors described herein may be for use in treatment or prevention of diseases associated with a demyelinating neuropathy and/or Schwann cell dysfunction by delivery of a wild-type copy or other therapeutically beneficial copy of the open reading frame or cDNA of a gene associated with such a disease.

Motor neuron disease (MND) (also called amyotrophic lateral sclerosis) is a neurodegenerative disorder with complex causes that have not been fully determined. In some embodiments, the viral vectors described herein may be used to deliver polynucleotides encoding trophic factors (for example brain-derived neurotrophic factor (BDNF), glial cell-derived neurotrophic factor (GDNF), neurotrophin-3 (NT-3), vascular endothelial growth factor (VEGF)). Expression of such trophic factors in target cells is considered to be useful in regenerating and saving stressed motor neurons.

It follows that in some embodiments, the viral vectors described herein are for use in methods of treating or preventing MND.

It would be clear to the skilled person that the wild-type or therapeutically beneficial form of the proteins disclosed herein could be expressed either from the nucleotide sequence of the full gene, just from the open reading frame sequence (ORF), or just from the cDNA sequence. All of these types of sequences would be readily accessed by the skilled person from a sequence database e.g. GenBank (accessible here: https://www.ncbi.nlm.nih.gov/genbank/).

In some embodiments, the first polynucleotide encodes and is translated into a first polypeptide or protein. In some embodiments, the first polynucleotide encodes a wild-type form of a protein. In some embodiments, the wild-type form of the protein is used to replace or supplement expression of a mutant form of the same protein that is expressed by a subject in need thereof.

In some embodiments, the first polynucleotide may encode a wild-type or therapeutically beneficial form of one or more of the following proteins: connexin-32 (Cx32); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1); N-Myc downstream regulated 1 (NDRG1). The skilled person would understand that the amino acid sequences of the proteins disclosed herein could be readily accessed from a sequence database e.g. the NCBI Protein Database (accessible here: https://www.ncbi.nlm.nih.gov/protein).

Therefore, in some embodiments the invention can be applied to methods of gene replacement by providing an AAV vector containing a wild-type form or other therapeutically beneficial form of a gene to be replaced. In some non-limiting examples, the gene to be replaced may be mutated in such a way that it does not encode protein, it encodes a truncated version of the wild-type protein (for example there is a premature stop codon), it encodes a reduced amount of functional protein or it encodes a non-functional mutant form of the protein.

In an additional or alternative embodiment, the first nucleic acid encodes and is translated into a trophic factor (for example brain-derived neurotrophic factor (BDNF), glial cell-derived neurotrophic factor (GDNF), neurotrophin-3 (NT-3), vascular endothelial growth factor (VEGF)). By trophic factor we include biomolecules (for example proteins or peptides) which support the growth, differentiation and/or development of developing and mature neurons. In another additional or alternative embodiment, the first polynucleotide encodes a regenerative factor (for example Angiogenin, Oct-6, Egr2, Sox-10). In another additional or alternative embodiment, the first polynucleotide encodes a growth factor (for example IGF).

Using the vectors described herein to deliver nucleic acids encoding the trophic factors, regenerative factors and/or growth factors described above may be used in some embodiments to treat or prevent acquired peripheral nerve disorders. In one example, diabetic and other toxic peripheral neuropathies could be treated by delivering vectors as described herein encoding trophic factors and/or growth factors to Schwann cells and axons. In another example, motor neuron disease (MND) (also known as amyotrophic lateral sclerosis) may be treated by delivering vectors as described herein encoding trophic factors that can be delivered to axons of stressed motor neurons to retroactively save said motor neurons.

In another embodiment, the administration of a viral vector comprising a first nucleic acid that encodes a first protein or polypeptide leads to improved functioning of Schwann cells and/or increased formation of myelin sheath. In some embodiments this improvement in function is achieved by increased formation of myelin sheath by Schwann cells when compared to the formation of myelin sheath by Schwann cells in the subject prior to treatment and the improvement in function can be detected via the detection of an increased production of myelin sheath. In some embodiments, the improvement in function can be measured by an improvement in muscle strength and/or improved sciatic nerve conduction velocity and/or changes to potential response of blood biomarkers when compared to these measures in the subject prior to treatment. The skilled person is aware of techniques to determine an improvement in the function of Schwann cells and/or increased formation of myelin sheath. Some such techniques are provided in the Examples.

In some specific embodiments, the increased formation of myelin sheath by the Schwann cells leads to improved myelination of the peripheral nerves. By improved myelination of the peripheral nerves we mean that there is increased myelination of peripheral nerves compared to the subject before treatment. This includes a decrease in demyelinated and remyelinated fibers and/or a reduction in abnormally myelinated fibers. Improved myelination may also be associated with a reduction in the number of foamy macrophages, which is a marker of inflammation, in some embodiments. Improved myelination may also be associated with increased myelin thickness and reduced g-ratios (axonal diameter divided by myelinated fiber diameter).

As described above, the first nucleic acid may encode a polypeptide or protein that has therapeutic benefits, for example when the native protein is mutated or expressed at a level which is too low to result in normal functionality.

It will be appreciated that in an alternative embodiment, the first nucleic acid may be transcribed into an RNA that is not an mRNA, i.e. is not an RNA that is translated into a protein. Accordingly, the first nucleic acid may be transcribed into a non-coding RNA.

By "non-coding RNA" we mean any RNA molecule that is not translated into a polypeptide or protein. The skilled person will be aware of such RNA polymers and how they can be used to affect the expression of polypeptides. In one embodiment the first nucleic acid is transcribed into a non-coding micro-RNA (miR). In a further additional alternative embodiment, the first nucleic acid is transcribed into a short-hairpin RNA (shRNA). In a further embodiment the first nucleic acid is transcribed into a guide RNA (gRNA), for example as part of a CRISPR-based system.

Expression of the non-coding RNA described above when the viral vector is in a target organism may lead to reduction in expression of a target polynucleotide, optionally wherein the target polynucleotide is a gene located in a target organism, optionally wherein it is located in a cell in a target organism. In some embodiments the target polynucleotide is a gene sequence. Therefore, in some embodiments the invention described herein can be used to knock-down expression of a target gene. By "knock-down" we mean that the expression of the target gene is reduced compared to expression levels prior to treatment with the viral vector.

For example, the invention can be applied to situations where a target nucleic acid, for example a target gene, is over-expressed. The viral vector can be used to deliver a first nucleic acid that is transcribed into a non-coding RNA to, for example, target the mRNA produced by the gene that this over-expressed for degradation (e.g. by the RISC complex, which is well known in the art) or to directly block translation of said mRNA into protein. This embodiment of the invention also applies to situations in which the target nucleic acid is itself transcribed into a non-coding RNA, and it is beneficial to reduce the levels of the host non-coding RNA in the cell.

This embodiment of the invention can also be used to target deleterious gain-of-function mutants and reduce their protein or mRNA expression levels.

Therefore, in some embodiments, expression of non-coding RNA results in reduction in expression of a target nucleic acid, polynucleotide or gene. In one embodiment expression or overexpression of the target polynucleotide in a target organism is considered to be associated with a disease associated with Schwann cells, optionally wherein the disease is a dominant demyelinating neuropathy (CMT1), optionally wherein the target polynucleotide is a mutated allele of myelin protein zero (Mpz/P0) and the disease associated with Schwann cells is CMT1B, or wherein the target polynucleotide is another dominant gene associated with CMT1.

In some embodiments, the administration of a viral vector encoding a first nucleic acid results in expression of a non-coding RNA that leads to improved functioning of Schwann cells. As discussed above, in some embodiments this improvement in function is achieved by increased formation of myelin sheath by Schwann cells when compared to the formation of myelin sheath by Schwann cells in the subject prior to treatment. In some embodiments, this improvement in function can be measured by an improvement in muscle strength and/or improved sciatic nerve conduction velocity and/or changes to potential response of blood biomarkers when compared to these measures in the subject prior to treatment.

In some embodiments, the viral vectors described herein comprises a first nucleic acid sequence that encodes a first polypeptide or protein, and the vector can also comprise a second nucleic acid that is transcribed into a non-coding RNA. Therefore, the invention can be used in some embodiments to knock-down expression of a mutant gene using a non-coding RNA and to also replace the mutant gene with a wild-type copy of said gene, resulting in complete gene replacement. This approach is considered to be particularly useful where the subject in need of therapy has a gain of function mutation in a particular protein.

In some embodiments, the viral vector also contains a second or third nucleic acid sequence that encodes a transcription factor capable to driving expression or increased expression from the Schwann cell specific promoter, optionally the myelin specific promoter or minimal myelin specific promoters as defined herein. Examples of such transcription factors that can drive expression of polynucleotides under the control of Schwann cell specific promoters include Egr2 and Sox10.

The viral vector may also comprise a nucleic acid sequence that encodes a Cas9 polypeptide or similar that is routinely used in CRISPR techniques and variations thereof, such as dead-Cas9.

It will be understood that the viral vectors described herein can be administered to the subject in a variety of ways. In a preferred embodiment, the viral vectors described herein are administered by intrathecal injection. By "intrathecal injection" we include injection into the spinal canal which results in the injected material reaching the cerebrospinal fluid (CSF). In a particularly preferred embodiment, the viral vectors described herein are administered by lumbar intrathecal injection. The viral vectors described herein are also suitable for administration by thoracic intrathecal injection or cervical intrathecal injection. Alternatively, the viral vectors described herein could be administered by direct injection into peripheral nerves. Alternatively, the viral vectors described herein could be administered by direct intravenous injection.

Intrathecal injection provides advantages over other administration methods such as intraneural and intraveneous injection. Compared to intraneural injection, intrathecal injection provides a more widespread distribution to multiple spinal roots and nerves. In contrast, intraneural injection provides distribution only within the injected nerve. In addition, intrathecal injection can be done routinely in the clinic, does not require surgical procedure and is considered safe, while intraneural injections will require surgical procedure, and multiple nerves to be exposed, higher risk, so much more difficult to translate in the clinic.

While intravenous injection is easier to administer in the clinic, it has the disadvantage of requiring much higher doses of the vector to reach the nervous system compared to intrathecal delivery. Intravenous delivery can also lead to more toxicity, due to higher doses of the virus and liver toxicity risk. In addition, intravenous injection is likely to cause more immune reactions, whereas intrathecal delivery provides a possibility to evade the immune system with lower immune response.

Once the AAV vectors described herein have transduced the target cell the genetic material that is delivered remains stable and episomal, providing the target cell has differentiated and is not dividing, as is the case with mature Schwann cells. Therefore, a single administration of an AAV vector should be sufficient to achieve therapeutic effects, and in some embodiments the viral vectors described herein are administered by a single intrathecal injection. However, in some cases, it may be necessary to administer multiple doses of different AAV vectors to the subject at different time points. These different vectors may express different first polynucleotides, or may express the same first polynucleotide and differ in the type of AAV that is used. Therefore, in some embodiments the viral vectors disclosed herein may be useful in treating or preventing diseases associated with Schwann cells that are associated with multiple different genes.

It will be appreciated that the viral vectors disclosed herein are suitable for use in human subjects. The viral vectors are also suitable for use in mammals in general such as: cat, dog, mouse, rabbit, horse. The subjects may be treated with the viral vectors disclosed herein either prior to the onset of symptoms of the disease associated with Schwann cells or after the onset of symptoms of said disease. The subjects to be treated may be any age at the onset of treatment. For example, the subjects may be treated with the vector(s) of the invention as soon as it is confirmed that the subject has a mutation or other defect compromising performance of the Schwann cells. This may be before any symptoms are exhibited.

It will be appreciated that the dose of viral vector used will be adjusted according to the requirement of the subject in need thereof, for example it may be adjusted due to the age, weight or height of the subject. As a general example, a dose of (for intrathecal delivery) escalating doses at $3.5\times10^{13}$ vector genomes (vg), 3.3× higher dose of $1.2\times10^{14}$ vg, and the 5 times higher dose of $1.8\times10^{14}$ vg, could be used. Doses such as these have been used previously in clinical trials using AAVs (e.g. https://clinicaltrials.gov/ct2/show/NCT02362438), and the skilled person would be aware that they could be applied to the present invention.

It will be clear to the skilled person that in addition to therapeutic methods of preventing or treating a disease associate with Schwann cells, the invention also provides the viral vector per se. Accordingly, in another aspect, the invention provides a viral vector as described herein comprising a nucleic acid sequence as defined herein. In a preferred embodiment the viral vector is an AAV. In a particularly preferred embodiment the AAV is an AAV9. Preferences for features of this aspect are as described elsewhere in this specification, for example the preferences for the vector, nucleic acid, promoter, Schwann cell associated disease are as defined herein.

In a further aspect, the invention provides a minimal myelin specific promoter comprising or consisting of the sequence as defined in SEQ ID NO. 5 or a sequence with at least 75% sequence homology or sequence identity with SEQ ID NO. 5, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 5. Preferences for features of this aspect are as described in this specification, for example the preferences for the vector, nucleic acid, promoter, Schwann cell associated disease are as defined herein.

In a further aspect, the invention provides a minimal myelin specific promoter comprising or consisting of the sequence as defined in SEQ ID NO. 22 or a sequence with at least 75% sequence homology or sequence identity with SEQ ID NO. 22, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 22. Preferences for features of this aspect are as described in this specification, for example the preferences for the vector, nucleic acid, promoter, Schwann cell associated disease are as defined herein. In some embodiments, the invention provides a human minimal myelin specific promoter, wherein the human minimal myelin specific promoter has a sequence homology with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 22.

In a further aspect, the invention provides a polynucleotide construct comprising a first nucleic acid sequence that is a Schwann cell specific promoter, optionally a myelin specific promoter, optionally comprising the myelin protein zero (Mpz) promoter or a minimal myelin specific promoter as defined herein, operably linked to a second nucleic acid sequence which is transcribed into a first polynucleotide, wherein the second nucleic acid: a) is the open reading frame or cDNA or other elements of a gene; or b) is transcribed into a non-coding RNA.

The invention also provides a viral vector comprising such a polynucleotide construct, for example provides an AAV vector comprising the construct. Preferences for features of this aspect are as described in this specification, for example the preferences for the vector, nucleic acid, promoter, Schwann cell associated disease are as defined herein. For example in one embodiment the polynucleotide construct of the invention comprises a Schwann cell specific promoter, wherein the promoter is a) a minimal Schwann cell specific promoter, optionally a minimal Mpz promoter as described herein, for example where the promoter has a sequence with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 5 or SEQ ID NO. 22; or b) a full-length Mpz promoter optionally wherein the promoter has a sequence with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 4 or SEQ ID NO. 18.

Preferably the polynucleotide construct of the invention comprises a human minimal Mpz or human full-length Mpz promoter as described herein.

In a further aspect, the invention provides the following viral vectors:

a) An AAV-Mpz.Egfp vector comprising an AAV9 vector, the myelin protein zero (Mpz) promoter and the EGFP reporter gene (SEQ ID NO. 1), optionally wherein the promoter has a sequence with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 4 or SEQ ID NO. 18;
b) An AAV9-Mpz-GJB1 vector comprising an AAV9 vector, the myelin protein zero (Mpz) promoter and the open reading frame (ORF) of the gap junction beta 1 (GJB1) gene (SEQ ID NO. 2), optionally wherein the promoter has a sequence with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 4 or SEQ ID NO. 18;
c) An AAV9-miniMpz.Egfp vector comprising an AAV9 vector, the minimal myelin protein zero (miniMpz) promoter and the EGFP reporter gene (SEQ ID NO. 3), optionally wherein the miniMPZ promoter has a sequence homology with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 5 or SEQ ID NO. 22;
d) An AAV9-human Mpz-GJB1 vector comprising an AAV9 vector, the human myelin protein zero (hP0) promoter and the open reading frame (ORF) of the gap junction beta 1 (GJB1) gene (SEQ ID NO. 17);
e) An AAV9-human Mpz-Egfp vector comprising an AAV9 vector, the human myelin protein zero (hP0) promoter and the EGFP reporter gene (SEQ ID NO. 19);
f) An AAV9-miniMpz-SH3TC2.myc.ITR vector comprising an AAV9 vector, a minimal myelin protein zero (Mpz) promoter and the open reading frame (ORF) of the SH3TC2 gene (SEQ ID NO. 20);

g) An AAV9-human-miniMpz-SH3TC2 vector comprising an AAV9 vector, a human minimal myelin protein zero (hP0) promoter and the open reading frame (ORF) of the SH3TC2 gene (SEQ ID NO. 21);

h) An AAV9-human-miniMpz-Egfp vector comprising an AAV9 vector, a human minimal myelin protein zero (hP0) promoter and the EGFP reporter gene (SEQ ID NO. 23);

or i) an AAV, optionally wherein the AAV vector is an AAV9

Preferences for features of this aspect are as described in this specification, for example the preferences for the vector, nucleic acid, promoter, Schwann cell associated disease are as defined herein.

In one specific embodiment, the invention also provides a viral vector for use in treating or preventing a disease associated with Schwann cells in a subject in need thereof, wherein the viral vector comprises a first nucleic acid sequence that is transcribed into a first polynucleotide, and wherein transcription of said first nucleic acid is under the control of a minimal myelin specific promoter, optionally comprising or consisting of the sequence defined in SEQ ID NO. 5 or SEQ ID NO. 22 or that has at least 75% sequence homology or sequence identity with SEQ ID NO. 5 or 22, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 5 or 22. In one embodiment, the viral vector may be an AAV vector. In another alternative embodiment, the viral vector may be a lentiviral vector. Preferences for features of this aspect are as described in this specification, for example the preferences for the vector, nucleic acid, promoter, Schwann cell associated disease are as defined herein.

In another aspect, the invention also provides pharmaceutical compositions comprising any of the viral vectors as described herein. In some embodiments, the pharmaceutical composition comprises an appropriate amount of the viral vector and further comprises a pharmaceutically acceptable excipient, diluent, carrier, buffer or adjuvant. Preferences for features of this aspect are as described in this specification, for example the preferences for the vector, nucleic acid, promoter, Schwann cell associated disease are as defined herein.

As used herein, "pharmaceutical composition" means a therapeutically effective formulation for use in the treatment or prevention of diseases associated with Schwann cells.

The pharmaceutical compositions may be prepared in a manner known in the art that is sufficiently storage stable and suitable for administration to humans.

By "pharmaceutically acceptable" we mean a non-toxic material that does not decrease the effectiveness of the biological activity of the active ingredients, i.e. the viral vector. Such pharmaceutically acceptable carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the viral vector in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the viral vector. The adjuvant may be one or more of colloidal silver, or zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as PHMB, cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, poly(lactic acid), poly(glycholic acid) or copolymers thereof with various composition, and polyvinylpyrrolidone, all of different molecular weight, which are added to the composition, e.g. for viscosity control, for achieving bioadhesion, or for protecting the active ingredient from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

In another aspect the invention provides the use of a viral vector as described herein in a method of manufacture of a medicament for the treatment or prevention of a disease associated with Schwann cells. In some embodiments the disease causes destruction and/or reduced formation of myelin sheath by Schwann cells. In a preferred embodiment the disease is Charcot-Marie-Tooth disease. Preferences for features of this aspect are as described in this specification, for example the preferences for the vector, nucleic acid, promoter, Schwann cell associated disease are as defined herein.

In yet another aspect, the invention provides methods of treatment or prevention of a disease associated with Schwann cells using any of the viral vectors described herein. In a specific embodiment, the invention provides methods of treatment or prevention of Charcot-Marie-Tooth disease. In a preferred embodiment, the disease is Charcot-Marie-Tooth disease type 1X or type 4C. Preferences for features of this aspect are as described in this specification, for example the preferences for the vector, nucleic acid, promoter, Schwann cell associated disease are as defined herein.

The skilled person will appreciate that the viral vectors described herein could be used in a CRISPR/Cas system for use in gene editing or gene silencing, for example by using a dead-Cas9 polypeptide. Accordingly, in another aspect the invention includes a viral vector or polynucleotide construct as described herein for use in a CRISPR/Cas9 system comprising any one or more of:

a) a polynucleotide encoding a single guide RNA (sgRNA) targeting a gene of interest;
b) a polynucleotide encoding a Cas9 polypeptide;
c) a polynucleotide encoding a polypeptide of interest.

Preferences for features of this aspect are as described in this specification, for example the preferences for the vector, nucleic acid, promoter, Schwann cell associated disease are as defined herein.

It would be clear to the skilled person that the viral vectors disclosed herein could have a variety of uses other than for the treatment or prevention of diseases associated with Schwann cells. For example, the viral vectors disclosed herein may be used in a method of labelling Schwann cells, for example with fluorescent protein, for example green fluorescent protein (GFP) or enhanced green fluorescent protein (EGFP), or with other non-fluorescent reporters. In some examples, the labelling of Schwann cells can be used in a method of diagnosing a disease associated with Schwann cells.

Preferences for features of this aspect are as described in this specification, for example the preferences for the vector, nucleic acid, promoter, Schwann cell associated disease are as defined herein.

In another example, the viral vectors disclosed herein may be used in methods of inducing Schwann cells to differentiate into alternative cell types, for example neurons, oligodednrocytes, or astrocytes.

In yet another example, the viral vectors disclosed herein may be used in methods of stimulating Schwann cells to support regeneration in a subject in need thereof, for example after an injury or trauma. Preferences for features of this aspect are as described in this specification, for example the preferences for the vector, nucleic acid, promoter, Schwann cell associated disease are as defined herein.

In yet another example, the viral vectors disclosed herein may be suitable for use in ex vivo methods of treating diseases associated with Schwann cells. For example, target cells could be removed from the subject in need of treatment and transduced with a viral vector as described herein before being introduced back into the subject.

Preferences for features of this aspect are as described in this specification, for example the preferences for the vector, nucleic acid, promoter, Schwann cell associated disease are as defined herein.

The invention also provides a cell that has been transduced by the viral vector of the invention, for example a Schwann cell.

The invention also provides a cell that comprises the nucleic acid construct of the invention that comprises the relevant promoter and first nucleic acid. The skilled person would be aware that the viral vectors of the present invention can be produced in cultured cells, preferably HEK293 cells, for example as described in (58).

It will be appreciated that the vectors and methods described herein can be performed in vivo, but may also be used ex vivo or in vitro, for example cells such as Schwann cells may be transduced in vitro or ex vivo for subsequent therapeutic or research purposes.

The invention also provides kits that can be used to implement any of the viral vectors described herein. For example, the invention provides a kit for use with the viral vector or polynucleotide of any of the preceding claims wherein the kit comprises one or more of:

a) a viral vector as defined herein;
b) a polynucleotide construct as defined herein;
c) a viral vector;
d) a viral vector comprising the polynucleotide construct as defined herein;
e) a pharmaceutically acceptable carrier and/or excipient;
f) a single-use syringe, for example a single-use syringe suitable for intrathecal lumbar injection;
g) instructions for use.

In one embodiment the kit comprises more than on viral vector according to the invention, for example the kit may comprise two different viral vectors as defined herein.

It will be clear to the skilled person that in any of the therapeutic uses of the invention, more than one viral vector according to the invention may be administered to the subject. It will be clear to the skilled person that in some situations this is advantageous, for example if more than one gene is known to be associated with the Schwann cell associated disease, multiple viral vectors may be administered, each vector directed towards expressing a different therapeutic protein. Alternatively, a single vector may express more than one therapeutic protein or non-coding RNA. in other situations, such as those described above, one viral vector can be used to express for example a Cas9 protein in Schwann cells, and a different viral vector can be used to express the relevant gRNA to target Cas9 to the required nucleic acid.

The listing or discussion of an apparently prior published document in this specification should not necessarily be taken as an acknowledgement that the document is part of the state of the art or is common general knowledge.

Preferences and options for a given aspect, feature or parameter of the invention should, unless the context indicates otherwise, be regarded as having been disclosed in combination with any and all preferences and options for all other aspects, features and parameters of the invention.

Accordingly, and to exemplify how the disclosure of one aspect of the invention relates to other aspects of the invention, and to demonstrate how these aspects may be combined, the invention, in some embodiments, provides:

A viral vector for use in the treatment or prevention of a disease associated with Schwann cells wherein the viral vector is an AAV and wherein the viral vector comprises a first nucleic acid that can be transcribed into a first polynucleotide, wherein expression of the first polynucleotide is under the control of a minimal myelin specific (Mpz) promoter;

A viral vector for use in the treatment or prevention of a disease associated with Schwann cells wherein the viral vector is an AAV and wherein the viral vector comprises a first nucleic acid that can be transcribed into a first polynucleotide, wherein expression of the first polynucleotide is under the control of a) a myelin protein zero (Mpz) promoter, optionally wherein the promoter has a sequence with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 4 or SEQ ID NO. 1; or b) a minimal myelin specific promoter (miniMpz), optionally comprising or consisting of the sequence defined in SEQ ID NO. 5 or SEQ ID NO. 22, optionally wherein the miniMPZ promoter has a sequence homology with at least 75%, 80%, or 82%, or 84%, or 86%, or 88%, or 90%, or 92%, or 94%, or 96%, or 97%, or 98%, or 99%, or 100% sequence homology or sequence identity with SEQ ID NO. 5 or SEQ ID NO. 22;

A polynucleotide construct comprising a first nucleic acid sequence that is a minimal myelin specific (Mpz) promoter which is operably linked to a second nucleic acid sequence, wherein the second nucleic acid sequence is either the open reading frame of a gene sequence or encodes a non-coding RNA;

A minimal myelin specific (Mpz) promoter that drives high levels of expression in Schwann cells and is suitable for use in the viral vectors described herein.

The invention also provides:

a viral vector for use in treating or preventing CMT1X, wherein the vector comprises a human Mpz promoter (according to SEQ ID NO: 18) operably linked to the GJB1 gene, wherein the viral vector is AAV9;

use of a viral vector in a method of manufacture of a medicament for the treatment or prevention of CMT1X, wherein the vector comprises a human Mpz promoter (according to SEQ ID NO: 18) operably linked to the GJB1 gene, where the viral vector is AAV9; and a method of treating or preventing CMT1X wherein the method comprises administering a viral vector to a patient in need thereof, wherein the viral vector comprises a human Mpz promoter (according to SEQ ID NO: 18) operably linked to the GJB1 gene, and where the viral vector is AAV9.

The invention also provides:

a viral vector for use in treating or preventing CMT4C, wherein the vector comprises the human minimal Mpz promoter (according to SEQ ID NO: 22) operably linked to the SH3TC2 gene, where the viral vector is AAV9; use of a viral vector in a method of manufacture of a medicament for the treatment of prevention of CMT4C, wherein the vector comprises a human Mpz promoter (according to SEQ ID NO: 22) operably linked to the SH3TC2 gene, where the viral vector is AAV9; and a method of treating or preventing CMT4C wherein the method comprises administering a viral vector to a patient in need thereof, wherein the viral vector comprises a human Mpz promoter (according to SEQ ID NO: 22) operably linked to the SH3TC2 gene, and where the viral vector is AAV9.

A patient in need thereof includes a patient that has displayed symptoms or has otherwise received a diagnosis of one of the diseases disclosed herein, and also includes a patient that is suspected of having, or will develop, one of the diseases disclosed herein.

DESCRIPTION OF THE FIGURES

FIG. 12C shows a significant improvement over time following treatment, whereas mock treated mice did not show any improvement.

Sequences

Figure 1:
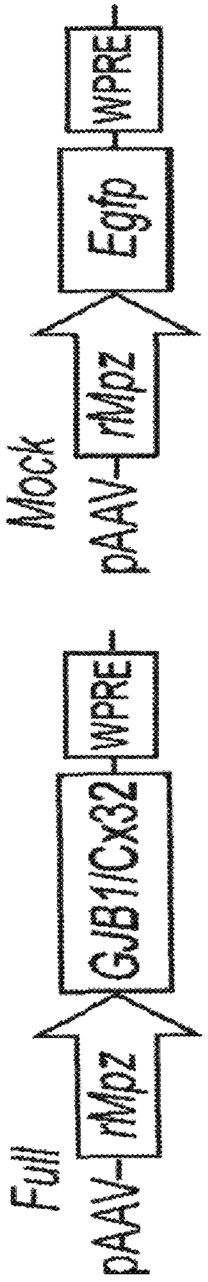
FIG. 1: AAV vector transfer plasmids generated for Schwann cell-targeted gene expression: pAAV-Mbz.GJB1 vector containing the human GJB1 open reading frame expressing Cx32 (Full) and pAAV-Mpz.Egfp expressing the reporter gene EGFP (Mock).

SEQ ID NO. 1: AAV-Mpz.Egfp construct
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta
cttatctacgtagccatgctctaggtaccgggccccccctcgaggtcgacggtatcgataagctt*cctgttcagactcgtttcctgctgtac*
*cctttcaatggccccacatcaaatcaaacacagatggcacatatctactctaaatatatgcagagcttcacaaacgtcatacacgtacgtg*
*tgtcacacacgcacacacacacccttccacctctgcccttacctttgctgtcccatctagacattatccctcccatccccttatttcccttatcaa*
*aatggctgctccttcaaggttccaaataacactgcttcctggacctgactcctctttcctctgaacttcctgtgttaagtgtattcctagtgcactg*
*tgccttggtagttgttgagattgccctctgcttctcccttctgcctcctcatctagtgatcttgagcttgtagaaagaactgaattaccattctaata*
*cgagcattctcgaactctccaaatagccaccaagcaggacaataggcagtcttgatcatttaaactgctgcatggcaaaaggaatcgaa*
*ggatttcttaacagaagtgggggggggggagatctgggcttcttcctggaagtttcctgatagagaaaatcttctgcctgggtagaatctcc*
*caggatgcagggagatggaaaaagtgttccccaaggactttgtagtctacaggttgtggagccatcggaacaacgagacaccctaattt*
*gggagtgctctgaaagaaacttgcctctaggccctagggctctcaggcaaggaggctaagaaggaatcctttgctgtagccttttggattt*
*aggtttctcagcttatctatccctcagagaagtgtgtctatgtccctttctgtccctctgcctcaccccaccccaacattccaacctagggtag*
*ggggaggtcagtatacacaaagccctctgtgtaaggggtggtatgtgtcccccaccccctacccagagtatacaatgccccttctgctc*
*catgcccctgccaccctcccaccacctctcaattgcacatgccaggctgcaattggtcactggctcaggacagcccctcatgctgggga*
*tccaggggattttaagcaggttccagaaaacaccactcagttccttgtccccgctctctccaccccacagacgctctgcc*aagcttgatat
cgaattgatccaccggtcgccaccatggtgagcaagggcgaggagctgttcaccggggtggtgcccatcctggtcgagctggacggcg
acgtaaacggccacaagttcagcgtgtccggcgagggcgagggcgatgccacctacggcaagctgaccctgaagttcatctgcacca
ccggcaagctgcccgtgccctggcccaccctcgtgaccaccctgacctacggcgtgcagtgcttcagccgctaccccgaccacatgaa
gcagcacgacttcttcaagtccgccatgcccgaaggctacgtccaggagcgcaccatcttcttcaaggacgacggcaactacaagacc
cgcgccgaggtgaagttcgagggcgacaccctggtgaaccgcatcgagctgaagggcatcgacttcaaggaggacggcaacatcct
ggggcacaagctggagtacaactacaacagccacaacgtctatatcatggccgacaagcagaagaacggcatcaaggtgaacttca
agatccgccacaacatcgaggacggcagcgtgcagctcgccgaccactaccagcagaacacccccatcggcgacggccccgtgct
gctgcccgacaaccactacctgagcacccagtccgccctgagcaaagaccccaacgagaagcgcgatcacatggtcctgctggagtt
cgtgaccgccgccgggatcactctcggcatggacgagctgtacaagtaaagcggccctagatcaagctt*atcgataatcaacctctgga*
*ttacaaaatttgtgaaagattgactggtattcttaactatgttgctccttttacgctatgtggatacgctgctttaatgcctttgtatcatgctattgctt*
*cccgtatggctttcattttctcctccttgtataaatcctggttgctgtctctttatgaggagttgtggcccgttgtcaggcaacgtggcgtggtgtgc*
*actgtgtttgctgacgcaacccccactggttggggcattgccaccacctgtcagctcctttccgggactttcgotttccccctccctattgccac*
*ggcggaactcatcgccgcctgccttgcccgctgctggacaggggctcggctgttgggcactgacaattccgtggtgttgtcggggaaatc*
*atcgtcctttccttggctgctcgcctgtgttgccacctggattctgcgcgggacgtccttctgctacgtcccttcggccctcaatccagcggacc*
*ttccttcccgcggcctgctgccggctctgcggcctcttccgcgtcttcgccttcgccctcagacgagtcggatctccctttgggccgcctcccc*
gcatcgataccgtcgactcgctgatcagcctcgactgtgccttctagttgccagccatctgttgtttgcccctcccccgtgccttccttgaccct
ggaaggtgccactcccactgtcctttcctaataaaatgaggaaattgcatcgcattgtctgagtaggtgtcattctattctggggggtggggt
ggggcaggacagcaagggggaggattgggaagacaatagcaggcatgctggggatgcggtgggctctatggcttctgaggcggaa
agaaccagctggggctcgactagagcatggctacgtagataagtagcatggcgggttaatcattaactacaaggaacccctagt
gatggagttggccactccctctctgcgcgctcgctcgctcactgaggccgggcgaccaaaggtcgcccgacgcccgggctt
tgcccgggcggcctcagtgagcgagcgagcgcgcagagctttttgcaaaagcctaggcctccaaaaaagcctcctcactacttct
ggaatagctcagaggccgaggcggcctcggcctctgcataaataaaaaaaattagtcagccatggggcggagaatgggcggaactg
ggcggagttaggggcgggatgggcggagttaggggcgggactatggttgctgactaattgagatgcatgctttgcatacttctgcctgctg
gggagcctggggactttccacacctggttgctgactaattgagatgcatgctttgcatacttctgcctgctggggagcctggggactttccac
accctaactgacacacattccacagctgcattaatgaatcggccaacgcgcggggagaggcggtttgcgtattgggcgctcttccgcttc
ctcgctcactgactcgctgcgctcggtcgttcggctgcggcgagcggtatcagctcactcaaaggcggtaatacggttatccacagaatc
aggggataacgcaggaaagaacatgtgagcaaaaggccagcaaaaggccaggaaccgtaaaaaggccgcgttgctggcgtttttc
cataggctccgcccccctgacgagcatcacaaaaatcgacgctcaagtcagaggtggcgaaacccgacaggactataaagatacca
ggcgtttccccctggaagctccctcgtgcgctctcctgttccgaccctgccgcttaccggatacctgtccgcctttctcccttcgggaagcgtg
gcgctttctcatagctcacgctgtaggtatctcagttcggtgtaggtcgttcgctccaagctgggctgtgtgcacgaaccccccgttcagccc
gaccgctgcgccttatccggtaactatcgtcttgagtccaacccggtaagacacgacttatcgccactggcagcagccactggtaacag
gattagcagagcgaggtatgtaggcggtgctacagagttcttgaagtggtggcctaactacggctacactagaagaacagtatttggtatc
tgcgctctgctgaagccagttaccttcggaaaaagagttggtagctcttgatccggcaaacaaaccaccgctggtagcggtggtttttttgttt
gcaagcagcagattacgcgcagaaaaaaaggatctcaagaagatcdttgatcttttctacggggtctgacgctcagtggaacgaaaa
ctcacgttaagggattttggtcatgagattatcaaaaaggatcttcacctagatcdtttaaattaaaaatgaagttttaaatcaatctaaagta
tatatgagtaaacttggtctgacagttaccaatgcttaatcagtgaggcacctatctcagcgatctgtctatttcgttcatccatagttgcctgac
tccccgtcgtgtagataactacgatacgggagggcttaccatctggccccagtgctgcaatgataccgcgagacccacgctcaccggct
ccagatttatcagcaataaaccagccagccggaagggccgagcgcagaagtggtcctgcaactttatccgcctccatccagtctattaat
tgttgccgggaagctagagtaagtagttcgccagttaatagtttgcgcaacgttgttgccattgctacaggcatcgtggtgtcacgctcgtcgt
ttggtatggcttcattcagctccggttcccaacgatcaaggcgagttacatgatcccccatgttgtgcaaaaaagcggttagctccttcggtc
ctccgatcgttgtcagaagtaagttggccgcagtgttatcactcatggttatggcagcactgcataattctcttactgtcatgccatccgtaag
atgcttttctgtgactggtgagtactcaaccaagtcattctgagaatagtgtatgcggcgaccgagttgctcttgcccggcgtcaatacggga
taataccgcgccacatagcagaactttaaaagtgctcatcattggaaaacgttcttcggggcgaaaactctcaaggatcttaccgctgttg
agatccagttcgatgtaacccactcgtgcacccaactgatcttcagcatcttttactttcaccagcgtttctgggtgagcaaaaacaggaag
gcaaaatgccgcaaaaaagggaataagggcgacacggaaatgttgaatactcatactcttcctttttcaatattattgaagcatttatcagg
gttattgtctcatgagcggatacatatttgaatgtatttagaaaaataaacaaataggggttccgcgcacatttccccgaaaagtgccacct
gacgtctaagaaaccattattatcatgacattaacctataaaaataggcgtatcacgaggccctttcgtctcgcgcgtttcggtgatgacggt
gaaaacctctgacacatgcagctcccggagacggtcacagcttgtctgtaagcggatgccgggagcagacaagcccgtcagggcgc
gtcagcgggtgttggcgggtgtcggggctggcttaactatgcggcatcagagcagattgtactgagagtgcaccattcgacgctctccctt
atgcgactcctgcattaggaagcagcccagtagtaggttgaggccgttgagcaccgccgccgcaaggaatggtgcatgcaaggagat
ggcgcccaacagtcccccggccacggggcctgccaccatacccacgccgaaacaagcgctcatgagcccgaagtggcgagcccg
atcttccccatcggtgatgtcggcgatataggcgccagcaaccgcacctgtggcgccggtgatgccggccacgatgcgtccggcgtag
aggatctggctagcgatgaccctgctgattggttcgctgaccatttccgggtgcgggacggcgttaccagaaactcagaaggttcgtcca
accaaaccgactctgacggcagtttacgagagagatgatagggtctgcttcagtaagccagatgctacacaattaggcttgtacatattgt
cgttagaacgcggctacaattaatacataaccttatgtatcatacacatacgatttaggtgacactatagaatacacggaattaattc
Bold = ITR sequence
Italics = Mpz promoter
Underline = EGFP
Italic underline = WPRE sequence SEQ ID NO. 2: AAV-Mpz.GJB1 construct
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta

-continued

| Sequences |
| --- |

cttatctacgtagccatgctctaggtacccctcgaagctt*cctgttcagactcgtttcctgctgtaccattcaatggccccacatcaaatca*
*aacacagatggcacatatctactctaaatatatgcagagcttcacaaacgtcatacacgtacgtgtgtcacacacgcacacacacaccc*
*ttccacctctgcccttacctttgctgtcccatctagacattatccctcccatccccttatttcccttatcaaaatggctgctccttcaaggttccaaa*
*taacactgcttcctggacctgactcctctttcctctgaacttcctgtgttaagtgtattcctagtgcactgtgccttggtagttgttgagattgccctc*
*tgcttctcccttctgcctcctcatctagtgatcttgagcttgtagaaagaactgaattaccattctaatacgagcattctcgaactctccaaatag*
*ccaccaagcaggacaataggcagtcttgatcatttaaactgctgcatggcaaaaggaatcgaaggatttcttaacagaagtgggggg*
*ggggagatctgggcttcttcctggaagtttcctgatagagaaaatcttctgcctgggtagaatctcccaggatgcagggagatggaaaaa*
*gtgttccccaaggactttgtagtctacaggttgtggagccatcggaacaacgagacaccctaatttgggagtgctctgaaagaaacttgcc*
*tctaggccctagggctctcaggcaaggaggctaagaaggaatcctttgctgtagccttttggatttaggtttctcagcttatctatccctcaga*
*gaagtgtgtctatgtccctttctgtccctctgcctcaccccaccccaacattccaacctagggtagggggaggtcagtatacacaaagccc*
*tctgtgtaaggggtggtatgtgtccccccaccccctacccagagtatacaatgccccttctgctccatgcccctgccaccctcccaccacc*
*tctcaattgcacatgccaggctgcaattggtcactggctcaggacagcccccctcatgctggggatccaggggatttaagcaggttccaga*
*aaacaccactcagttccttgtcccccgctctctccaccccacagacgctctgcc*aagcttcgagaatgaggcaggatgaactggacagg
tttgtacaccttgctcagtggcgtgaaccggcattctactgccattggccgagtatggctctcggtcatcttcatcttcagaatcatggtgctggt
ggtggctgcagagagtgtgtggggtgatgagaaatcttccttcatctgcaacacactccagcctggctgcaacagcgtttgctatgaccaa
ttcttccccatctcccatgtgcggctgtggtccctgcagctcatcctagtttccaccccagctctcctcgtggccatgcacgtggctcaccagc
aacacatagagaagaaaatgctacggcttgagggccatggggacccccctacacctggaggaggtgaagaggcacaaggtccacat
ctcagggacactgtggtggacctatgtcatcagcgtggtgttccggctgttgtttgaggccgtcttcatgtatgtcttttatctgctctaccctggc
tatgccatggtgcggctggtcaagtgcgacgtctacccctgccccaacacagtggactgcttcgtgtcccgccccaccgagaaaaccgt
cttcaccgtcttcatgctagctgcctctggcatctgcatcatcctcaatgtggccgaggtggtgtacctcatcatccgggcctgtgcccgccg
agcccagcgccgctccaatccaccttcccgcaagggctcgggcttcggccaccgcctctcacctgaatacaagcagaatgagatcaac
aagctgctgagtgagcaggatggctccctgaaagacatactgcgccgcagccctggcaccggggctgggctggctgaaaagagcga
ccgctgctcggcctgctgaggatccctcgaggtcgacggtatcgataagctt*atcgataatcaacctctggattacaaaatttgtgaaagat*
*tgactggtattcttaactatgttgctccttttacgctatgtggatacgctgctttaatgcctttgtatcatgctattgcttcccgtatggctttcattttctc*
*ctccttgtataaatcctggttgctgtctctttatgaggagttgtggcccgttgtcaggcaacgtggcgtggtgtgcactgtgtttgctgacgcaac*
*ccccactggttggggcattgccaccacctgtcagctcctttccgggactttcgctttccccctccctattgccacggeggaactcatcgccgc*
*ctgccttgcccgctgctggacaggggctcggctgttgggcactgacaattccgtggtgttgtcggggaaatcatcgtcctttccttggctgctc*
*gcctgtgttgccacctggattctgcgcgggacgtccttctgctacgtcccttcggccctcaatccagcggaccttccttcccgcggcctgctg*
*ccggctctgcggcctcttccgcgtcttcgccttcgccctcagacgagtcggatctccctttgggccgcctcccc*gcatcgataccgtcgactc
gctgatcagcctcgactgtgccttctagttgccagccatctgttgtttgcccctcccccgtgccttccttgaccctggaaggtgccactcccact
gtcctttcctaataaaatgaggaaattgcatcgcattgtctgagtaggtgtcattctattctggggggtggggtggggcaggacagcaagg
gggaggattgggaagacaatagcaggcatgctggggatgcggtgggctctatggcttctgaggcggaaagaaccagctggggctcga
ctagagcatggctacgtagataagtagcatggcgggttaatcattaactacaaggaacccctagtgatggagttggccactcc
ctctctgcgcgctcgctcgctcactgaggccgggcgaccaaaggtcgcccgacgcccgggctttgcccgggcggcctcag
tgagcgagcgagcgcgcagagctttttgcaaaagcctaggcctccaaaaaagcctcctcactacttctggaatagctcagaggccg
aggcggcctcggcctctgcataaataaaaaaaattagtcagccatggggcggagaatgggcggaactgggcggagttaggggcggg
atgggcggagttaggggcgggactatggttgctgactaattgagatgcatgctttgcatacttctgcctgctggggagcctggggactttcc
acacctggttgctgactaattgagatgcatgctttgcatacttctgcctgctggggagcctggggactttccacaccctaactgacacacatt
ccacagctgcattaatgaatcggccaacgcgcggggagaggcggtttgcgtattgggcgctcttccgcttcctcgctcactgactcgctgc
gctcggtcgttcggctgcggcgagcggtatcagctcactcaaaggcggtaatacggttatccacagaatcaggggataacgcaggaaa
gaacatgtgagcaaaaggccagcaaaaggccaggaaccgtaaaaaggccgcgttgctggcgtttttccataggctccgcccccctga
cgagcatcacaaaaatcgacgctcaagtcagaggtggcgaaacccgacaggactataaagataccaggcgtttccccctggaagctc
cctcgtgcgctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgccttatccggt
aactatcgtcttgagtccaacccggtaagacacgacttatcgccactggcagcagccactggtaacaggattagcagagcgaggtatgt
aggcggtgctacagagttcttgaagtggtggcctaactacggctacactagaagaacagtatttggtatctgcgctctgctgaagccagtt
accttcggaaaaagagttggtagctcttgatccggcaaacaaaccaccgctggtagcggtggtttttttgtttgcaagcagcagattacgcg
cagaaaaaaaggatctcaagaagatcctttgatcttttctacggggtctgacgctcagtggaacgaaaactcacgttaagggattttggtc
atgagattatcaaaaaggatcttcacctagatccttttaaattaaaaatgaagttttaaatcaatctaaagtatatatgagtaaacttggtctga
cagttaccaatgcttaatcagtgaggcacctatctcagcgatctgtctatttcgttcatccatagttgcctgactccccgtcgtgtagataacta
cgatacgggagggcttaccatctggccccagtgctgcaatgataccgcgagacccacgctcaccggctccagatttatcagcaataaa
ccagccagccggaagggccgagcgcagaagtggtcctgcaactttatccgcctccatccagtctattaattgttgccgggaagctagagt
aagtagttcgccagttaatagtttgcgcaacgttgttgccattgctacaggcatcgtggtgtcacgctcgtcgtttggtatggcttcattcagctc
cggttcccaacgatcaaggcgagttacatgatcccccatgttgtgcaaaaaagcggttagctccttcggtcctccgatcgttgtcagaagta
agttggccgcagtgttatcactcatggttatggcagcactgcataattctcttactgtcatgccatccgtaagatgcttttctgtgactggtgagt
actcaaccaagtcattctgagaatagtgtatgcggcgaccgagttgctcttgcccggcgtcaatacgggataataccgcgccacatagca
gaactttaaaagtgctcatcattggaaaacgttcttcggggcgaaaactctcaaggatcttaccgctgttgagatccagttcgatgtaaccc
actcgtgcacccaactgatcttcagcatcrntactttcaccagcgtttctgggtgagcaaaaacaggaaggcaaaatgccgcaaaaaag
ggaataagggcgacacggaaatgttgaatactcatactcttcctttttcaatattattgaagcatttatcagggttattgtctcatgagcggata
catatttgaatgtatttagaaaaataaacaaataggggttccgcgcacatttccccgaaaagtgccacctgacgtctaagaaaccattatt
atcatgacattaacctataaaaataggcgtatcacgaggccctttcgtctcgcgcgtttcggtgatgacggtgaaaacctctgacacatgc
agctcccggagacggtcacagcttgtctgtaagcggatgccgggagcagacaagcccgtcagggcgcgtcagcgggtgttggcgggt
gtcggggctggcttaactatgcggcatcagagcagattgtactgagagtgcaccattcgacgctctcccttatgcgactcctgcattagga
agcagcccagtagtaggttgaggccgttgagcaccgccgccgcaaggaatggtgcatgcaaggagatggcgcccaacagtccccg
gccacggggcctgccaccatacccacgccgaaacaagcgctcatgagcccgaagtggcgagcccgatcttccccatcggtgatgtcg
gcgatataggcgccagcaaccgcacctgtggcgccggtgatgccggccacgatgcgtccggcgtagaggatctggctagcgatgacc
ctgctgattggttcgctgaccatttccgggtgcgggacggcgttaccagaaactcagaaggttcgtccaaccaaaccgactctgacggca
grnacgagagagatgatagggtctgcttcagtaagccagatgctacacaattaggcttgtacatattgtcgttagaacgcggctacaatta
atacataaccttatgtatcatacacatacgatttaggtgacactatagaatacacggaattaattc
Bold = ITR sequence
Italics = Mpz promoter
Underline = Cx32
Italic underline = WPRE sequence SEQ ID NO. 3: AAV-miniMpz.Egfp construct
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta

-continued

Sequences cttatctacgtagccatgctctaggtacc*gctctcaggcaaggaggctaagaaggaatcctttgctgtagccttttggatttaggtttctca*
*gcttatctatccctcagagaagtgtgtctatgtccctttttctgtccctctgcctcaccccaccccaacattccaacctagggtagggggaggtc*
*agtatacacaaagccctctgtgtaaggggtggtatgtgtcccccaccccctacccagagtatacaatgccccttctgctccatgcccct*
*gccaccctcccaccacctctcaattgcacatgccaggctgcaattggtcactggctcaggacagccccctcatgctggggatccagggg*
*attttaagcaggttccagaaaacaccactcagttccttgtcccccgctctctccaccccacagacgctctgccaaccggtcgccacc*atgg
tgagcaagggcgaggagctgttcaccggggtggtgcccatcctggtcgagctggacggcgacgtaaacggccacaagttcagcgtgt
ccggcgagggcgagggcgatgccacctacggcaagctgaccctgaagttcatctgcaccaccggcaagctgcccgtgccctggccc
accctcgtgaccaccctgacctacggcgtgcagtgcttcagccgctaccccgaccacatgaagcagcacgacttcttcaagtccgccat
gcccgaaggctacgtccaggagcgcaccatcttcttcaaggacgacggcaactacaagacccgcgccgaggtgaagttcgagggcg
acaccctggtgaaccgcatcgagctgaagggcatcgacttcaaggaggacggcaacatcctggggcacaagctggagtacaactac
aacagccacaacgtctatatcatggccgacaagcagaagascggcatcaaggtgaacttcaagatccgccacaacatcgaggacg
gcagcgtgcagctcgccgaccactaccagcagaacacccccatcggcgacggccccgtgctgctgcccgacaaccactacctgagc
acccagtccgccctgagcaaagaccccaacgagaagcgccatcacatggtcctgctggagttcgtgaccgccgccgggatcactctc
ggcatggacgagctgtacaagtaaagcggccctagatcaagctt*atcgataatcaacctctggattacaaaatttgtgaaagattgactg*
*gtattcttaactatgttgctccttttacgctatgtggatacgctgctttaatgcctttgtatcatgctattgcttcccgtatggctttcattttctcctccttg*
*tataaatcctggttgctgtctctttatgaggagttgtggcccgttgtcaggcaacgtggcgtggtgtgcactgtgtttgctgacgcaacccccca*
*ctggttggggcattgccaccacctgtcagctcctttccgggactttcgctttccccctccctattgccacggcggaactcategccgcctgcct*
*tgcccgctgctggacaggggctcggctgttgggcactgacaattccgtggtgttgtcggggaaatcatcgtcctttccttggctgctcgcctgt*
*gttgccacctggattctgcgcgggacgtccttctgctacgtcccttcggccctcaatccagcggaccttccttcccgcggcctgctgccggct*
*ctgcggcctcttccgcgtcttcgccttcgccctcagacgagtcggatctccctttgggccgcctccccg*catcgataccgtcgactcgctgat
cagcctcgactgtgccttctagttgccagccatctgttgtttgcccctcccccgtgccttccttgaccctggaaggtgccactcccactgtccttt
cctaataaaatgaggaaattgcatcgcattgtctgagtaggtgtcattctattctggggggtggggtggggcaggacagcaagggggag
gattgggaagacaatagcaggcatgctggggatgcggtgggctctatggcttctgaggcggaaagaaccagctggggctcgactaga
gcatggctacgtagataagtagcatggcgggttaatcattaactacaaggaacccctagtgatggagttggccactccctctct
gcgcgctcgctcgctcactgaggccgggcgaccaaaggtcgcccgacgcccgggctttgcccgggcggcctcagtgagc
gagcgagcgcgcagagctttttgcaaaagcctaggcctccaaaaaagcctcctcactacttctggaatagctcagaggccgaggcg
gcctcggcctctgcataaataaaaaaaattagtcagccatggggcggagaatgggcggaactgggcggagttaggggcgggatggg
cggagttaggggcgggactatggttgctgactaattgagatgcatgctttgcatacttctgcctgctggggagcctggggactttccacacct
ggttgctgactaattgagatgcatgctttgcatacttctgcctgctggggagcctggggactttccacaccctaactgacacacattccacag
ctgcattaatgaatcggccaacgcgcggggagaggcggtttgcgtattgggcgctcttccgcttcctcgctcactgactcgctgcgctcggt
cgttcggctgcggcgagcggtatcagctcactcaaaggcggtaatacggttatccacagaatcaggggataacgcaggaaagaacat
gtgagcaaaaggccagcaaaaggccaggaaccgtaaaaaggccgcgttgctggcgtttttccataggctccgcccccctgacgagca
tcacaaaaatcgacgctcaagtcagaggtggcgaaacccgacaggactataaagataccaggcgtttccccctggaagctccctcgtg
cgctctcctgttccgaccctgccgcttaccggatacctgtccgcctttctcccttcgggaagcgtggcgctttctcatagctcacgctgtaggta
tctcagttcggtgtaggtcgttcgctccaagctgggctgtgtgcacgaaccccccgttcagcccgaccgctgcgccttatccggtaactatc
gtcttgagtccaacccggtaagacacgacttatcgccactggcagcagccactggtaacaggattagcagagcgaggtatgtaggcgg
tgctacagagttcttgaagtggtggcctaactacggctacactagaagaacagtatttggtatctgcgctctgctgaagccagttaccttcgg
aaaaagagttggtagctcttgatccggcaaacaaaccaccgctggtagcggtggtttttttgtttgcaagcagcagattacgcgcagaaa
aaaaggatctcaagaagatcctttgatcttttctacggggtctgacgctcagtggaacgaaaactcacgttaagggattttggtcatgagatt
atcaaaaaggatcttcacctagatccttttaaattaaaaatgaagttttaaatcaatctaaagtatatatgagtaaacttggtctgacagttac
caatgcttaatcagtgaggcacctatctcagcgatctgtctatttcgttcatccatagttgcctgactccccgtcgtgtagataactacgatacg
ggagggcttaccatctggccccagtgctgcaatgataccgcgagacccacgctcaccggctccagatttatcagcaataaaccagcca
gccggaagggccgagcgcagaagtggtcctgcaactttatccgcctccatccagtctattaattgttgccgggaagctagagtaagtagtt
cgccagttaatagtttgcgcaacgttgttgccattgctacaggcatcgtggtgtcacgctcgtcgtttggtatggcttcattcagctccggttccc
aacgatcaaggcgagttacatgatcccccatgttgtgcaaaaaagcggttagctccttcggtcctccgatcgttgtcagaagtaagttggc
cgcagtgttatcactcatggttatggcagcactgcataattctcttactgtcatgccatccgtaagatgcttttctgtgactggtgagtactcaac
caagtcattctgagaatagtgtatgcggcgaccgagttgctcttgcccggcgtcaatacgggataataccgcgccacatagcagaacttt
aaaagtgctcatcattggaaaacgttcttcggggcgaaaactctcaaggatcttaccgctgttgagatccagttcgatgtaacccactcgtg
cacccaactgatcttcagcatcttttactttcaccagcgtttctgggtgagcaaaaacaggaaggcaaaatgccgcaaaaaagggaata
agggcgacacggaaatgttgaatactcatactcttcctttttcaatattattgaagcatttatcagggttattgtctcatgagcggatacatatttg
aatgtatttagaaaaataaacaaataggggttccgcgcacatttccccgaaaagtgccacctgacgtctaagaaaccattattatcatgac
attaacctataaaaataggcgtatcacgaggccdttcgtctcgcgcgtttcggtgatgacggtgaaaacctctgacacatgcagctcccg
gagacggtcacagcttgtctgtaagcggatgccgggagcagacaagcccgtcagggcgcgtcagcgggtgttggcgggtgtcggggc
tggcttaactatgcggcatcagagcagattgtactgagagtgcaccattcgacgctctcccttatgcgactcctgcattaggaagcagccc
agtagtaggttgaggccgttgagcaccgccgccgcaaggaatggtgcatgcaaggagatggcgcccaacagtcccccggccacggg
gcctgccaccatacccacgccgaaacaagcgctcatgagcccgaagtggcgagcccgatcttccccatcggtgatgtcggcgatatag
gcgccagcaaccgcacctgtggcgccggtgatgccggccacgatgcgtccggcgtagaggatctggctagcgatgaccctgctgattg
gttcgctgaccatttccgggtgcgggacggcgttaccagaaactcagaaggttcgtccaaccaaaccgactctgacggcagtttacgag
agagatgatagggtctgcttcagtaagccagatgctacacaattaggcttgtacatattgtcgttagaacgcggctacaattaatacataac
cttatgtatcatacacatacgatttaggtgacactatagaatacacggaattaattc
Bold = ITR sequence
Italics = mini-Mpz promoter
Underline = EGFP
Italic underline = WPRE sequence SEQ ID NO. 4: Mpz promoter
cctgttcagactcgtttcctgctgtaccctttcaatggccccacatcaaatcaaacacagatggcacatatctactctaaatatatgcagagc
ttcacaaacgtcatacacgtacgtgtgtcacacacgcacacacacacccttccacctctgcccttacctttgctgtcccatctagacattatc
cctcccatccccttatttcccttatcaaaatggctgctccttcaaggttccaaataacactgcttcctggacctgactcctctttcctctgaacttc
ctgtgttaagtgtattcctagtgcactgtgccttggtagttgttgagattgccctctgcttctcccttctgcctcctcatctagtgatcttgagcttgta
gaaagaactgaattaccattctaatacgagcattctcgaactctccaaatagccaccaagcaggacaataggcagtcttgatcatttaaa
ctgctgcatggcaaaaggaatcgaaggatttcttaacagaagtgggggggggggagatctgggcttcttcctggaagtttcctgatagag
aaaatcttctgcctgggtagaatctcccaggatgcagggagatggaaaaagtgttccccaaggactttgtagtctacaggttgtggagcc
atcggaacaacgagacaccctaatttgggagtgctctgaaagaaacttgcctctaggccctagggctctcaggcaaggaggctaagaa
ggaatcctttgctgtagccttttggatttaggtttctcagcttatctatccctcagagaagtgtgtctatgtccctttttctgtccctctgcctcacccc -continued

| Sequences |
|---|

accccaacattccaacctagggtagggggaggtcagtatacacaaagccctctgtgtaaggggtggtatgtgtcccccaccccccctac
ccagagtatacaatgccccttctgctccatgcccctgccaccctcccaccacctctcaattgcacatgccaggctgcaattggtcactggct
caggacagcccccctcatgctggggatccaggggattttaagcaggttccagaaaacaccactcagttccttgtcccccgctctctccacc
ccacagacgctctgcc SEQ ID NO. 5: MiniMpz promoter
gctctcaggcaaggaggctaagaaggaatcctttgctgtagccttttggatttaggtttctcagcttatctatccctcagagaagtgtgtctatg
tcccttttctgtccctctgcctcaccccaccccaacattccaacctagggtagggggaggtcagtatacacaaagccctctgtgtaaggggt
ggtatgtgtcccccaccccccctacccagagtatacaatgccccttctgctccatgcccctgccaccctcccaccacctctcaattgcacat
gccaggctgcaattggtcactggctcaggacagcccccctcatgctggggatccaggggattttaagcaggttccagaaaacaccactca
gttccttgtcccccgctctctccaccccacagacgctctgcc SEQ ID NO. 6: Connexin-32 (Cx32): GenBank: AY408135.1
atgaactggacaggtttgtacaccttgctcagtggcgtgaaccggcattctactgccattggccgagtatggctctcggtcatcttcatcttca
gaatcatggtgctggtggtggctgcagagagtgtgtggggtgatgagaaatcttccttcatctgcaacacactccagcctggctgcaacag
cgtttgctatgaccaattcttccccatctcccatgtgcggctgtggtccctgcagctcatcctagtttccaccccagctctcctcgtggccatgc
acgtggctcaccagcaacacatagagaagaaaatgctacggcttgagggccatggggacccccctacacctggaggaggtgaagag
gcacaaggtccacatctcagggacactgtggtggacctatgtcatcagcgtggtgttccggctgttgtttgaggccgtcttcatgtatgtctttt
atctgctctaccctggctatgccatggtgcggctggtcaagtgcgacgtctacccctgccccaacacagtggactgcttcgtgtcccgcccc
accgagaaaaccgtcttcaccgtcttcatgctagctgcctctggcatctgcatcatcctcaatgtggccgaggtggtgtacctcatcatccgg
gcctgtgcccgccgagcccagcgccgctccaatccaccttcccgcaagggctcgggcttcggccaccgcctctcacctgaatacaagc
agaatgagatcaacaagctgctgagtgagcaggatggctccctgaaagacatactgcgccgcagccctggcaccggggctgggctg
gctgaaaagagcgaccgctgctcggcctgctga SEQ ID NO. 7: SH3 domain and tetratricopeptide repeats 2 (SH3TC2): GenBank: BC114486.1
atgggtggctgcttctgcatccccagggagcggagtctgacccggggcccaggtaaagaaactccttccaaggatccaa
ctgtatcgagtgagtgtatagcctcatctgaatacaaggaaaaatgttttctgccacagaacattaatccagacctgacactctccttctgtgt
aaagagccgctccaggaggtgtgtaaatggacccctacaggaagctgctcggaggcggctctgggcactggagaatgaggaccagg
aggtgcgcgcatgctgtttaaggacctctcagcaaggttggtcagtatccagtctcagagggcccagtttctcatcaccttcaagaccatgga
ggaaatctggaagttctccacctaccttaatttagaacatctcctctttgaccacaagtactggctcaactgcatattggtggaggatacaga
gatccaagtgtctgtagatgataaacacctggaaacaatatacctgggactcctgatacaggaaggccacttcttctgcagagccctgtg
ctccgtgactccaccagccgagaaggaaggggaatgcttgacactttgcaagaatgagttaatctcagtgaagatggcagaagctggc
tccgagttggaaggcgtgtctttggtgacaggtcagcggggcctggtactggtgtcagccttggagcctctgcctctccctttccaccagtgg
ttcctaaagaattatccaggaagctgtggcctttccaggaagagggattggacaggctcctatcagattggcagaggacgctgtaaggc
cttgacgggttatgagccaggagaaaaggatgaactgaatttctaccagggagaaagcattgagatcatcggctttgtcatacctgggctt
cagtggttcattggaaagtcgacaagttcaggacaagtgggctttgtccccaccaggaacatagatcctgattcttattccccaatgagca
ggaactctgcctttctcagtgatgaggagagatgctccctgttggccctgggaagtgataagcagactgagtgttccagcttcctccacact
cttgctcgcactgacatcacatctgtctaccggctcagtgggtttgaatccatccagaatcctccaaatgatctgagtgcatcccagcctga
aggcttcaaggaggtcaggcctggcagagcctgggaggagcatcaggccgtggggtccagacagtccagcagctctgaggactcca
gcctggaggaggagctcctctcggccacctcagacagctatcgcctgccggagcctgatgaccttgatgacccggaactgctcatggac
ctaagcactggtcaggaggaggaggctgagaacttcgcccccatattggcttttctggatcatgagggttatgctgaccactttaagagtct
ctatgacttctccttctctttcctcacttcttccttttatagcttctctgaggaggatgagtttgtggcctacctggaggcatcaagaaagtgggcc
aagaagagccacatgacctgggcccatgcccggctctgcttcctcctgggcggctgagcatcaggaaggtcaaactctctcaggcca
gggtgtacttcgaggaggccatccacattctcaatggagcatttgaggacctatccttggtggccactctgtacatcaatttggctgccatct
acctgaaacagaggctgagacataaaggctccgccctgttggaaaaggcaggtgccctgctggcctgcctgcctgaccgtgagtctagt
gccaagcatgaactcgacgtggtggcctacgtgctgcgccaggggattgtggtgggcagcagcccgctggaggccagggcctgctttct
ggccatccgcttgctcctgagcctaggccggcacgaggaggtcctgccctttgccgagcgcctgcagctcctctctggacaccctcctgc
ctctgaggctgtggccagtgttttgagttttctgtatgacaagaaatatcttccacaccttgcagtggcctctgtccagcaacatggtatccag
agtgcccaagggatgtctcttcctatttggcaggtccaccttgtcctccagaacacaaccaagctccttggctttccttccccaggctggggt
gaagtttctgccttggcctgcccaatgctcagacaggccctggctgcctgtgaggaactagcagaccggagcacccagagggccctgt
gtctcatcctttccaaagtgtacctcgagcacaggtctcctgacggtgccatccactacctgagccaggccttggtgctagggcagctgctg
ggtgagcaggaatcctttgagtcttctctgcctggcatgggcctatctcttagccagcaggccaagaaggctttggatgtgcttgagcc
actgctatgctccctgaaggagacagagagtctcactcaaaggggagtcatctataacctcctgggacttgcactccaaggtgaaggcc
gggtgaacagggcagccaagagctatcttcgggccttgaacagagcccaggaggtgggagatgtgcataaccaggcagtggctatg
gccaatcttggccacctgagccttaagtcctgggctcagcatccagccagaaactatctcctgcaggctgtacgactctattgtgaacttca
ggccagtaaggagacagacatggaattagtacaggtgtttctctggttggcccaagttctggtgtctggacaccagctgacccatggcctt
ctttgttatgaaatggcattgctgtttggcttaaggcatcgacatctaaagagtcagcttcaggccaccaaatccctctgccatttctacagctc
tgtgtccccaaaccctgaggcatgcatcacctaccatgagcactggctggccctggctcagcaactcagggaccgggagatggaagg
gaggctgctggagtccctggggcagctttatcggaacctaaataccgccaggtccctcaggaggtcactcacatgcatcaaggagagc
ctgcgtatcttcattgacctgggggagacagacaaggctgctgaggcctggcttggggcggggcgactccactacctcatgcaggaag
acgagctggtggagctgtgcctgcaggcagccatccagacagccctgaagtcagaggagcctttgctggctctcaaactttatgaagaa
gcaggtgatgtgttcttcaatgggacccgccacaggcatcatgcagtggagtactaccgagctggagctgttcctttagcaaggaggttga
aggcggtgagaactgagctccggattttcaataagctgacagagctgcagattagcctcgaaggctatgagaaggctttggaatttgcca
ccctggccgccaggctcagcacagtcacaggagatcagaggcaagagctggtggcctttcaccgcctggctacagtgtactactccctg
cacatgtatgagatggctgaggactgctacctgaagaccctgtccctctgtccaccctggctgcagagtcccaaggaggccctgtactat
gccaaggtgtattatcgcctgggcagactcaccttctgccagctgaaggatgcccatgatgccactgagtacttccttctggccctggcag
cagcggtcctgctgggtgatgaggagcttcaggacaccattaggagcaggctggacaacatctgccagagccccctgtggcacagca
ggccctccgggtgctcctcagagagggcgcggtggctgagtggtggtggcctggccctctga SEQ ID NO. 8: Peripheral myelin protein 22 (PMP22): NCBI Reference Sequence:
NM_000304.4
agttacagggagcaccaccagggaacatctcggggagcctggttggaagctgcaggcttagtctgtcggctgcgggtctctgactgccc
tgtggggagggtcttgccttaacatcccttgcatttggctgcaaagaaatctgcttggaagaaggggttacgctgtttggccgggcagaaa
ctccgctgagcagaacttgccgccagaatgctcctcctgttgctgagtatcatcgtcctccacgtcgcggtgctggtgctgctgttcgtctcca
cgatcgtcagccaatggatcgtgggcaatggacacgcaactgatctctggcagaactgtagcacctcttcctcaggaaatgtccaccact
gtttctcatcatcaccaaacgaatggctgcagtctgtccaggccaccatgatcctgtcgatcatcttcagcattctgtctctgttcctgttcttctg
ccaactcttcaccctcaccaagggggcaggttttacatcactggaatcttccaaattcttgctggtctgtgcgtgatgagtgctgcggccat -continued Sequences ctacacggtgaggcacccggagtggcatctcaactcggattactcctacggtttcgcctacatcctggcctgggtggccttcccctggcc
cttctcagcggtgtcatctatgtgatcttgcggaaacgcgaatgaggcgcccagacggtctgtctgaggctctgagcgtacatagggaag
ggaggaagggaaaacagaaagcagacaaagaaaaaagagctagcccaaaatcccaaactcaaaccaaaccaaacagaaagc
agtggaggtggggggttgctgttgattgaagatgtatataatatctccggtttataaaacctatttataacactttttacatatatgtacatagtattg
tttgctttttatgttgaccatcagcctcgtgttgagccttaaagaagtagctaaggaactttacatcctaacagtataatccagctcagtatttttg
ttttgtttttgtttgtttgttttgttttacccagaaataagataactccatctcgccccttccctttcatctgaaagaagatacctccctcccagtcca
cctcatttagaaaaccaaagtgtgggtagaaaccccaaatgtccaaaagcccttttctggtgggtgacccagtgcatccaacagaaaca
gccgctgcccgaacctctgtgtgaagctttacgcgcacacggacaaaatgcccaaactggagcccttgcaaaaacacggcttgtggca
ttggcatacttgcccttacaggtggagtatcttcgtcacacatctaaatgagaaatcagtgacaacaagtctttgaaatggtgctatggattta
ccattccttattatcactaatcatctaaacaactcactggaaatccaattaacaattttacaacataagatagaatggagacctgaataattct
gtgtaatataaatggtttataactgcttttgtacctagctaggctgctattattactataatgagtaaatcataaagccttcatcactcccacatttt
tcttacggtcggagcatcagaacaagcgtctagactccttggaccgtgagttcctagagcttggctgggtctaggctgttctgtgcctcca
aggactgtctggcaatgacttgtattggccaccaactgtagatgtatatatggtgcccttctgatgctaagactccagaccttttgtttttgctttg
cattttctgattttataccaactgtgtggactaagatgcattaaaataaacatcagagtaactca SEQ ID NO. 9: Myelin Protein Zero (MPZ): GenBank: AK313555.1
agttcctggtccccccactttctcaaccccacagatgctccgggcccctgcccctgccccagctatggctcctggggctccctcatccagcc
ccagccctatcctggctgtgctgctcttctcttctttggtgctgtccccggcccaggccatcgtggtttacaccgacagggaggtccatggtgc
tgtgggctcccgggtgaccctgcactgctccttctggtccagtgagtgggtctcagatgacatctccttcacctggcgctaccagcccgaag
ggggcagagatgccatttcgatcttccactatgccaagggacaaccctacattgacgaggtggggaccttcaaagagcgcatccagtg
ggtaggggaccctcgctggaaggatggctccattgtcatacacaacctagactacagtgacaatggcacgttcacttgtgacgtcaaaa
accctccagacatagtgggcaagacctctcaggtcacgctgtatgtctttgaaaaagtgccaactaggtacggggtcgttctgggagctgt
gatcgggggtgtcctcggggtggtgctgttgctgctgctgcttttctacgtggttcggtactgctggctacgcaggcaggcggccctgcaga
ggaggctcagtgctatggagaaggggaaattgcacaagccaggaaaggacgcgtcgaagcgcgggcggcagacgccagtgctgt
atgcaatgctggaccacagcagaagcaccaaagctgtcagtgagaagaaggccaaggggctgggggagtctcgcaaggataaga
aatag SEQ ID NO. 10: Early Growth Response 2 (EGR2): NCBI Reference Sequence: NM_000399.5
aactgagcgaggagcaattgattaatagctcggcgaggggactcactgactgttataataacactacaccagcaactcctggcttccca
gcagccggaacacagacaggagagagtcagtggcaaatagacatttttcttatttcttaaaaaacagcaacttgtttgctacttttatttctgtt
gattttttttttcttggtgtgtgtggtggttgtttttaagtgtggagggcaaaaggagataccatcccaggctcagtccaacccctctccaaaacg
gcttttctgacactccaggtagcgagggagttgggtctccaggttgtgcgaggagcaaatgatgaccgccaaggccgtagacaaaatcc
cagtaactctcagtggttttgtgcaccagctgtctgacaacatctacccggtggaggacctcgccgccacgtcggtgaccatctttcccaat
gccgaactgggaggcccctttgaccagatgaacggagtggccggagatggcatgatcaacattgacatgactggagagaagaggtc
gttggatctcccatatcccagcagctttgctcccgtctctgcacctagaaaccagaccttcacttacatgggcaagttctccattgaccctca
gtaccctggtgccagctgctacccagaaggcataatcaatattgtgagtgcaggcatcttgcaaggggtcacttccccagcttcaaccac
agcctcatccagcgtcacctctgcctcccccaacccactggccacaggacccctgggtgtgtgcaccatgtcccagacccagcctgacc
tggaccacctgtactctccgccaccgcctcctcctccttattctggctgtgcaggagacctctaccaggacccttctgcgttcctgtcagcag
ccaccacctccacctcttcctctctggcctacccaccacctccttcctatccatcccccaagccagccacggacccaggtctcttcccaatg
atcccagactatcctggattctttccatctcagtgccagagagacctacatggtacagctggcccagaccgtaagccctttccctgcccact
ggacaccctgcgggtgccccctccactcactccactctctacaatccgtaactttaccctgggggggccccagtgctggggtgaccggacc
aggggccagtggaggcagcgagggaccccggctgcctggtagcagctcagcagcagcagcagccgccgccgccgccgcctataa
cccacaccacctgccactgcggcccattctgaggcctcgcaagtaccccaacagacccagcaagacgccggtgcacgagaggccct
acccgtgcccagcagaaggctgcgaccggcggttctcccgctctgacgagctgacacggcacatccgaatccacactgggcataagc
ccttccagtgtcggatctgcatgcgcaacttcagccgcagtgaccacctcaccacccatatccgcacccacaccggtgagaagcccttc
gcctgtgactactgtggccgaaagtttgcccggagtgatgagaggaagcgccacaccaagatccacctgagacagaaagagcggaa
aagcagtgccccctctgcatcggtgccagccccctctacagcctcctgctctgggggcgtgcagcctggggggtaccctgtgcagcagta
acagcagcagtcttggcggagggccgctcgccccttgctcctctcggacccggacaccttgagatgagactcaggctgatacaccagct
cccaaaggtcccggaggccctttgtccactggagctgcacaacaaacactaccaccctttcctgtccctctctccctttgttgggcaaagg
gctttggtggagctagcactgccccdttccacctagaagcaggttcttcctaaaacttagcccattctagtctctcttaggtgagttgactatc
aacccaaggcaaaggggaggctcagaaggaggtggtgtggggacccctggccaagagggctgaggtctgaccctgctttaaagggt
tgtttgactaggttttgctaccccacttccccttattttgacccatcacaggtttttgaccctggatgtcagagttgatctaagacgttttctacaat
aggttgggagatgctgatcccttcaagtggggacagcaaaaagacaagcaaaactgatgtgcactttatggcttgggactgatttgggg
gacattgtacagtgagtgaagtatagcctttatgccacactctgtggccctaaaatggtgaatcagagcatatctagttgtctcaacccttga
agcaatatgtattataaactcagagaacagaagtgcaatgtgatgggaggaacatagcaatatctgctccttttcgagttgtttgagaaatg
taggctatttttttcagtgtatatccactcagattttgtgtatttttgatgtacactgttctctaaattctgaatctttgggaaaaaatgtaaagcatttat
gatctcagaggttaacttatttaaggggggatgtacatatattctctgaaactaggatgcatgcaattgtgttggaagtgtccttggtgccttgtgt
gatgtagacaatgttacaaggtctgcatgtaaatgggttgccttattatggagaaaaaaaatcactccctgagtttagtatggctgtatatttct
gcctattaatatttggaattttttttagaaagtatatttttgtatgctttgttttgtgacttaaaagtgttacctttgtagtcaaatttcagataagaatgt
acataatgttaccggagctgatttgtttggtcattagctcttaatagttgtgaaaaaataaatctattctaacgcaaaaccactaactgaagttc
agataatggatggtttgtgactatagtgtaaataaatacttttcaacaata SEQ ID NO. 11: Ganglioside induced differentiation associated protein 1 (GDAP1): NCBI Reference Sequence: NM_018972.3
atggctgagaggcaggaagagcagagagggagcccgcccttgagggcggaaggcaaggccgacgcggaggttaagctcattctgt
accattggacgcattccttcagctctcaaaaggtgcgcttggtaattgctgaaaaggcattgaagtgcgaggaacatgatgtaagtctgcc
cttgagtgagcacaatgagccttggtttatgcgtttgaactcaactggagaagtgcctgtccttatccacggggaaaacataatttgtgagg
ccactcagatcattgattatcttgaacagactttcctggatgaaagaacacccaggttaatgcctgataaagaaagcatgtattacccacg
ggtacaacattaccgagagctgcttgactccttgccaatggatgcctatacacatggctgcattttacatcctgagttaactgtggactccat
gatcccggcttatgcaactacaaggattcgtagccaaattggaaacacagagtctgagctgaagaaacttgctgaagaaaacccagat
ttacaagaagcatacattgcaaaacagaaacgacttaaatcaaagctgcttgatcatgacaatgtcaagtatttgaagaaaattcttgatg
agttggagaaagtcttggatcaggttgaaactgaattgcaaagaagaaatgaagaaaccccagaagagggccagcaaccttggctct
gcggtgaatccttcaccctggcagacgtctcactcgctgtcacattgcatcgactgaagttcctggggtttgcaaggagaaactggggaa
acggaaagcgaccaaacttggaaacctattacgagcgtgtcttgaagagaaaaacatttaacaaggttttaggacatgtcaacaatatat
taatctctgcagtgctgccaacagcattccgggtggccaagaaaagggccccaaaagttcttggcacgacccttgtggttggtttgcttgc
aggagtgggatattttgcttttatgcttttcagaaagaggcttggcagcatgatattagcatttagacccagaccaaattatttctag -continued Sequences SEQ ID NO. 12: N-Myc downstream regulated 1 (NDRG1): NCBI Reference Sequence: NM_001135242.1
atgtctcgggagatgcaggatgtagacctcgctgaggtgaagcctttggtggagaaaggggagaccatcaccggcctcctgcaagagt
ttgatgtccaggagcaggacatcgagactttacatggctctgttcacgtcacgctgtgtgggactcccaagggaaaccggcctgtcatcct
cacctaccatgacatcggcatgaaccacaaaacctgctacaacccccctcttcaactacgaggacatgcaggagatcacccagcacttt
gccgtctgccacgtggacgcccctggccagcaggacggcgcagcctccttccccgcagggtacatgtacccctccatggatcagctgg
ctgaaatgcttcctggagtccttcaacagtttgggctgaaaagcattattggcatgggaacaggagcaggcgcctacatcctaactcgattt
gctctaaacaaccctgagatggtggagggccttgtccttatcaacgtgaacccttgtgcggaaggctggatggactgggccgcctccaa
gatctcaggatggacccaagctctgccggacatggtggtgtcccaccttttttgggaaggaagaaatgcagagtaacgtggaagtggtcc
acacctaccgccagcacattgtgaatgacatgaaccccggcaacctgcacctgttcatcaatgcctacaacagccggcgcgacctgga
gattgagcgaccaatgccgggaacccacacagtcaccctgcagtgccctgctctgttggtggttggggacagctcgcctgcagtggatg
ccgtggtggagtgcaactcaaaattggacccaacaaagaccactctcctcaagatggcggactgtggcggcctcccgcagatctccca
gccggccaagctcgctgaggccttcaagtacttcgtgcagggcatgggatacatgccctcggctagcatgacccgcctgatgcggtccc
gcacagcctctggttccagcgtcacttctctggatggcacccgcagccgctcccacaccagcgagggcacccgaagccgctcccaca
ccagcgagggcacccgcagccgctcgcacaccagcgagggggcccacctggacatcacccccaactcgggtgctgctgggaaca
gcgccgggcccaagtccatggaggtctcctgctag SEQ ID NO. 17: AAV-human-Mpz-GJB1 construct
tagctgcgcgctcgctcgctcactgaggccgcccgggcaaagcccgggcgtcgggcgacattggtcgcccggcctcagt
gagcgagcgagcgcgcagagagggagtggccaactccatcactaggggttccttgtagttaatgattaacccgccatgcta
cttatctacgtagccatgctctaggtaccg*cctggcataaacttcatttattaaagtttattttgtctttaatctctcatataacttagtcttcctga*
*tattgcagctgtgtgtgcccctcttttgtactcccagcattttgttcattactaaaggaagtgtcatggcttattatacttgattgttgatgggtttgtc*
*ctctgatcttcccatctccacctccccaaaccaaatttcaactccttgctggaaggacttaatttttattcctctctctattacctgcattctcatac*
*tttacatattgctggcacttaatacaattttgtagccttgaaataaattgaaatggacttaaacagcagcatgaagcactgaaggacttcttga*
*caaacggaaaggtcaggggcttcttgcctggaaatagtccagtggagaaaaacttctgtctgggaagaatcgcacaggatgaaggga*
*ggtgcggggaaaaaaactcccataggacttggtcatctcaagaagtctgtaatgcagcccacattagaggagataacaggggatatcc*
*tattttcagagttctctgggggaaacctccctctagttcctagggctgtgaggcagcctctctcaggcaaggaggctgaggagaaatccctt*
*tttatggcattaaattgaggttccatatctatccctcagagaagtgtgtctgtgtccctgtttttgtccctctccctcaccacccccccacaacattc*
*cagcctggggcaggggggaggccagtggacacaaagccctctgtgtatggggtggtatgtgtcccccacccctccacccagactatac*
*aatgccccttctgctccctgcactctgcccccctccccaccacctctcaactgcacatgccaggctgcaattggttactggctgaggacag*
*ccccctcatgctggggccctaggggatttaagcaggttccaggaacccccgttcagttcctggtcccccactttctcaaccccacagatg*
*ctccgggcccctgcccctgccccagc*accggtcgcggatcctgaggcaggatgaactggacaggtttgtacaccttgctcagtggcgtg
aaccggcattctactgccattggccgagtatggctctcggtcatcttcatcttcagaatcatggtgctggtggtggctgcagagagtgtgtgg
ggtgatgagaaatcttccttcatctgcaacacactccagcctggctgcaacagcgtttgctatgaccaattcttccccatctcccatgtgcgg
ctgtggtccctgcagctcatcctagtttccaccccagctctcctcgtggccatgcacgtggctcaccagcaacacatagagaagaaaatg
ctacggcttgagggccatggggacccccctacacctggaggaggtgaagaggcacaaggtccacatctcagggacactgtggtggac
ctatgtcatcagcgtggtgttccggctgttgtttgaggccgtcttcatgtatgtcttttatctgctctaccctggctatgccatggtgcggctggtca
agtgcgacgtctaccctgccccaacacagtggactgcttcgtgtcccgccccaccgagaaaaccgtcttcaccgtcttcatgctagctgc
ctctggcatctgcatcatcctcaatgtggccgaggtggtgtacctcatcatccgggcctgtgcccgccgagcccagcgccgctccaatcca
ccttcccgcaagggctcgggcttcggccaccgcctctcacctgaatacaagcagaatgagatcaacaagctgctgagtgagcaggatg
gctccctgaaagacatactgcgccgcagccctggcaccggggctgggctggctgaaaagagcgaccgctgctcggcctgctgactcg
agatcgatatccatcacactggcggccgcaagctt*atcgataatcaacctctggattacaaaatttgtgaaagattgactggtattcttaact*
*atgttgctccttttacgctatgtggatacgctgctttaatgcctttgtatcatgctattgcttcccgtatggctttcattttctcctccttgtataaatcctg*
*gttgctgtctctttatgaggagttgtggcccgttgtcaggcaacgtggcgtggtgtgcactgtgtttgctgacgcaacccccactggttggggc*
*attgccaccacctgtcagctcctttccgggactttcgctttccccctccctattgccacggcggaactcatcgccgcctgccttgcccgctgct*
*ggacaggggctcggctgttgggcactgacaattccgtggtgttgtcggggaaatcatcgtcctttccttggctgctcgcctgtgttgccacctg*
*gattctgcgcgggacgtccttctgctacgtcccttcggccctcaatccagcggaccttccttcccgcggcctgctgccggctctgcggcctct*
*tccgcgtcttcgccttcgccctcagacgagtcggatctccctttgggccgcctcccc*gcatcgataccgtcgactcgctgatcagcctcgac
tgtgccttctagttgccagccatctgttgtttgcccctcccccgtgccttccttgaccctggaaggtgccactcccactgtcctttcctaataaaat
gaggaaattgcatcgcattgtctgagtaggtgtcattctattctggggggtggggtggggcaggacagcaagggggaggattgggaaga
caatagcaggcatgctggggatgcggtgggctctatggcttctgaggcggaaagaaccagctggggctcgactagagcatggctacg
tagataagtagcatggcgggttaatcattaactacaaggaacccctagtgatggagttggccactccctctctgcgcgctcgct
cgctcactgaggccgggcgaccaaaggtcgcccgacgcccgggctttgcccgggcggcctcagtgagcgagcgagcgc
gcagagctttttgcaaaagcctaggcctccaaaaaagcctcctcactacttctggaatagctcagaggccgaggcggcctcggcctctg
cataaataaaaaaaattagtcagccatggggcggagaatgggcggaactgggcggagttaggggcgggatgggcggagttagggg
cgggactatggttgctgactaattgagatgcatgctttgcatacttctgcctgctggggagcctggggactttccacacctggttgctgactaa
ttgagatgcatgctttgcatacttctgcctgctggggagcctggggactttccacaccctaactgacacacattccacagctgcattaatgaa
tcggccaacgcgcggggagaggcggtttgcgtattgggcgctcttccgcttcctcgctcactgactcgctgcgctcggtcgttcggctgcgg
cgagcggtatcagctcactcaaaggcggtaatacggttatccacagaatcaggggataacgcaggaaagaacatgtgagcaaaagg
ccagcaaaaggccaggaaccgtaaaaaggccgcgttgctggcgtttttccataggctccgcccccctgacgagcatcacaaaaatcg
acgctcaagtcagaggtggcgaaacccgacaggactataaagataccaggcgtttccccctggaagctccctcgtgcgctctcctgttcc
gaccctgccgcttaccggatacctgtccgcctttctcccttcgggaagcgtggcgctttctcatagctcacgctgtaggtatctcagttcggtgt
aggtcgttcgctccaagctgggctgtgtgcacgaaccccccgttcagcccgaccgctgcgccttatccggtaactatcgtcttgagtccaa
cccggtaagacacgacttatcgccactggcagcagccactggtaacaggattagcagagcgaggtatgtaggcggtgctacagagttc
ttgaagtggtggcctaactacggctacactagaagaacagtatttggtatctgcgctctgctgaagccagttaccttcggaaaaagagttg
gtagctcttgatccggcaaacaaaccaccgctggtagcggtggtttttttgtttgcaagcagcagattacgcgcagaaaaaaaggatctca
agaagatcdttgatcttttctacggggtctgacgctcagtggaacgaaaactcacgttaagggattttggtcatgagattatcaaaaaggat
cttcacctagatcdtttaaattaaaaatgaagttttaaatcaatctaaagtatatatgagtaaacttggtctgacagttaccaatgcttaatcag
tgaggcacctatctcagcgatctgtctatttcgttcatccatagttgcctgactccccgtcgtgtagataactacgatacgggagggcttacca
tctggccccagtgctgcaatgataccgcgagacccacgctcaccggctccagatttatcagcaataaaccagccagccggaagggcc
gagcgcagaagtggtcctgcaactttatccgcctccatccagtctattaattgttgccgggaagctagagtaagtagttcgccagttaatagt
ttgcgcaacgttgttgccattgctacaggcatcgtggtgtcacgctcgtcgtttggtatggcttcattcagctccggttcccaacgatcaaggc
gagttacatgatcccccatgttgtgcaaaaaagcggttagctccttcggtcctccgatcgttgtcagaagtaagttggccgcagtgttatcac
tcatggttatggcagcactgcataattctcttactgtcatgccatccgtaagatgcttttctgtgactggtgagtactcaaccaagtcattctgag
aatagtgtatgcggcgaccgagttgctcttgcccggcgtcaatacgggataataccgcgccacatagcagaactttaaaagtgctcatca
ttggaaaacgttcttcggggcgaaaactctcaaggatcttaccgctgttgagatccagttcgatgtaacccactcgtgcacccaactgatctt
cagcatcttttactttcaccagcgtttctgggtgagcaaaaacaggaaggcaaaatgccgcaaaaagggaataagggcgacacgga -continued Sequences aatgttgaatactcatactcttcctttttcaatattattgaagcatttatcagggttattgtctcatgagcggatacatatttgaatgtatttagaaaa
ataaacaaataggggttccgcgcacatttccccgaaaagtgccacctgacgtctaagaaaccattattatcatgacattaacctataaaa
ataggcgtatcacgaggccctttcgtctcgcgcgtttcggtgatgacggtgaaaacctctgacacatgcagctcccggagacggtcacag
cttgtctgtaagcggatgccgggagcagacaagcccgtcagggcgcgtcagcgggtgttggcgggtgtcggggctggcttaactatgcg
gcatcagagcagattgtactgagagtgcaccattcgacgctctcccttatgcgactcctgcattaggaagcagcccagtagtaggttgag
gccgttgagcaccgccgccgcaaggaatggtgcatgcaaggagatggcgcccaacagtcccccggccacggggcctgccaccata
cccacgccgaaacaagcgctcatgagcccgaagtggcgagcccgatcttccccatcggtgatgtcggcgatataggcgccagcaacc
gcacctgtggcgccggtgatgccggccacgatgcgtccggcgtagaggatctggctagcgatgaccctgctgattggttcgctgaccattt
ccgggtgcgggacggcgttaccagaaactcagaaggttcgtccaaccaaaccgactctgacggcagtttacgagagagatgataggg
tctgcttcagtaagccagatgctacacaattaggcttgtacatattgtcgttagaacgcggctacaattaatacataaccttatgtatcataca
catacgatttaggtgacactatagaatacacggaattaattc
Bold = ITR sequence
Italics = human Mpz promoter
Underline = Cx32
Italic underline = WPRE sequence SEQ ID NO. 18: Human hP0 promoter
gcctggcataaacttcatttattaaagtttatttgtctttaatctctcatataacttagtcttcctgatattgcagctgtgtgtgcccctcttttgtactc
ccagcattttgttcattactaaaggaagtgtcatggcttattatacttgattgttgatgggtttgtcctctgatcttcccatctccacctccccaaac
caaattttcaactccttgctggaaggacttaattttattcctctctctattacctgcattctcatactttacatattgctggcacttaatacaattttgt
agccttgaaataaattgaaatggacttaaacagcagcatgaagcactgaaggacttcttgacaaacggaaaggtcaggggcttcttgcc
tggaaatagtccagtggagaaaaacttctgtctgggaagaatcgcacaggatgaagggaggtgcggggaaaaaaactcccatagga
cttggtcatctcaagaagtctgtaatgcagcccacattagaggagataacaggggatatcctattttcagagttctctggggggaaacctccc
tctagttcctagggctgtgaggcagcctctctcaggcaaggaggctgaggagaaatccctttttatggcctttaaattgaggttccatatctat
ccctcagagaagtgtgtctgtgtccctgtttttgtccctctccctcaccaccccccacaacattccagcctggggcagggggaggccagtg
gacacaaagccctctgtgtatggggtggtatgtgtccccccacccctccacccagactatacaatgccccttctgctccctgcactctgccc
ccctccccaccacctctcaactgcacatgccaggctgcaattggttactggctgaggacagccccctcatgctggggccctaggggatttt
aagcaggttccaggaaccccccgttcagttcctggtcccccactttctcaaccccacagatgctccgggcccctgcccctgccccagc SEQ ID NO. 19: AAV-human-Mpz-Egfp mock construct
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta
cttatctacgtagccatgctctaggtacc*gcctggcataaacttcatttattaaagtttatttgtctttaatctctcatataacttagtcttcctga*
*tattgcagctgtgtgtgcccctcttttgtactcccagcattttgttcattactaaaggaagtgtcatggcttattatacttgattgttgatgggtttgtc*
*ctctgatcttcccatctccacctccccaaaccaaattttcaactccttgctggaaggacttaattttattcctctctctattacctgcattctcatac*
*tttacatattgctggcacttaatacaattttgtagccttgaaataaattgaaatggacttaaacagcagcatgaagcactgaaggacttcttga*
*caaacggaaaggtcaggggcttcttgcctggaaatagtccagtggagaaaaacttctgtctgggaagaatcgcacaggatgaaggga*
*ggtgcggggaaaaaaactcccataggacttggtcatctcaagaagtctgtaatgcagcccacattagaggagataacaggggatatcc*
*tattttcagagttctctggggggaaacctccctctagttcctagggctgtgaggcagcctctctcaggcaaggaggctgaggagaaatccctt*
*tttatggcattaaattgaggttccatatctatccctcagagaagtgtgtctgtgtccctgtttttgtccctctccctcaccaccccccacaacattc*
*cagcctggggcagggggaggccagtggacacaaagccctctgtgtatggggtggtatgtgtccccccacccctccacccagactatac*
*aatgccccttctgctccctgcactctgccccccctccccaccacctctcaactgcacatgccaggctgcaattggttactggctgaggacag*
*ccccctcatgctggggccctaggggatttaagcaggttccaggaaccccccgttcagttcctggtcccccactttctcaaccccacagatg*
*ctccgggcccctgcccctgccccagc*accggtcgccaccatggtgagcaagggcgaggagctgttcaccggggtggtgcccatcctg
gtcgagctggacggcgacgtaaacggccacaagttcagcgtgtccggcgagggcgagggcgatgccacctacggcaagctgaccct
gaagttcatctgcaccaccggcaagctgcccgtgccctggcccaccctcgtgaccaccctgacctacggcgtgcagtgcttcagccgct
accccgaccacatgaagcagcacgacttcttcaagtccgccatgcccgaaggctacgtccaggagcgcaccatcttcttcaaggacga
cggcaactacaagacccgcgccgaggtgaagttcgagggcgacaccctggtgaaccgcatcgagctgaagggcatcgacttcaagg
aggacggcaacatcctggggcacaagctggagtacaactacaacagccacaacgtctatatcatggccgacaagcagaagaacgg
catcaaggtgaacttcaagatccgccacaacatcgaggacggcagcgtgcagctcgccgaccactaccagcagaacacccccatcg
gcgacggccccgtgctgctgcccgacaaccactacctgagcacccagtccgccctgagcaaagaccccaacgagaagcgcgatca
catggtcctgctggagttcgtgaccgccgccgggatcactctcggcatggacgagctgtacaagtaaagcggccctagatcaagctt*atc*
*gataatcaacctctggattacaaaatttgtgaaagattgactggtattcttaactatgttgctccttttacgctatgtggatacgctgctttaatgc*
*ctttgtatcatgctattgcttcccgtatggctttcattttctcctccttgtataaatcctggttgctgtctctttatgaggagttgtggcccgttgtcagg*
*caacgtggcgtggtgtgcactgtgtttgctgacgcaacccccactggttggggcattgccaccacctgtcagctcctttccgggactttcgctt*
*tccccctccctattgccacggcggaactcatcgccgcctgccttgcccgctgctggacaggggctcggctgttgggcactgacaattccgt*
*ggtgttgtcggggaaatcatcgtcctttccttggctgctcgcctgtgttgccacctggattctgcgcgggacgtccttctgctacgtcccttcggc*
*cctcaatccagcggaccttccttcccgcggcctgctgccggctctgcggcctcttccgcgtcttcgccttcgccctcagacgagtcggatctc*
*cctttgggccgcctcccc*gcatcgataccgtcgactcgctgatcagcctcgactgtgccttctagttgccagccatctgttgtttgcccctccc
ccgtgccttccttgaccctggaaggtgccactcccactgtcctttcctaataaaatgaggaaattgcatcgcattgtctgagtaggtgtcattct
attctggggggtggggtggggcaggacagcaagggggaggattgggaagacaatagcaggcatgctggggatgcggtgggctctat
ggcttctgaggcggaaagaaccagctggggctcgactagagcatggctacgtagataagtagcatggcgggttaatcattaacta
caaggaacccctagtgatggagttggccactccctctctgcgcgctcgctcgctcactgaggccgggcgaccaaaggtcgc
ccgacgcccgggctttgcccgggcggcctcagtgagcgagcgagcgcgcagagcttttgcaaaagcctaggcctccaaaa
aagcctcctcactacttctggaatagctcagaggccgaggcggcctcggcctctgcataaataaaaaaaattagtcagccatggggcg
gagaatgggcggaactgggcggagttaggggcgggatgggcggagttaggggcgggactatggttgctgactaattgagatgcatgct
ttgcatacttctgcctgctggggagcctggggactttccacacctggttgctgactaattgagatgcatgctttgcatacttctgcctgctgggg
agcctggggactttccacaccctaactgacacacattccacagctgcattaatgaatcggccaacgcgcggggagaggcggtttgcgta
ttgggcgctcttccgcttcctcgctcactgactcgctgcgctcggtcgttcggctgcggcgagcggtatcagctcactcaaaggcggtaata
cggttatccacagaatcaggggataacgcaggaaagaacatgtgagcaaaaggccagcaaaaggccaggaaccgtaaaaaggc
cgcgttgctggcgtttttccataggctccgcccccctgacgagcatcacaaaaatcgacgctcaagtcagaggtggcgaaacccgaca
ggactataaagataccaggcgtttccccctggaagctccctcgtgcgctctcctgttccgaccctgccgcttaccggatacctgtccgccttt
ctcccttcgggaagcgtggcgctttctcatagctcacgctgtaggtatctcagttcggtgtaggtcgttcgctccaagctgggctgtgtgcacg
aaccccccgttcagcccgaccgctgcgccttatccggtaactatcgtcttgagtccaacccggtaagacacgacttatcgccactggcag
cagccactggtaacaggattagcagagcgaggtatgtaggcggtgctacagagttcttgaagtggtggcctaactacggctacactaga
agaacagtatttggtatctgcgctctgctgaagccagttaccttcggaaaaagagttggtagctcttgatccggcaaacaaaccaccgctg
gtagcggtggtttttttgtttgcaagcagcagattacgcgcagaaaaaaaggatctcaagaagatcctttgatcttttctacggggtctgacg -continued Sequences ctcagtggaacgaaaactcacgttaagggattttggtcatgagattatcaaaaaggatcttcacctagatccttttaaattaaaaatgaagtt
ttaaatcaatctaaagtatatatgagtaaacttggtctgacagttaccaatgcttaatcagtgaggcacctatctcagcgatctgtctatttcgtt
catccatagttgcctgactccccgtcgtgtagataactacgatacgggagggcttaccatctggccccagtgctgcaatgataccgcgag
acccacgctcaccggctccagatttatcagcaataaaccagccagccggaagggccgagcgcagaagtggtcctgcaactttatccgc
ctccatccagtctattaattgttgccgggaagctagagtaagtagttcgccagttaatagtttgcgcaacgttgttgccattgctacaggcatc
gtggtgtcacgctcgtcgtttggtatggcttcattcagctccggttcccaacgatcaaggcgagttacatgatcccccatgttgtgcaaaaaa
gcggttagctccttcggtcctccgatcgttgtcagaagtaagttggccgcagtgttatcactcatggttatggcagcactgcataattctcttac
tgtcatgccatccgtaagatgcttttctgtgactggtgagtactcaaccaagtcattctgagaatagtgtatgcggcgaccgagttgctcttgc
ccggcgtcaatacgggataataccgcgccacatagcagaactttaaaagtgctcatcattggaaaacgttcttcggggcgaaaactctc
aaggatcttaccgctgttgagatccagttcgatgtaacccactcgtgcacccaactgatcttcagcatcttttactttcaccagcgtttctgggt
gagcaaaaacaggaaggcaaaatgccgcaaaaaagggaataagggcgacacggaaatgttgaatactcatactcttcctttttcaata
ttattgaagcatttatcagggttattgtctcatgagcggatacatatttgaatgtatttagaaaaataaacaaataggggttccgcgcacatttc
cccgaaaagtgccacctgacgtctaagaaaccattattatcatgacattaacctataaaaataggcgtatcacgaggccctttcgtctcgc
gcgtttcggtgatgacggtgaaaacctctgacacatgcagctcccggagacggtcacagcttgtctgtaagcggatgccgggagcaga
caagcccgtcagggcgcgtcagcgggtgttggcgggtgtcggggctggcttaactatgcggcatcagagcagattgtactgagagtgca
ccattcgacgctctcccttatgcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaaacaagcgctcatgagcc
cgaagtggcgagcccgatcttccccatcggtgatgtcggcgatataggcgccagcaaccgcacctgtggcgccggtgatgccggccac
gatgcgtccggcgtagaggatctggctagcgatgaccctgctgattggttcgctgaccatttccgggtgcgggacggcgttaccagaaac
tcagaaggttcgtccaaccaaaccgactctgacggcagtttacgagagagatgatagggtctgcttcagtaagccagatgctacacaatt
aggcttgtacatattgtcgttagaacgcggctacaattaatacataaccttatgtatcatacacatacgatttaggtgacactatagaataca
cggaattaattc
Bold = ITR sequence
Italics = human Mpz promoter
Underline = EGFP
Italic underline = WPRE sequence SEQ ID NO. 20: AAV-minMpz-SH3TC2.myc.ITR for therapeutic SH3TC2 gene replacement
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta
cttatctacgtagccatgctctaggtacc*gctctcaggcaaggaggctaagaaggaatcctttgctgtagccttttggatttaggtttctca*
*gcttatctatccctcagagaagtgtgtctatgtccctttttctgtccctctgcctcaccccaccccaacattccaacctagggtagggggaggtc*
*agtatacacaaagccctctgtgtaaggggtggtatgtgtcccccaccccccctacccagagtatacaatgccccttctgctccatgcccct*
*gccacccctcccaccacctctcaattgcacatgccaggctgcaattggtcactggctcaggacagcccccctcatgctggggatccaggg*
*gattttaagcaggttccagaaaacaccactcagttccttgtcccccgctctctccaccccacagacgctctgccaaccggtacc*atgggtg
gctgcttctgcatccccagggagcggagtctgacccgcmcccaggtaaagaaactccttccaaggatccaactgtatcgagtgagtgt
atagcctcatctgaatacaaggaaaaatgttttctgccacagaacattaatccagacctgacactctccttctgtgtaaagagccgctccag
gaggtgtgtaaatggacccctacaggaagctgctcggaggcggctctgggcactggagaatgaggaccaggaggtgcgcatgctgttt
aaggacctctcagcaaggttggtcagtatccagtctcagagggcccagtttctcatcaccttcaagaccatggaggaaatctggaagttct
ccacctaccttaatttaggctacgtatccatgtgtctagaacatctcctctttgaccacaagtactggctcaactgcatattggtggaggatac
agagatccaagtactgtagatgataaacacctggaaacaatatacctgggactcctgatacaggaaggccacttcttctgcagagccct
gtgctccgtgactccaccagccgagaaggaaggggaatgcttgacactttgcaagaatgagttaatctcagtgaagatggcagaagct
ggctccgagttggaaggcgtgtctttggtgacaggtcagcggggcctggtactggtgtcagccttggagcctctgcctctccctttccacca
gtggttcctaaagaattatccaggaagctgtggcctttccaggaagagggattggacaggctcctatcagattggcagaggacgctgtaa
ggccttgacgggttatgagccaggagaaaaggatgaactgaatttctaccagggagaaagcattgagatcatcggctttgtcatacctgg
gcttcagtggttcattggaaagtcgacaagttcaggacaagtgggctttgtccccaccaggaacatagatcctgattcttattccccaatga
gcaggaactctgcctttctcagtgatgaggagagatgctccctgttggccctgggaagtgataagcagactgagtgttccagcttcctcca
cactcttgctcgcactgacatcacatctgtctaccggctcagtgggtttgaatccatccagaatcctccaaatgatctgagtgcatcccagcc
tgaaggtttcaaggaggtcaggcctggcagagcctgggaggagcatcaggccgtggggtccagacagtccagcagctctgaggactc
cagcctggaggaggagctcctctcggccacctcagacagctatcgcctgccggagcctgatgaccttgatgacccggaactgctcatgg
acctaagcactggtcaggaggaggaggctgagaacttcgccccccatattggcttttctggatcatgagggttatgctgaccactttaagagt
ctctatgacttctccttctctttcctcacttcttcgtttatagcttctctgaggaggatgagtttgtggcctacctggaggcatcaagaaagtgggc
caagaagagccacatgacctgggcccatgcccggctctgcttcctcctgggccggctgagcatcaggaaggtcaaactctctcaggcc
agggtgtacttcgaggaggccatccacattctcaatggagcatttgaggacctatccttggtggccactctgtacatcaatttggctgccatc
tacctgaaacagaggctgagacataaaggctccgccctgttggaaaaggcaggtgccctgctggcctgcctgcctgaccgtgagtctag
tgccaagcatgaactcgacgtggtggcctacgtgctgcgccaggggattgtggtgggcagcagcccgctggaggccagggcctgctttc
tggccatccgcttgctcctgagcctaggccggcacgaggaggtcctgccctttgccgagcgcctgcagctcctctctggacaccctcctgc
ctctgaggctgtggccagtgttttgagttttctgtatgacaagaaatatcttccacaccttgcagtggcctctgtccagcaacatggtatccag
agtgcccaagggatgtctcttcctatttggcaggtccaccttgtcctccagaacacaaccaagctccttggctttccttccccaggctggggt
gaagtttctgccttggcctgcccaatgctcagacaggccctggctgcctgtgaggaactagcagaccggagcacccagagggccctgt
gtctcatcctttccaaagtgtacctcgagcacaggtctcctgacggtgccatccactacctgagccaggccttggtgctagggcagctgctg
ggtgagcaggaatcctttgagtcttctctctgcctggcatgggcctatctcttagccagccaggccaagaaggctttggatgtgcttgagcc
actgctatgctccctgaaggagacagagagtctcactcaaaggggagtcatctataacctcctgggacttgcactccaaggtgaaggcc
gggtgaacagggcagccaagagctatcttcgggccttgaacagagcccaggaggtgggagatgtgcataaccaggcagtggctatg
gccaatcttggccacctgagccttaagtcctgggctcagcatccagccagaaactatctcctgcaggctgtacgactctattgtgaacttca
ggccagtaaggagacagacatggaattagtacaggtgtttctctggttggcccaagttctggtgtctggacaccagctgacccatggcctt
ctttgttatgaaatggcattgctgtttggcttaaggcatcgacatctaaagagtcagcttcaggccaccaaatccctctgccatttctacagctc
tgtgtccccaaaccctgaggcatgcatcacctaccatgagcactggctggccctggctcagcaactcagggaccgggagatggaagg
gaggctgctggagtccctggggcagctttatcggaacctaaataccgccaggtccctcaggaggtcactcacatgcatcaaggagagc
ctgcgtatcttcattgacctgggggagacagacaaggctgctgaggcctggcttggggcggggcgactccactacctcatgcaggaag
acgagctggtggagctgtgcctgcaggcagccatccagacagccctgaagtcagaggagcctttgctggctctcaaactttatgaagaa
gcaggtgatgtgttcttcaatgggacccgccacaggcatcatgcagtggagtactaccgagctggagctgttcctttagcaaggaggttga
aggcggtgagaactgagctccggattttcaataagctgacagagctgcagattagcctcgaaggctatgagaaggctttggaatttgcca
ccctggccgccaggctcagcacagtcacaggagatcagaggcaagagctggtggcctttcaccgcctggctacagtgtactactccctg
cacatgtatgagatggctgaggactgctacctgaagaccctgtccctctgtccaccatggctgcagagtcccaaggaggccctgtactat
gccaaggtgtattatcgcctgggcagactcaccttctgccagctgaaggatgcccatgatgccactgagtacttccttctggccctggcag
cagcggtcctgctgggtgatgaggagcttcaggacaccattaggagcaggctggacaacatctgccagagcccccctgtggcacagca -continued Sequences ggccctccgggtgctcctcagagagggcgcggtggctgagtggtggtggcctggccctcgagcagaagctgatcagcgaggaggac
ctgtaagatatccatcacactggcggccgc*ggagctctcgagaggcctaataaagagctcagatgcatcgatcagagtgtgttggtttttttg*
*tgtgagatct*aagcttagcatggctacgtagataagtagcatggcgggttaatcattaactacaaggaacccctagtgatggagtt
ggccactccctctctgcgcgctcgctcgctcactgaggccgggcgaccaaaggtcgcccgacgcccgggctttgcccggg
cggcctcagtgagcgagcgagcgcgcagagctttttgcaaaagcctaggcctccaaaaaagcctcctcactacttctggaatagct
cagaggccgaggcggcctcggcctctgcataaataaaaaaaattagtcagccatggggcggagaatgggcggaactgggcggagtt
aggggcgggatgggcggagttaggggcgggactatggttgctgactaattgagatgcatgctttgcatacttctgcctgctggggagcctg
gggactttccacacctggttgctgactaattgagatgcatgctttgcatacttctgcctgctggggagcctggggactttccacaccctaactg
acacacattccacagctgcattaatgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggttatccacagaatcaggggataac
gcaggaaagaacatgtgagcaaaaggccagcaaaaggccaggaaccgtaaaaaggccgcgttgctggcgtttttccataggctccg
cccccctgacgagcatcacaaaaatcgacgctcaagtcagaggtggcgaaacccgacaggactataaagataccaggcgtttcccc
ctggaagctccctcgtgcgctctcctgttccgaccctgccgcttaccggatacctgtccgcctttctcccttcgggaagcgtggcgctttctcat
agctcacgctgtaggtatctcagttcggtgtaggtcgttcgctccaagctgggctgtgtgcacgaaccccccgttcagcccgaccgctgcg
ccttatccggtaactatcgtcttgagtccaacccggtaagacacgacttatcgccactggcagcagccactggtaacaggattagcagag
cgaggtatgtaggcggtgctacagagttcttgaagtggtggcctaactacggctacactagaagaacagtatttggtatctgcgctctgctg
aagccagttaccttcggaaaaagagttggtagctcttgatccggcaaacaaaccaccgctggtagcggtggtttttttgtttgcaagcagca
gattacgcgcagaaaaaaaggatctcaagaagatcctttgatcttttctacggggtctgacgctcagtggaacgaaaactcacgttaagg
gattttggtcatgagattatcaaaaaggatcttcacctagatccttttaaattaaaaatgaagttttaaatcaatctaaagtatatatgagtaaa
cttggtctgacagttaccaatgcttaatcagtgaggcacctatctcagcgatctgtctatttcgttcatccatagttgcctgactccccgtcgtgt
agataactacgatacgggagggcttaccatctggccccagtgctgcaatgataccgcgagacccacgctcaccggctccagatttatca
gcaataaaccagccagccggaagggccgagcgcagaagtggtcctgcaactttatccgcctccatccagtctattaattgttgccggga
agctagagtaagtagttcgccagttaatagtttgcgcaacgttgttgccattgctacaggcatcgtggtgtcacgctcgtcgtttggtatggctt
cattcagctccggttcccaacgatcaaggcgagttacatgatcccccatgttgtgcaaaaaagcggttagctccttcggtcctccgatcgtt
gtcagaagtaagttggccgcagtgttatcactcatggttatggcagcactgcataattctcttactgtcatgccatccgtaagatgcttttctgtg
actggtgagtactcaaccaagtcattctgagaatagtgtatgcggcgaccgagttgctcttgcccggcgtcaatacgggataataccgcg
ccacatagcagaactttaaaagtgctcatcattggaaaacgttcttcggggcgaaaactctcaaggatcttaccgctgttgagatccagttc
gatgtaacccactcgtgcacccaactgatcttcagcatcttttactttcaccagcgtttctgggtgagcaaaaacaggaaggcaaaatgcc
gcaaaaaagggaataagggcgacacggaaatgttgaatactcatactcttcctttttcaatattattgaagcatttatcagggttattgtctcat
gagcggatacatatttgaatgtatttagaaaaataaacaaataggggttccgcgcacatttccccgaaaagtgccacctgacgtctaaga
aaccattattatcatgacattaacctataaaaataggcgtatcacgaggccgttcgtctcgcgcgtttcggtgatgacggtgaaaacctctg
acacatgcagctcccggagacggtcacagcttgtctgtaagcggatgccgggagcagacaagcccgtcagggcgcgtcagcgggtgt
tggcgggtgtcggggctggcttaactatgcggcatcagagcagattgtactgagagtgcaccattcgacgctctcccttatgcgactcctgc
attaggaagcagcccagtagtaggttgaggccgttgagcaccgccgccgcaaggaatggtgcatgcaaggagatggcgcccaacag
tcccccggccacggggcctgccaccatacccacgccgaaacaagcgctcatgagcccgaagtggcgagcccgatcttccccatcggt
gatgtcggcgatataggcgccagcaaccgcacctgtggcgccggtgatgccggccacgatgcgtccggcgtagaggatctggctagc
gatgaccctgctgattggttcgctgaccatttccgggtgcgggacggcgttaccagaaactcagaaggttcgtccaaccaaaccgactct
gacggcagtttacgagagagatgatagggtctgcttcagtaagccagatgctacacaattaggcttgtacatattgtcgttagaacgcggc
tacaattaatacataaccttatgtatcatacacatacgatttaggtgacactatagaatacacggaattaattc
Bold = ITR sequence
Italics = mini Mpz promoter
Underline = SH3TC2
Italic underline = synthetic minimal polyA SEQ ID NO. 21: AAV-human-miniMpz-SH3TC2
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta
cttatctacgtagccatgctctaggtacc*tctctcaggcaaggaggctgaggagaaatccctttttatggcctttaaattgaggttccatat*
*ctatccctcagagaagtgtgtctgtgtccctgtttttgtccctctccctcaccaccccccacaacattccagcctggggcaggggggaggcca*
*gtggacacaaagccctctgtgtatggggtggtatgtgtcccccaccccctccacccagactatacaatgccccttctgctccctgcactctg*
*ccccctccccaccacctctcaactgcacatgccaggctgcaattggttactggctgaggacagccccctcatgctggggccctagggg*
*attttaagcaggttccaggaacccccgttcagttcctggtcccccactttctcaaccccacagatgctccgggcccctgcccctgccccag*
*c*ggtaccatgaataactacttctacatccccaaaaagcgaaatctaacccgaggcccaaataaaaaaactccttccaaaaatccaact
gtatcgagtgagtgtatagcctcatctgaatacaaggaaaaatgttttctgccacagaacattaatccagacctgacactctccttctgtgta
aagagccgctccaggaggtgtgtaaatggacccctacaggaagctgctcggaggcggctctgggcactggagaatgaggaccagga
ggtgcgcatgctgtttaaggacctctcagcaaggttggtcagtatccagtctcagagggcccagtttctcatcaccttcaagaccatggag
gaaatctggaagttctccacctaccttaatttaggctacgtatccatgtgtctagaacatctcctctttgaccacaagtactggctcaactgcat
attggtggaggatacagagatccaagtgtctgtagatgataaacacctggaaacaatatacctgggactcctgatacaggaaggccact
tcttctgcagagccctgtgctccgtgactccaccagccgagaaggaaggggaatgcttgacactttgcaagaatgagttaatctcagtga
agatggcagaagctggctccgagttggaaggcgtgtctttggtgacaggtcagcggggcctggtactggtgtcagccttggagcctctgc
ctctccctttccaccagtggttcctaaagaattatccaggaagctgtggcctttccaggaagagggattggacaggctcctatcagattggc
agaggacgctgtaaggccttgacgggtlatgagccaggagaaaaggatgaactgaatttctaccagggagaaagcattgagatcatc
ggctttgtcatacctgggcttcagtggttcattggaaagtcgacaagttcaggacaagtgggctttgtccccaccaggaacatagatcctga
ttcttattccccaatgagcaggaactctgcctttctcagtgatgaggagagatgctccctgttggccctgggaagtgataagcagactgagt
gttccagcttcctccacactcttgctcgcactgacatcacatctgtctaccggctcagtgggtttgaatccatccagaatcctccaaatgatct
gagtgcatcccagcctgaaggtttcaaggaggtcaggcctggcagagcctgggaggagcatcaggccgtggggtccagacagtcca
gcagctctgaggactccagcctggaggaggagctcctctcggccacctcagacagctatcgcctgccggagcctgatgaccttgatgac
ccggaactgctcatggacctaagcactggtcaggaggaggaggctgagaacttcgcccccatattggcttttctggatcatgagggttatg
ctgaccactttaagagtctctatgacttctccttctctttcctcacttcttccttttatagcttctctgaggaggatgagtttgtggcctacctggagg
catcaagaaagtgggccaagaagagccacatgacctgggcccatgcccggctctgcttcctcctgggccggctgagcatcaggaagg
tcaaactctctcaggccagggtgtacttcgaggaggccatccacattctcaatggagcatttgaggacctatccttggtggccactctgtac
atcaatttggctgccatctacctgaaacagaggctgagacataaaggctccgccctgttggaaaaggcaggtgccctgctggcctgcctg
cctgaccgtgagtctagtgccaagcatgaactcgacgtggtggcctacgtgctgcgccaggggattgtggtgggcagcagcccgctgg
aggccagggcctgctttctggccatccgcttgctcctgagcctaggccggcacgaggaggtcctgccctttgccgagcgcctgcagctcc
tctctggacaccctcctgcctctgaggctgtggccagtgttttgagttttotgtatgacaagaaatatcttccacaccttgcagtggcctctgtcc
agcaacatggtatccagagtgcccaagggatgtctcttcctatttggcaggtccaccttgtcctccagaacacaaccaagctccttggcttt
ccttccccaggctggggtgaagtttctgccttggcctgcccaatgctcagacaggccctggctgcctgtgaggaactagcagaccggag -continued Sequences cacccagagggccctgtgtctcatcctttccaaagtgtacctcgagcacaggtctcctgacggtgccatccactacctgagccaggccttg
gtgctagggcagctgctgggtgagcaggaatcctttgagtcttctctctgcctggcatgggcctatctcttagccagccaggccaagaagg
ctttggatgtgcttgagccactgctatgctccctgaaggagacagagagtctcactcaaaggggagtcatctataacctcctgggacttgc
actccaaggtgaaggccgggtgaacagggcagccaagagctatcttcgggccttgaacagagcccaggaggtgggagatgtgcata
accaaacaataactatagccaatcttagccacctaaaccttaaatcctagactcaacatccagccaaaaactatctcctacaaactgtac
gactctattgtgaacttcaggccagtaaggagacagacatggaattagtacaggtgtttctctggttggcccaagttctggtgtctggacac
cagctgacccatggccttctttgttatgaaatggcattgctgttlggcttaaggcatcgacatctaaagagtcagcttcaggccaccaaatcc
ctctgccatttctacagctctgtgtccccaaaccctgaggcatgcatcacctaccatgagcactggctggccctggctcagcaactcaggg
accgggagatggaagggaggctgctggagtccctggggcagctttatcggaacctaaataccgccaggtccctcaggaggtcactca
catgcatcaaggagagcctgcgtatcttcattgacctgggggagacagacaaggctgctgaggcctggcttggggcggggcgactcca
ctacctcatgcaggaagacgagctggtggagctgtgcctgcaggcagccatccagacagccctgaagtcagaggagcctttgctggct
ctcaaactttatgaagaagcaggtgatgtgttcttcaatgggacccgccacaggcatcatgcagtggagtactaccgagctggagctgttc
ctttagcaaggaggttgaaggcggtgagaactgagctccggattttcaataagctgacagagctgcagattagcctcgaaggctatgag
aaggctttggaatttgccaccctggccgccaggctcagcacagtcacaggagatcagaggcaagagctggtggcctttcaccgcctgg
ctacagtgtactactccctgcacatgtatgagatggctgaggactgctacctgaagaccctgtccctctgtccaccatggctgcagagtccc
aaggaggccctgtactatgccaaggtgtattatcgcctgggcagactcaccttctgccagctgaaggatgcccatgatgccactgagtact
tccttctggccctggcagcagcggtcctgctgggtgatgaggagcttcaggacaccattaggagcaggctggacaacatctgccagagc
cccctgtggcacagcaggccctccgggtgctcctcagagagggcgcggtggctgagtggtggtggcctggccctctgagcggccgc*g*
*gagctctcgagaggcctaataaagagctcagatgcatcgatcagagtgtgttggtttttttgtgtgagatct*aagcttagcatggctacgta
gataagtagcatggcgggttaatcattaactacaaggaacccctagtgatggagttggccactccctctctgcgcgctcgctc
gctcactgaggccgggcgaccaaaggtcgcccgacgcccgggctttgcccgggcggcctcagtgagcgagcgagcgcg
cagagctttttgcaaaagcctaggcctccaaaaaagcctcctcactacttctggaatagctcagaggccgaggcggcctcggcctctgc
ataaataaaaaaaattagtcagccatggggcggagaatgggcggaactgggcggagttaggggcgggatgggcggagttaggggc
gggactatggttgctgactaattgagatgcatgctttgcatacttctgcctgctggggagcctggggactttccacacctggttgctgactaatt
gagatgcatgctttgcatacttctgcctgctggggagcctggggactttccacaccctaactgacacacattccacagctgcattaatgaat
cggccaacgcgcggggagaggcggtttgcgtattgggcgctcttccgcttcctcgctcactgactcgctgcgctcggtcgttcggctgcgg
cgagcggtatcagctcactcaaaggcggtaatacggttatccacagaalcaggggataacgcaggaaagaacatgtgagcaaaagg
ccagcaaaaggccaggaaccgtaaaaaggccgcgttgctggcgtttttccataggctccgcccccctgacgagcatcacaaaaatcg
acgctcaagtcagaggtggcgaaacccgacaggactataaagataccaggcgtttccccctggaagctccctcgtgcgctctcctgttcc
gaccctgccgcttaccggatacctgtccgcctttctcccttcgggaagcgtggcgctttctcatagctcacgctgtaggtatctcagttcggtgt
aggtcgttcgctccaagctgggctgtgtgcacgaaccccccgttcagcccgaccgctgcgccttatccggtaactatcgtcttgagtccaa
cccggtaagacacgacttatcgccactggcagcagccactggtaacaggattagcagagcgaggtatgtaggcggtgctacagagttc
ttgaagtggtggcctaactacggctacactagaagaacagtatttggtatctgcgctctgctgaagccagttaccttcggaaaaagagttg
gtagctcttgatccggcaaacaaaccaccgctggtagcggtggtttttttgtttgcaagcagcagattacgcgcagaaaaaaaggatctca
agaagatcctttgatcttttctacggggtctgacgctcagtggaacgaaaactcacgttaagggattttggtcatgagattatcaaaaaggat
cttcacctagatccttttaaattaaaaatgaagttttaaatcaatctaaagtatatatgagtaaacttggtctgacagttaccaatgcttaatcag
tgaggcacctatctcagcgatctgtctatttcgttcatccatagttgcctgactccccgtcgtgtagataactacgatacgggagggcttacca
tctggccccagtgctgcaatgataccgcgagacccacgctcaccggctccagatttatcagcaataaaccagccagccggaagggcc
gagcgcagaagtggtcctgcaactttatccgcctccatccagtctattaattgttgccgggaagctagagtaagtagttcgccagttaatagt
ttgcgcaacgttgttgccattgctacaggcatcgtggtgtcacgctcgtcgtttggtatggcttcattcagctccggttcccaacgatcaaggc
gagttacatgatcccccatgttgtgcaaaaaagcggttagctccttcggtcctccgatcgttgtcagaagtaagttggccgcagtgttatcac
tcatggttatggcagcactgcataattctcttactgtcatgccatccgtaagatgcttttctgtgactggtgagtactcaaccaagtcattctgag
aatagtgtatgcggcgaccgagttgctcttgcccggcgtcaatacgggataataccgcgccacatagcagaactttaaaagtgctcatca
ttggaaaacgttcttcggggcgaaaactctcaaggatcttaccgctgttgagatccagttcgatgtaacccactcgtgcacccaactgatctt
cagcatcttttactttcaccagcgtttctgggtgagcaaaaacaggaaggcaaaatgccgcaaaaaagggaataagggcgacacgga
aatgttgaatactcatactcttcctttttcaatattattgaagcatttatcagggttattgtctcatgagcggatacatatttgaatgtatttagaaaa
ataaacaaataggggttccgcgcacatttccccgaaaagtgccacctgacgtctaagaaaccattattatcatgacattaacctataaaa
ataggcgtatcacgaggccctttcgtctcgcgcgtttcggtgatgacggtgaaaacctctgacacatgcagctcccggagacggtcacag
cttgtctgtaagcggatgccgggagcagacaagcccgtcagggcgcgtcagcgggtgttggcgggtgtcggggctggcttaactatgcg
gcatcagagcagattgtactgagagtgcaccattcgacgctctcccttatgcgactcctgcattaggaagcagcccagtagtaggttgag
gccgttgagcaccgccgccgcaaggaatggtgcatgcaaggagatggcgcccaacagtcccccggccacggggcctgccaccata
cccacgccgaaacaagcgctcatgagcccgaagtggcgagcccgatcttccccatcggtgatgtcggcgatataggcgccagcaacc
gcacctgtggcgccggtgatgccggccacgatgcgtccggcgtagaggatctggctagcgatgaccctgctgattggttcgctgaccattt
ccgggtgcgggacggcgttaccagaaactcagaaggttcgtccaaccaaaccgactctgacggcagtttacgagagagatgataggg
tctgcttcagtaagccagatgctacacaattaggcttgtacatattgtcgttagaacgcggctacaattaatacataaccttatgtatcataca
catacgatttaggtgacactatagaatacacggaattaattc
Bold = ITR sequence
Italics = mini-human hP0 promoter
Underline = SH3TC2
Italic underline = synthetic minimal polyA SEQ ID NO. 22: Mini-human hP0 promoter
tctctcaggcaaggaggctgaggagaaatccctttttatggcctttaaattgaggttccatatctatccctcagagaagtgtgtctgtgtccctg
tttttgtccctctccctcaccacccccacaacattccagcctggggcagggggaggccagtggacacaaagccctctgtgtatggggtg
gtatgtgtcccccacccctccacccagactatacaatgccccttctgctccctgcactctgccccctccccaccacctctcaactgcaca
tgccaggctgcaattggttactggctgaggacagcccctcatgctggggccctaggggattttaagcaggttccaggaacccccgttc
agttcctggtcccccactttctcaaccccacagatgctccgggcccctgcccctgccccagc SEQ ID NO. 23: AAV-human-miniMpz-Egfp
tagctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccatgcta
cttatctacgtagccatgctctaggtacc*tctctcaggcaaggaggctgaggagaaatccctttttatggcctttaaattgaggttccatat*
*ctatccctcagagaagtgtgtctgtgtccctgtttttgtccctctccctcaccacccccacaacattccagcctggggcagggggaggcca*
*gtggacacaaagccctctgtgtatggggtggtatgtgtcccccacccctccacccagactatacaatgccccttctgctccctgcactctg*
*ccccctccccaccacctctcaactgcacatgccaggctgcaattggttactggctgaggacagcccctcatgctggggccctagggg*
*attttaagcaggttccaggaacccccgttcagttcctggtcccccactttctcaaccccacagatgctccgggcccctgcccctgccccag*
*caccggtcgccacc*atggtgagcaagggcgaggagctgttcaccggggtggtgcccatcctggtcgagctggacggcgacgtaaacg -continued Sequences gccacaagttcagcgtgtccggcgagggcgagggcgatgccacctacggcaagctgaccctgaagttcatctgcaccaccggcaag
ctgcccgtgccctggcccaccctcgtgaccaccctgacctacggcgtgcagtgcttcagccgctaccccgaccacatgaagcagcacg
acttcttcaagtccgccatgcccgaaggctacgtccaggagcgcaccatcttcttcaggcagacggcaactacaagacccgcgccga
ggtgaagttcgagggcgacaccctggtgaaccgcatcgagctgaagggcatcgacttcaaggaggacggcaacatcctggggcaca
agctggagtacaactacaacagccacaacgtctatatcatggccgacaagcagaagaacggcatcaaggtgaacttcaagatccgc
cacaacatcgaggacggcagcgtgcagctcgccgaccactaccagcagaacacccccatcggcgacggccccgtgctgctgcccg
acaaccactacctgagcacccagtccgccctgagcaaagaccccaacgagaagcgcgatcacatggtcctgctggagttcgtgaccg
ccgccgggatcactctcggcatggacgagctgtacaagtaaagcggccctagatcaagctt*atcgataatcaacctctggattacaaaa*
*tttgtgaaagattgactggtattcttaactatgttgctccttttacgctatgtggatacgctgctttaatgcctttgtatcatgctattgcttcccgtatg*
*gctttcattttctcctccttgtataaatcctggttgctgtctctttatgaggagttgtggcccgttgtcaggcaacgtggcgtggtgtgcactgtgttt*
*gctgacgcaacccccactggttggggcattgccaccacctgtcagctcctttccgggactttcgctttccccctccctattgccacggcgga*
*actcatcgccgcctgccttgcccgctgctggacaggggctcggctgttgggcactgacaattccgtggtgttgtcggggaaatcatcgtcct*
*ttccttggctgctcgcctgtgttgccacctggattctgcgcgggacgtccttctgctacgtcccttcggccctcaatccagcggaccttccttcc*
*cgcggcctgctgccggctctgcggcctcttccgcgtcttcgccttcgccctcagacgagtcggatctccctttgggccgcctccccg*catcg
ataccgtcgactcgctgatcagcctcgactgtgccttctagttgccagccatctgttgtttgcccctcccccgtgccttccttgaccctggaagg
tgccactcccactgtcctttcctaataaaatgaggaaattgcatcgcattgtctgagtaggtgtcattctattctggggggtggggtggggca
ggacagcaagggggaggattgggaagacaatagcaggcatgctggggatgcggtgggctctatggcttctgaggcggaaagaacc
agctggggctcgactagagcatggctacgtagataagtagcatggcgggttaatcattaactacaaggaacccctagtgatgga
gttggccactccctctctgcgcgctcgctcgctcactgaggccgggcgaccaaaggtcgcccgacgcccgggctttgcccg
ggcggcctcagtgagcgagcgagcgcgcagagctttttgcaaaagcctaggcctccaaaaaagcctcctcactacttctggaata
gctcagaggccgaggcggcctcggcctctgcataaataaaaaaaattagtcagccatggggcggagaatgggcggaactgggcgg
agttaggggcgggatgggcggagttaggggcgggactatggttgctgactaattgagatgcatgctttgcatacttctgcctgctggggag
cctggggactttccacacctggttgctgactaattgagatgcatgctttgcatacttctgcctgctggggagcctggggactttccacaccta
actgacacacattccacagctgcattaatgaatcggccaacgcgcggggagaggcggtttgcgtattgggcgctcttccgcttcctcgctc
actgactcgctgcgctcggtcgttcggctgcggcgagcggtatcagctcactcaaaggcggtaatacggttatccacagaatcagggga
taacgcaggaaagaacatgtgagcaaaaggccagcaaaaggccaggaaccgtaaaaaggccgcgttgctggcgtttttccataggc
tccgcccccctgacgagcatcacaaaaatcgacgctcaagtcagaggtggcgaaacccgacaggactataaagataccaggcgtttc
cccctggaagctccctcgtgcgctctcctgttccgaccctgccgcttaccggatacctgtccgcctttctcccttcgggaagcgtggcgctttc
tcatagctcacgctgtaggtatctcagttcggtgtaggtcgttcgctccaagctgggctgtgtgcacgaaccccccgttcagcccgaccgct
gcgccttatccggtaactatcgtcttgagtccaacccggtaagacacgacttatcgccactggcagcagccactggtaacaggattagca
gagcgaggtatgtaggcggtgctacagagttcttgaagtggtggcctaactacggctacactagaagaacagtatttggtatctgcgctct
gctgaagccagttaccttcggaaaaagagttggtagctcttgatccggcaaacaaaccaccgctggtagcggtggtttttttgtttgcaagc
agcagattacgcgcagaaaaaaaggatctcaagaagatcctttgatcttttctacggggtctgacgctcagtggaacgaaaactcacgtt
aagggattttggtcatgagattatcaaaaaggatcttcacctagatccttttaaattaaaaatgaagttttaaatcaatctaaagtatatatgag
taaacttggtctgacagttaccaatgcttaatcagtgaggcacctatctcagcgatctgtctatttcgttcatccatagttgcctgactccccgtc
gtgtagataactacgatacgggagggcttaccatctggccccagtgctgcaatgataccgcgagacccacgctcaccggctccagattt
atcagcaataaaccagccagccggaagggccgagcgcagaagtggtcctgcaactttatccgcctccatccagtctattaattgttgccg
ggaagctagagtaagtagttcgccagttaatagtttgcgcaacgttgttgccattgctacaggcatcgtggtgtcacgctcgtcgtttggtatg
gcttcattcagctccggttcccaacgatcaaggcgagttacatgatcccccatgttgtgcaaaaaagcggttagctccttcggtcctccgat
cgttgtcagaagtaagttggccgcagtgttatcactcatggttatggcagcactgcataattctcttactgtcatgccatccgtaagatgcttttc
tgtgactggtgagtactcaaccaagtcattctgagaatagtgtatgcggcgaccgagttgctcttgcccggcgtcaatacgggataatacc
gcgccacatagcagaactttaaaagtgctcatcattggaaaacgttcttcggggcgaaaactctcaaggatcttaccgctgttgagatcca
gttcgatgtaacccactcgtgcacccaactgatcttcagcatcttttactttcaccagcgtttctgggtgagcaaaaacaggaaggcaaaat
gccgcaaaaaagggaataagggcgacacggaaatgttgaatactcatactcttcctttttcaatattattgaagcatttatcagggttattgtc
tcatgagcggatacatatttgaatgtatttagaaaaataaacaaataggggttccgcgcacatttccccgaaaagtgccacctgacgtcta
agaaaccattattatcatgacattaacctataaaaataggcgtatcacgaggccctttcgtctcgcgcgtttcggtgatgacggtgaaaacc
tctgacacatgcagctcccggagacggtcacagcttgtctgtaagcggatgccgggagcagacaagcccgtcagggcgcgtcagcgg
gtgttggcgggtgtcggggctggcttaactatgcggcatcagagcagattgtactgagagtgcaccattcgacgctctcccttatgcgactc
ctgcattaggaagcagcccagtagtaggttgaggccgttgagcaccgccgccgcaaggaatggtgcatgcaaggagatggcgccca
acagtcccccggccacggggcctgccaccatacccacgccgaaacaagcgctcatgagcccgaagtggcgagcccgatcttcccca
tcggtgatgtcggcgatataggcgccagcaaccgcacctgtggcgccggtgatgccggccacgatgcgtccggcgtagaggatctggc
tagcgatgaccctgctgattggttcgctgaccatttccgggtgcgggacggcgttaccagaaactcagaaggttcgtccaaccaaaccga
ctctgacggcagtttacgagagagatgatagggtctgcttcagtaagccagatgctacacaattaggcttgtacatattgtcgttagaacgc
ggctacaattaatacataaccttatgtatcatacacatacgatttaggtgacactatagaatacacggaattaattc
Bold = ITR sequence
Italics = mini-human hP0 promoter
Underline = EGFP
Italic underline = WPRE sequence SEQ ID NO. 24: Minimal synthetic poly A sequence
ggagctctcgagaggcctaataaagagctcagatgcatcgatcagagtgtgttggttttttgtgtgagatct

EXAMPLES

The invention shall now be described with reference to the following non-limiting examples.

Example 1: AAV Transfer Plasmid Cloning

Figure 9:
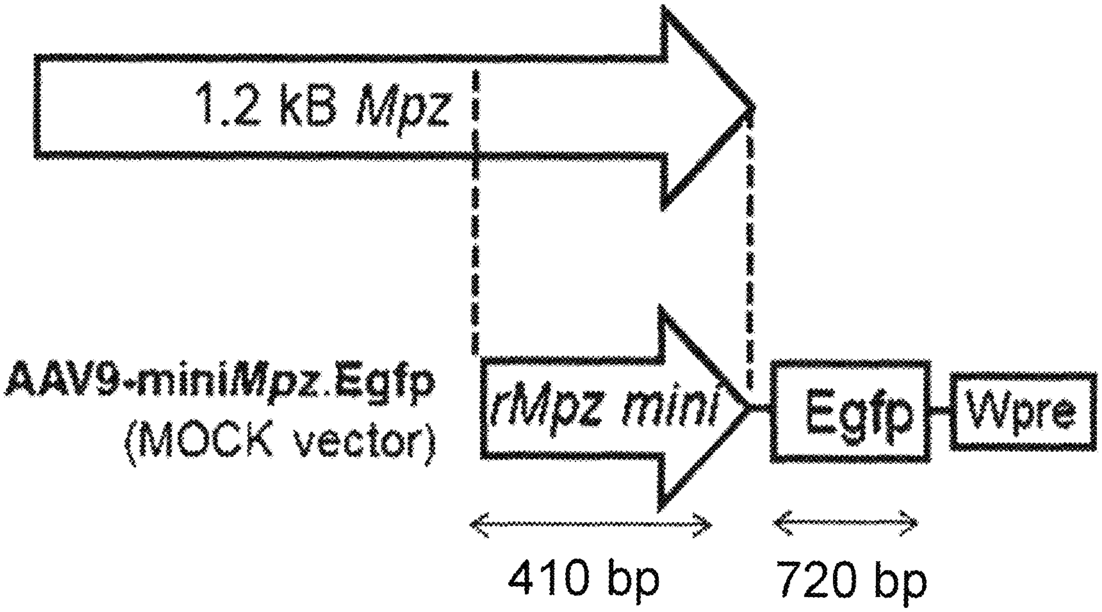
FIG. 9: The miniMpz-Egfp construct cloned into the AAV transfer plasmid after PCR amplification of a 410 bp sequence from the 1127 bp full-length rat Mpz promoter.

AAV vectors were designed to provide Schwann cell-specific expression of Cx32 (pAAV-Mpz.GJB1, full vector) or of the reporter gene EGFP (pAAV-Mpz.Egfp, mock vector), both under the 1.127 kB Mpz promoter shown to drive expression specifically in Schwann cells (26, 32). These vectors were cloned using as starting plasmid the AAV construct pAM/Mbp-EGFP-WPRE-bGH (57), containing the woodchuck hepatitis virus post-transcriptional regulatory element (WPRE) and the bovine growth hormone polyadenylation sequence (bGHpA) flanked by AAV2 inverted terminal repeats (FIGS. 1 and 9).

Specific details of how the three constructs AAV-Mpz.Egfp, AAV-Mpz.GJB1 and AAV-miniMpz.Egfp were cloned are as follows:

264-P0-EGFP-WPRE (=AAV-Mpz.Egfp—SEQ ID NO. 1) pBluescript SK+ plasmid that contains the Mpz promoter sequence was used in order to digest out the promoter sequence using XhoI and EcoRV restriction enzymes. The AAV vector was also digested using the same enzymes. After ligation and transformation correct assembly of the expression cassette was confirmed by restriction digest mapping and direct sequencing using primers covering the entire coding sequence.

264-Mpz(P0)-Cx32-WPRE (=AAV-Mpz.GJB1—SEQ ID NO. 2)

The Mpz/Cx32 ORF was PCR amplified from a lentiviral construct previously made. The primers used for the amplification were P0-Cx32-F 5'-AGGGGTACCCTTCCTGTTCAGACT-3' (SEQ ID NO. 13) and P0-Cx32-R 5'-CCGCTCGAGGGATCCTC AGCAG-3' (SEQ ID NO. 14). The PCR product (2030 bp) was gel purified using the Qiagen gel extraction kit and digested with KpnI and XhoI. The AAV vector was also digested with the same restriction enzymes. The entire expression cassette was confirmed by direct sequencing of the ORFs.

264-Mpz(P0) min-EGFP-WPRE (=AAV-miniMpz.Eqfp—SEQ ID NO. 3)

The AAV vector 264 was digested with HindIII and was self-ligated. Then a linker was inserted to the vector. Mpzmin was PCR amplified from the rat Mpz promoter sequence, using the following primers: KpnI-P0-F: 5'-GGGGTACCGCTCTCAGGCAAG-3' (SEQ ID NO. 15) and AgeI-P0-R: 5'-AAACCGGTTGGCAGAGCGTCTGT-3' (SEQ ID NO. 16). The insert (420 bp) was then directionally cloned to our AAV vector 264. EGFP was digested from another construct using AgeI and HindIII and was directly ligated in.

Example 2: AAV Vector Production, Purification and Titration

The production of AAV9 vectors was performed according to published protocols (58). The pAAV-Mpz.Egfp and pAAV-Mpz.GJB1 plasmids were cross-packaged into AAV9 capsid (capsid plasmids provided by Dr. A. Bosch, University of Barcelona, Spain, and originally developed by Dr. James Wilson, University of Pennsylvania Vector Core, PA, USA).

AAV viral stocks for pseudotypes 9 were generated as previously described (59). Recombinant AAV (rAAV) vectors were produced by triple transfection of 2×108 HEK293 cells with 250 μg of pAAV, 250 μg of pRepCap, and 500 μg of pXX6 plasmid mixed with polyethylenimine (PEI; branched, MW 25,000; Sigma). Briefly, 48 hr after transfection, cells were harvested by centrifugation (200 g, 10 min); resuspended in 30 ml of 20 mM NaCl, 2 mM MgCl2, and 50 mM Tris-HCl (pH 8.5) and lysed by three freeze-thaw cycles. Cell lysate were clarified by centrifugation (2000 g, 10 min) and rAAV particles were purified from the supernatant by iodixanol gradient as follows: The clarified lysate was treated with 50 U/ml of Benzonase (Novagen; 1 hr, 37° C.) and centrifuged (3000 g, 20 min). The vector-containing supernatant was collected and adjusted to 200 mM NaCl using a 5 M stock solution. To precipitate the virus from the clarified cell lysate, polyethylene glycol (PEG 8000; Sigma) were added to a final concentration of 8% and the mixture incubated (3 hr, 4° C.) and centrifuged (8000 g, 15 min). The rAAV-containing pellets were resuspended in 20 mM NaCl, 2 mM MgCl2, and 50 mM Tris-HCl (pH 8.5) and incubated for 48 hr at 4° C. rAAV particles will be purified using the iodixanol method as described (59). If necessary, rAAV was concentrated and desalted in PBSMK using Amicon Ultra-15 Centrifugal Filter Device (Millipore). Titration was evaluated by picogreen quantification (60) and calculated as viral genomes per milliliter (vg/ml).

Example 3: Intrathecal Vector Delivery

Following a small skin incision along the lower lumbar spine level to visualize the spine, the AAV vector was delivered into the L5-L6 intervertebral space of anesthetized mice at a slow rate of 5 μl/min. A 50-μL Hamilton syringe (Hamilton, Giarmata, Romania) connected to a 26-gauge needle was used to inject a total volume of 20 μL containing 0.5-1×$10^{11}$ vector genomes (vg) of the AAV vector. A flick of the tail was considered indicative of successful intrathecal administration.

Example 4: AAV9-Mediated Schwann-Cell Targeted Gene Expression 2 month old wild-type mice were treated with the AAV9-Mpz-Egfp vector described in Examples 1 and 3 above. Samples were analyzed by DNA extraction from PNS tissues and determination of the presence of the viral DNA measured as vector copy numbers (VCNs) 4 and 6 weeks post-injection (Table 1) as we previously described (33). Immunofluorescence staining of lumbar root sections and immunoblot of lumbar root, femoral nerves and sciatic nerves were also carried out as described below 4 and 8 weeks post-injection (Table 2).

Immunofluorescence staining: For immunostaining, mice were anesthetized with avertin according to institutionally approved protocols, and then transcardially perfused with normal saline followed by fresh 4% paraformaldehyde in 0.1 M PB buffer. The lumbar-sacral spinal cords with spinal roots attached, as well as the bilateral sciatic and femoral motor nerves were dissected. All tissues were frozen for cryosections, while sciatic and femoral nerves were isolated and teased into fibers under a stereoscope. Teased fibers or sections were permeabilized in cold acetone and incubated at RT with a blocking solution of 5% BSA (Sigma-Aldrich, Munich, Germany) containing 0.5% Triton-X (Sigma-Aldrich, Munich, Germany) for 1 h. Primary antibodies used were: mouse monoclonal antibody against contactin-associated protein (Caspr, 1:50; gift of Dr Elior Peles, Weizmann Institute of Science), rabbit antisera against EGFP (1:1,000; Invitrogen, USA), Capr2 (1:200, Alomone Labs, Israel) and Cx32 (1:50; Sigma, Munich, Germany) all diluted in blocking solution and incubated overnight at 4° C. Slides were then washed in PBS and incubated with fluorescein- and rhodamine-conjugated mouse and rabbit cross-affinity purified secondary antibodies (1:500; Jackson ImmunoResearch, USA) for 1 h at RT. Cell nuclei were visualized with DAPI (1 μg/ml; Sigma, Munich, Germany). Slides were mounted with fluorescent mounting medium and images photographed under a fluorescence microscope with a digital camera using Axiovision software (Carl Zeiss MicroImaging; Oberkochen, Germany).

Expression rates for the Egfp reporter gene were quantified by counting the number of EGFP-positive Schwann cells as a percentage of total Schwann cells in lumbar roots and sciatic nerves. Expression of Cx32 was quantified by visualizing nodal areas of myelinated fibers with axonal domain markers including juxtaparanodal Kv1.2 and paranodal Caspr in double staining with Cx32. The number of nodal areas positive for Cx32 immunoreactivity was counted as a percentage of total nodal areas in lumbar roots and sciatic nerves.

Immunoblot analysis: Immunoblot analysis of root and peripheral nerve lysates was used to detect the expression of either the reporter gene Egfp or Cx32 in tissues of injected mice. Immunoblots of lumbar root, femoral and sciatic nerve lysates collected 4 weeks post-injection were incubated with rabbit anti-Egfp (1:1000; Abcam) and anti-Cx32 (clone 918, 1:3,000) primary antibodies followed by HRP-conjugated anti-rabbit secondary antibodies (Jackson ImmunoResearch, diluted 1:3,000). The bound antibody was visualized by an enhanced chemiluminescence system (GE Healthcare Life Sciences).

Figure 2:
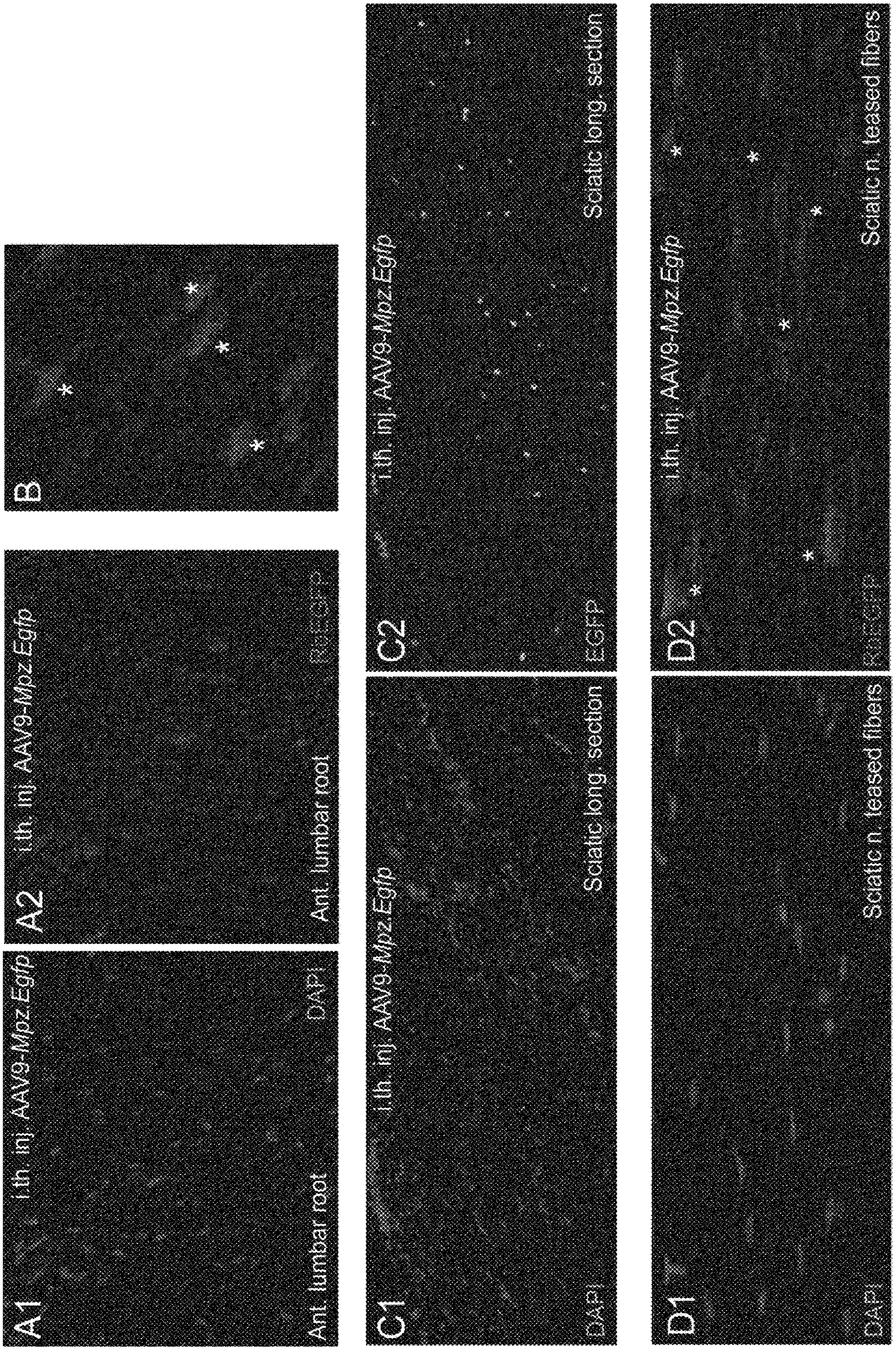
FIG. 2: AAV9-mediated Schwann-cell targeted gene expression. A-D: Four weeks following lumbar intrathecal (i.th.) injection of the AAV9-Mpz-Egfp vector in 2-month old wild-type (WT) mice, immunostaining of lumbar root sections (A-B) with EGFP antibody (A2, B) shows perinuclear expression (asterisks) in a subset of Schwann cells at low (left) and higher (right) magnification. EGFP expression is also seen in the sciatic nerve section at low magnification without antibody staining (C2) and at higher magnification of teased sciatic nerve fibers immunostained with EGFP antibody (D2). A1, C1, and D1 show only nuclear staining with DAPI of the same areas shown in A2, C2, D2. E: Quantification of EGFP-positive Schwann cell ratios in lumbar roots and sciatic nerves. F: Vector copy numbers (VCNs) in lumbar roots, proximal and distal sections of the sciatic nerves demonstrate a gradient of biodistribution of the vector towards peripheral nerves after intrathecal injection. G: Immunoblot analysis of lumbar root (LR), femoral nerves (FN) and sciatic nerves (SN) lysates from different mice (1-4) shows the specific EGFP specific band in most of the tissue of injected mice corresponding to the positive control (+) from a transgenic sample, while it is absent in negative (−) control (Kagiava et al., unpublished).
Figure 2:
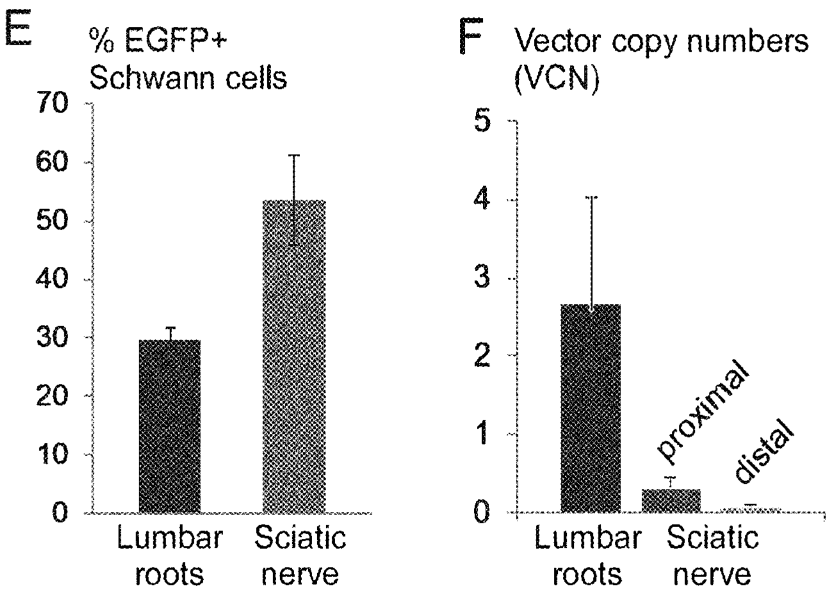
Figure 2:
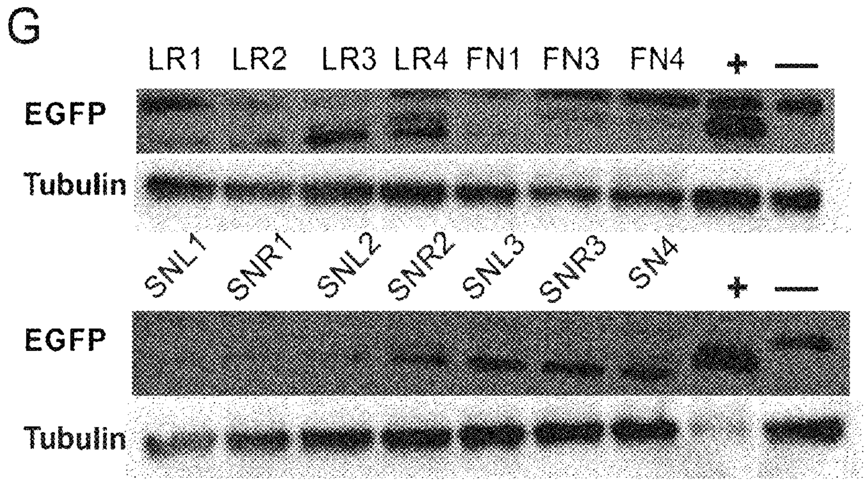

Results are shown in FIG. 2 and Tables 1 and 2 below. It was possible to detect high expression levels of the reporter gene EGFP (enhanced green fluorescent protein) specifically in Schwann cells, the myelinating cells of the PNS, including the lumbar spinal nerve roots and distal sciatic nerves and this shows specific expression of the EGFP reporter gene in lumbar root and sciatic nerve samples, indicating that tissue specific expression in Schwann cells is achieved using this vector delivery system.

TABLE 1

Vector copy numbers (VCN) in all tissues examined in WT mice injected with AAV9-Mpz.Egfp:

| | 4 weeks | | | 6 weeks | | | 8 weeks | | |
|---|---|---|---|---|---|---|---|---|---|
| | Lumbar roots | Sciatic nerve proximal | Sciatic nerve distal | Lumbar roots | Sciatic nerve proximal | Sciatic nerve distal | Lumbar roots | Sciatic nerve proximal | Sciatic nerve distal |
| VCN | 2.66 ± 1.37 | 0.31 ± 0.13 | 0.07 ± 0.03 | 0.62 ± 0.28 | 0.23 ± 0.13 | 0.02 ± 0.01 | 0.24 ± 0.1 | 0.82 ± 0.45 | 0.18 ± 0.08 |
| N number of mice | 4 | 2 | 4 | 4 | 4 | 4 | 3 | 4 | 4 |

TABLE 2

EGFP expression rates (% Egfp-postive Schwann cells) in lumbar roots and sciatic nerves of AAV9-Mpz.EGFP injected WT mice 4-and 8-weeks post-injection:

| | Sciatic | | Roots | |
|---|---|---|---|---|
| | 4 weeks | 8 weeks | 4 weeks | 8 weeks |
| EGFP expression | 53.6 ± 7.66 | 39.9 ± 2.49 | 29.7 ± 1.89 | 35.0 ± 3.23 |
| N | 4 | 3 | 4 | 3 |

Example 5: Expression of Intrathecally Delivered AAV9-Mpz.GJB1 Vector in 2-Month Cx32KO and R75W KO Mice The AAV9-Mpz.GJB1 vector was produced as described in Example 1 above ($5\times10^{12}$ vg/ml) and delivered to 2- and 6-month old Cx32 KO mice by lumbar intrathecal (i.th.) injection ($5\times10^{10}$ vg in 20 μl). Analysis of VCNs from DNA extracted from PNS tissues as previously described (33) per cell in different tissues revealed widespread biodistribution (FIG. 3A), including in spinal roots and sciatic nerves with highest levels in the liver (55). Immunostaining and immunoblot analysis were carried out as described above. Cx32 was expressed at paranodal myelin areas in over 60-70% of myelinating Schwann cells in lumbar spinal roots and in sciatic nerve fibers (FIGS. 3B-D). AAV9-delivered Cx32 expression at high levels could be also detected by Western blot of PNS tissue lysates from injected as opposed to non-injected Cx32 KO mice (FIG. 3F).

In order to clarify whether the AAV9-Mpz.GJB1 viral vector allowing higher expression levels could overcome the interfering effects of Golgi-retained mutants observed with the lentiviral vector in our previous studies (29, 34), the inventors also injected 2-month old R75W knockout (R75W KO) mice. Importantly, paranodal localization of AAV9-delivered Cx32 was also detected in R75W/KO tissues, despite the co-expression of the interfering Golgi-retained R75W mutant showing the typical perinuclear localization (FIG. 3E). Thus, AAV9 shows the potential to provide widespread, high level and Schwann-cell targeted gene expression that may also overcome the interfering effect of a representative Golgi-retained CMT1X mutant.

Figure 3:
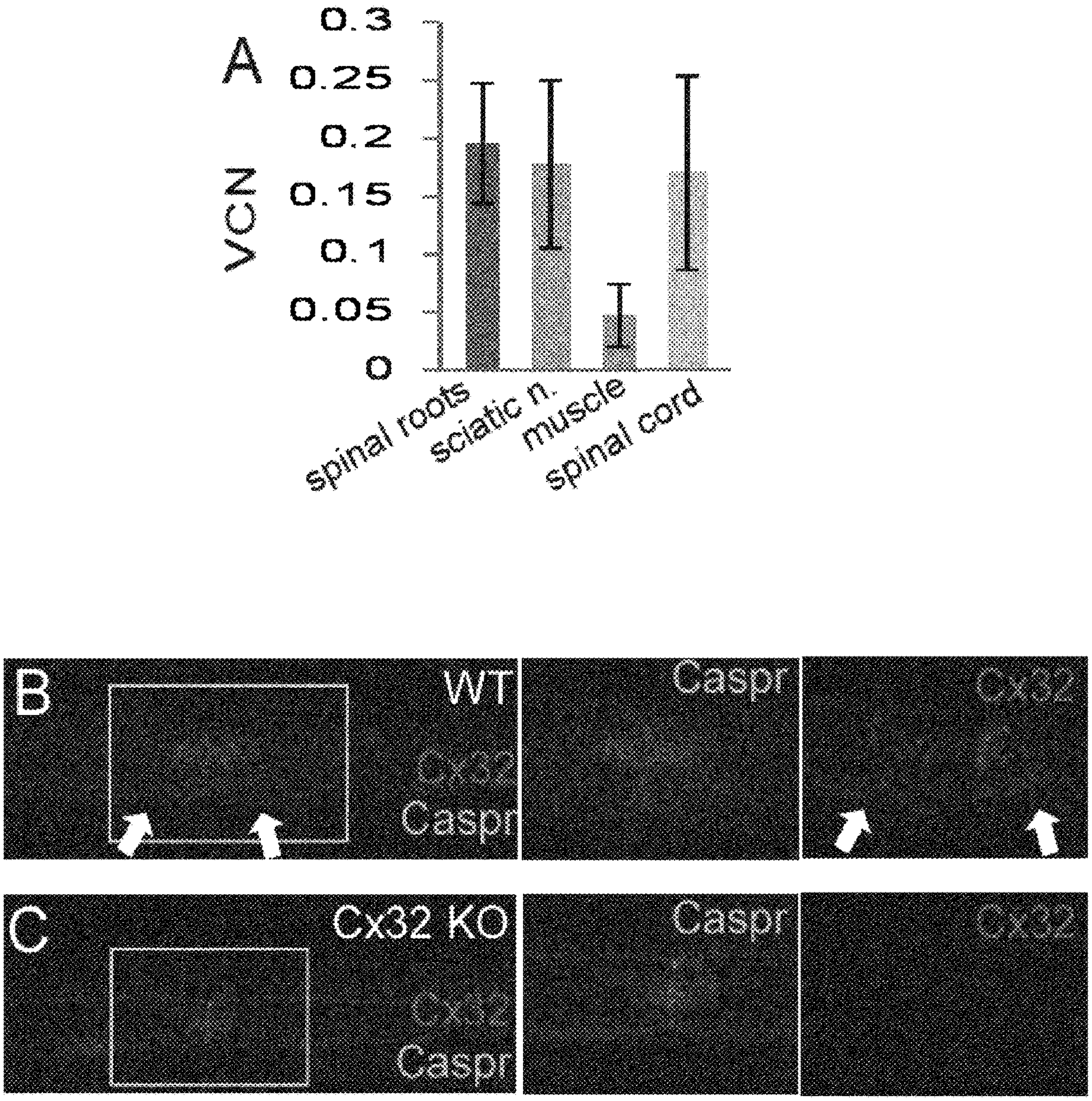
FIG. 3: Expression of intrathecally delivered AAV9-Mpz.GJB1 vector in 2-month Cx32KO and R75W KO mice. A. Vector copy numbers (VCN) in relevant tissues. Immunostaining of WT (B) and Cx32 KO (C) sciatic teased fibers demonstrates the specific Cx32 localization at paranodal myelin areas in the WT fiber (arrows) which is absent in the Cx32 KO. AAV9-Mpz.GJB1 i.th. injection results in paranodal Cx32 expression not only in Cx32 KO sciatic fibers (D), but also in R75W KO fibers (E), despite the presence of R75W mutant in perinuclear areas (asterisk and open arrowheads). F: Western blot analysis of Cx32 expression in lumbar root and sciatic nerve samples (TG+: transgenic-positive; KO: untreated Cx32 KO–negative controls) (Kagiava et al., unpublished).
Figure 3:
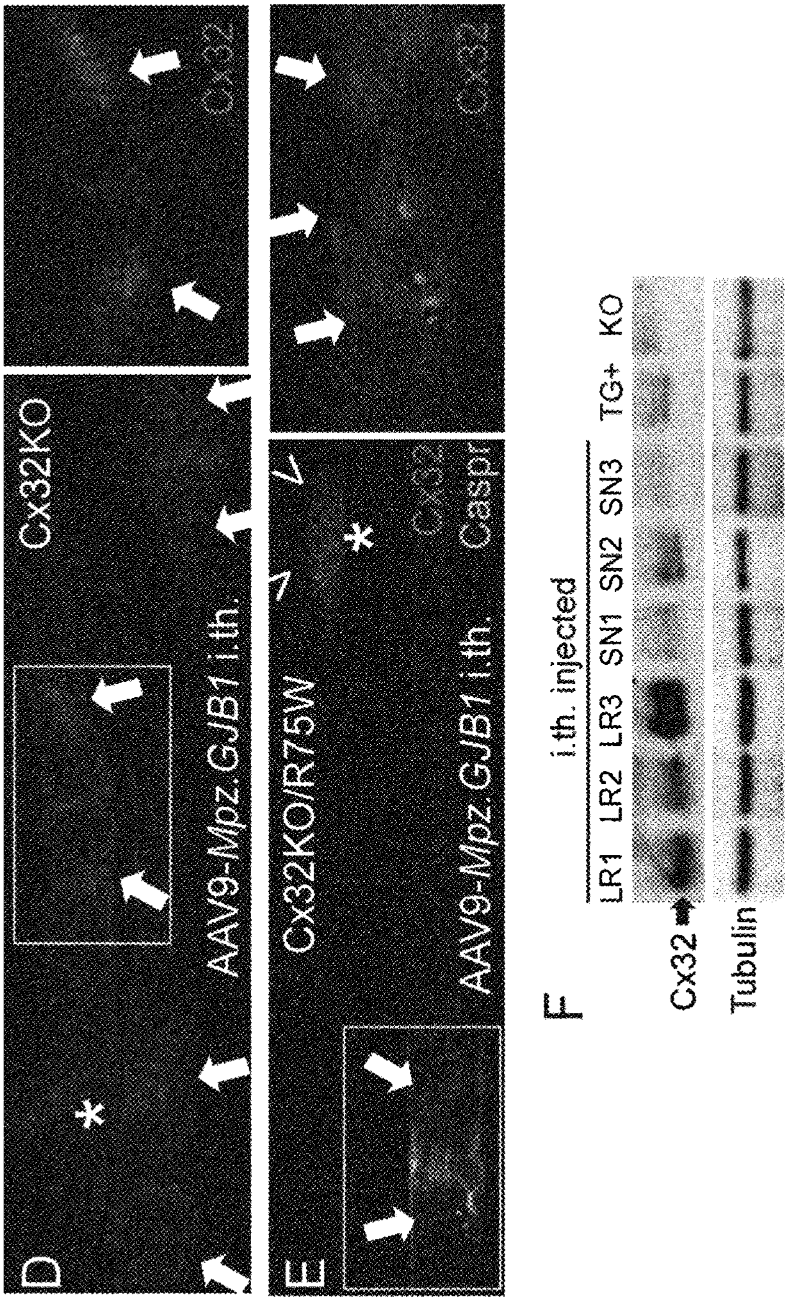

These results are shown in FIG. 3 and Tables 3 and 4 below, demonstrating that using the vectors to deliver copies of the wild-type GJB1 gene results in successful expression of Cx32 in both Cx32 knockout mice and R75W knockout mice. The R75W Golgi-retained mutant (FIG. 3E) also achieves expression of Cx32 despite the presence of R75W Cx32 mutant protein in perinuclear areas, whereas this had not been possible in previous work not using the AAV vector.

TABLE 3

Vector copy numbers in all tissues examined in Cx32 KO mice injected with AAV9-Mpz.GJB1:

| | Lumbar roots | Sciatic nerve | Muscle | Spinal cord |
|---|---|---|---|---|
| VCN | 0.20 ± 0.05 | 0.18 ± 0.07 | 0.05 ± 0.03 | 0.17 ± 0.08 |
| N | 12 | 12 | 3 | 5 |

TABLE 4

Cx32 expression rates (% Cx32-positive paranodal myelin areas) in lumbar roots and sciatic nerves of AAV9-Mpz.GJB1 injected 2-and 6-month-old Cx32 KO and Cx32 KO/R75W transgenic mice:

| | Sciatic | | | Lumbar roots | | |
|---|---|---|---|---|---|---|
| | KO 2 mo | KO 6 mo | KO R75W | KO 2 mo | KO 6 mo | KO R75W |
| Cx32 expression | 71.5 ± 5.8 | 71.7 ± 6.0 | 73.2 ± 5.1 | 63.1 ± 3.1 | 62.7 ± 8.1 | 64.9 ± 3.8 |
| N | 6 | 3 | 6 | 6 | 3 | 6 |

Example 6: Behavioral Analysis of AAV9-Mpz.GJB1 (Full) Injected 6-mo old Cx32 KO Mice Compared to AAV9-Mpz.Egfp (Mock) Treated Littermates Treatment of mice: A gene therapy trial was conducted using two groups of 6-month old Cx32 knockout (KO) mice. A minimum of 8-12 mice per treatment group for each outcome measured was considered adequate for assessing statistically significant differences based on the previous studies using similar models (32, 33). Animals were treated at the age of 6 months, after the onset of the pathology (known to start after 3 months of age).

Littermate mice were randomized to receive either AAV9-Mpz.GJB1 (full) treatment or AAV9-Mpz.Egfp (mock treatment, as a control group) and were assigned a coding number for further identification.

Figure 4:
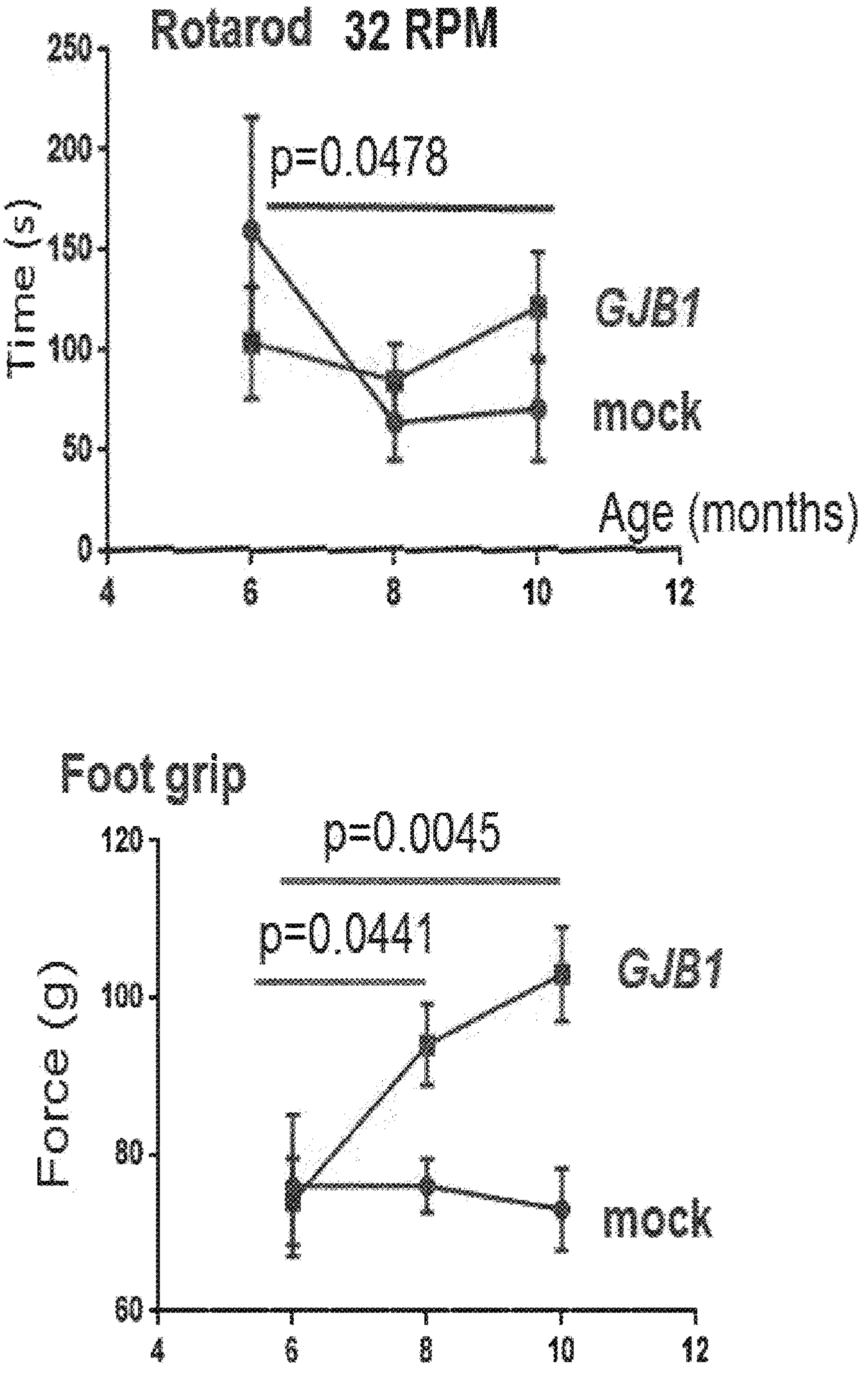
FIG. 4: Behavioral analysis of AAV9-Mpz.GJB1 (full) injected post-onset at 6 months of age Cx32 KO mice compared to AAV9-Mpz.Egfp (mock) treated littermates. Results of rotarod (left) and foot grip (right) testing of motor performance in AAV9-Mpz.GJB1 treated (GJB1) compared to mock treated Cx32 KO mice, as indicated. Time course analysis of each group showed improved motor performance of fully treated Cx32 KO mice in rotarod and foot grip analysis 2 months post-injection (8 months of age) and then motor performance remained stable up to 10 months of age. In contrast, mock treated mice did not improve over time as indicated by both behavioral tests.

Behavioral testing: Mice were then evaluated by behavioral testing as set out below before treatment, and again at the ages of 8 and 10 months, by an examiner blinded to the treatment condition (FIG. 4 and Table 5).

Rotarod testing: Motor balance and coordination was determined as described previously (61) using an accelerating rotarod apparatus (Ugo Basile, Varese, Italy). Training of animals consisted of three trials per day with 15-min rest period between trials, for 3 consecutive days. The mice were placed on the rod and the speed was gradually increased from 4 to 40 rotations per minute (rpm). Testing was performed on the fourth day using two different speeds, 20 and 32 rpm. Latency to fall was calculated for each speed. The test lasted until the mouse fell from the rod or after the mouse remained on the rod for 600 s and was then removed. Each mouse was placed on the rotarod three times at each speed used and three different values were obtained for each speed. Mean values were used for each mouse at the two different speeds.

Grip strength testing: To measure grip strength, mice were held by the tail and lowered towards the apparatus (Ugo Basile, Varese, Italy) until they grabbed the grid with the hind paws. Mice were gently pulled back until they released the grid. Measurements of the force in g were indicated on the equipment. Each session consisted of three consecutive trials and measurements were averaged. Hind limb force was compared between AAV9.Mpz-GJB1 and AAV9.Mpz-Egfp treated mice.

Older Cx32 KO mice treated with the AAV9-Mpz.GJB1 full therapeutic vector performed significantly better in those tests compared to AAV9-Mpz.Egfp mock (non-therapeutic) vector injected littermates (n=20 mice per group).

Results are shown in FIG. 4 and Table 5 below, which show that motor performance (as measured by both rotarod and foot grip testing) in the GJB1 treated group was improved 2 months after injection (at 8 months of age) and that this improvement remained stable up to 10 months of age. Mock treated mice did not show an improvement in motor performance.

TABLE 5

Longitudinal comparison of motor behavioural performance of Cx32 KO treatment groups:

| Time point comparison | Full treatment group AAV9.Mpz-GJB1 (Mann-Whitney test compared to mock) | | | Mock treatment group AAV9.Mpz-Egfp | | |
|---|---|---|---|---|---|---|
| (months of age) | Rotarod 20 RPM (sec) | Rotarod 32 RPM (sec) | Food grip test (gram) | Rotarod 20 RPM (sec) | Rotarod 32 RPM (sec) | Food grip test (gram) |
| 6 | 317.7 ± 45.62 $p > 0.05$ | 103.5 ± 27.90 $p > 0.05$ | 74.5 ± 5.46 $p > 0.05$ | 345.1 ± 85.60 | 159.7 ± 56.34 | 76.0 ± 9.14 |
| 8 | 241.3 ± 35.92 $p > 0.05$ | 84.6 ± 26.89 $p > 0.05$ | 93.5 ± 5.18 $p = 0.0196$ | 207.7 ± 38.43 | 64.5 ± 18.60 | 76.2 ± 3.41 |
| 10 | 312.7 ± 39.79 $p > 0.05$ | 121.9 ± 27.42 $p = 0.0427$ | 103.4 ± 6.01 $p = 0.0025$ | 288.9 ± 42.44 | 71.2 ± 25.86 | 73.2 ± 5.15 |

Example 7: Sciatic Nerve Motor Conduction Studies

Cx32 KO mice were treated as described in Example 6 above at the age of 6 months, after the onset of neuropathy, and then motor nerve conduction studies carried out as described below at the age of 10 months.

Motor nerve conduction velocity (MNCV): MNCV was measured in vivo using published methods (62) from bilateral sciatic nerves following stimulation in anesthetized animals at the sciatic notch and distally at the ankle via bipolar electrodes with supramaximal square-wave pulses (5 V) of 0.05 ms. The latencies of the compound muscle action potentials (CMAP) were recorded by a bipolar electrode inserted between digits 2 and 3 of the hind paw and measured from the stimulus artifact to the onset of the negative M-wave deflection. MNCV was calculated by dividing the distance between the stimulating and recording electrodes by the result of subtracting distal from proximal latency.

Figure 5:
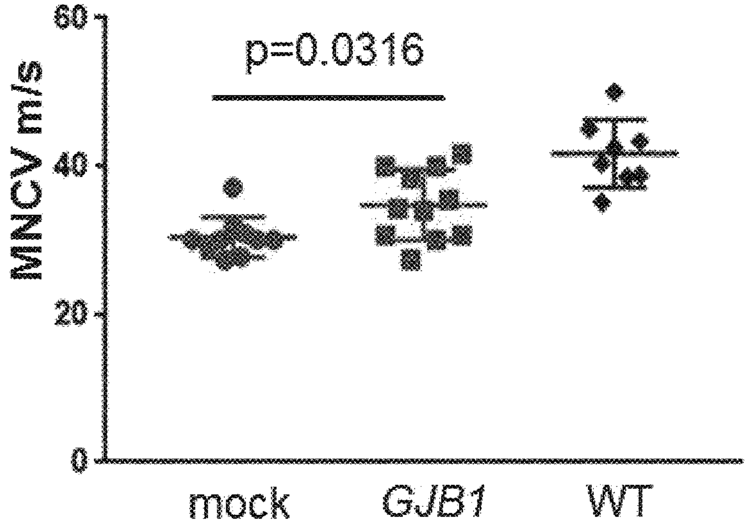
FIG. 5: Results of sciatic nerve motor conduction studies. Motor nerve conduction velocities (MNCV) were improved in the 10-month old fully treated Cx32 KO mice compared to the mock vector injected littermates approaching the values of WT.

Results from the MNCV study carried out at 10 months of age are shown in FIG. 5 and Table 6 below which shows that motor nerve conduction velocity was improved when measured at 10 months in Cx32 KO mice treated with GJB1, and approaches wild-type levels, compared to the mock treated control group (n=10 mice).

TABLE 6

Motor nerve conduction velocities and amplitude measurements of AAV9.Mpz.EGFP (Mock, Cx32 KO control group), AAV9.Mpz.GJB1 (Full, full treatment group) and WT:

| | Mock | Full | p value mock vs full | WT | p value WT vs full |
|---|---|---|---|---|---|
| MNCV (m/s) | 30.4 ± 0.87 | 34.8 ± 1.44 | 0.0316 | 41.7 ± 1.62 | 0.0068 |
| Amplitude | 3.2 ± 0.35 | 4.15 ± 3.22 | >0.05 | 3.3 ± 0.29 | >0.05 |
| N | 10 | 11 | | 8 | |

Example 8: Morphological Analysis of Anterior Spinal Roots, Sciatic Nerves and Femoral Nerves of Cx32 KO mice Following Intrathecal Delivery of the AAV9-Mpz.GJB1 Compared to Mock-Treated Mice Vector Cx32 KO mice were treated as described in Example 6 above at the age of 6 months and examined 4 months later, at the age of 10 months.

Mice were transcardially perfused with 2.5% glutaraldehyde in 0.1 M PB buffer. The lumbar spinal cord with multiple spinal roots attached, as well as the femoral and sciatic nerves, were dissected and fixed overnight at 4° C., then osmicated, dehydrated, and embedded in araldite resin (all purchased from Agar Scientific, Essex, UK). Transverse semi-thin sections (1 μm) of the lumbar spinal cord with roots and the middle portion of the femoral motor and sciatic nerves were obtained and stained with alkaline toluidine blue (Sigma-Aldrich, Munich, Germany). Sections were visualized with 10×, 20×, and 40× objective lenses and captured with a Nikon DS-L3 camera (Nikon Eclipse-Ni; Tokyo, Japan). Images of whole root or transverse nerve sections were obtained at 100-200× final magnification, and a series of partially overlapping fields covering the cross-sectional area of the roots or the nerves were captured at 400× final magnification. These images were used to examine the degree of abnormal myelination in both groups as described previously (22, 32, 63). In brief, all demyelinated, remyelinated, and normally myelinated axons were counted using the following criteria: axons larger than 1 μm without a myelin sheath were considered demyelinated, axons with myelin sheaths <10% of the axonal diameter and/or axons surrounded by "onion bulbs" (i.e., circumferentially arranged Schwann cell processes and extracellular matrix) were considered remyelinated, and other myelinated axons were considered normally myelinated.

In addition, the number of foamy macrophages present within the entire cross section of each root or nerve were counted, as an indication of inflammation. Macrophages were identified in semi-thin sections at 400× magnification as cells laden with myelin debris, devoid of a basement membrane, and extending small, microvilli-like processes, as described previously (64, 65). The macrophage count was calculated as the ratio per 1,000 myelinated fibers, to account for size differences between different spinal roots and nerves. All pathological analyses were performed blinded to the treatment condition of each mouse.

Figure 6:
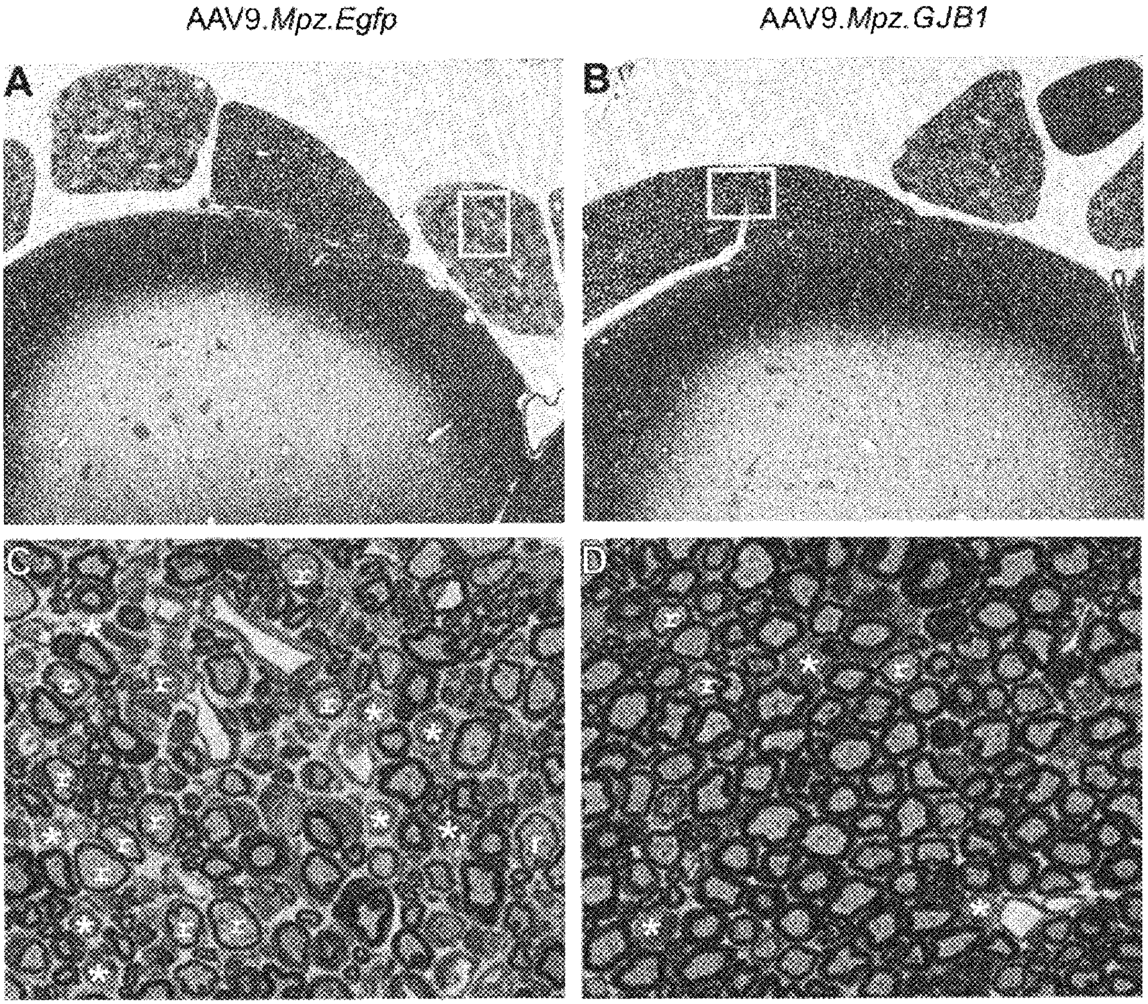
FIG. 6: Morphological analysis of anterior spinal roots of Cx32 KO mice following post-onset intrathecal delivery of the AAV9-Mpz.GJB1 compared to mock-treated mice vector. Representative images of semithin sections of anterior lumbar spinal roots attached to the spinal cord at low (A-B) and higher (C-D) magnification, as well as morphometric analysis results (E-F) from mock or full (GJB1) vector treated mice as indicated, at 10 months of age (4 months after treatment). AAV9-Mpz.GJB1 injected mouse roots (B, D) show improved myelination compared with roots of a mock-treated littermate (A, C) with fewer demyelinated (*) and remyelinated (r) fibers. Quantification of the ratios of abnormally myelinated fibers in multiple roots confirms significant improvement in the numbers of abnormally myelinated fibers (E) as well as significant reduction in the numbers of foamy macrophages (F) in fully treated compared to mock vector treated littermates.
Figure 6:
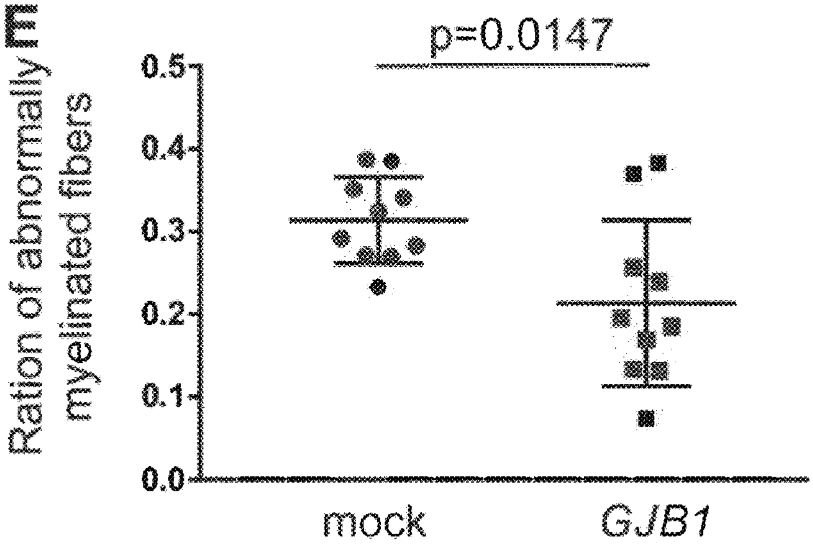
Figure 6:
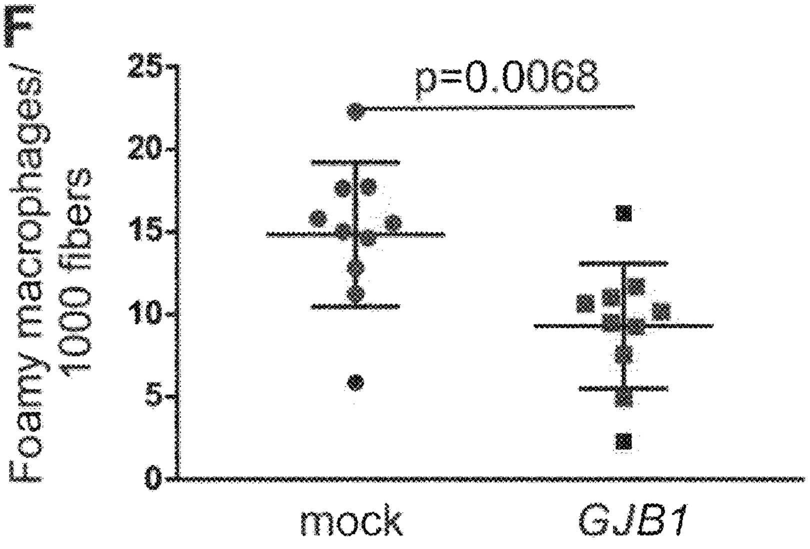
Figure 7:
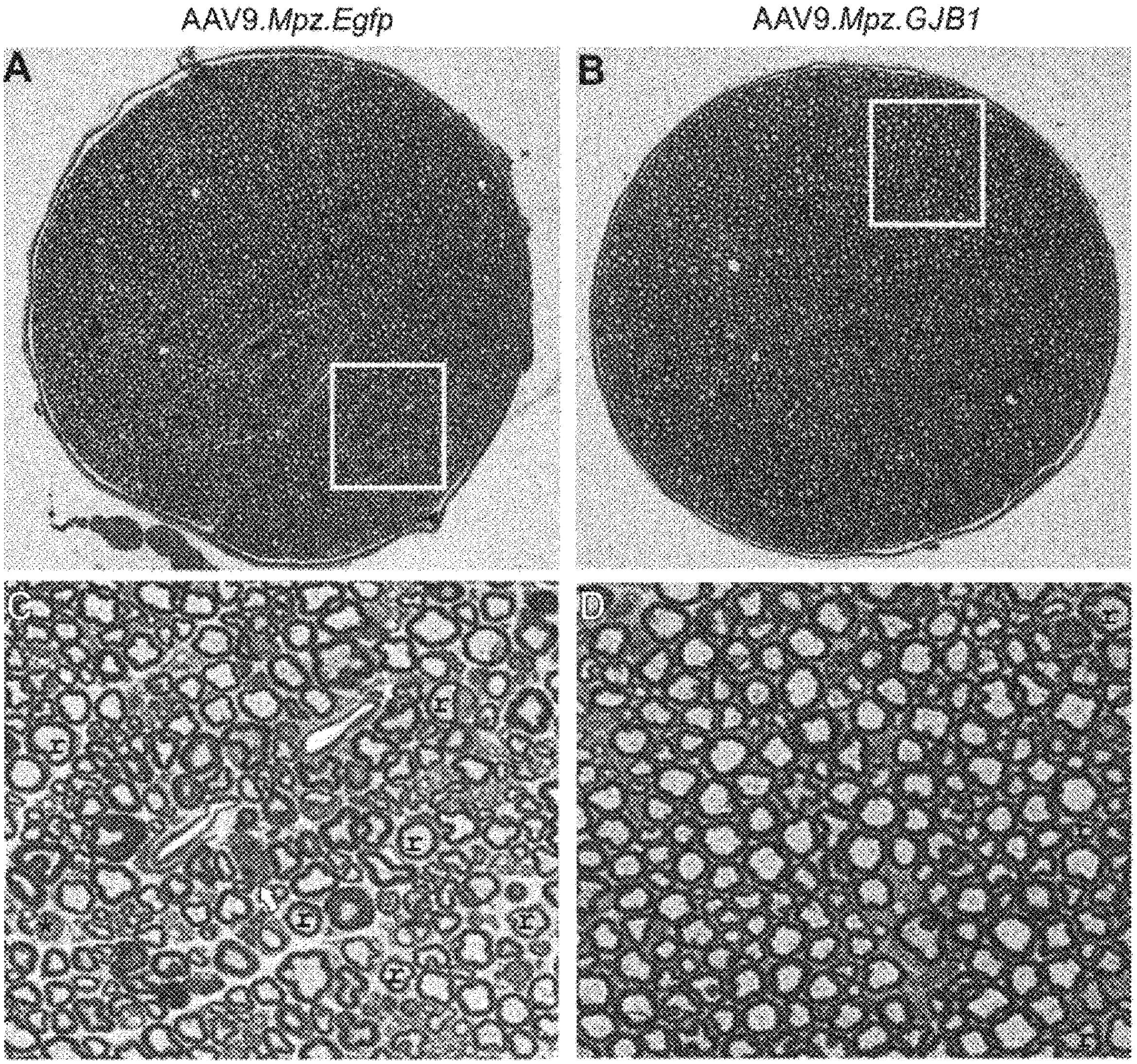
FIG. 7: Morphological analysis of sciatic nerves of Cx32 KO mice following post-onset intrathecal delivery of the AAV9-Mpz.GJB1 vector. Representative images of semithin sections of sciatic nerves at low (A-B) and higher (C-D) magnification, as well as morphometric analysis results (E-F) from mock or full (GJB1) vector treated mice as indicated, at 10 months of age (4 months after treatment). AAV9-Mpz.GJB1 injected mouse nerves (B, D) show improved myelination compared with nerves of a mock-treated littermate (A, C) with fewer demyelinated (*) and remyelinated (r) fibers. Quantification of the ratios of abnormally myelinated fibers in multiple nerves confirms significant improvement in the numbers of abnormally myelinated fibers (E) as well as significant reduction in the numbers of foamy macrophages (F) in fully treated compared to mock vector treated littermates.
Figure 7:
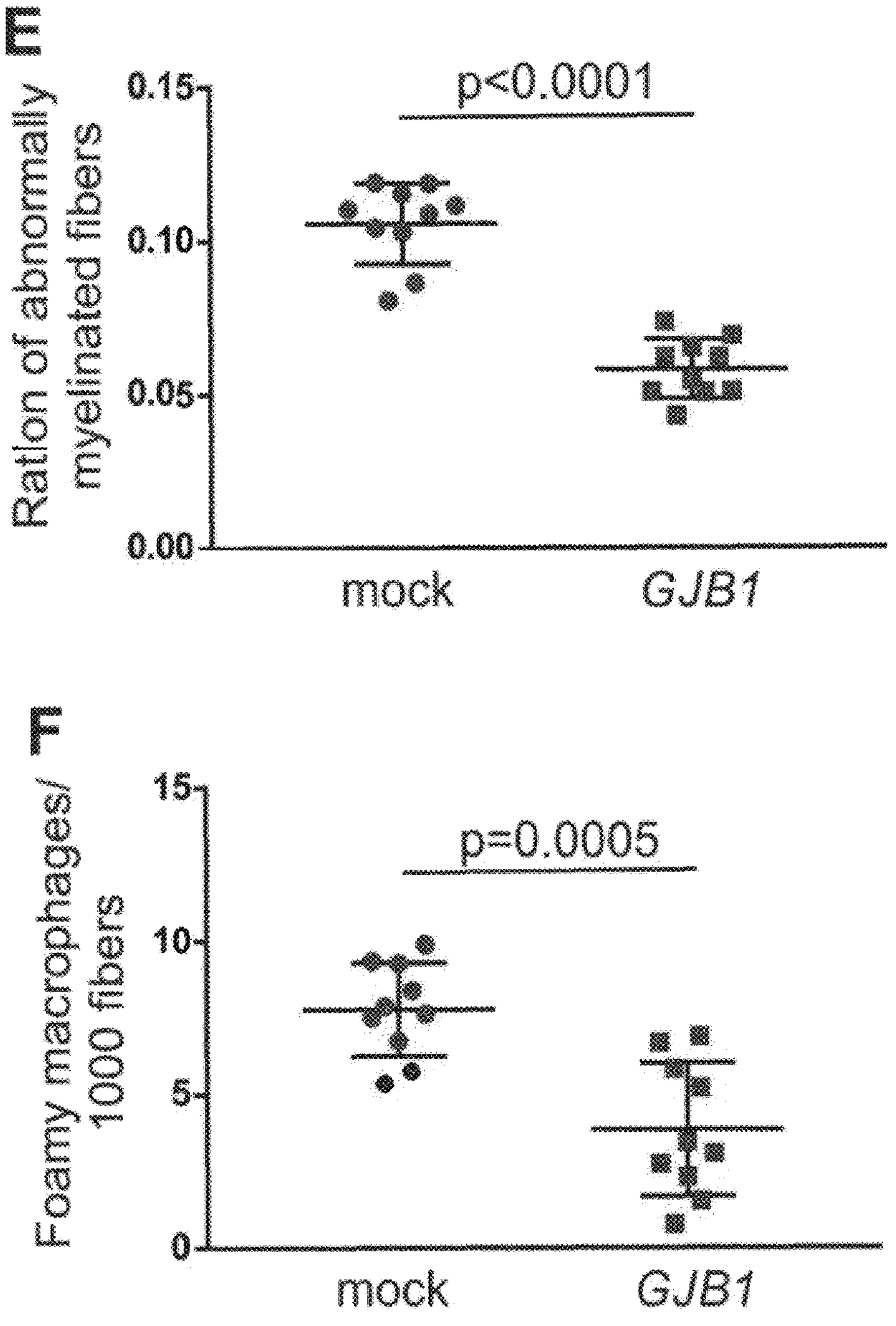
Figure 8:
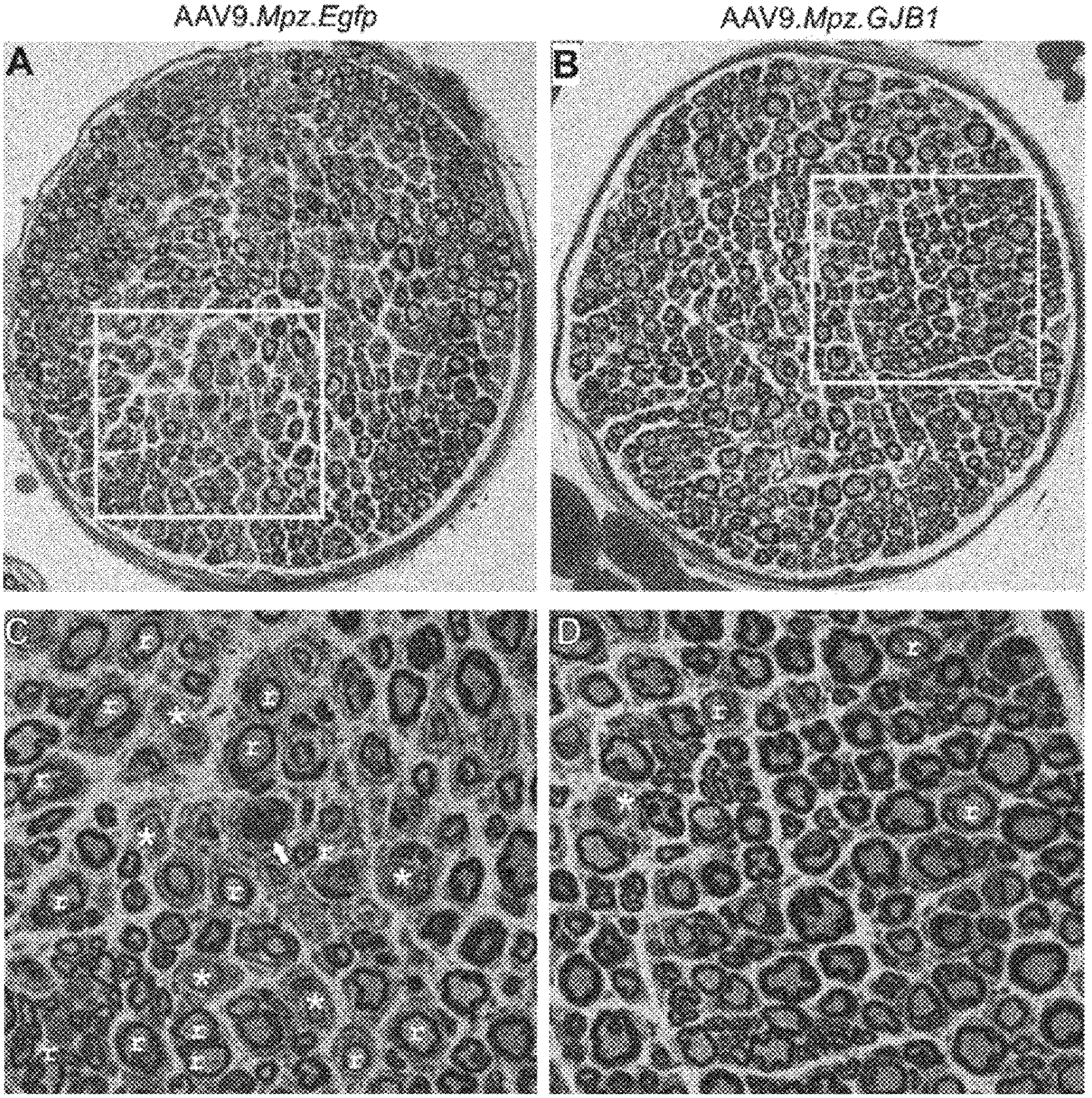
FIG. 8: Morphological analysis of femoral nerves of Cx32 KO mice following post-onset intrathecal delivery of the AAV9-Mpz.GJB1 vector. Representative images of semithin sections of femoral nerves at low (A-B) and higher (C-D) magnification, as well as morphometric analysis results (E-F) from mock or full (GJB1) vector treated mice as indicated, at 10 months of age (4 months after treatment). AAV9-Mpz.GJB1 injected mouse nerves (B, D) show improved myelination compared with nerves of a mock-treated littermate (A, C) with fewer demyelinated (*) and remyelinated (r) fibers. Quantification of the ratios of abnormally myelinated fibers in multiple nerves confirms significant improvement in the numbers of abnormally myelinated fibers (E) as well as significant reduction in the numbers of foamy macrophages (F) in fully treated compared to mock vector treated littermates.
Figure 8:
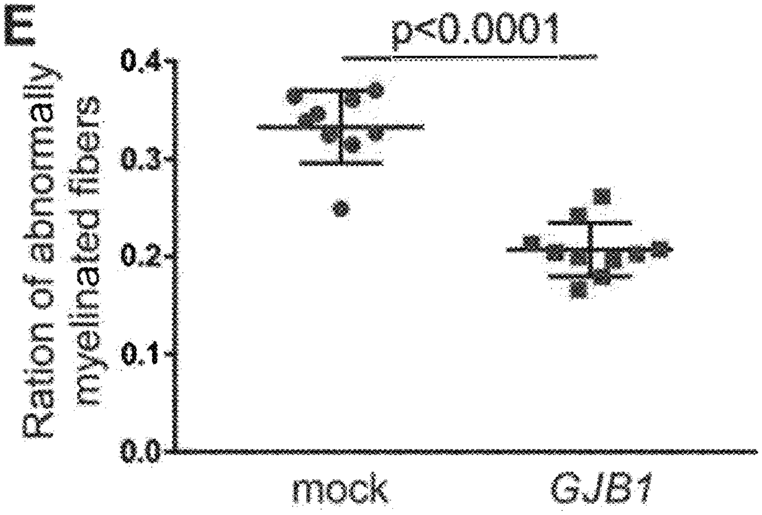
Figure 8:
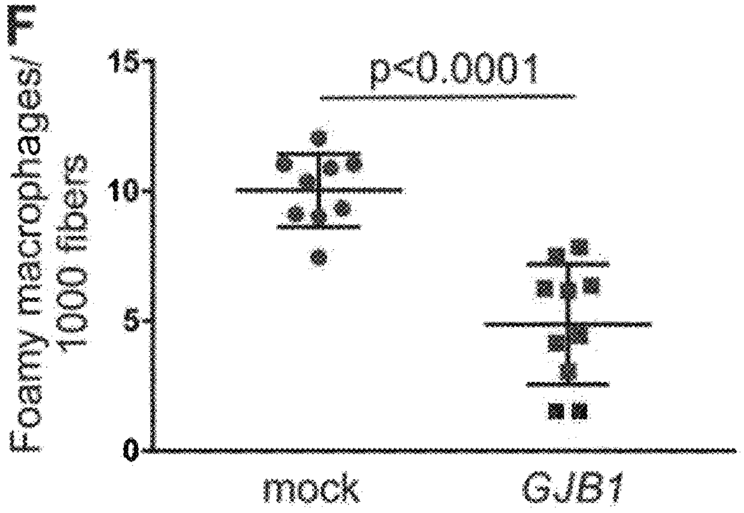

Results are shown in FIG. 6 and Table 7 (for anterior spinal roots), FIG. 7 and Table 8 (for sciatic nerves) and FIG. 8 and Table 9 (for femoral motor nerves). These results show improved myelination of spinal roots, sciatic nerves and femoral nerves compared to the mock-treated control group with fewer demyelinated and re-myelinated fibers, along with an improved ratio of abnormally myelinated fibers. All samples showed a reduction in the number of foamy macrophages in the GJB1 treated group, indicating a reduction in inflammation in the treated group.

TABLE 7

Results of morphometric analysis of anterior lumbar roots in intrathecally treated Cx32 KO mice at 10 months of age:

| | AAV9-Mpz.Egfp (mock) injected | AAV9-Mpz.GJB1 (full) injected | Mann-Whitney test |
|---|---|---|---|
| Anterior lumbar roots | (n = 10 mice) | (n = 10 mice) | |
| Ratio abnormally myelinated fibers | 0.315 ± 0.016 | 0.215 ± 0.032 | p = 0.0147 |

TABLE 7-continued

Results of morphometric analysis of anterior lumbar roots in intrathecally treated Cx32 KO mice at 10 months of age:

| | AAV9-Mpz.Egfp (mock) injected | AAV9-Mpz.GJB1 (full) injected | Mann-Whitney test |
|---|---|---|---|
| Number of macrophages/ 1000 fibers | 14.85 ± 1.38 | 9.31 ± 1.20 | p = 0.0068 |

TABLE 8

Results of morphometric analysis of sciatic nerves in intrathecally treated Cx32 KO mice at 10 months of age:

| | AAV9-Mpz.Egfp (mock) injected | AAV9-Mpz.GJB1 (full) injected | Mann-Whitney test |
|---|---|---|---|
| Sciatic nerves | (n = 10 mice) | (n = 10 mice) | |
| Ratio abnormally myelinated fibers | 0.105 ± 0.004 | 0.058 ± 0.003 | p < 0.0001 |
| Number of macrophages/ 1000 fibers | 7.76 ± 0.48 | 3.84 ± 0.69 | p = 0.0005 |

TABLE 9

Results of morphometric analysis of femoral motor nerves in intrathecally treated Cx32 KO mice at 10 months of age:

| | AAV9-Mpz.Egfp injected | AAV9-Mpz.GJB1 injected | Mann-Whitney test |
|---|---|---|---|
| Femoral nerves | (n = 9 mice) | (n = 10 mice) | |
| Ratio abnormally myelinated fibers | 0.333 ± 0.012 | 0.207 ± 0.009 | p < 0.0001 |
| Number of macrophages/ 1000 fibers | 10.03 ± 0.47 | 4.87 ± 0.73 | p < 0.0001 |

Example 9: Development of AAV Vectors for Schwann Cell Targeted Expression Driven by Minimal Promoter (miniMpz) Elements The AAV9-based approach described in the above examples has a high potential for clinical translation to treat other demyelinating CMT types including CMT4C. However, the limitation of smaller transgene capacity in AAV vectors needs to be overcome.

In order to facilitate an AAV-mediated Schwann cell targeted gene expression, the inventors cloned a minimal version of the Mpz promoter. Starting from the 1.127 kb full length Mpz promoter (SEQ ID NO. 4) and based on enhancer/ChIP-seq data indicating that functional regulatory elements (Egr2 and Sox10 binding sites) of the full-length Mpz promoter are located within 400 bp upstream of the start codon (56), the inventors selected this strategy to achieve targeted expression in Schwann cells with a minimal size promoter in order remain within the carrying capacity of the AAV vector. The inventors PCR-amplified the 410 bp from the Mpz promoter upstream of the start codon, and then further cloned this miniMpz promoter into the AAV transfer plasmid along with downstream Egfp as a reporter gene and produced the AAV9-miniMpz.Egfp vector (SEQ ID NO. 3 and FIG. 9).

This AAV9-miniMpz.Egfp vector was also validated in vivo in 2-month old wild type (WT) mice using the same delivery method as described in Example 3 by a single lumbar intrathecal injection, and shown to drive expression of reporter gene EGFP in a high percentage of myelinating Schwann cells throughout the PNS. This showed widespread expression of the vector which was mostly restricted to myelinating Schwann cells in PNS tissues, with over 50% expression ratios and high vector copy numbers (VCNs) in lumbar spinal roots and peripheral nerves (FIG. 10).

Figure 11:
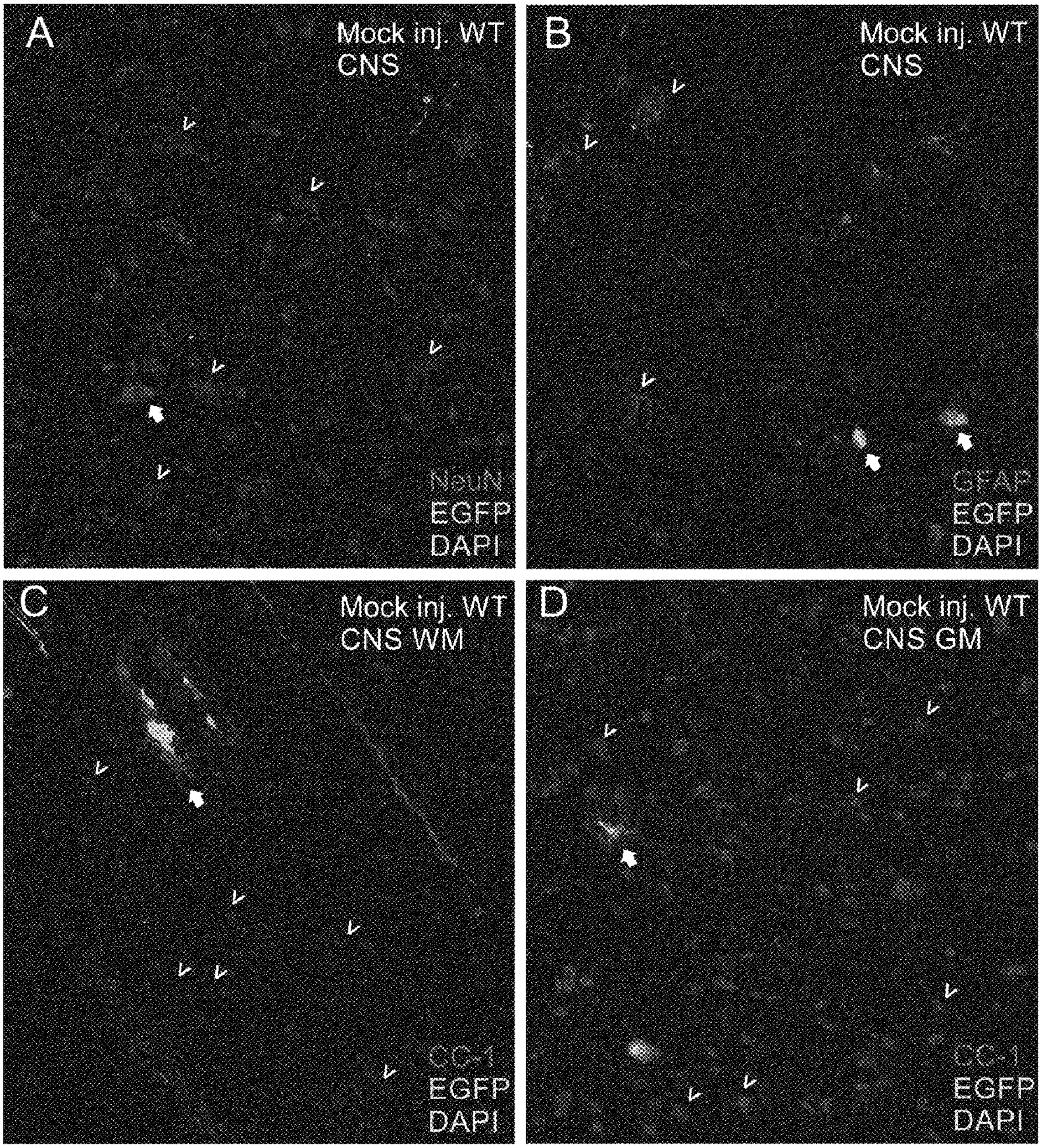
FIG. 11: Minimal CNS expression of the AAV9-miniMpz-Egfp vector. Immunostaining of lumbar spinal cord longitudinal sections 4 weeks following lumbar intrathecal injection of the AAV9-miniMpz-Egfp vector in 2-mo old WT mice with EGFP antibody in combination with cell markers NeuN (A, labelling neurons), GFAP (B, labeling astrocytes), CC-1 (C-D, labeling oligodendrocytes) shows that only a few cells of each cell type express EGFP (examples indicated by arrows) while most are EGFP-negative (examples are indicated by open arrowheads). E. Quantification in n=3-5 mice per cell marker staining shows low expression rates in all three CNS cell types of around 2-3%.
Figure 11:
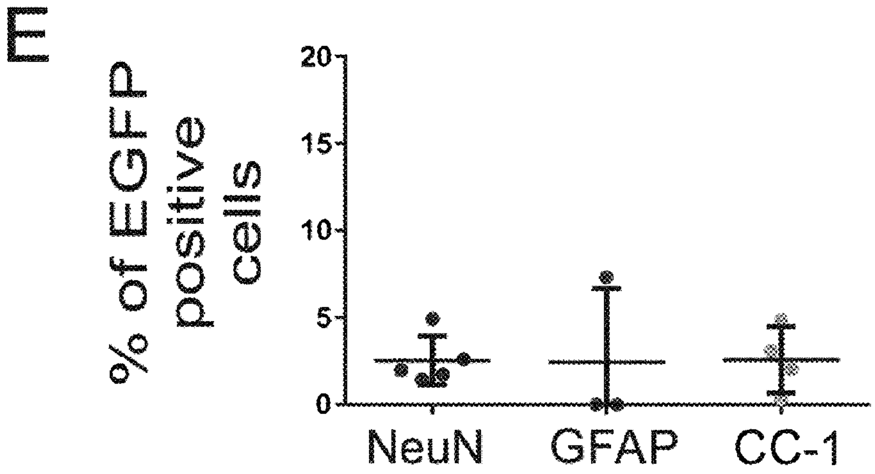

Immunostaining of spinal cord tissue from AAV9-miniMpz-Egfp injected mice that was carried out similarly to as described in Example 4 with cell markers including neuronal NeuN, astrocytic GFAP, and oligodendrocytic CC-1 in white and gray matter combined with EGFP showed expression of the miniMpz-driven construct only in a very small subset of around 2-3% of both neurons and glia cells in the CNS as quantified from n=3-5 mice (FIG. 11).

Figure 10:
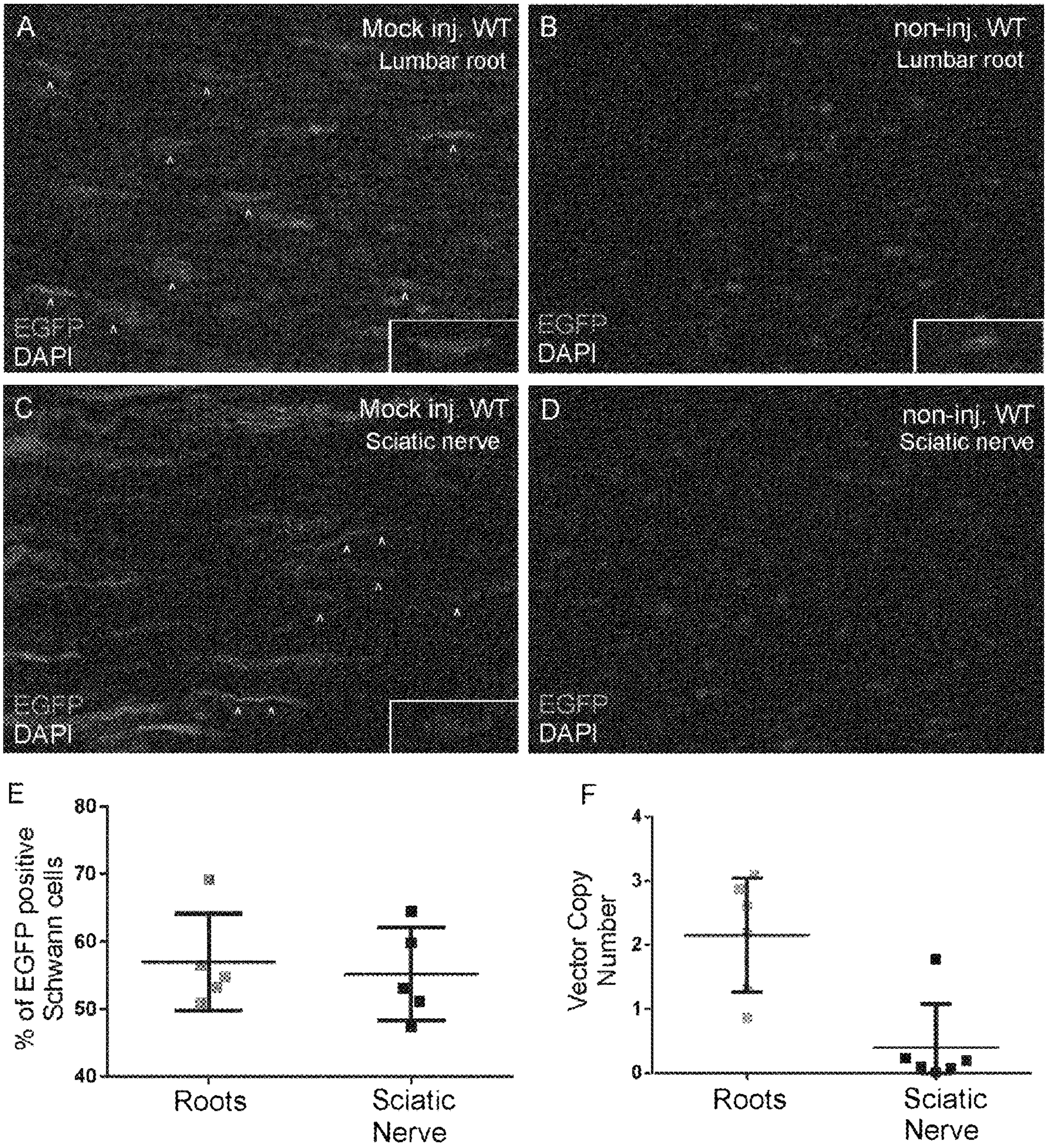
FIG. 10: Immunostaining of lumbar root and sciatic nerve longitudinal sections 4 weeks following lumbar intrathecal injection of the AAV9-miniMpz-Egfp vector in 2-mo old WT mice with EGFP antibody shows perinuclear expression in a subset of Schwann cells (A, C). B and C are negative controls showing only the nuclear staining with DAPI. E: Percentage of EGFP-positive Schwann cells (n=5-6 mice). F: Vector copy numbers in lumbar roots and sciatic nerves demonstrate adequate biodistribution of the vector after intrathecal injection (n=6 mice).

Results are shown in FIG. 10 (lumbar root and sciatic nerve) and FIG. 11 (lumbar spinal cord), and demonstrate that EGFP expression is distributed adequately in the lumbar root and sciatic nerve and that there is minimal expression in the lumbar spinal cord, showing that after injection there is biodistribution of vector and expression of EGFP reporter protein in Schwann cells in the peripheral nervous system.

Example 10: Efficacy of Gene Therapy Treatment in a Model of CMT1X when Treated Pre-Onset at Early Stages of the Neuropathy Groups of 2-month old Cx32 knockout (KO) mice, a model of CMT1X (n=10 mice per group), were injected at the age of 2 months with either the therapeutic (full) AAV9-Mpz-GJB1 vector or with the negative control (mock) vector AAV9-Mpz-Egfp. Behavioral analysis was performed before treatment, and at 4 and 6 months of age. Electrophysiological analysis was carried out at 6 months of age, followed by morphological analysis of semithin sections of peripheral nerve tissues. The same protocols were used as described in Examples 6-8 above, aside from mice were treated at the age of 2 months.

This data provides a model for pre-onset treatment of mice at the early stages of neuopathy (2 months old) in addition to treatment after onset at a later stage of 6 months (Examples 6-8).

Behavioral Result in Treated Versus Mock-Treated 6-Month Old Cx32 KO Mice

Figure 12:
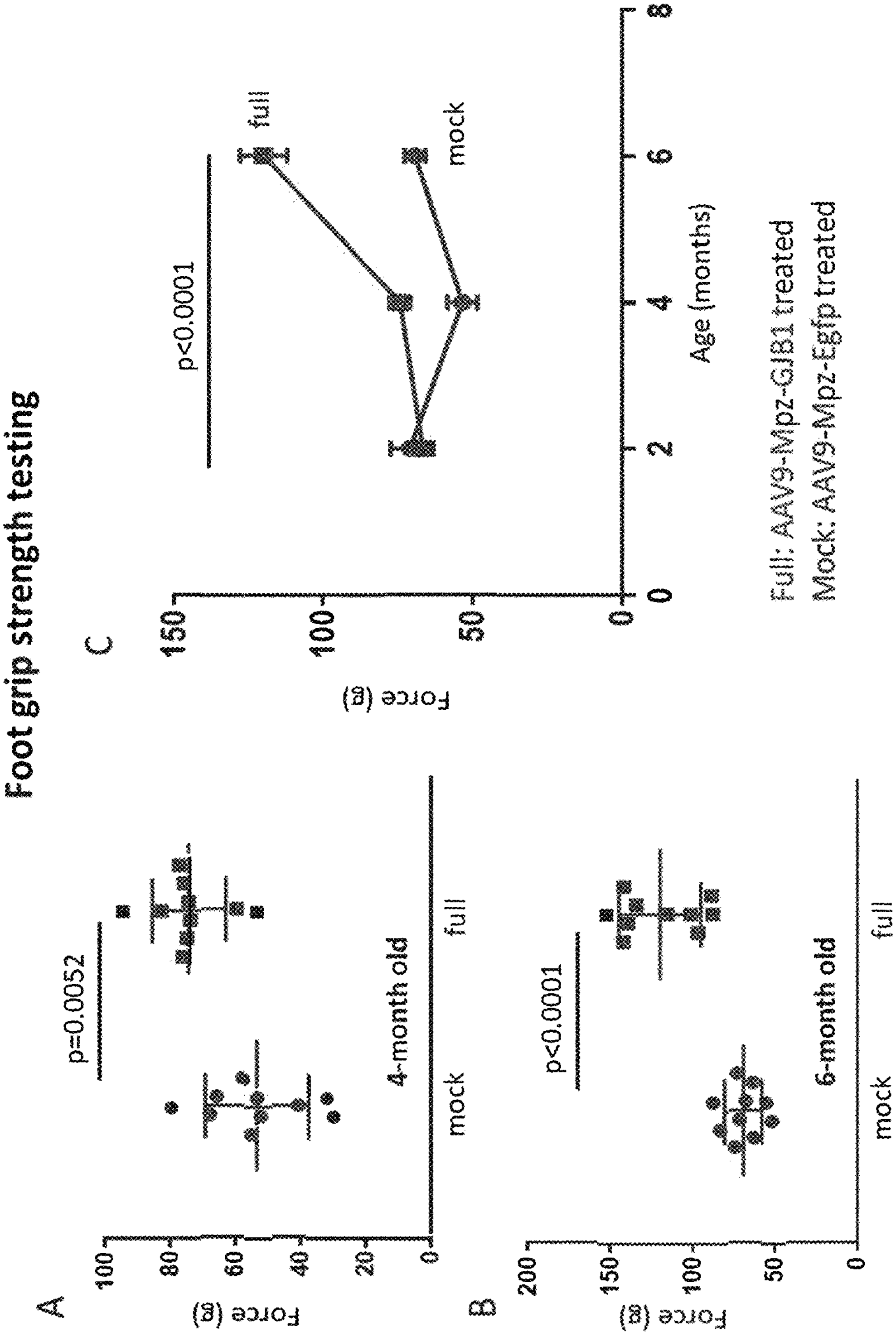
FIG. 12: Motor behavioural testing in groups of Cx32 KO mice (CMT1X model) treated pre-onset at the age of 2 months with either the full therapeutic (AAV9-Mpz-GJB1) vector or the mock vector (AAV9-Mpz-Egfp). Foot grip strength testing was carried out before treatment (2 months of age) and at 4 (FIG. 12A) and 6 (FIG. 12B) months of age. There is significant functional improvement in the treated groups at 4 and 6 months.

Treatment of groups of 2-month old Cx32 knockout (KO) mice, a model of CMT1X, with either the therapeutic (full) or negative control (mock) vector was performed and mice were examined for motor strength at 4 and 6 months of age. The fully treated group showed significantly improved muscle strength at both time points compared to the mock-treated (FIGS. 12A and B). The fully treated group also showed significant improvement over time following treatment (FIG. 12C), whereas the mock treated mice did not show any improvement.

Figure 13:
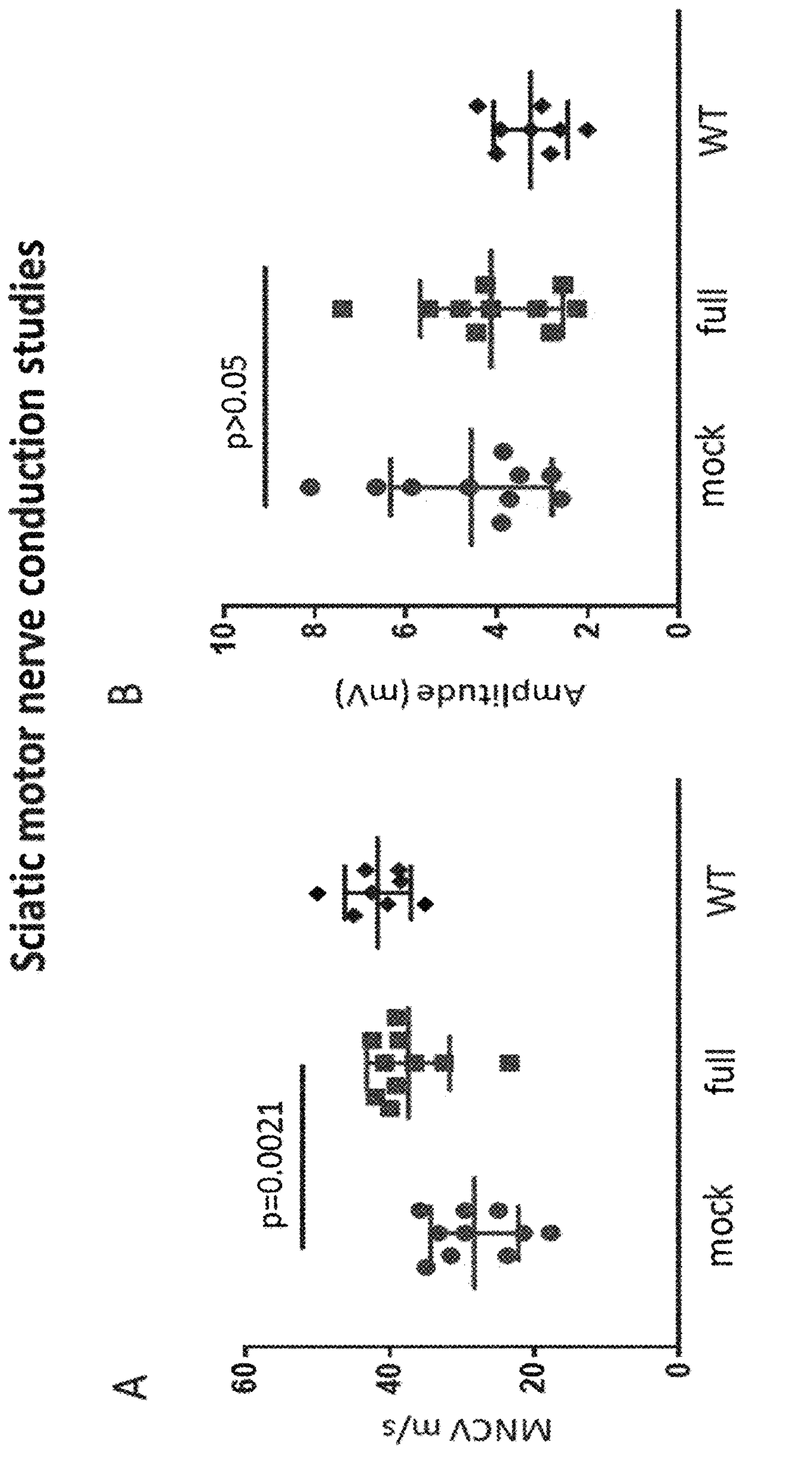
FIG. 13: Electrophysiological studies of pre-onset treated (full) and mock-treated 6-month old Cx32 KO mice. Sciatic motor nerve conduction studies were carried out at 6 months of age, and showed significant improvement of sciatic nerve conduction velocities after gene therapy treatment at the age of 2 months, compared to the mock treatment.

Electrophysiological Studies in Pre-Onset Treated Versus Mock-Treated 6-Month Old Cx32 KO Mice Electrophysiological studies in treated (full) and mock-treated 6-month old Cx32 KO mice showed significant improvement of sciatic nerve conduction velocities after gene therapy treatment are shown in FIG. 13.

FIG. 13 shows a significantly improved sciatic nerve conduction velocities in AAV9-Mpz-GJB1 (full vector) pre-onset treated compared to mock vector treated Cx32 KO mice.

Figure 14:
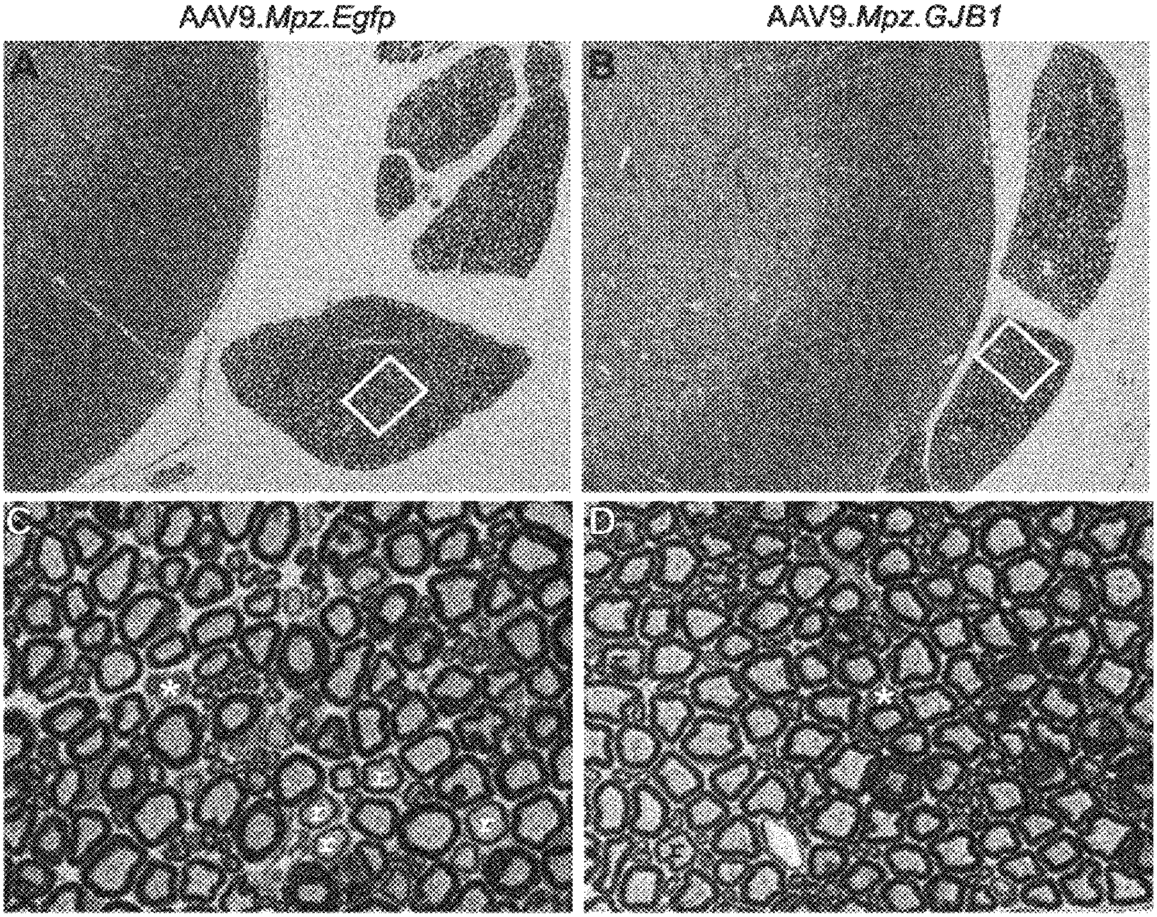
FIG. 14: Morphological analysis of anterior (motor) lumbar roots of 6 month old Cx32 KO mice following pre-onset treatment with either the full therapeutic (AAV9-Mpz-GJB1) vector or the mock vector (AAV9-Mpz-Egfp) at 2 months old. Representative images of semithin sections of anterior (motor) lumbar roots. AAV9-Mpz-GJB1 treated mice (B, D) show improved myelination compared to mock treated mice (A, C) with fewer demyelinated (*) and remyelinated (r) fibers. As confimred by quantitative analysis (E, F), fewer demyelinated (*) or remyelimated (r) fibers (E) and fewer foamy macrphages (F) were found in treated compared to mock treated mice.
Figure 14:
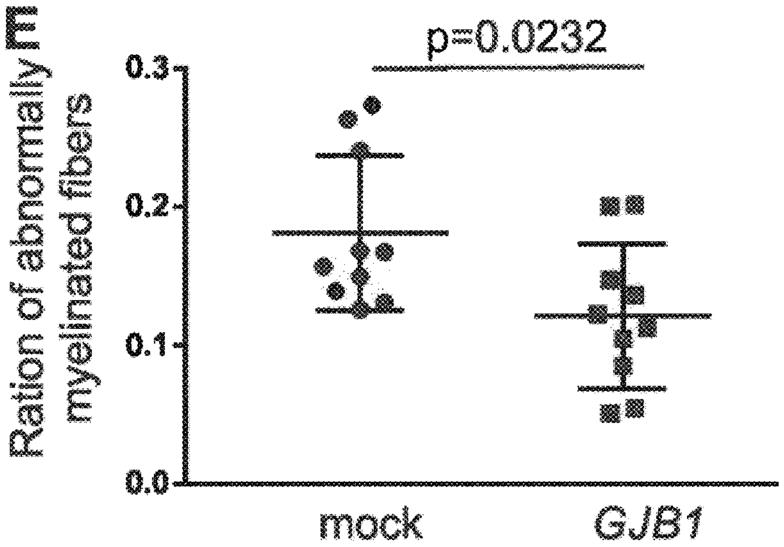
Figure 14:
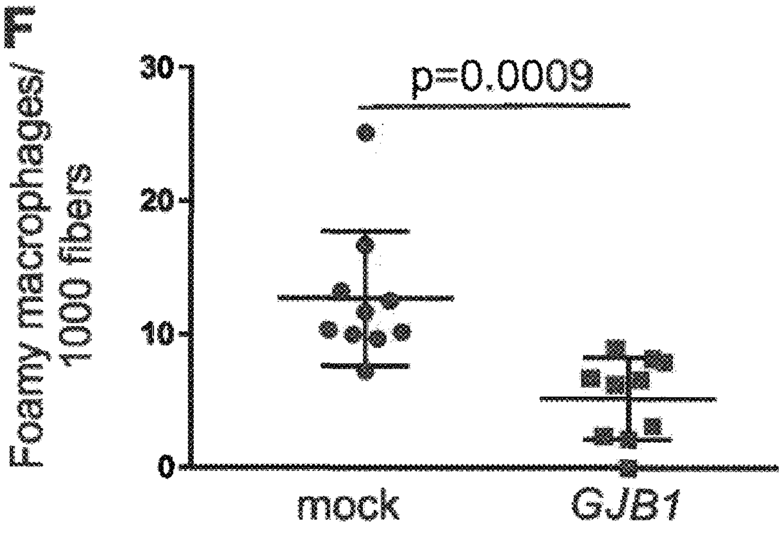
Figure 15:
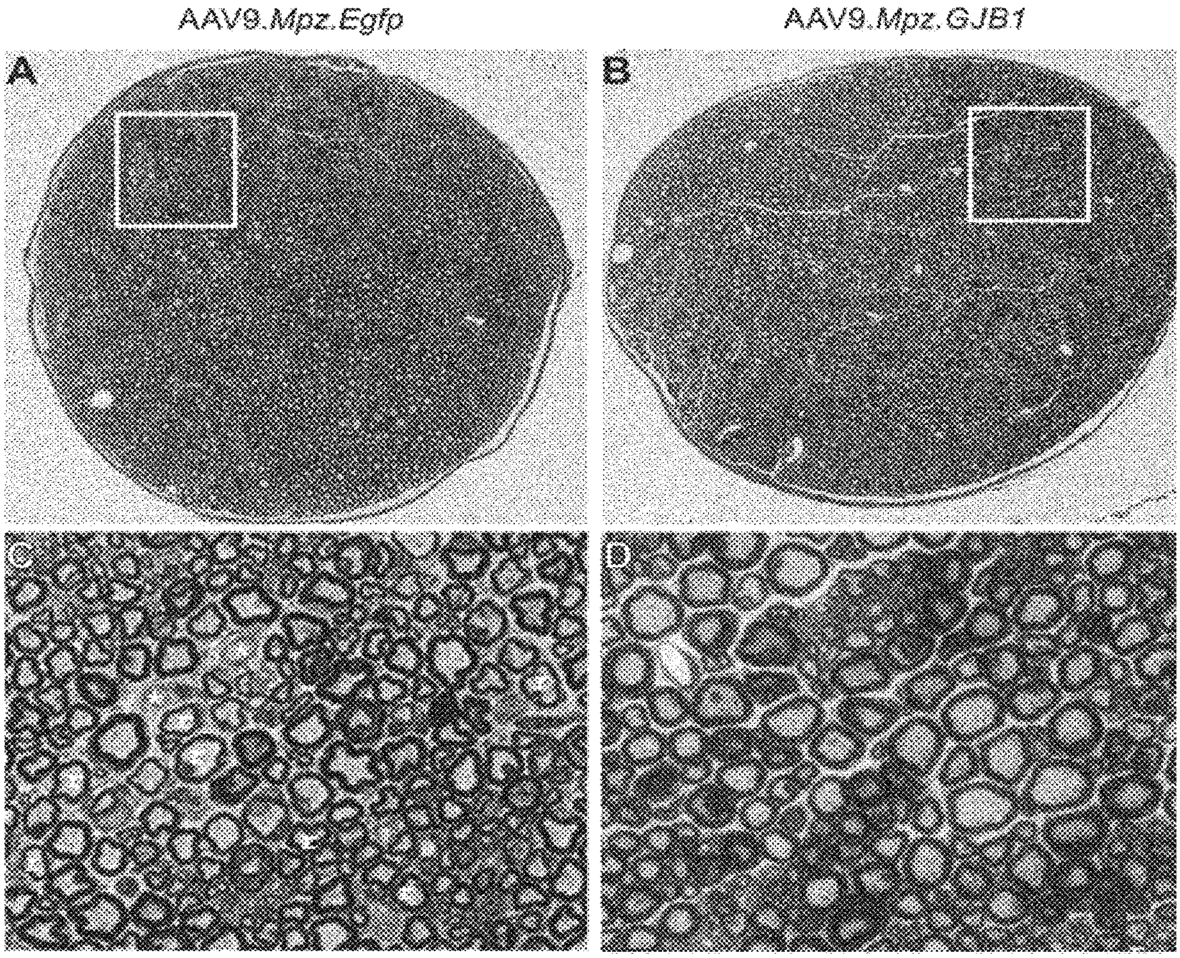
FIG. 15: Morphological analysis of mid-sciatic nerves of 6 month old Cx32 KO mice following pre-onset treatment with either the full therapeutic (AAV9-Mpz-GJB1) vector or the mock vector (AAV9-Mpz-Egfp) at 2 months old. Representative images of semithin sections of mid-sciatic nerves. AAV9-Mpz-GJB1 treated mice (B, D) show improved myelination compared to mock treated mice (A, C) with fewer demyelinated (*) and remyelinated (r) fibers. As confimred by quantitative analysis (E, F), fewer demyelinated (*) or remyelimated (r) fibers (E) and fewer foamy macrphages (F) were found in treated compared to mock treated mice.
Figure 15:
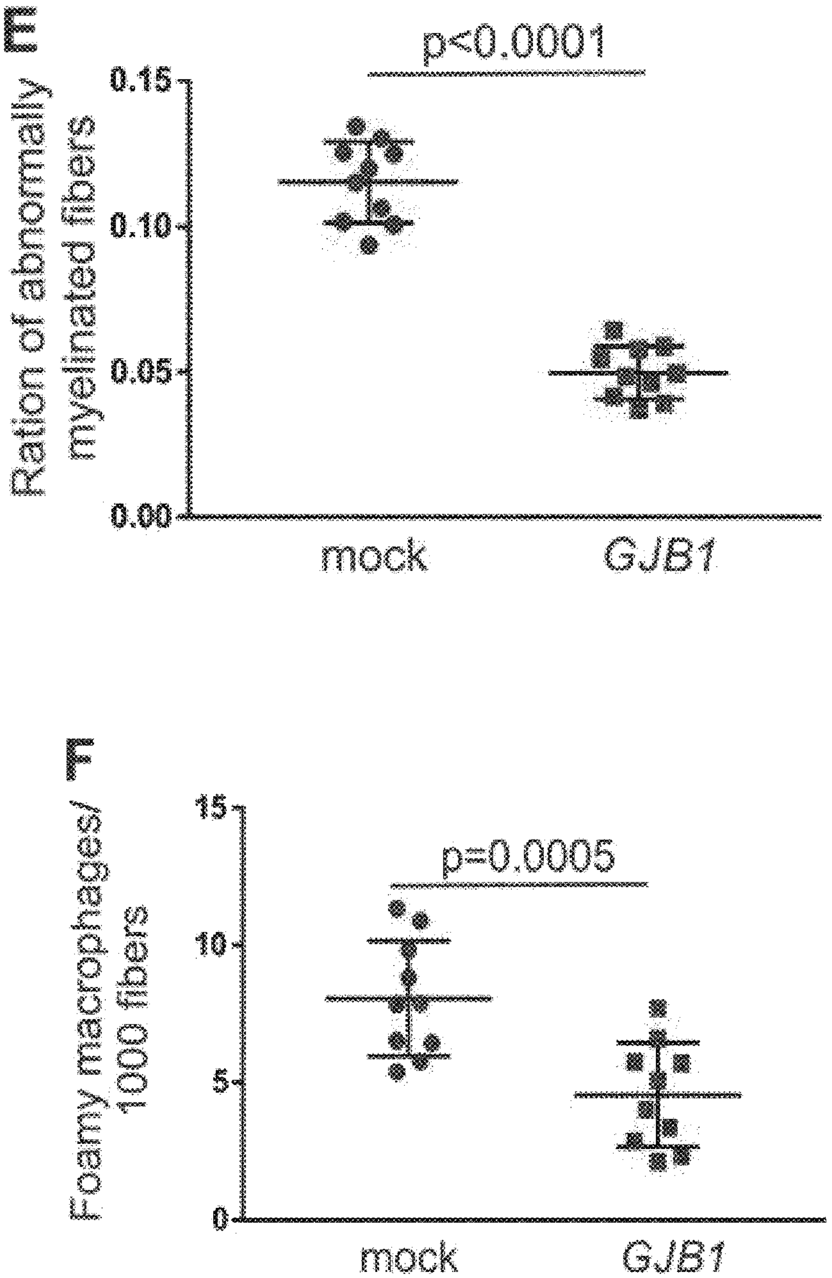
Figure 16:
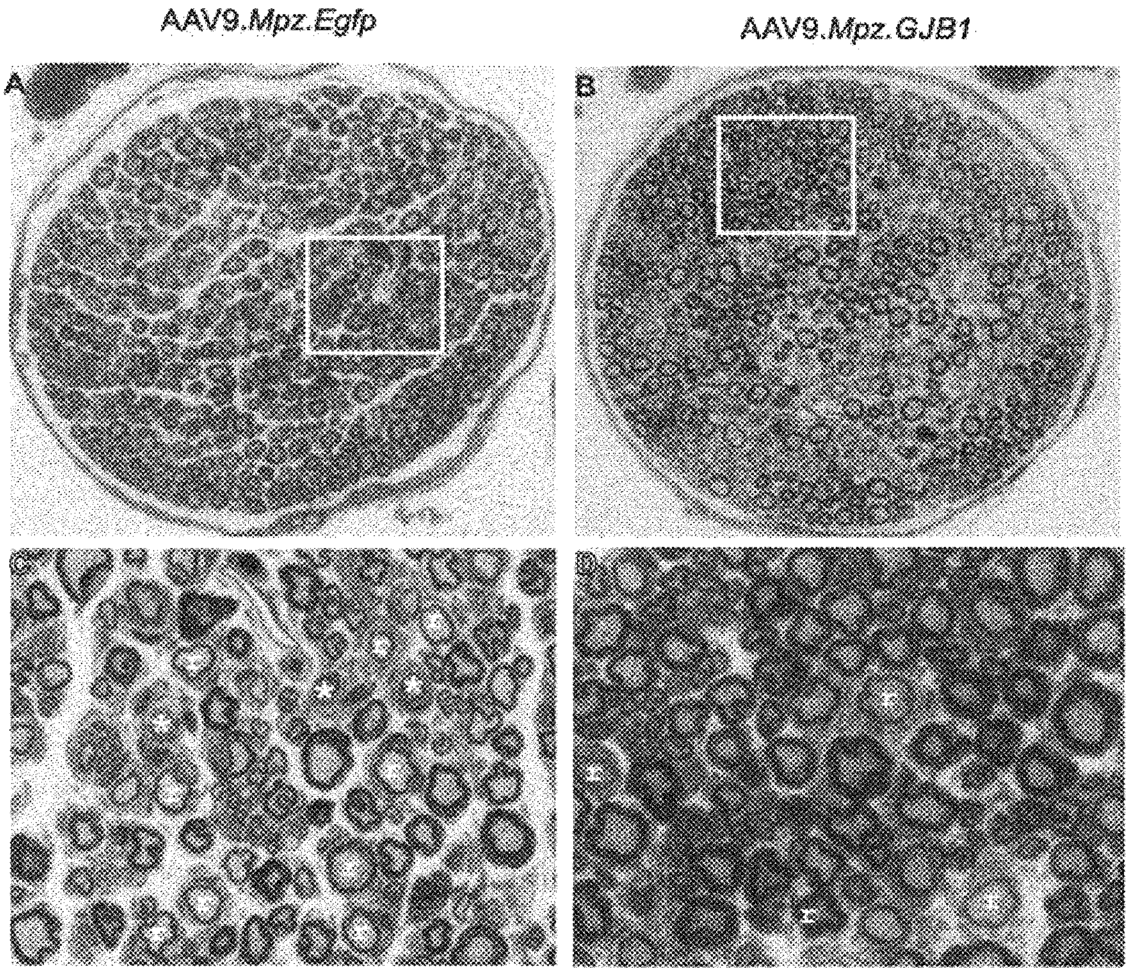
FIG. 16: Morphological analysis of femoral motor nerves of 6 month old Cx32 KO mice following pre-onset treatment with either the full therapeutic (AAV9-Mpz-GJB1) vector or the mock vector (AAV9-Mpz-Egfp) at 2 months old. Representative images of semithin sections of femoral motor nerves. AAV9-Mpz-GJB1 treated mice (B, D) show improved myelination compared to mock treated mice (A, C) with fewer demyelinated (*) and remyelinated (r) fibers. As confimred by quantitative analysis (E, F), fewer demyelinated (*) or remyelimated (r) fibers (E) and fewer foamy macrphages (F) were found in treated compared to mock treated mice.
Figure 16:
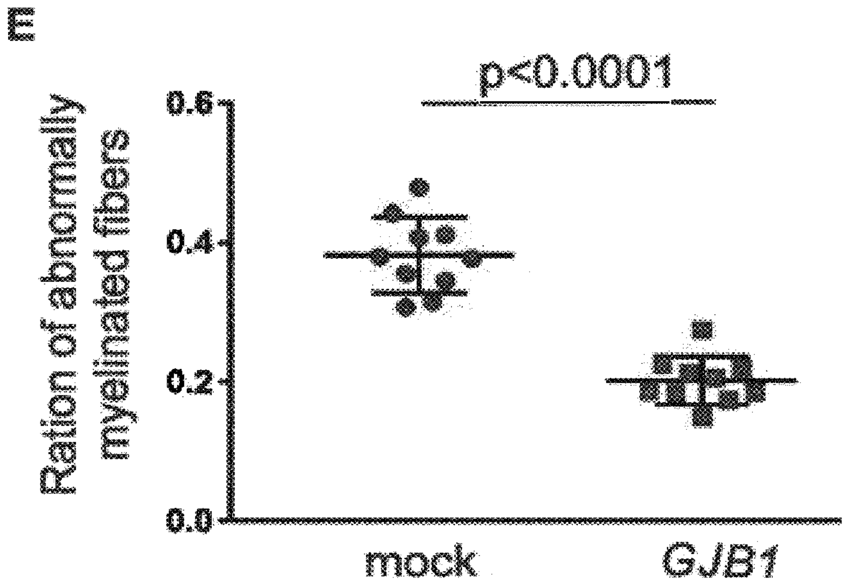
Figure 16:
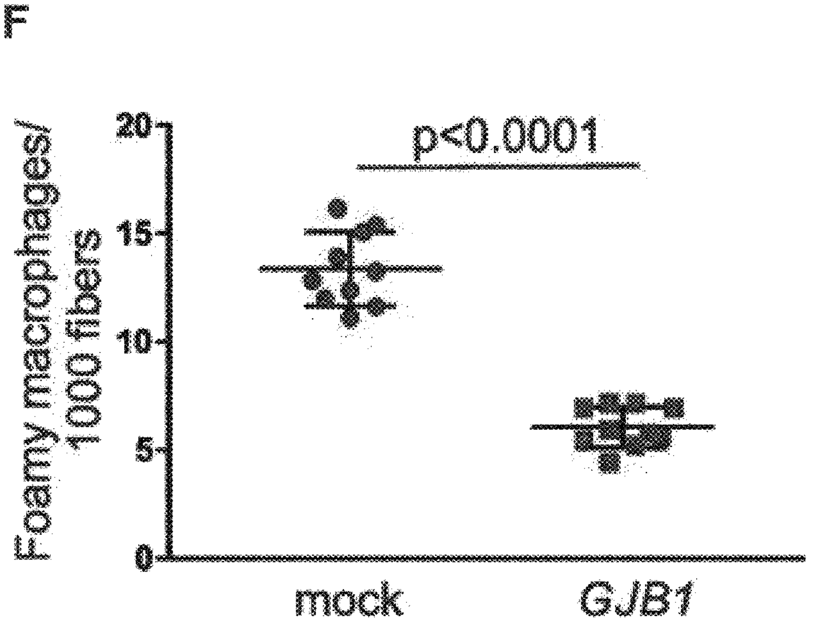
Figure 17:
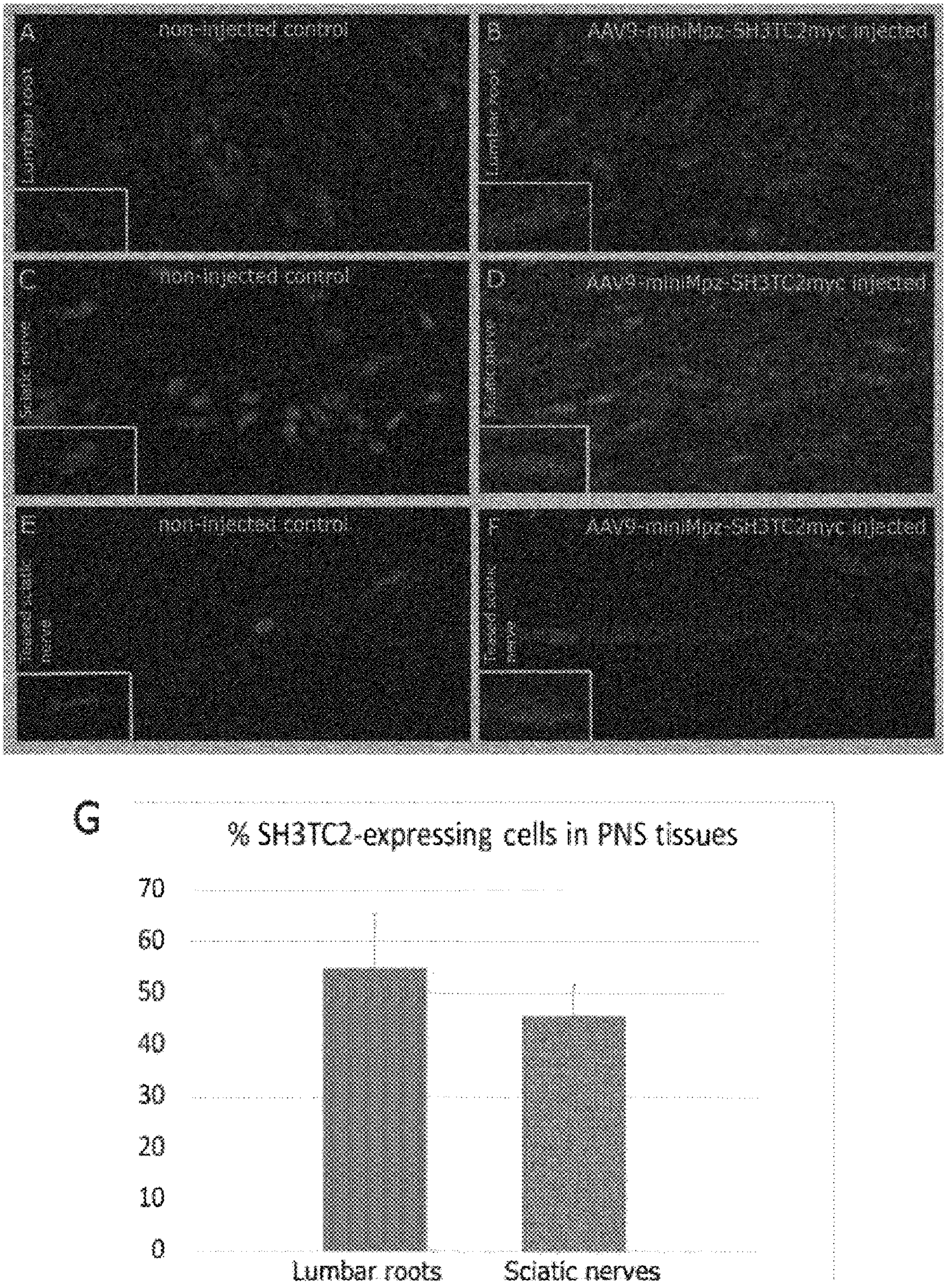
FIG. 17: Expression analysis of SH3TC2 in peripheral nervous system of Sh3tc2−/− mice following intrathecal delivery of novel therapeutic vector AAV9-mini-Mpz-SH3TC2.myc. Expression of human normal SH3TC2 protein (red) mainly in the perinuclear cytoplasm of myelinating Schwann cells in lumbar roots (A) and sciatic nerves (section in D and teased fibers in F) 4 weeks following intrathecal injection of the AAV9-miniMpz-SH3TC2myc vector into Sh3tc2−/− mice. Tissues of non-injected mice are shown in A, C, E as negative control. Cell nuclei are stained blue. Quantification of the expression rates (% SH3TC2-positive cells) in lumbar roots and sciatic nerves in n=5 mice is shown in FIG. 17G.

Morphological Studies in Peripheral Nerve Tissues in Treated Versus Mock-Treated 6-Month Old Cx32 KO Mice Morphological studies in peripheral nerve tissues in treated versus mock-treated 6-month old Cx32 KO mice. Semithin sections of anterior lumbar roots (FIG. 14), mid-sciatic nerves (FIG. 15), and femoral motor nerves (FIG. 16) were examined and the ratio of abnormally myelinated fibers as well as the number of macrophages were quantified in groups of fully treated compared to mock-treated Cx32 KO mice at the age of 6 months. As shown in each of FIGS. 14, 15 and 16, fewer demyelinated (*) or remyelimated (r) fibers and fewer foamy macrphages were found in treated compared to mock treated mice. This is indicative of improved myelination and a reduction in inflammation in the treated group.

Example 11: Development of a Humanised Therapetic Vector to Treat CMT1X

The vectors described in Example 1 are controlled by the rat Mpz promoter. In order to humanize this construct and make it more suitable for clinical applications, the inventors have also cloned a human-Mpz-GJB1 construct (SEQ ID NO: 17) using a human hP0 promoter (SEQ ID NO: 18) that can be used for preclinical dose-response testing and non-human primate (NHP) toxicity and biodistribution studies. Human P0 sequence was PCR amplified from genomic DNA using primers to introduce Kpnl and Agel restriction enzymes. The primers were: KpnhP0-F-5'-AGGGGTACCGCCTGGCATAAAC-3' (SEQ ID NO. 25) and AgehP0-R-5'-AATTTACCGGTGCTGGGGCAG-3' (SEQ ID NO. 26). After ligation of hP0, Cx32 ORF was cut from a pre-existing construct using BamHl and Xhol. Cx32 was ligated in the AAV transfer construct and correct assembly of the expression cassette was confirmed by restriction digest mapping and direct sequencing.

A humanized mock vector plasmid (human-Mpz-Egfp) has also been generated for use as a control (SEQ ID NO: 19).

Example 12: Development of and expression analysis of a therapeutic vector to treat CMT4C A mini-Mpz-SH3TC2.myc contruct similar to those described in Example 9 utilising the mini Mpz rat dervied promoter of SEQ ID NO. 5, above was developed using the SH3TC2 gene insert, and with further modifications in the ITR-ITR segment (including removal of WPRE and replacement of polyA with a minimal synthetic polyA) (68, 69) to remain within the approximate 4700 bp limit to allow for efficient packaging into the AAV9. The sequence of this therapeutic vector is shown in SEQ ID NO: 20.

Expression analysis of this novel therapeutic vector (mini-Mpz-SH3TC2.myc) was conducted in groups of CMT4C model mice. These results complement the development of the minimal Mpz promoter vector driving reporter gene expresison described in Example 9 above.

The novel AAV-miniMpz-SH3TC2.myc contruct was produced and packaged into the AAV9 serotype achieving titers of $5\times10^{12}$ vg/ml. The vector (total of $1\times10^{11}$ vg in a volume of 20 μl) was delivered by lumbar intrathecal injection into 5-month old Sh3tc2−/− mice (n=5), and expression was examined 5 weeks after injection in fixed lumbar spinal root and bilateral sciatic nerve sections.

Expression of SH3TC2 was detected in a high percentage of myelinating Schwann cells throughout the PNS including roots and sciatic nerves, in a characteristic perinuclear granular appearance, and occasionally along the entire length of the Schwann cell (FIGS. 17A-F). Quantification of the percentage of SH3TC2-immunoreactive Schwann cells showed an average of 54.67% expression rate in lumbar roots and 45.39% in sciatic nerves (FIG. 17G).

These results indicate that the construct achieved a good level of expression in myelinating Schwann cells throughout the PNS.

Example 13: Development of a Humanised Therapeutic Vector to Treat CMT4C

The mini-Mpz-SH3TC2.myc (SEQ ID NO: 20) construct (as described in Example 12 above) that is well suited for preclinical testing (due to inclusion of the minimial version of rat Mpz promoter and myc tag on SH3TC2 to facilitate preclinical expression analysis) has been modified in order to be more suitable for clinical application (SEQ ID NO: 21).

The myc tag has been removed, and the minimal version of the rat promoter has been replaced by the corresponding sequence of the minimal human Mpz promoter (SEQ ID NO: 22). This vector can be used for final preclinical dose-response testing and NHP toxicity and biodistribution studies before proceeding to clinical applications. A humanized mock vector plasmid (human-miniMpz-Egfp) has also been generated (SEQ ID NO: 23).

REFERENCES

1. Baets J, De Jonghe P, Timmerman V. Recent advances in Charcot-Marie-Tooth disease. Curr Opin Neurol. 2014; 27(5):532-40.
2. Kleopa K A, Scherer S S. Inherited Neuropathies. Neurol Clinics North America. 2002; 20:679-709.
3. Kleopa K A, Kagiava A, Sargiannidou I. Gene Therapy for CMT Inherited Neuropathy. In: Duan D, Mendell J (eds): Muscle Gene Therapy. 2019; https://doi.org/10.1007/978-3-030-03095-7_35 (Springer, Cham).
4. Bergoffen J, Scherer S S, Wang S, Oronzi-Scott M, Bone L, Paul D L, et al. Connexin mutations in X-linked Charcot-Marie-Tooth disease. Science. 1993; 262:2039-42.
5. Kleopa K A, Scherer S S. Molecular genetics of X-linked Charcot-Marie-Tooth disease. Neuromolecular Med. 2006; 8:107-22.
6. Hahn A F, Brown W F, Koopman W J, Feasby T E. X-linked dominant hereditary motor and sensory neuropathy. Brain. 1990; 113:1511-25.
7. Birouk N, Le Guern E, Maisonobe T, Rouger H, Gouider R, Gugenheim M, et al. X-linked Charcot-Marie-Tooth disease with connexin 32 mutations—clinical and electrophysiological study. Neurology. 1998; 50:1074-82.
8. Shy M E, Siskind C, Swan E R, Krajewski K M, Doherty T, Fuerst D R, et al. CMT1X phenotypes represent loss of GJB1 gene function. Neurology. 2007; 68:849-55.
9. Dubourg O, Tardieu S, Birouk N, Gouider R, Léger J M, Maisonobe T, et al. Clinical, electrophysiological and molecular genetic characteristics of 93 patients with X-linked Charcot-Marie-Tooth disease. Brain. 2001; 124:1958-67.
10. Liang G S L, de Miguel M, Gomez-Hernandez J M, Glass J D, Scherer S S, Mintz M, et al. Severe neuropathy with leaky connexin32 hemichannels. Ann Neurol. 2005; 57:749-54.
11. Al-Mateen M, Craig A K, Chance P F. The Central Nervous System Phenotype of X-Linked Charcot-Marie-Tooth Disease: A Transient Disorder of Children and Young Adults. J Child Neurol. 2014; 29:342-8
12. Hahn A F, Ainsworth P J, Bolton C F, Bilbao J M, Vallat J-M. Pathological findings in the X-linked form of Charcot-Marie-Tooth disease: a morphometric and ultrastructural analysis. Acta Neuropathol. 2001; 101:129-39.
13. Hattori N, Yamamoto M, Yoshihara T, Koike H, Nakagawa M, Yoshikawa H, et al. Demyelinating and axonal features of Charcot-Marie-Tooth disease with mutations of myelin-related proteins (PMP22, MPZ and Cx32): a clinicopathological study of 205 Japanese patients. Brain. 2003; 126:134-51.
14. Kleopa K A, Zamba-Papanicolaou E, Alevra X, Nicolaou P, Georgiou D-M, Hadjisawas A, et al. Phenotypic and cellular expression of two novel connexin32 mutations causing CMT1X. Neurology. 2006; 66:396-402.
15. Omori Y, Mesnil M, Yamasaki H. Connexin 32 mutations from X-linked Charcot-Marie-Tooth disease patients: functional defects and dominant negative effects. Mol Biol Cell. 1996; 7(6):907-16.
16. Yoshimura T, Satake M, Ohnishi A, Tsutsumi Y, Fujikura Y. Mutations of connexin32 in Charcot-Marie-Tooth disease type X interfere with cell-to-cell communication but not cell proliferation and myelin-specific gene expression. J Neurosci Res. 1998; 51(2):154-61.
17. Yum S W, Kleopa K A, Shumas S, Scherer S S. Diverse trafficking abnormalities of Connexin32 mutants causing CMTX. Neurobiol Dis. 2002; 11:43-52.
18. Deschênes S M, Walcott J L, Wexler T L, Scherer S S, Fischbeck K H. Altered trafficking of mutant connexin32. J Neurosci. 1997; 17:9077-84.
19. Oh S, Ri Y, Bennett M V L, Trexler E B, Verselis V K, Bargiello T A. Changes in permeability caused by connexin 32 mutations underlie X-linked Charcot-Marie-Tooth disease. Neuron. 1997; 19(4):927-38.
20. Martin P E M, Mambetisaeva E T, Archer D A, George C H, Evans W H. Analysis of gap junctions assembly using mutated connexins detected in Charcot-Marie-Tooth X-linked disease. J Neurochem. 2000; 74:711-20.
21. Kleopa K A, Yum S W, Scherer S S. Cellular mechanisms of connexin32 mutations associated with CNS manifestations. J Neurosci Res. 2002; 68:522-34.
22. Sargiannidou I, Vavlitou N, Aristodemou S, Hadjisavvas A, Kyriacou K, Scherer S S, et al. Connexin32 mutations cause loss of function in Schwann cells and oligodendrocytes leading to PNS and CNS myelination defects. J Neurosci. 2009; 29:4748-61.
23. Sargiannidou I, Kim G H, Kyriakoudi S, Eun BL, Kleopa K A. A start codon CMT1X mutation associated with transient encephalomyelitis causes complete loss of Cx32. Neurogenetics. 2015; 16(3):193-200.
24. Anzini P, Neuberg D H-H, Schachner M, Nelles E, Willecke K, Zielasek J, et al. Structural abnormalities and deficient maintenance of peripheral nerve myelin in mice lacking the gap junction protein connexin32. J Neurosci. 1997; 17:4545-61.
25. Scherer S S, Xu Y-T, Nelles E, Fischbeck K, Willecke K, Bone L J. Connexin32-null mice develop a demyelinating peripheral neuropathy. Glia. 1998; 24:8-20.
26. Scherer S S, Xu Y T, Messing A, Willecke K, Fischbeck K H, Jeng L J. Transgenic expression of human connexin32 in myelinating Schwann cells prevents demyelination in connexin32-null mice. J Neurosci. 2005; 25:1550-9.

27. Abel A, Bone L J, Messing A, Scherer S S, Fischbeck K F. Studies in transgenic mice indicate a loss of connexin32 function in X-linked Charcot-Marie-Tooth disease. J Neuropathol Exp Neurol. 1999; 58:702-10.
28. Jeng L J, Balice-Gordon R J, Messing A, Fischbeck K H, Scherer S S. The effects of a dominant connexin32 mutant in myelinating Schwann cells. Mol Cell Neurosci. 2006; 32:283-98.
29. Kagiava A, Karaiskos C, Richter J, Tryfonos C, Lapathitis G, Sargiannidou I, et al. Intrathecal gene therapy in mouse models expressing CMT1X mutations. Hum Mol Genet. 2018; 27(8):1460-73.
30. Huang Y, Sirkowski E E, Stickney J T, Scherer S S. Prenylation-defective human connexin32 mutants are normally localized and function equivalently to wild-type connexin32 in myelinating Schwann cells. J Neurosci. 2005; 25:7111-20.
31. Hahn A F, Ainsworth PJ, Naus C C G, Mao J, Bolton C F. Clinical and pathological observations in men lacking the gap junction protein connexin 32. Muscle Nerve. 2000:S39-S48.
32. Sargiannidou I, Kagiava A, Bashiardes S, Richter J, Christodoulou C, Scherer S S, et al. Intraneural GJB1 gene delivery improves nerve pathology in a model of CMT1X. Ann Neurol. 2015; 78:303-16.
33. Kagiava A, Sargiannidou I, Theophilidis G, Karaiskos C, Richter J, Bashiardes S, et al. Intrathecal gene therapy rescues a model of demyelinating peripheral neuropathy. Proc Natl Acad Sci USA. 2016; 113(17):E2421-9. doi: 10.1073/pnas.1522202113.
34. Kyriakoudi S, Sargiannidou I, Kagiava A, Olympiou M, Kleopa K A. Golgi-retained Cx32 mutants interfere with gene addition therapy for CMT1X. Hum Mol Genet. 2017; 26(9):1622-33.
35. Fridman V, Bundy B, Reilly M M, Pareyson D, Bacon C, Burns J, et al. CMT subtypes and disease burden in patients enrolled in the Inherited Neuropathies Consortium natural history study: a cross-sectional analysis. J Neurol Neurosurg Psychiatry. 2015; 86(8):873-8.
36. Kessali M, Zemmouri R, Guilbot A, Maisonobe T, Brice A, LeGuern E, et al. A clinical, electrophysiologic, neuropathologic, and genetic study of two large Algerian families with an autosomal recessive demyelinating form of Charcot-Marie-Tooth disease. Neurology. 1997; 48(4): 867-73.
37. Gabreels-Festen A, van Beersum S, Eshuis L, LeGuern E, Gabreels F, van Engelen B, et al. Study on the gene and phenotypic characterisation of autosomal recessive demyelinating motor and sensory neuropathy (Charcot-Marie-Tooth disease) with a gene locus on chromosome 5q23-q33. J Neurol Neurosurg Psychiatry. 1999; 66(5):569-74.
38. Azzedine H, Ravise N, Verny C, Gabreels-Festen A, Lammens M, Grid D, et al. Spine deformities in Charcot-Marie-Tooth 4C caused by SH3TC2 gene mutations. Neurology. 2006; 674(4):602-6
39. Gooding R, Colomer J, King R, Angelicheva D, Marns L, Parman Y, et al. A novel Gypsy founder mutation, p.Arg1109X in the CMT4C gene, causes variable peripheral neuropathy phenotypes. J Med Genet. 2005; 42(12): e69.
40. Colomer J, Gooding R, Angelicheva D, King R H, Guillen-Navarro E, Parman Y, et al. Clinical spectrum of CMT4C disease in patients homozygous for the p.Arg1109X mutation in SH3TC2. Neuromuscul Disord. 2006; 16(7):449-53.
41. Varley T L, Bourque P R, Baker S K. Phenotypic variability of CMT4C in a French-Canadian kindred. Muscle Nerve. 2015.
42. Senderek J, Bergmann C, Stendel C, Kirfel J, Verpoorten N, De Jonghe P, et al. Mutations in a Gene Encoding a Novel SH3/TPR Domain Protein Cause Autosomal Recessive Charcot-Marie-Tooth Type 4C Neuropathy. Am J Hum Genet. 2003; 73:1106-19.
43. LeGuern E, Guilbot A, Kessali M, Ravise N, Tassin J, Maisonobe T, et al. Homozygosity mapping of an autosomal recessive form of demyelinating Charcot-Marie-Tooth disease to chromosome 5q23-q33. Hum Mol Genet. 1996; 5(10):1685-8.
44. Lassuthova P, Mazanec R, Vondracek P, Siskova D, Haberlova J, Sabova J, et al. High frequency of SH3TC2 mutations in Czech HMSN I patients. Clin Genet. 2011; 80(4):334-45.
45. Lupo V, Galindo M I, Martinez-Rubio D, Sevilla T, Vilchez J J, Palau F, et al. Missense mutations in the SH3TC2 protein causing Charcot-Marie-Tooth disease type 4C affect its localization in the plasma membrane and endocytic pathway. Hum Mol Genet. 2009; 18(23):4603-14.
46. Arnaud E, Zenker J, de Preux Charles A S, Stendel C, Roos A, Medard J J, et al. SH3TC2/KIAA1985 protein is required for proper myelination and the integrity of the node of Ranvier in the peripheral nervous system. Proc Natl Acad Sci USA. 2009; 106(41):17528-33.
47. Gouttenoire E A, Lupo V, Calpena E, Bartesaghi L, Schupfer F, Medard J J, et al. Sh3tc2 deficiency affects neuregulin-1/ErbB signaling. Glia. 2013; 61(7):1041-51.
48. Zoupi L, Sawaki M, Karagogeos D. Axons and myelinating glia: An intimate contact. IUBMB Life. 2011; 63(9):730-5.
49. Schiza N, Georgiou E, Kagiava A, Médard J-J, Richter J, Tryfonos C, et al. Gene replacement therapy in a model of Charcot-Marie-Tooth 4C neuropathy. Brain. 2019; 142 (5):1227-1241
50. Tanguy Y, Biferi M G, Besse A, Astord S, Cohen-Tannoudji M, Marais T, et al. Systemic AAVrh10 provides higher transgene expression than AAV9 in the brain and the spinal cord of neonatal mice. Front Mol Neurosci. 2015; 8:36.
51. Foust K D, Nurre E, Montgomery C L, Hernandez A, Chan C M, Kaspar B K. Intravascular AAV9 preferentially targets neonatal neurons and adult astrocytes. Nat Biotechnol. 2009; 27(1):59-65.
52. Gurda B L, De Guilhem De Lataillade A, Bell P, Zhu Y, Yu H, Wang P, et al. Evaluation of AAV-mediated Gene Therapy for Central Nervous System Disease in Canine Mucopolysaccharidosis VII. Mol Ther. 2016; 24(2):206-16.
53. Calcedo R, Wilson J M. Humoral Immune Response to AAV. Front Immunol. 2013; 4:341.
54. Jackson K L, Dayton R D, Klein R L. AAV9 supports wide-scale transduction of the CNS and TDP-43 disease modeling in adult rats. Mol Ther Methods Clin Dev. 2015; 2:15036.
55. Meyer K, Ferraiuolo L, Schmelzer L, Braun L, McGovern V, Likhite S, et al. Improving single injection CSF delivery of AAV9-mediated gene therapy for SMA: a dose-response study in mice and nonhuman primates. Mol Ther. 2015; 23(3):477-87.

56. Jang S W, Svaren J. Induction of myelin protein zero by early growth response 2 through upstream and intragenic elements. J Biol Chem. 2009; 284(30):20111-20.
57. von Jonquieres G, Mersmann N, Klugmann C B, Harasta A E, Lutz B, Teahan O, et al. Glial promoter selectivity following AAV-delivery to the immature brain. PLoS One. 2013; 8(6):e65646.
58. Georgiou E, Sidiropoulou K, Richter J, Papaneophytou C, Sargiannidou I, Kagiava A, et al. Gene therapy targeting oligodendrocytes provides therapeutic benefit in a leukodystrophy model. Brain. 2017; 140(3):599-616.
59. Zolotukhin S, Byrne B J, Mason E, Zolotukhin I, Potter M, Chesnut K, et al. Recombinant adeno-associated virus purification using novel methods improves infectious titer and yield. Gene Ther. 1999; 6(6):973-85.
60. Piedra J, Ontiveros M, Miravet S, Penalva C, Monfar M, Chillon M. Development of a rapid, robust, and universal picogreen-based method to titer adeno-associated vectors. Hum Gene Ther Methods. 2015; 26(1):35-42.
61. Sawaki M, Panagiotaropoulos T, Stamatakis A, Sargiannidou I, Karatzioula P, Watanabe K, et al. Impairment of learning and memory in TAG-1 deficient mice associated with shorter CNS internodes and disrupted juxtaparanodes. Mol Cell Neurosci. 2008; 39:478-90.
62. Zielasek J, Martini R, Toyka K V. Functional abnormalities in P0-deficient mice resemble human hereditary neuropathies linked to P0 gene mutations. Muscle Nerve. 1996; 19(8):946-52.
63. Vavlitou N, Sargiannidou I, Markoullis K, Kyriacou K, Scherer S S, Kleopa K A. Axonal pathology precedes demyelination in a mouse model of X-linked demyelinating/type I Charcot-Marie Tooth neuropathy. J Neuropathol Exp Neurol. 2010; 69:945-58.
64. Kobsar I, Berghoff M, Samsam M, Wessig C, Maurer M, Toyka K V, et al. Preserved myelin integrity and reduced axonopathy in connexin32-deficient mice lacking the recombination activating gene-1. Brain. 2003; 126:804-13.
65. Groh J, Heinl K, Kohl B, Wessig C, Greeske J, Fischer S, et al. Attenuation of MCP-1/CCL2 expression ameliorates neuropathy in a mouse model for Charcot-Marie-Tooth 1X. Hum Mol Genet. 2010; 19:3530-43.
66. Shevtsova, Z., et al. (2005). "Promoters and serotypes: targeting of adeno-associated virus vectors for gene transfer in the rat central nervous system in vitro and in vivo." Exp Physiol; 90(1): 53-59
67. von Jonquieres, G., et al. (2016). "Recombinant Human Myelin-Associated Glycoprotein Promoter Drives Selective AAV-Mediated Transgene Expression in Oligodendrocytes." Front Mol Neurosci; 9: 13
68. Levitt, N., Briggs, D., Gil, A., and Proudfoot, N. J. (1989). Definition of an efficient synthetic poly(A) site. Genes Dev. 3,1019-1025.
69. Bailey R M, Armao D, Nagabhushan Kalburgi S, Gray S J. Development of Intrathecal AAV9 Gene Therapy for Giant Axonal Neuropathy. Mol Ther Methods Clin Dev. 2018 Feb. 15; 9:160-171.

Embodiments of the invention will now be described in the following numbered paragraphs:

1. A viral vector for use in treating or preventing a disease associated with Schwann cells in a subject in need thereof, wherein the viral vector comprises a first nucleic acid sequence that can be transcribed into a first polynucleotide, and wherein the viral vector is an AAV vector.

2. The viral vector for use of paragraph 1, wherein the expression of the first polynucleotide is under the control of a Schwann cell specific promoter, optionally a myelin specific promoter.

3. The viral vector for use of paragraphs 1 or 2, wherein the expression of the first polynucleotide is under the control of the full-length myelin protein zero (Mpz) promoter, wherein the full-length promoter is a full-length rat or human myelin protein zero promoter.

4. The viral vector for use of paragraphs 1-3 wherein the expression of the first polynucleotide is under the control of a promoter that is between 100 bp and 1100 bp in length, optionally wherein the promoter ranges from 200 bp to 900 bp in length, 300 bp to 800 bp in length, 400 bp to 700 bp in length, optionally wherein the promoter ranges from 500 bp to 600 bp in length, optionally wherein the promoter is 410 bp in length.

5. The viral vector for use of paragraph 4 wherein the promoter is a full-length or a minimal myelin specific promoter, optionally a minimal myelin protein zero (Mpz) promoter, optionally wherein the promoter has a sequence with at least 75% sequence homology or sequence identity with SEQ ID NO. 5 or SEQ ID NO. 22, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 5 or SEQ ID NO. 22.

6. The viral vector for use of any one of the preceding paragraphs, wherein the vector has the ability to transduce Schwann cells.

7. The viral vector for use of any one of the preceding paragraphs, wherein the vector does not integrate into the genome of the host cell.

8. The viral vector for use of any one of the preceding paragraphs, wherein the AAV vector is selected from the group comprising: AAV9 and AAVrh10.

9. The viral vector for use of paragraph 8, wherein the AAV vector is an AAV9.

10. The viral vector for use of any one of the preceding paragraphs wherein the first polynucleotide encodes and is translated into a first polypeptide or protein.

11. The viral vector for use of paragraph 10 wherein the first nucleic acid comprises:

a) a wild-type or therapeutically beneficial sequence of a neuropathy-associated gene, optionally selected from the group comprising or consisting of any one of the following genes: gap junction beta 1 (GJB1); SH3 domain and tetratricopeptide repeats 2 (SH3TC2) peripheral myelin protein 22 (PMP22); myelin protein zero (MPZ); early growth response 2 (EGR2); ganglioside induced differentiation associated protein 1 (GDAP1); N-Myc downstream regulated 1 (NDRG1) or other genes associated with demyelinating neuropathy and Schwann cell dysfunction; or b) a sequence with at least 75% sequence homology or sequence identity, optionally at least 80%, or 82%, or 84%, or 86%, or 88%, or 90%, or 92%, or 94%, or 96%, or 97%, or 98%, or 99%, or 100% sequence identity or sequence homology to a wild-type sequence of a neuropathy-associated gene, for example one of the following genes: gap junction beta 1 (GJB1); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1);

N-Myc downstream regulated 1 (NDRG1) or other genes associated with demyelinating neuropathy and Schwann cell dysfunction;

optionally wherein the first nucleic acid comprises a sequence with at least 75% sequence homology or sequence identity with SEQ ID NOs. 6-12, optionally at least 80%, or 82%, or 84%, or 86%, or 88%, or 90%, or 92%, or 94%, or 96%, or 97%, or 98%, or 99%, or 100% sequence identity or sequence homology to SEQ ID NOs. 6-12.

12. The viral vector for use of paragraphs 10 or 11 wherein the first nucleic acid comprises the wild-type form of the open reading frame (ORF) or cDNA that is transcribed into a first polynucleotide encoding one or more polypeptides, optionally selected from the group comprising or consisting of: connexin-32 (Cx32); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1); N-Myc downstream regulated 1 (NDRG1).

13. The viral vector for use of paragraphs 10-11 wherein the first nucleic acid comprises the wild-type open reading frame (ORF) of the gap junction beta 1 (GJB1) gene.

14. The viral vector for use of any one of paragraphs 1-13 wherein the vector is capable of driving expression from the first polynucleotide, optionally driving expression of a first polypeptide, optionally wherein the first polypeptide is connexin 32 (Cx32) protein, optionally wild-type Cx32.

15. The viral vector for use of any one of paragraphs 1-10 wherein the first polynucleotide encodes one or more of the following: a trophic factor (e.g. BDNF, GDNF, NT-3, VEGF), a regenerative factor (e.g. Angiogenin, Oct-6, Egr2, Sox-10), a growth factor (e.g. IGF).

16. The viral vector for use of any one of the preceding paragraphs, wherein administration of the viral vector results in an expression of a first protein from the first polynucleotide that leads to improved functioning of Schwann cells and/or increased formation of myelin sheath.

17. The viral vector for use of paragraphs 1-9 wherein the first polynucleotide does not encode a polypeptide, optionally wherein the first polynucleotide is a non-coding RNA.

18. The viral vector for use of paragraph 17 wherein the non-coding RNA is a short hairpin RNA (shRNA); microRNA (miRNA); guide RNA (gRNA).

19. The viral vector for use of any one of paragraphs 17 or 18 wherein when the viral vector is in a target organism, expression of the non-coding RNA causes a reduction in expression of a target polynucleotide, optionally wherein the target polynucleotide is a gene located in a target organism, optionally located in a cell in a target organism.

20. The viral vector for use of paragraph 19 wherein expression or overexpression of the target polynucleotide in a target organism is considered to be associated with a disease associated with Schwann cells, optionally wherein the disease is a dominant demyelinating neuropathy (CMT1), optionally wherein the target polynucleotide is a mutated allele of myelin protein zero (Mpz/P0) and the disease associated with Schwann cells is CMT1B, or wherein the target polynucleotide is another dominant gene associated with CMT1.

21. The viral vector for use of any one of paragraphs 17-20, wherein administration of the viral vector results in improved functioning of Schwann cells and/or increased formation of myelin sheath.

22. The viral vector for use of any one of the preceding paragraphs wherein the disease associated with Schwann cells causes destruction and/or reduced formation of myelin sheath by Schwann cells.

23. The viral vector for use of any one of the preceding paragraphs, where the disease is selected from the group consisting of: Charcot-Marie-Tooth disease (CMT); hereditary neuropathy with liability to pressure palsies (HNPP); diabetic and other toxic peripheral neuropathies; motor neuron disease (MND).

24. The viral vector for use of any one of the preceding paragraphs, wherein the disease is Charcot-Marie-Tooth disease (CMT).

25. The viral vector for use of paragraph 24, wherein the disease is selected from: Charcot-Marie-Tooth type 1X (CMT1X); Charcot-Marie-Tooth types 1A-1F (CMT1A-1F); Charcot-Marie-Tooth types 4A-4H (CMT4A-4H).

26. The viral vector for use of paragraph 25, wherein the disease is Charcot-Marie-Tooth type 1X (CMT1X).

27. The viral vector for use of paragraph 25, wherein the disease is Charcot-Marie-Tooth type 4C (CMT4C).

28. The viral vector for use of paragraphs 16 or 21, wherein the improved function results from increased formation of myelin sheath by Schwann cells when compared to the formation of myelin sheath by Schwann cells in the subject prior to treatment.

29. The viral vector for use of paragraph 28, wherein the increased formation of myelin sheath by Schwann cells leads to an improvement in any one or more of the following paramters:

a) muscle strength;

b) sciatic nerve conduction velocity; and/or c) response of blood biomarkers, when compared to the subject prior to treatment.

30. The viral vector for use of paragraph 28 or 29, wherein the improved formation of myelin sheath by Schwann cells leads to improved myelination of the peripheral nerves.

31. The viral vector for use of any one of the preceding paragraphs, wherein the AAV is administered to the subject by intrathecal injection or intravenous injection, preferably wherein the AAV is administered by intrathecal injection.

32. The viral vector for use of paragraph 31 wherein the AAV is administered by one of the following routes: lumbar intrathecal injection; thoracic intrathecal injection; cervical intrathecal injection.

33. The viral vector for use of paragraph 32, wherein the viral vector is administered by lumbar intrathecal injection.

34. The viral vector for use of paragraphs 31-33, wherein the AAV is administered by a single intrathecal injection.

35. The viral vector for use of any one of the preceding paragraphs, wherein the subject in need thereof is a human subject.

36. A viral vector as defined by any of the preceding paragraphs.

37. A cell that has been transduced with a viral vector as defined by any of the preceding paragraphs, optionally wherein the cell is a Schwann cell.

38. A minimal myelin specific promoter, wherein the minimal myelin specific promoter has a sequence homology with at least 75% sequence homology or sequence identity with SEQ ID NO. 5 or SEQ ID NO. 22, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 5 or SEQ ID NO. 22.

39. A minimal myelin specific promoter comprising or consisting of the sequence of SEQ ID NO. 5 or SEQ ID NO. 22.

40. A polynucleotide construct comprising a first nucleic acid sequence that is a Schwann cell specific promoter, optionally a myelin specific promoter, optionally comprising the myelin protein zero (Mpz) promoter or a minimal myelin specific promoter as defined in paragraphs 38 or 39, operably linked to a second nucleic acid sequence, wherein the second nucleic acid is transcribed into a first polynucleotide and wherein the second nucleic acid sequence: a) is the open reading frame or cDNA or other elements of a gene; or b) is transcribed into a non-coding RNA.

41. A viral vector comprising the minimal myelin specific promoter according to any of paragraphs 38 or 39 or the polynucleotide construct of paragraph 40.

42. The viral vector for use of any one of paragraphs 1-35 or the viral vector of paragraphs 36 or 41, wherein the vector has the ability to transduce Schwann cells.

43. The viral vector for use of any one of the preceding paragraphs, wherein the vector does not integrate into the genome of the host cell.

44. A viral vector according to one any one of paragraphs 42 or 43 comprising:
- a) an AAV, optionally wherein the AAV vector is an AAV9;
- b) an AAV-Mpz.Egfp vector comprising an AAV9 vector, the myelin protein zero (Mpz) promoter and the EGFP reporter gene;
- c) an AAV9-Mpz-GJB1 vector comprising an AAV9 vector, the myelin protein zero (Mpz) promoter and the open reading frame (ORF) of the gap junction beta 1 (GJB1) gene;
- d) an AAV9-miniMpz.Egfp vector comprising an AAV9 vector, the minimal myelin protein zero (miniMpz) promoter and the EGFP reporter gene;
- e) an AAV9-human Mpz-GJB1 vector comprising an AAV9 vector, the full-length human myelin protein zero (hP0) promoter and the open reading frame (ORF) of the gap junction beta 1 (GJB1) gene (SEQ ID NO. 17);
- f) an AAV9-human Mpz-Egfp vector comprising an AAV9 vector, the full-length human myelin protein zero (hP0) promoter and the EGFP reporter gene (SEQ ID NO. 19);
- g) an AAV9-miniMpz-SH3TC2.myc.ITR vector comprising an AAV9 vector, a minimal rat myelin protein zero (Mpz) promoter and the open reading frame (ORF) of the SH3TC2 gene (SEQ ID NO. 20);
- h) an AAV9-human-miniMpz-SH3TC2 vector comprising an AAV9 vector, a human minimal myelin protein zero (hP0) promoter and the open reading frame (ORF) of the SH3TC2 gene (SEQ ID NO. 21); or
- i) an AAV9-human-miniMpz-Egfp vector comprising an AAV9 vector, a human minimal myelin protein zero (hP0) promoter and the EGFP reporter gene (SEQ ID NO. 23).

45. A pharmaceutical composition comprising the viral vector of any one of the preceding paragraphs.

46. The pharmaceutical composition of paragraph 45, wherein the composition comprises an appropriate amount of the viral vector and further comprises a pharmaceutically acceptable carrier and/or excipient.

45. Use of a viral vector according to any of the preceding paragraphs in a method of manufacture of a medicament for the treatment or prevention of a disease associated with Schwann cells, optionally wherein the disease causes destruction and/or reduced formation of myelin sheath by Schwann cells, optionally wherein the disease is Charcot-Marie-Tooth disease.

46. A viral vector or polynucleotide construct according to any of the preceding paragraphs for use in a CRISPR/Cas9 system wherein the viral vector or polynucleotide comprises any one or more of:
- a) a polynucleotide encoding a single guide RNA (sgRNA) targeting a gene of interest;
- b) a polynucleotide encoding a Cas9 polypeptide;
- c) a polynucleotide encoding a polypeptide of interest.

47. A viral vector according to any of the preceding paragraphs, for use in a method of labelling Schwann cells, for example labelling with fluorescent protein, for example green fluorescent protein (GFP) or enhanced green fluorescent protein (EGFP), or another non-fluorescent reporter, optionally wherein the labelling of Schwann cells can be used in a method of diagnosing a disease associated with Schwann cells.

48. A viral vector according to any one of paragraphs 1-43, for use in a method wherein Schwann cells are induced to differentiate into an alternative cell type (for example oligodendrocytes, astrocytes or neurons).

49. A viral vector according to any one of paragraphs 1-43, for use in a method of stimulating Schwann cells to support regeneration in a subject in need thereof, optionally after an injury or trauma.

50. A kit for use preventing or treating a disease associated with Schwann cells, labelling Schwann cells or regenerating Schwann cells wherein the kit comprises one or more of:
- a) a viral vector as defined in any of the preceding paragraphs;
- b) a polynucleotide construct as defined by paragraph 40;
- c) a viral vector;
- d) a viral vector comprising the polynucleotide construct as defined by paragraph 40;
- e) a pharmaceutically acceptable carrier and/or excipient;
- f) a single-use syringe, for example a single-use syringe suitable for intrathecal lumbar injection;
- g) instructions for use.

51. A kit according to paragraph 50, wherein the kit comprises more than one viral vector as defined by any one of the preceding paragraphs, optionally wherein the kit comprises 2, 3, 4, 5, 6, 7, 8, 9 or 10 different viral vectors as defined by any one of the preceding paragraphs.

52. A viral vector for use in treating or preventing a disease associated with Schwann cells in a subject in need thereof, wherein the viral vector comprises a first nucleic acid sequence that can be transcribed into a first polynucleotide, and wherein expression of said first polynucleotide is under the control of a minimal myelin specific promoter, optionally comprising or consisting of the sequence defined in SEQ ID NO. 5 or SEQ ID NO. 22, optionally wherein the viral vector is an AAV vector.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the following claims.

The invention claimed is:

1. A method of treating Charcot-Marie-Tooth disease in a subject in need thereof, wherein the method comprises: selecting the subject as suffering from Charcot-Marie-Tooth disease; administering to said subject a viral vector that comprises a first nucleic acid sequence that can be transcribed into a therapeutic related polynucleotide, and wherein the viral vector is an adeno-associated virus (AAV) vector, wherein the expression of the first therapeutic related polynucleotide is under the control of a promoter selected from:

a) a full-length myelin protein zero (Mpz) promoter, wherein the full-length Mpz promoter is a full-length rat or full-length human Mpz promoter, wherein the promoter has a sequence with at least 75% sequence homology or sequence identity with SEQ ID NO. 4 or SEQ ID NO. 18, optionally at least 80%, or 82%, or 84%, or 86%, or 88%, or 90%, or 92%, or 94%, or 96%, or 97%, or 98%, or 99%, or 100% sequence identity or sequence homology to SEQ ID NO. 4 or SEQ ID NO. 18; or b) a minimal myelin protein zero (miniMpZ) promoter, wherein the minimal Mpz promoter is a rat or human minimal Mpz promoter, wherein the promoter has a sequence with at least 75% sequence homology or sequence identity with SEQ ID NO. 5 or SEQ ID NO. 22.

2. The method of claim 1, wherein the AAV vector is selected from the group comprising: AAV9 and AAVrh10.

3. The method of claim 1, wherein the first nucleic acid sequence encodes and is translated into a first polypeptide or protein, wherein the first nucleic acid sequence comprises:

a) a wild-type or therapeutically beneficial sequence of a neuropathy-associated gene, optionally selected from the group comprising or consisting of any one of the following genes: gap junction beta 1 (GJB1); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1); N-Myc downstream regulated 1 (NDRG1); or other genes associated with demyelinating neuropathy and Schwann cell dysfunction; or b) a sequence with at least 75% sequence homology or sequence identity, optionally at least 80%, or 82%, or 84%, or 86%, or 88%, or 90%, or 92%, or 94%, or 96%, or 97%, or 98%, or 99%, or 100% sequence identity or sequence homology to a wild-type sequence of a neuropathy-associated gene, for example one of the following genes: gap junction beta 1 (GJB1); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1); N-Myc downstream regulated 1 (NDRG1); or other genes associated with demyelinating neuropathy and Schwann cell dysfunction.

4. The method of claim 1, wherein the first nucleic acid sequence comprises the wild-type form of the open reading frame (ORF) or cDNA that is transcribed into the first therapeutic related polynucleotide encoding one or more polypeptides, optionally selected from the group comprising or consisting of: connexin-32 (Cx32); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1); N-Myc downstream regulated 1 (NDRG1); or wherein the vector is capable of driving expression from the first nucleic acid sequence, optionally driving expression of a first polypeptide, optionally wherein the first polypeptide is selected from the group comprising or consisting of connexin-32 (Cx32); SH3 domain and tetratricopeptide repeats 2 (SH3TC2); peripheral myelin protein 22 (PMP22); myelin protein zero (MPZ); early growth response 2 (EGR2); ganglioside induced differentiation associated protein 1 (GDAP1); N-Myc downstream regulated 1 (NDRG1).

5. The method of claim 1, wherein the first nucleic acid sequence is a non-coding RNA that causes a reduction in expression of a target polynucleotide.

6. The method of claim 5, wherein expression or overexpression of the target polynucleotide in a target organism is considered to be associated with Charcot-Marie-Tooth disease, wherein the disease is: a dominant demyelinating neuropathy (CMT1), wherein the target polynucleotide is a mutated allele of myelin protein zero (Mpz/P0) and the Charcot-Marie-Tooth disease is CMT1B, or wherein the target polynucleotide is another dominant gene associated with CMT1.

7. The method of claim 1, wherein the Charcot-Marie-Tooth disease is selected from the group consisting of:

Charcot-Marie-Tooth type 1X (CMT1X);
Charcot-Marie-Tooth type 1A;
Charcot-Marie-Tooth type 1B;
Charcot-Marie-Tooth type 1C;
Charcot-Marie-Tooth type 1D;
Charcot-Marie-Tooth type 1E;
Charcot-Marie-Tooth type 1F;
Charcot-Marie-Tooth type 4A;
Charcot-Marie-Tooth type 4B;
Charcot-Marie-Tooth type 4C;
Charcot-Marie-Tooth type 4D;
Charcot-Marie-Tooth type 4E;
Charcot-Marie-Tooth type 4F;
Charcot-Marie-Tooth type 4G; and
Charcot-Marie-Tooth type 4H.

8. The method of claim 1, wherein administration of the viral vector results in improved functioning of Schwann cells and/or increased formation of myelin sheath by Schwann cells when compared to the formation of myelin sheath by Schwann cells in the subject prior to treatment.

9. The method of claim 1, wherein the AAV vector is administered to the subject by intrathecal injection; intravenous injection;

lumbar intrathecal injection; thoracic intrathecal injection; or cervical intrathecal injection.

10. The method of claim 5, wherein the non-coding RNA is a short hairpin RNA (shRNA); a microRNA (miRNA); or a guide RNA (gRNA).

* * * * *

SEQUENCE LISTING

```
<160> NUMBER OF SEQ ID NOS: 26

<210> SEQ ID NO 1
<211> LENGTH: 6323
<212> TYPE: DNA
<213> ORGANISM: Artificial Sequence
<220> FEATURE:
<223> OTHER INFORMATION: AAV-Mpz.Egfp construct

<400> SEQUENCE: 1

tagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctaggtacc gggccccccc tcgaggtcga cggtatcgat aagcttcctg ttcagactcg    240
tttcctgctg taccctttca atggccccac atcaaatcaa acacagatgg cacatatcta    300
ctctaaatat atgcagagct tcacaaacgt catacacgta cgtgtgtcac acacgcacac    360
acacaccctt ccacctctgc ccttaccttt gctgtcccat ctagacatta tccctcccat    420
ccccttattt cccttatcaa aatggctgct ccttcaaggt tccaaataac actgcttcct    480
ggacctgact cctctttcct ctgaacttcc tgtgttaagt gtattcctag tgcactgtgc    540
cttggtagtt gttgagattg ccctctgctt ctcccttctg cctcctcatc tagtgatctt    600
gagcttgtag aaagaactga attaccattc taatacgagc attctcgaac tctccaaata    660
gccaccaagc aggacaatag gcagtcttga tcatttaaac tgctgcatgg caaaaggaat    720
cgaaggattt cttaacagaa gtgggggggg gggagatctg ggcttcttcc tggaagtttc    780
ctgatagaga aaatcttctg cctgggtaga atctcccagg atgcagggag atggaaaaag    840
tgttccccaa ggactttgta gtctacaggt tgtggagcca tcggaacaac gagacaccct    900
aatttgggag tgctctgaaa gaaacttgcc tctaggccct agggctctca ggcaaggagg    960
ctaagaagga atcctttgct gtagcctttt ggatttaggt ttctcagctt atctatccct   1020
cagagaagtg tgtctatgtc ccttttctgt ccctctgcct caccccaccc caacattcca   1080
acctagggta gggggaggtc agtatacaca aagccctctg tgtaaggggt ggtatgtgtc   1140
cccccacccc cctacccaga gtatacaatg cccctctgc tccatgcccc tgccaccctc    1200
ccaccacctc tcaattgcac atgccaggct gcaattggtc actggctcag gacagccccc   1260
tcatgctggg gatccagggg attttaagca ggttccagaa aacaccactc agttccttgt   1320
cccccgctct ctccacccca cagacgctct gccaagcttg atatcgaatt gatccaccgg   1380
tcgccaccat ggtgagcaag ggcgaggagc tgttcaccgg ggtggtgccc atcctggtcg   1440
agctggacgg cgacgtaaac ggccacaagt tcagcgtgtc cggcgagggc gagggcgatg   1500
ccacctacgg caagctgacc ctgaagttca tctgcaccac cggcaagctg cccgtgccct   1560
ggcccaccct cgtgaccacc ctgacctacg gcgtgcagtg cttcagccgc taccccgacc   1620
acatgaagca gcacgacttc ttcaagtccg ccatgcccga aggctacgtc caggagcgca   1680
ccatcttctt caaggacgac ggcaactaca agacccgcgc cgaggtgaag ttcgagggcg   1740
acaccctggt gaaccgcatc gagctgaagg gcatcgactt caaggaggac ggcaacatcc   1800
tggggcacaa gctggagtac aactacaaca gccacaacgt ctatatcatg gccgacaagc   1860
agaagaacgg catcaaggtg aacttcaaga tccgccacaa catcgaggac ggcagcgtgc   1920
agctcgccga ccactaccag cagaacaccc ccatcggcga cggccccgtg ctgctgcccg   1980
acaaccacta cctgagcacc cagtccgccc tgagcaaaga ccccaacgag aagcgcgatc   2040
```

-continued

```
acatggtcct gctggagttc gtgaccgccg ccgggatcac tctcggcatg gacgagctgt   2100

acaagtaaag cggccctaga tcaagcttat cgataatcaa cctctggatt acaaaatttg   2160

tgaaagattg actggtattc ttaactatgt tgctcctttt acgctatgtg gatacgctgc   2220

tttaatgcct ttgtatcatg ctattgcttc ccgtatggct ttcattttct cctccttgta   2280

taaatcctgg ttgctgtctc tttatgagga gttgtggccc gttgtcaggc aacgtggcgt   2340

ggtgtgcact gtgtttgctg acgcaacccc cactggttgg ggcattgcca ccacctgtca   2400

gctcctttcc gggactttcg ctttccccct ccctattgcc acggcggaac tcatcgccgc   2460

ctgccttgcc cgctgctgga caggggctcg gctgttgggc actgacaatt ccgtggtgtt   2520

gtcggggaaa tcatcgtcct ttccttggct gctcgcctgt gttgccacct ggattctgcg   2580

cgggacgtcc ttctgctacg tcccttcggc cctcaatcca gcggaccttc cttcccgcgg   2640

cctgctgccg gctctgcggc ctcttccgcg tcttcgcctt cgccctcaga cgagtcggat   2700

ctccctttgg gccgcctccc cgcatcgata ccgtcgactc gctgatcagc ctcgactgtg   2760

ccttctagtt gccagccatc tgttgtttgc ccctcccccg tgccttcctt gaccctggaa   2820

ggtgccactc ccactgtcct ttcctaataa aatgaggaaa ttgcatcgca ttgtctgagt   2880

aggtgtcatt ctattctggg gggtggggtg gggcaggaca gcaaggggga ggattgggaa   2940

gacaatagca ggcatgctgg ggatgcggtg ggctctatgg cttctgaggc ggaaagaacc   3000

agctggggct cgactagagc atggctacgt agataagtag catggcgggt taatcattaa   3060

ctacaaggaa cccctagtga tggagttggc cactccctct ctgcgcgctc gctcgctcac   3120

tgaggccggg cgaccaaagg tcgcccgacg cccgggcttt gcccgggcgg cctcagtgag   3180

cgagcgagcg cgcagagctt tttgcaaaag cctaggcctc caaaaaagcc tcctcactac   3240

ttctggaata gctcagaggc cgaggcggcc tcggcctctg cataaataaa aaaaattagt   3300

cagccatggg gcggagaatg ggcggaactg ggcggagtta ggggcgggat gggcggagtt   3360

aggggcggga ctatggttgc tgactaattg agatgcatgc tttgcatact tctgcctgct   3420

ggggagcctg gggactttcc acacctggtt gctgactaat tgagatgcat gctttgcata   3480

cttctgcctg ctggggagcc tggggacttt ccacacccta actgacacac attccacagc   3540

tgcattaatg aatcggccaa cgcgcgggga gaggcggttt gcgtattggg cgctcttccg   3600

cttcctcgct cactgactcg ctgcgctcgg tcgttcggct gcggcgagcg gtatcagctc   3660

actcaaaggc ggtaatacgg ttatccacag aatcagggga taacgcagga aagaacatgt   3720

gagcaaaagg ccagcaaaag gccaggaacc gtaaaaaggc cgcgttgctg gcgtttttcc   3780

ataggctccg cccccctgac gagcatcaca aaaatcgacg ctcaagtcag aggtggcgaa   3840

acccgacagg actataaaga taccaggcgt ttccccctgg aagctccctc gtgcgctctc   3900

ctgttccgac cctgccgctt accggatacc tgtccgcctt tctcccttcg ggaagcgtgg   3960

cgctttctca tagctcacgc tgtaggtatc tcagttcggt gtaggtcgtt cgctccaagc   4020

tgggctgtgt gcacgaaccc cccgttcagc ccgaccgctg cgccttatcc ggtaactatc   4080

gtcttgagtc caacccggta agacacgact tatcgccact ggcagcagcc actggtaaca   4140

ggattagcag agcgaggtat gtaggcggtg ctacagagtt cttgaagtgg tggcctaact   4200

acggctacac tagaagaaca gtatttggta tctgcgctct gctgaagcca gttaccttcg   4260

gaaaaagagt tggtagctct tgatccggca aacaaaccac cgctggtagc ggtggttttt   4320

ttgtttgcaa gcagcagatt acgcgcagaa aaaaaggatc tcaagaagat cctttgatct   4380
```

-continued

```
tttctacggg gtctgacgct cagtggaacg aaaactcacg ttaagggatt ttggtcatga   4440

gattatcaaa aaggatcttc acctagatcc ttttaaatta aaaatgaagt tttaaatcaa   4500

tctaaagtat atatgagtaa acttggtctg acagttacca atgcttaatc agtgaggcac   4560

ctatctcagc gatctgtcta tttcgttcat ccatagttgc ctgactcccc gtcgtgtaga   4620

taactacgat acgggagggc ttaccatctg gccccagtgc tgcaatgata ccgcgagacc   4680

cacgctcacc ggctccagat ttatcagcaa taaaccagcc agccggaagg gccgagcgca   4740

gaagtggtcc tgcaacttta tccgcctcca tccagtctat taattgttgc cgggaagcta   4800

gagtaagtag ttcgccagtt aatagtttgc gcaacgttgt tgccattgct acaggcatcg   4860

tggtgtcacg ctcgtcgttt ggtatggctt cattcagctc cggttcccaa cgatcaaggc   4920

gagttacatg atcccccatg ttgtgcaaaa aagcggttag ctccttcggt cctccgatcg   4980

ttgtcagaag taagttggcc gcagtgttat cactcatggt tatggcagca ctgcataatt   5040

ctcttactgt catgccatcc gtaagatgct tttctgtgac tggtgagtac tcaaccaagt   5100

cattctgaga atagtgtatg cggcgaccga gttgctcttg cccggcgtca atacgggata   5160

ataccgcgcc acatagcaga actttaaaag tgctcatcat tggaaaacgt tcttcggggc   5220

gaaaactctc aaggatctta ccgctgttga gatccagttc gatgtaaccc actcgtgcac   5280

ccaactgatc ttcagcatct tttactttca ccagcgtttc tgggtgagca aaaacaggaa   5340

ggcaaaatgc cgcaaaaaag ggaataaggg cgacacggaa atgttgaata ctcatactct   5400

tcctttttca atattattga agcatttatc agggttattg tctcatgagc ggatacatat   5460

ttgaatgtat ttagaaaaat aaacaaatag gggttccgcg cacatttccc cgaaaagtgc   5520

cacctgacgt ctaagaaacc attattatca tgacattaac ctataaaaat aggcgtatca   5580

cgaggccctt tcgtctcgcg cgtttcggtg atgacggtga aaacctctga cacatgcagc   5640

tcccggagac ggtcacagct tgtctgtaag cggatgccgg gagcagacaa gcccgtcagg   5700

gcgcgtcagc gggtgttggc gggtgtcggg gctggcttaa ctatgcggca tcagagcaga   5760

ttgtactgag agtgcaccat tcgacgctct cccttatgcg actcctgcat taggaagcag   5820

cccagtagta ggttgaggcc gttgagcacc gccgccgcaa ggaatggtgc atgcaaggag   5880

atggcgccca acagtccccc ggccacgggg cctgccacca tacccacgcc gaaacaagcg   5940

ctcatgagcc cgaagtggcg agcccgatct tccccatcgg tgatgtcggc gatataggcg   6000

ccagcaaccg cacctgtggc gccggtgatg ccggccacga tgcgtccggc gtagaggatc   6060

tggctagcga tgaccctgct gattggttcg ctgaccattt ccgggtgcgg gacggcgtta   6120

ccagaaactc agaaggttcg tccaaccaaa ccgactctga cggcagttta cgagagagat   6180

gatagggtct gcttcagtaa gccagatgct acacaattag gcttgtacat attgtcgtta   6240

gaacgcggct acaattaata cataacctta tgtatcatac acatacgatt taggtgacac   6300

tatagaatac acggaattaa ttc                                           6323
```

<210> SEQ ID NO 2
<211> LENGTH: 6429
<212> TYPE: DNA
<213> ORGANISM: Artificial Sequence
<220> FEATURE:
<223> OTHER INFORMATION: AAV-Mpz.GJB1 construct

<400> SEQUENCE: 2

```
tagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120
```

-continued

```
actaggggtt ccttgtagtt aatgattaac ccgccatgct acttatctac gtagccatgc    180
tctaggtacc cctcgaagct tcctgttcag actcgtttcc tgctgtaccc tttcaatggc    240
cccacatcaa atcaaacaca gatggcacat atctactcta aatatatgca gagcttcaca    300
aacgtcatac acgtacgtgt gtcacacacg cacacacaca cccttccacc tctgccctta    360
cctttgctgt cccatctaga cattatccct cccatcccct tatttccctt atcaaaatgg    420
ctgctccttc aaggttccaa ataacactgc ttcctggacc tgactcctct ttcctctgaa    480
cttcctgtgt taagtgtatt cctagtgcac tgtgccttgg tagttgttga gattgccctc    540
tgcttctccc ttctgcctcc tcatctagtg atcttgagct tgtagaaaga actgaattac    600
cattctaata cgagcattct cgaactctcc aaatagccac caagcaggac aataggcagt    660
cttgatcatt taaactgctg catggcaaaa ggaatcgaag gatttcttaa cagaagtggg    720
gggggggag atctgggctt cttcctggaa gtttcctgat agagaaaatc ttctgcctgg    780
gtagaatctc ccaggatgca gggagatgga aaaagtgttc cccaaggact ttgtagtcta    840
caggttgtgg agccatcgga acaacgagac accctaattt gggagtgctc tgaaagaaac    900
ttgcctctag gccctagggc tctcaggcaa ggaggctaag aaggaatcct ttgctgtagc    960
cttttggatt taggtttctc agcttatcta tccctcagag aagtgtgtct atgtcccttt   1020
tctgtccctc tgcctcaccc caccccaaca ttccaaccta gggtaggggg aggtcagtat   1080
acacaaagcc ctctgtgtaa ggggtggtat gtgtcccccc acccccctac ccagagtata   1140
caatgcccct tctgctccat gcccctgcca ccctcccacc acctctcaat tgcacatgcc   1200
aggctgcaat tggtcactgg ctcaggacag ccccctcatg ctggggatcc aggggatttt   1260
aagcaggttc cagaaaacac cactcagttc cttgtccccc gctctctcca ccccacagac   1320
gctctgccaa gcttcgagaa tgaggcagga tgaactggac aggtttgtac accttgctca   1380
gtggcgtgaa ccggcattct actgccattg gccgagtatg gctctcggtc atcttcatct   1440
tcagaatcat ggtgctggtg gtggctgcag agagtgtgtg gggtgatgag aaatcttcct   1500
tcatctgcaa cacactccag cctggctgca acagcgtttg ctatgaccaa ttcttcccca   1560
tctcccatgt gcggctgtgg tccctgcagc tcatcctagt ttccacccca gctctcctcg   1620
tggccatgca cgtggctcac cagcaacaca tagagaagaa aatgctacgg cttgagggcc   1680
atggggaccc cctacacctg gaggaggtga agaggcacaa ggtccacatc tcagggacac   1740
tgtggtggac ctatgtcatc agcgtggtgt tccggctgtt gtttgaggcc gtcttcatgt   1800
atgtctttta tctgctctac cctggctatg ccatggtgcg gctggtcaag tgcgacgtct   1860
acccctgccc caacacagtg gactgcttcg tgtcccgccc caccgagaaa accgtcttca   1920
ccgtcttcat gctagctgcc tctggcatct gcatcatcct caatgtggcc gaggtggtgt   1980
acctcatcat ccgggcctgt gcccgccgag cccagcgccg ctccaatcca ccttcccgca   2040
agggctcggg cttcggccac cgcctctcac ctgaatacaa gcagaatgag atcaacaagc   2100
tgctgagtga gcaggatggc tccctgaaag acatactgcg ccgcagccct ggcaccgggg   2160
ctgggctggc tgaaaagagc gaccgctgct cggcctgctg aggatccctc gaggtcgacg   2220
gtatcgataa gcttatcgat aatcaacctc tggattacaa aatttgtgaa agattgactg   2280
gtattcttaa ctatgttgct ccttttacgc tatgtggata cgctgcttta atgcctttgt   2340
atcatgctat tgcttcccgt atggctttca ttttctcctc cttgtataaa tcctggttgc   2400
tgtctcttta tgaggagttg tggcccgttg tcaggcaacg tggcgtggtg tgcactgtgt   2460
```

-continued ttgctgacgc aacccccact ggttggggca ttgccaccac ctgtcagctc ctttccggga 2520
ctttcgcttt ccccctccct attgccacgg cggaactcat cgccgcctgc cttgcccgct 2580
gctggacagg ggctcggctg ttgggcactg acaattccgt ggtgttgtcg gggaaatcat 2640
cgtcctttcc ttggctgctc gcctgtgttg ccacctggat tctgcgcggg acgtccttct 2700
gctacgtccc ttcggccctc aatccagcgg accttccttc ccgcggcctg ctgccggctc 2760
tgcggcctct tccgcgtctt cgccttcgcc ctcagacgag tcggatctcc ctttgggccg 2820
cctccccgca tcgataccgt cgactcgctg atcagcctcg actgtgcctt ctagttgcca 2880
gccatctgtt gtttgcccct cccccgtgcc ttccttgacc ctggaaggtg ccactcccac 2940
tgtcctttcc taataaaatg aggaaattgc atcgcattgt ctgagtaggt gtcattctat 3000
tctggggggt ggggtggggc aggacagcaa gggggaggat tgggaagaca atagcaggca 3060
tgctggggat gcggtgggct ctatggcttc tgaggcggaa agaaccagct ggggctcgac 3120
tagagcatgg ctacgtagat aagtagcatg gcgggttaat cattaactac aaggaacccc 3180
tagtgatgga gttggccact ccctctctgc gcgctcgctc gctcactgag gccgggcgac 3240
caaaggtcgc ccgacgcccg ggctttgccc gggcggcctc agtgagcgag cgagcgcgca 3300
gagctttttg caaaagccta ggcctccaaa aaagcctcct cactacttct ggaatagctc 3360
agaggccgag gcggcctcgg cctctgcata aataaaaaaa attagtcagc catggggcgg 3420
agaatgggcg gaactgggcg gagttagggg cgggatgggc ggagttaggg gcgggactat 3480
ggttgctgac taattgagat gcatgctttg catacttctg cctgctgggg agcctgggga 3540
ctttccacac ctggttgctg actaattgag atgcatgctt tgcatacttc tgcctgctgg 3600
ggagcctggg gactttccac accctaactg acacacattc cacagctgca ttaatgaatc 3660
ggccaacgcg cggggagagg cggtttgcgt attgggcgct cttccgcttc ctcgctcact 3720
gactcgctgc gctcggtcgt tcggctgcgg cgagcggtat cagctcactc aaaggcggta 3780
atacggttat ccacagaatc aggggataac gcaggaaaga acatgtgagc aaaaggccag 3840
caaaaggcca ggaaccgtaa aaaggccgcg ttgctggcgt ttttccatag gctccgcccc 3900
cctgacgagc atcacaaaaa tcgacgctca agtcagaggt ggcgaaaccc gacaggacta 3960
taaagatacc aggcgtttcc ccctggaagc tccctcgtgc gctctcctgt tccgaccctg 4020
ccgcttaccg gatacctgtc cgcctttctc ccttcgggaa gcgtggcgct ttctcatagc 4080
tcacgctgta ggtatctcag ttcggtgtag gtcgttcgct ccaagctggg ctgtgtgcac 4140
gaaccccccg ttcagcccga ccgctgcgcc ttatccggta actatcgtct tgagtccaac 4200
ccggtaagac acgacttatc gccactggca gcagccactg gtaacaggat tagcagagcg 4260
aggtatgtag gcggtgctac agagttcttg aagtggtggc ctaactacgg ctacactaga 4320
agaacagtat ttggtatctg cgctctgctg aagccagtta ccttcggaaa aagagttggt 4380
agctcttgat ccggcaaaca aaccaccgct ggtagcggtg gtttttttgt ttgcaagcag 4440
cagattacgc gcagaaaaaa aggatctcaa gaagatcctt tgatcttttc tacggggtct 4500
gacgctcagt ggaacgaaaa ctcacgttaa gggattttgg tcatgagatt atcaaaaagg 4560
atcttcacct agatcctttt aaattaaaaa tgaagtttta aatcaatcta aagtatatat 4620
gagtaaactt ggtctgacag ttaccaatgc ttaatcagtg aggcacctat ctcagcgatc 4680
tgtctatttc gttcatccat agttgcctga ctccccgtcg tgtagataac tacgatacgg 4740
gagggcttac catctggccc cagtgctgca atgataccgc gagacccacg ctcaccggct 4800
ccagatttat cagcaataaa ccagccagcc ggaagggccg agcgcagaag tggtcctgca 4860

-continued actttatccg cctccatcca gtctattaat tgttgccggg aagctagagt aagtagttcg 4920
ccagttaata gtttgcgcaa cgttgttgcc attgctacag gcatcgtggt gtcacgctcg 4980
tcgtttggta tggcttcatt cagctccggt tcccaacgat caaggcgagt tacatgatcc 5040
cccatgttgt gcaaaaaagc ggttagctcc ttcggtcctc cgatcgttgt cagaagtaag 5100
ttggccgcag tgttatcact catggttatg gcagcactgc ataattctct tactgtcatg 5160
ccatccgtaa gatgcttttc tgtgactggt gagtactcaa ccaagtcatt ctgagaatag 5220
tgtatgcggc gaccgagttg ctcttgcccg gcgtcaatac gggataatac cgcgccacat 5280
agcagaactt taaaagtgct catcattgga aaacgttctt cggggcgaaa actctcaagg 5340
atcttaccgc tgttgagatc cagttcgatg taacccactc gtgcacccaa ctgatcttca 5400
gcatctttta ctttcaccag cgtttctggg tgagcaaaaa caggaaggca aaatgccgca 5460
aaaaagggaa taagggcgac acggaaatgt tgaatactca tactcttcct ttttcaatat 5520
tattgaagca tttatcaggg ttattgtctc atgagcggat acatatttga atgtatttag 5580
aaaaataaac aaataggggt tccgcgcaca tttccccgaa aagtgccacc tgacgtctaa 5640
gaaaccatta ttatcatgac attaacctat aaaaataggc gtatcacgag gccctttcgt 5700
ctcgcgcgtt tcggtgatga cggtgaaaac ctctgacaca tgcagctccc ggagacggtc 5760
acagcttgtc tgtaagcgga tgccgggagc agacaagccc gtcagggcgc gtcagcgggt 5820
gttggcgggt gtcggggctg gcttaactat gcggcatcag agcagattgt actgagagtg 5880
caccattcga cgctctccct tatgcgactc ctgcattagg aagcagccca gtagtaggtt 5940
gaggccgttg agcaccgccg ccgcaaggaa tggtgcatgc aaggagatgg cgcccaacag 6000
tcccccggcc acggggcctg ccaccatacc cacgccgaaa caagcgctca tgagcccgaa 6060
gtggcgagcc cgatcttccc catcggtgat gtcggcgata taggcgccag caaccgcacc 6120
tgtggcgccg gtgatgccgg ccacgatgcg tccggcgtag aggatctggc tagcgatgac 6180
cctgctgatt ggttcgctga ccatttccgg gtgcgggacg gcgttaccag aaactcagaa 6240
ggttcgtcca accaaaccga ctctgacggc agtttacgag agagatgata gggtctgctt 6300
cagtaagcca gatgctacac aattaggctt gtacatattg tcgttagaac gcggctacaa 6360
ttaatacata accttatgta tcatacacat acgatttagg tgacactata gaatacacgg 6420
aattaattc 6429

<210> SEQ ID NO 3
<211> LENGTH: 5549
<212> TYPE: DNA
<213> ORGANISM: Artificial Sequence
<220> FEATURE:
<223> OTHER INFORMATION: AAV-miniMpz.Egfp construct

<400> SEQUENCE: 3
tagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctaggtacc gctctcaggc aaggaggcta agaaggaatc ctttgctgta gccttttgga 240
tttaggtttc tcagcttatc tatccctcag agaagtgtgt ctatgtccct tttctgtccc 300
tctgcctcac cccaccccaa cattccaacc tagggtaggg ggaggtcagt atacacaaag 360
ccctctgtgt aaggggtggt atgtgtcccc ccaccccct acccagagta tacaatgccc 420

-continued

```
cttctgctcc atgcccctgc caccctccca ccacctctca attgcacatg ccaggctgca    480
attggtcact ggctcaggac agccccctca tgctggggat ccaggggatt ttaagcaggt    540
tccagaaaac accactcagt tccttgtccc ccgctctctc caccccacag acgctctgcc    600
aaccggtcgc caccatggtg agcaagggcg aggagctgtt caccggggtg gtgcccatcc    660
tggtcgagct ggacggcgac gtaaacggcc acaagttcag cgtgtccggc gagggcgagg    720
gcgatgccac ctacggcaag ctgaccctga agttcatctg caccaccggc aagctgcccg    780
tgccctggcc caccctcgtg accaccctga cctacggcgt gcagtgcttc agccgctacc    840
ccgaccacat gaagcagcac gacttcttca agtccgccat gcccgaaggc tacgtccagg    900
agcgcaccat cttcttcaag gacgacggca actacaagac ccgcgccgag gtgaagttcg    960
agggcgacac cctggtgaac cgcatcgagc tgaagggcat cgacttcaag gaggacggca   1020
acatcctggg gcacaagctg gagtacaact acaacagcca caacgtctat atcatggccg   1080
acaagcagaa gaacggcatc aaggtgaact tcaagatccg ccacaacatc gaggacggca   1140
gcgtgcagct cgccgaccac taccagcaga acacccccat cggcgacggc cccgtgctgc   1200
tgcccgacaa ccactacctg agcacccagt ccgccctgag caaagacccc aacgagaagc   1260
gcgatcacat ggtcctgctg gagttcgtga ccgccgccgg gatcactctc ggcatggacg   1320
agctgtacaa gtaaagcggc cctagatcaa gcttatcgat aatcaacctc tggattacaa   1380
aatttgtgaa agattgactg gtattcttaa ctatgttgct ccttttacgc tatgtggata   1440
cgctgcttta atgcctttgt atcatgctat tgcttcccgt atggctttca ttttctcctc   1500
cttgtataaa tcctggttgc tgtctcttta tgaggagttg tggcccgttg tcaggcaacg   1560
tggcgtggtg tgcactgtgt ttgctgacgc aacccccact ggttggggca ttgccaccac   1620
ctgtcagctc ctttccggga ctttcgcttt ccccctccct attgccacgg cggaactcat   1680
cgccgcctgc cttgcccgct gctggacagg ggctcggctg ttgggcactg acaattccgt   1740
ggtgttgtcg gggaaatcat cgtcctttcc ttggctgctc gcctgtgttg ccacctggat   1800
tctgcgcggg acgtccttct gctacgtccc ttcggccctc aatccagcgg accttccttc   1860
ccgcggcctg ctgccggctc tgcggcctct tccgcgtctt cgccttcgcc ctcagacgag   1920
tcggatctcc ctttgggccg cctccccgca tcgataccgt cgactcgctg atcagcctcg   1980
actgtgcctt ctagttgcca gccatctgtt gtttgcccct cccccgtgcc ttccttgacc   2040
ctggaaggtg ccactcccac tgtcctttcc taataaaatg aggaaattgc atcgcattgt   2100
ctgagtaggt gtcattctat tctggggggt ggggtggggc aggacagcaa gggggaggat   2160
tgggaagaca atagcaggca tgctggggat gcggtgggct ctatggcttc tgaggcggaa   2220
agaaccagct ggggctcgac tagagcatgg ctacgtagat aagtagcatg gcgggttaat   2280
cattaactac aaggaacccc tagtgatgga gttggccact ccctctctgc gcgctcgctc   2340
gctcactgag gccgggcgac caaaggtcgc ccgacgcccg ggctttgccc gggcggcctc   2400
agtgagcgag cgagcgcgca gagctttttg caaaagccta ggcctccaaa aaagcctcct   2460
cactacttct ggaatagctc agaggccgag gcggcctcgg cctctgcata aataaaaaaa   2520
attagtcagc catggggcgg agaatgggcg gaactgggcg gagttagggg cgggatgggc   2580
ggagttaggg gcgggactat ggttgctgac taattgagat gcatgctttg catacttctg   2640
cctgctgggg agcctgggga ctttccacac ctggttgctg actaattgag atgcatgctt   2700
tgcatacttc tgcctgctgg ggagcctggg gactttccac accctaactg acacacattc   2760
cacagctgca ttaatgaatc ggccaacgcg cggggagagg cggtttgcgt attgggcgct   2820
```

-continued cttccgcttc ctcgctcact gactcgctgc gctcggtcgt tcggctgcgg cgagcggtat 2880
cagctcactc aaaggcggta atacggttat ccacagaatc aggggataac gcaggaaaga 2940
acatgtgagc aaaaggccag caaaaggcca ggaaccgtaa aaaggccgcg ttgctggcgt 3000
ttttccatag gctccgcccc cctgacgagc atcacaaaaa tcgacgctca agtcagaggt 3060
ggcgaaaccc gacaggacta taaagatacc aggcgtttcc ccctggaagc tccctcgtgc 3120
gctctcctgt tccgaccctg ccgcttaccg gatacctgtc cgcctttctc ccttcgggaa 3180
gcgtggcgct ttctcatagc tcacgctgta ggtatctcag ttcggtgtag gtcgttcgct 3240
ccaagctggg ctgtgtgcac gaaccccccg ttcagcccga ccgctgcgcc ttatccggta 3300
actatcgtct tgagtccaac ccggtaagac acgacttatc gccactggca gcagccactg 3360
gtaacaggat tagcagagcg aggtatgtag gcggtgctac agagttcttg aagtggtggc 3420
ctaactacgg ctacactaga agaacagtat ttggtatctg cgctctgctg aagccagtta 3480
ccttcggaaa aagagttggt agctcttgat ccggcaaaca aaccaccgct ggtagcggtg 3540
gtttttttgt ttgcaagcag cagattacgc gcagaaaaaa aggatctcaa gaagatcctt 3600
tgatcttttc tacggggtct gacgctcagt ggaacgaaaa ctcacgttaa gggattttgg 3660
tcatgagatt atcaaaaagg atcttcacct agatcctttt aaattaaaaa tgaagtttta 3720
aatcaatcta aagtatatat gagtaaactt ggtctgacag ttaccaatgc ttaatcagtg 3780
aggcacctat ctcagcgatc tgtctatttc gttcatccat agttgcctga ctccccgtcg 3840
tgtagataac tacgatacgg gagggcttac catctggccc cagtgctgca atgataccgc 3900
gagacccacg ctcaccggct ccagatttat cagcaataaa ccagccagcc ggaagggccg 3960
agcgcagaag tggtcctgca actttatccg cctccatcca gtctattaat tgttgccggg 4020
aagctagagt aagtagttcg ccagttaata gtttgcgcaa cgttgttgcc attgctacag 4080
gcatcgtggt gtcacgctcg tcgtttggta tggcttcatt cagctccggt tcccaacgat 4140
caaggcgagt tacatgatcc cccatgttgt gcaaaaaagc ggttagctcc ttcggtcctc 4200
cgatcgttgt cagaagtaag ttggccgcag tgttatcact catggttatg gcagcactgc 4260
ataattctct tactgtcatg ccatccgtaa gatgcttttc tgtgactggt gagtactcaa 4320
ccaagtcatt ctgagaatag tgtatgcggc gaccgagttg ctcttgcccg gcgtcaatac 4380
gggataatac cgcgccacat agcagaactt taaaagtgct catcattgga aaacgttctt 4440
cggggcgaaa actctcaagg atcttaccgc tgttgagatc cagttcgatg taacccactc 4500
gtgcacccaa ctgatcttca gcatctttta ctttcaccag cgtttctggg tgagcaaaaa 4560
caggaaggca aaatgccgca aaaaagggaa taagggcgac acggaaatgt tgaatactca 4620
tactcttcct ttttcaatat tattgaagca tttatcaggg ttattgtctc atgagcggat 4680
acatatttga atgtatttag aaaaataaac aaataggggt tccgcgcaca tttccccgaa 4740
aagtgccacc tgacgtctaa gaaaccatta ttatcatgac attaacctat aaaaataggc 4800
gtatcacgag gccctttcgt ctcgcgcgtt tcggtgatga cggtgaaaac ctctgacaca 4860
tgcagctccc ggagacggtc acagcttgtc tgtaagcgga tgccgggagc agacaagccc 4920
gtcagggcgc gtcagcgggt gttggcgggt gtcggggctg gcttaactat gcggcatcag 4980
agcagattgt actgagagtg caccattcga cgctctccct tatgcgactc ctgcattagg 5040
aagcagccca gtagtaggtt gaggccgttg agcaccgccg ccgcaaggaa tggtgcatgc 5100
aaggagatgg cgcccaacag tcccccggcc acggggcctg ccaccatacc cacgccgaaa 5160

-continued

```
caagcgctca tgagcccgaa gtggcgagcc cgatcttccc catcggtgat gtcggcgata      5220

taggcgccag caaccgcacc tgtggcgccg gtgatgccgg ccacgatgcg tccggcgtag      5280

aggatctggc tagcgatgac cctgctgatt ggttcgctga ccatttccgg gtgcgggacg      5340

gcgttaccag aaactcagaa ggttcgtcca accaaaccga ctctgacggc agtttacgag      5400

agagatgata gggtctgctt cagtaagcca gatgctacac aattaggctt gtacatattg      5460

tcgttagaac gcggctacaa ttaatacata accttatgta tcatacacat acgatttagg      5520

tgacactata gaatacacgg aattaattc                                       5549
```

<210> SEQ ID NO 4
<211> LENGTH: 1127
<212> TYPE: DNA
<213> ORGANISM: Rattus sp.
<220> FEATURE:
<223> OTHER INFORMATION: Mpz promoter

<400> SEQUENCE: 4

```
cctgttcaga ctcgtttcct gctgtaccct ttcaatggcc ccacatcaaa tcaaacacag        60

atggcacata tctactctaa atatatgcag agcttcacaa acgtcataca cgtacgtgtg       120

tcacacacgc acacacacac ccttccacct ctgcccttac ctttgctgtc ccatctagac       180

attatccctc ccatcccctt atttcccttp tcaaaatggc tgctccttca aggttccaaa       240

taacactgct tcctggacct gactcctctt tcctctgaac ttcctgtgtt aagtgtattc       300

ctagtgcact gtgccttggt agttgttgag attgccctct gcttctccct tctgcctcct       360

catctagtga tcttgagctt gtagaaagaa ctgaattacc attctaatac gagcattctc       420

gaactctcca aatagccacc aagcaggaca ataggcagtc ttgatcattt aaactgctgc       480

atggcaaaag gaatcgaagg atttcttaac agaagtgggg gggggggaga tctgggcttc       540

ttcctggaag tttcctgata gagaaaatct tctgcctggg tagaatctcc caggatgcag       600

ggagatggaa aaagtgttcc ccaaggactt tgtagtctac aggttgtgga gccatcggaa       660

caacgagaca ccctaatttg ggagtgctct gaaagaaact tgcctctagg ccctagggct       720

ctcaggcaag gaggctaaga aggaatcctt tgctgtagcc ttttggattt aggtttctca       780

gcttatctat ccctcagaga agtgtgtcta tgtccctttt ctgtccctct gcctcacccc       840

accccaacat tccaacctag ggtaggggga ggtcagtata cacaaagccc tctgtgtaag       900

gggtggtatg tgtccccca cccccctacc cagagtatac aatgcccctt ctgctccatg       960

cccctgccac cctcccacca cctctcaatt gcacatgcca ggctgcaatt ggtcactggc      1020

tcaggacagc cccctcatgc tggggatcca ggggatttta agcaggttcc agaaaacacc      1080

actcagttcc ttgtcccccg ctctctccac cccacagacg ctctgcc                   1127
```

<210> SEQ ID NO 5
<211> LENGTH: 410
<212> TYPE: DNA
<213> ORGANISM: Artificial Sequence
<220> FEATURE:
<223> OTHER INFORMATION: MiniMpz promoter

<400> SEQUENCE: 5

```
gctctcaggc aaggaggcta agaaggaatc ctttgctgta gccttttgga tttaggtttc        60

tcagcttatc tatccctcag agaagtgtgt ctatgtccct tttctgtccc tctgcctcac       120

cccaccccaa cattccaacc tagggtaggg ggaggtcagt atacacaaag ccctctgtgt       180

aaggggtggt atgtgtcccc ccacccccct acccagagta tacaatgccc cttctgctcc       240
```

atgcccctgc caccctccca ccacctctca attgcacatg ccaggctgca attggtcact 300
ggctcaggac agccccctca tgctggggat ccaggggatt ttaagcaggt tccagaaaac 360
accactcagt tccttgtccc ccgctctctc caccccacag acgctctgcc 410

<210> SEQ ID NO 6
<211> LENGTH: 852
<212> TYPE: DNA
<213> ORGANISM: Homo sapiens
<220> FEATURE:
<223> OTHER INFORMATION: Connexin-32 (Cx32): GenBank: AY408135.1

<400> SEQUENCE: 6
atgaactgga caggtttgta caccttgctc agtggcgtga accggcattc tactgccatt 60
ggccgagtat ggctctcggt catcttcatc ttcagaatca tggtgctggt ggtggctgca 120
gagagtgtgt ggggtgatga gaaatcttcc ttcatctgca acacactcca gcctggctgc 180
aacagcgttt gctatgacca attcttcccc atctcccatg tgcggctgtg gtccctgcag 240
ctcatcctag tttccacccc agctctcctc gtggccatgc acgtggctca ccagcaacac 300
atagagaaga aaatgctacg gcttgagggc catggggacc ccctacacct ggaggaggtg 360
aagaggcaca aggtccacat ctcagggaca ctgtggtgga cctatgtcat cagcgtggtg 420
ttccggctgt tgtttgaggc cgtcttcatg tatgtctttt atctgctcta ccctggctat 480
gccatggtgc ggctggtcaa gtgcgacgtc taccccctgcc ccaacacagt ggactgcttc 540
gtgtcccgcc ccaccgagaa aaccgtcttc accgtcttca tgctagctgc ctctggcatc 600
tgcatcatcc tcaatgtggc cgaggtggtg tacctcatca tccgggcctg tgcccgccga 660
gcccagcgcc gctccaatcc accttcccgc aagggctcgg gcttcggcca ccgcctctca 720
cctgaataca agcagaatga gatcaacaag ctgctgagtg agcaggatgg ctccctgaaa 780
gacatactgc gccgcagccc tggcaccggg gctgggctgg ctgaaaagag cgaccgctgc 840
tcggcctgct ga 852

<210> SEQ ID NO 7
<211> LENGTH: 3846
<212> TYPE: DNA
<213> ORGANISM: Homo sapiens
<220> FEATURE:
<223> OTHER INFORMATION: SH3 domain and tetratricopeptide repeats 2
(SH3TC2): GenBank: BC114486.1

<400> SEQUENCE: 7
atgggtggct gcttctgcat ccccagggag cggagtctga cccggggccc aggtaaagaa 60
actccttcca aggatccaac tgtatcgagt gagtgtatag cctcatctga atacaaggaa 120
aaatgttttc tgccacagaa cattaatcca gacctgacac tctccttctg tgtaaagagc 180
cgctccagga ggtgtgtaaa tggaccccta caggaagctg ctcggaggcg gctctgggca 240
ctggagaatg aggaccagga ggtgcgcatg ctgtttaagg acctctcagc aaggttggtc 300
agtatccagt ctcagagggc ccagtttctc atcaccttca agaccatgga ggaaatctgg 360
aagttctcca cctaccttaa tttagaacat ctcctctttg accacaagta ctggctcaac 420
tgcatattgg tggaggatac agagatccaa gtgtctgtag atgataaaca cctggaaaca 480
atatacctgg gactcctgat acaggaaggc cacttcttct gcagagccct gtgctccgtg 540
actccaccag ccgagaagga aggggaatgc ttgacacttt gcaagaatga gttaatctca 600
gtgaagatgg cagaagctgg ctccgagttg gaaggcgtgt ctttggtgac aggtcagcgg 660

-continued

```
ggcctggtac tggtgtcagc cttggagcct ctgcctctcc ctttccacca gtggttccta    720
aagaattatc caggaagctg tggcctttcc aggaagaggg attggacagg ctcctatcag    780
attggcagag gacgctgtaa ggccttgacg ggttatgagc caggagaaaa ggatgaactg    840
aatttctacc agggagaaag cattgagatc atcggctttg tcatacctgg gcttcagtgg    900
ttcattggaa agtcgacaag ttcaggacaa gtgggctttg tccccaccag gaacatagat    960
cctgattctt attccccaat gagcaggaac tctgcctttc tcagtgatga ggagagatgc   1020
tccctgttgg ccctgggaag tgataagcag actgagtgtt ccagcttcct ccacactctt   1080
gctcgcactg acatcacatc tgtctaccgg ctcagtgggt ttgaatccat ccagaatcct   1140
ccaaatgatc tgagtgcatc ccagcctgaa ggcttcaagg aggtcaggcc tggcagagcc   1200
tgggaggagc atcaggccgt ggggtccaga cagtccagca gctctgagga ctccagcctg   1260
gaggaggagc tcctctcggc cacctcagac agctatcgcc tgccggagcc tgatgacctt   1320
gatgacccgg aactgctcat ggacctaagc actggtcagg aggaggaggc tgagaacttc   1380
gcccccatat tggcttttct ggatcatgag ggttatgctg accactttaa gagtctctat   1440
gacttctcct tctctttcct cacttcttcc ttttatagct tctctgagga ggatgagttt   1500
gtggcctacc tggaggcatc aagaaagtgg gccaagaaga gccacatgac ctgggcccat   1560
gcccggctct gcttcctcct gggccggctg agcatcagga aggtcaaact ctctcaggcc   1620
agggtgtact tcgaggaggc catccacatt ctcaatggag catttgagga cctatccttg   1680
gtggccactc tgtacatcaa tttggctgcc atctacctga aacagaggct gagacataaa   1740
ggctccgccc tgttggaaaa ggcaggtgcc ctgctggcct gcctgcctga ccgtgagtct   1800
agtgccaagc atgaactcga cgtggtggcc tacgtgctgc gccaggggat tgtggtgggc   1860
agcagcccgc tggaggccag ggcctgcttt ctggccatcc gcttgctcct gagcctaggc   1920
cggcacgagg aggtcctgcc ctttgccgag cgcctgcagc tcctctctgg acaccctcct   1980
gcctctgagg ctgtggccag tgttttgagt tttctgtatg acaagaaata tcttccacac   2040
cttgcagtgg cctctgtcca gcaacatggt atccagagtg cccaagggat gtctcttcct   2100
atttggcagg tccaccttgt cctccagaac acaaccaagc tccttggctt tccttcccca   2160
ggctggggtg aagtttctgc cttggcctgc ccaatgctca gacaggccct ggctgcctgt   2220
gaggaactag cagaccggag cacccagagg gccctgtgtc tcatcctttc caaagtgtac   2280
ctcgagcaca ggtctcctga cggtgccatc cactacctga gccaggcctt ggtgctaggg   2340
cagctgctgg gtgagcagga atcctttgag tcttctctct gcctggcatg ggcctatctc   2400
ttagccagcc aggccaagaa ggctttggat gtgcttgagc cactgctatg ctccctgaag   2460
gagacagaga gtctcactca aaggggagtc atctataacc tcctgggact tgcactccaa   2520
ggtgaaggcc gggtgaacag ggcagccaag agctatcttc gggccttgaa cagagcccag   2580
gaggtgggag atgtgcataa ccaggcagtg gctatggcca atcttggcca cctgagcctt   2640
aagtcctggg ctcagcatcc agccagaaac tatctcctgc aggctgtacg actctattgt   2700
gaacttcagg ccagtaagga gacagacatg gaattagtac aggtgtttct ctggttggcc   2760
caagttctgg tgtctggaca ccagctgacc catggccttc tttgttatga aatggcattg   2820
ctgtttggct taaggcatcg acatctaaag agtcagcttc aggccaccaa atccctctgc   2880
catttctaca gctctgtgtc cccaaaccct gaggcatgca tcacctacca tgagcactgg   2940
ctggccctgg ctcagcaact cagggaccgg gagatggaag ggaggctgct ggagtccctg   3000
```

-continued

```
gggcagcttt atcggaacct aaataccgcc aggtccctca ggaggtcact cacatgcatc   3060

aaggagagcc tgcgtatctt cattgacctg gggagacag acaaggctgc tgaggcctgg   3120

cttggggcgg ggcgactcca ctacctcatg caggaagacg agctggtgga gctgtgcctg   3180

caggcagcca tccagacagc cctgaagtca gaggagcctt tgctggctct caaactttat   3240

gaagaagcag gtgatgtgtt cttcaatggg acccgccaca ggcatcatgc agtggagtac   3300

taccgagctg gagctgttcc tttagcaagg aggttgaagg cggtgagaac tgagctccgg   3360

attttcaata agctgacaga gctgcagatt agcctcgaag gctatgagaa ggctttggaa   3420

tttgccaccc tggccgccag gctcagcaca gtcacaggag atcagaggca agagctggtg   3480

gcctttcacc gcctggctac agtgtactac tccctgcaca tgtatgagat ggctgaggac   3540

tgctacctga agaccctgtc cctctgtcca ccctggctgc agagtcccaa ggaggccctg   3600

tactatgcca aggtgtatta tcgcctgggc agactcacct tctgccagct gaaggatgcc   3660

catgatgcca ctgagtactt ccttctggcc ctggcagcag cggtcctgct gggtgatgag   3720

gagcttcagg acaccattag gagcaggctg gacaacatct gccagagccc cctgtggcac   3780

agcaggccct ccgggtgctc ctcagagagg gcgcggtggc tgagtggtgg tggcctggcc   3840

ctctga                                                              3846
```

```
<210> SEQ ID NO 8
<211> LENGTH: 1828
<212> TYPE: DNA
<213> ORGANISM: Homo sapiens
<220> FEATURE:
<223> OTHER INFORMATION: Peripheral myelin protein 22 (PMP22): NCBI
      Reference Sequence: NM_000304.4

<400> SEQUENCE: 8
```

```
agttacaggg agcaccacca gggaacatct cggggagcct ggttggaagc tgcaggctta     60

gtctgtcggc tgcgggtctc tgactgccct gtggggaggg tcttgcctta acatcccttg    120

catttggctg caaagaaatc tgcttggaag aaggggttac gctgtttggc cgggcagaaa    180

ctccgctgag cagaacttgc cgccagaatg ctcctcctgt tgctgagtat catcgtcctc    240

cacgtcgcgg tgctggtgct gctgttcgtc tccacgatcg tcagccaatg gatcgtgggc    300

aatggacacg caactgatct ctggcagaac tgtagcacct cttcctcagg aaatgtccac    360

cactgtttct catcatcacc aaacgaatgg ctgcagtctg tccaggccac catgatcctg    420

tcgatcatct tcagcattct gtctctgttc ctgttcttct gccaactctt caccctcacc    480

aagggggca ggttttacat cactggaatc ttccaaattc ttgctggtct gtgcgtgatg    540

agtgctgcgg ccatctacac ggtgaggcac ccggagtggc atctcaactc ggattactcc    600

tacggtttcg cctacatcct ggcctgggtg gccttccccc tggcccttct cagcggtgtc    660

atctatgtga tcttgcggaa acgcgaatga ggcgcccaga cggtctgtct gaggctctga    720

gcgtacatag ggaagggagg aagggaaaac agaaagcaga caaagaaaaa agagctagcc    780

caaaatccca aactcaaacc aaaccaaaca gaaagcagtg gaggtggggg ttgctgttga    840

ttgaagatgt atataatatc tccggtttat aaaacctatt tataacactt tttacatata    900

tgtacatagt attgtttgct ttttatgttg accatcagcc tcgtgttgag ccttaaagaa    960

gtagctaagg aactttacat cctaacagta taatccagct cagtattttt gttttgtttt   1020

ttgtttgttt gttttgtttt acccagaaat aagataactc catctcgccc cttccctttc   1080

atctgaaaga agatacctcc ctcccagtcc acctcattta gaaaaccaaa gtgtgggtag   1140
```

-continued

```
aaaccccaaa tgtccaaaag cccttttctg gtgggtgacc cagtgcatcc aacagaaaca   1200

gccgctgccc gaacctctgt gtgaagcttt acgcgcacac ggacaaaatg cccaaactgg   1260

agcccttgca aaaacacggc ttgtggcatt ggcatacttg cccttacagg tggagtatct   1320

tcgtcacaca tctaaatgag aaatcagtga caacaagtct ttgaaatggt gctatggatt   1380

taccattcct tattatcact aatcatctaa acaactcact ggaaatccaa ttaacaattt   1440

tacaacataa gatagaatgg agacctgaat aattctgtgt aatataaatg gtttataact   1500

gcttttgtac ctagctaggc tgctattatt actataatga gtaaatcata aagccttcat   1560

cactcccaca tttttcttac ggtcggagca tcagaacaag cgtctagact ccttgggacc   1620

gtgagttcct agagcttggc tgggtctagg ctgttctgtg cctccaagga ctgtctggca   1680

atgacttgta ttggccacca actgtagatg tatatatggt gcccttctga tgctaagact   1740

ccagaccttt tgtttttgct ttgcattttc tgattttata ccaactgtgt ggactaagat   1800

gcattaaaat aaacatcaga gtaactca                                       1828


<210> SEQ ID NO 9
<211> LENGTH: 810
<212> TYPE: DNA
<213> ORGANISM: Homo sapiens
<220> FEATURE:
<223> OTHER INFORMATION: Myelin Protein Zero (MPZ): GenBank: AK313555.1

<400> SEQUENCE: 9

agttcctggt cccccacttt ctcaacccca cagatgctcc gggcccctgc ccctgcccca     60

gctatggctc ctggggctcc ctcatccagc cccagcccta tcctggctgt gctgctcttc    120

tcttctttgg tgctgtcccc ggcccaggcc atcgtggttt acaccgacag ggaggtccat    180

ggtgctgtgg gctcccgggt gaccctgcac tgctccttct ggtccagtga gtgggtctca    240

gatgacatct ccttcacctg gcgctaccag cccgaagggg gcagagatgc catttcgatc    300

ttccactatg ccaagggaca accctacatt gacgaggtgg ggaccttcaa agagcgcatc    360

cagtgggtag gggaccctcg ctggaaggat ggctccattg tcatacacaa cctagactac    420

agtgacaatg gcacgttcac ttgtgacgtc aaaaaccctc cagacatagt gggcaagacc    480

tctcaggtca cgctgtatgt ctttgaaaaa gtgccaacta ggtacggggt cgttctggga    540

gctgtgatcg gggtgtcct cggggtggtg ctgttgctgc tgctgctttt ctacgtggtt     600

cggtactgct ggctacgcag gcaggcggcc ctgcagagga ggctcagtgc tatggagaag    660

gggaaattgc acaagccagg aaaggacgcg tcgaagcgcg ggcggcagac gccagtgctg    720

tatgcaatgc tggaccacag cagaagcacc aaagctgtca gtgagaagaa ggccaagggg    780

ctgggggagt ctcgcaagga taagaaatag                                     810


<210> SEQ ID NO 10
<211> LENGTH: 2979
<212> TYPE: DNA
<213> ORGANISM: Homo sapiens
<220> FEATURE:
<223> OTHER INFORMATION: Early Growth Response 2 (EGR2): NCBI Reference
      Sequence: NM_000399.5

<400> SEQUENCE: 10

aactgagcga ggagcaattg attaatagct cggcgagggg actcactgac tgttataata     60

acactacacc agcaactcct ggcttcccag cagccggaac acagacagga gagagtcagt    120

ggcaaataga catttttctt atttcttaaa aaacagcaac ttgtttgcta cttttatttc    180
```

-continued

```
tgttgatttt tttttcttgg tgtgtgtggt ggttgttttt aagtgtggag ggcaaaagga    240

gataccatcc caggctcagt ccaacccctc tccaaaacgg cttttctgac actccaggta    300

gcgagggagt tgggtctcca ggttgtgcga ggagcaaatg atgaccgcca aggccgtaga    360

caaaatccca gtaactctca gtggttttgt gcaccagctg tctgacaaca tctacccggt    420

ggaggacctc gccgccacgt cggtgaccat ctttcccaat gccgaactgg gaggcccctt    480

tgaccagatg aacggagtgg ccggagatgg catgatcaac attgacatga ctggagagaa    540

gaggtcgttg gatctcccat atcccagcag ctttgctccc gtctctgcac ctagaaacca    600

gaccttcact tacatgggca agttctccat tgaccctcag taccctggtg ccagctgcta    660

cccagaaggc ataatcaata ttgtgagtgc aggcatcttg caaggggtca cttccccagc    720

ttcaaccaca gcctcatcca gcgtcacctc tgcctccccc aacccactgg ccacaggacc    780

cctgggtgtg tgcaccatgt cccagaccca gcctgacctg gaccacctgt actctccgcc    840

accgcctcct cctccttatt ctggctgtgc aggagacctc taccaggacc cttctgcgtt    900

cctgtcagca gccaccacct ccacctcttc ctctctggcc tacccaccac ctccttccta    960

tccatccccc aagccagcca cggacccagg tctcttccca atgatcccag actatcctgg   1020

attctttcca tctcagtgcc agagagacct acatggtaca gctggcccag accgtaagcc   1080

ctttccctgc ccactggaca ccctgcgggt gccccctcca ctcactccac tctctacaat   1140

ccgtaacttt accctggggg gccccagtgc tggggtgacc ggaccagggg ccagtggagg   1200

cagcgaggga ccccggctgc ctggtagcag ctcagcagca gcagcagccg ccgccgccgc   1260

cgcctataac ccacaccacc tgccactgcg gcccattctg aggcctcgca agtaccccaa   1320

cagacccagc aagacgccgg tgcacgagag gccctacccg tgcccagcag aaggctgcga   1380

ccggcggttc tcccgctctg acgagctgac acggcacatc cgaatccaca ctgggcataa   1440

gcccttccag tgtcggatct gcatgcgcaa cttcagccgc agtgaccacc tcaccaccca   1500

tatccgcacc cacaccggtg agaagccctt cgcctgtgac tactgtggcc gaaagtttgc   1560

ccggagtgat gagaggaagc gccacaccaa gatccacctg agacagaaag agcggaaaag   1620

cagtgccccc tctgcatcgg tgccagcccc ctctacagcc tcctgctctg ggggcgtgca   1680

gcctgggggt accctgtgca gcagtaacag cagcagtctt ggcggagggc cgctcgcccc   1740

ttgctcctct cggacccgga caccttgaga tgagactcag gctgatacac cagctcccaa   1800

aggtcccgga ggccctttgt ccactggagc tgcacaacaa acactaccac cctttcctgt   1860

ccctctctcc ctttgttggg caaagggctt tggtggagct agcactgccc cctttccacc   1920

tagaagcagg ttcttcctaa aacttagccc attctagtct ctcttaggtg agttgactat   1980

caacccaagg caaaggggag gctcagaagg aggtggtgtg gggacccctg gccaagaggg   2040

ctgaggtctg accctgcttt aaagggttgt ttgactaggt tttgctaccc cacttcccct   2100

tattttgacc catcacaggt ttttgaccct ggatgtcaga gttgatctaa gacgttttct   2160

acaataggtt gggagatgct gatcccttca agtggggaca gcaaaaagac aagcaaaact   2220

gatgtgcact ttatggcttg ggactgattt gggggacatt gtacagtgag tgaagtatag   2280

cctttatgcc acactctgtg gccctaaaat ggtgaatcag agcatatcta gttgtctcaa   2340

cccttgaagc aatatgtatt ataaactcag agaacagaag tgcaatgtga tgggaggaac   2400

atagcaatat ctgctccttt tcgagttgtt tgagaaatgt aggctatttt ttcagtgtat   2460

atccactcag attttgtgta tttttgatgt acactgttct ctaaattctg aatctttggg   2520

aaaaaatgta aagcatttat gatctcagag gttaacttat ttaaggggga tgtacatata   2580
```

-continued

```
ttctctgaaa ctaggatgca tgcaattgtg ttggaagtgt ccttggtgcc ttgtgtgatg   2640

tagacaatgt tacaaggtct gcatgtaaat gggttgcctt attatggaga aaaaaaatca   2700

ctccctgagt ttagtatggc tgtatatttc tgcctattaa tatttggaat tttttttaga   2760

aagtatattt ttgtatgctt tgttttgtga cttaaaagtg ttacctttgt agtcaaattt   2820

cagataagaa tgtacataat gttaccggag ctgatttgtt tggtcattag ctcttaatag   2880

ttgtgaaaaa ataaatctat tctaacgcaa aaccactaac tgaagttcag ataatggatg   2940

gtttgtgact atagtgtaaa taaatacttt tcaacaata                          2979
```

<210> SEQ ID NO 11
<211> LENGTH: 1077
<212> TYPE: DNA
<213> ORGANISM: Homo sapiens
<220> FEATURE:
<223> OTHER INFORMATION: Ganglioside induced differentiation associated protein 1 (GDAP1): NCBI Reference Sequence: NM_018972.3

<400> SEQUENCE: 11

```
atggctgaga ggcaggaaga gcagagaggg agcccgccct tgagggcgga aggcaaggcc     60

gacgcggagg ttaagctcat tctgtaccat tggacgcatt ccttcagctc tcaaaaggtg    120

cgcttggtaa ttgctgaaaa ggcattgaag tgcgaggaac atgatgtaag tctgcccttg    180

agtgagcaca atgagccttg gtttatgcgt ttgaactcaa ctggagaagt gcctgtcctt    240

atccacgggg aaaacataat ttgtgaggcc actcagatca ttgattatct tgaacagact    300

ttcctggatg aaagaacacc caggttaatg cctgataaag aaagcatgta ttacccacgg    360

gtacaacatt accgagagct gcttgactcc ttgccaatgg atgcctatac acatggctgc    420

attttacatc ctgagttaac tgtggactcc atgatcccgg cttatgcaac tacaaggatt    480

cgtagccaaa ttggaaacac agagtctgag ctgaagaaac ttgctgaaga aaacccagat    540

ttacaagaag catacattgc aaaacagaaa cgacttaaat caaagctgct tgatcatgac    600

aatgtcaagt atttgaagaa aattcttgat gagttggaga aagtcttgga tcaggttgaa    660

actgaattgc aaagaagaaa tgaagaaacc ccagaagagg gccagcaacc ttggctctgc    720

ggtgaatcct tcaccctggc agacgtctca ctcgctgtca cattgcatcg actgaagttc    780

ctggggtttg caaggagaaa ctggggaaac ggaaagcgac caaacttgga aacctattac    840

gagcgtgtct tgaagagaaa aacatttaac aaggttttag gacatgtcaa caatatatta    900

atctctgcag tgctgccaac agcattccgg gtggccaaga aaagggcccc aaaagttctt    960

ggcacgaccc ttgtggttgg tttgcttgca ggagtgggat attttgcttt tatgcttttc   1020

agaaagaggc ttggcagcat gatattagca tttagaccca gaccaaatta tttctag      1077
```

<210> SEQ ID NO 12
<211> LENGTH: 1185
<212> TYPE: DNA
<213> ORGANISM: Homo sapiens
<220> FEATURE:
<223> OTHER INFORMATION: N-Myc downstream regulated 1 (NDRG1): NCBI Reference Sequence: NM_001135242.1

<400> SEQUENCE: 12

```
atgtctcggg agatgcagga tgtagacctc gctgaggtga agcctttggt ggagaaaggg     60

gagaccatca ccggcctcct gcaagagttt gatgtccagg agcaggacat cgagacttta    120

catggctctg ttcacgtcac gctgtgtggg actcccaagg gaaaccggcc tgtcatcctc    180
```

-continued

```
acctaccatg acatcggcat gaaccacaaa acctgctaca accccctctt caactacgag    240

gacatgcagg agatcaccca gcactttgcc gtctgccacg tggacgcccc tggccagcag    300

gacggcgcag cctccttccc cgcagggtac atgtacccct ccatggatca gctggctgaa    360

atgcttcctg gagtccttca acagtttggg ctgaaaagca ttattggcat gggaacagga    420

gcaggcgcct acatcctaac tcgatttgct ctaaacaacc ctgagatggt ggagggcctt    480

gtccttatca acgtgaaccc ttgtgcggaa ggctggatgg actgggccgc ctccaagatc    540

tcaggatgga cccaagctct gccggacatg gtggtgtccc accttttgg gaaggaagaa     600

atgcagagta acgtggaagt ggtccacacc taccgccagc acattgtgaa tgacatgaac    660

cccggcaacc tgcacctgtt catcaatgcc tacaacagcc ggcgcgacct ggagattgag    720

cgaccaatgc cgggaaccca cacagtcacc ctgcagtgcc ctgctctgtt ggtggttggg    780

gacagctcgc ctgcagtgga tgccgtggtg gagtgcaact caaaattgga cccaacaaag    840

accactctcc tcaagatggc ggactgtggc ggcctcccgc agatctccca gccggccaag    900

ctcgctgagg ccttcaagta cttcgtgcag ggcatgggat acatgccctc ggctagcatg    960

acccgcctga tgcggtcccg cacagcctct ggttccagcg tcacttctct ggatggcacc   1020

cgcagccgct cccacaccag cgagggcacc cgaagccgct cccacaccag cgagggcacc   1080

cgcagccgct cgcacaccag cgagggggcc cacctggaca tcacccccaa ctcgggtgct   1140

gctgggaaca gcgccgggcc caagtccatg gaggtctcct gctag                   1185
```

<210> SEQ ID NO 13
<211> LENGTH: 24
<212> TYPE: DNA
<213> ORGANISM: Artificial Sequence
<220> FEATURE:
<223> OTHER INFORMATION: P0-Cx32 forward primer

<400> SEQUENCE: 13

```
aggggtaccc ttcctgttca gact                                            24
```

<210> SEQ ID NO 14
<211> LENGTH: 22
<212> TYPE: DNA
<213> ORGANISM: Artificial Sequence
<220> FEATURE:
<223> OTHER INFORMATION: P0-Cx32 reverse primer

<400> SEQUENCE: 14

```
ccgctcgagg gatcctcagc ag                                              22
```

<210> SEQ ID NO 15
<211> LENGTH: 21
<212> TYPE: DNA
<213> ORGANISM: Artificial Sequence
<220> FEATURE:
<223> OTHER INFORMATION: KpnI-P0 forward primer

<400> SEQUENCE: 15

```
ggggtaccgc tctcaggcaa g                                               21
```

<210> SEQ ID NO 16
<211> LENGTH: 23
<212> TYPE: DNA
<213> ORGANISM: Artificial Sequence
<220> FEATURE:
<223> OTHER INFORMATION: AgeI-P0 reverse primer

<400> SEQUENCE: 16
aaaccggttg gcagagcgtc tgt 23

<210> SEQ ID NO 17
<211> LENGTH: 6324
<212> TYPE: DNA
<213> ORGANISM: Artificial Sequence
<220> FEATURE:
<223> OTHER INFORMATION: AAV-human-Mpz-GJB1 construct

<400> SEQUENCE: 17
tagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctaggtacc gcctggcata aacttcattt attaaagttt attttgtctt taatctctca 240
tataacttag tcttcctgat attgcagctg tgtgtgcccc tcttttgtac tcccagcatt 300
ttgttcatta ctaaaggaag tgtcatggct tattatactt gattgttgat gggtttgtcc 360
tctgatcttc ccatctccac ctccccaaac caaattttca actccttgct ggaaggactt 420
aatttttatt cctctctcta ttacctgcat tctcatactt tacatattgc tggcacttaa 480
tacaattttg tagccttgaa ataaattgaa atggacttaa acagcagcat gaagcactga 540
aggacttctt gacaaacgga aaggtcaggg gcttcttgcc tggaaatagt ccagtggaga 600
aaaacttctg tctgggaaga atcgcacagg atgaagggag gtgcggggaa aaaaactccc 660
ataggacttg gtcatctcaa gaagtctgta atgcagccca cattagagga gataacaggg 720
gatatcctat tttcagagtt ctctgggggga aacctccctc tagttcctag ggctgtgagg 780
cagcctctct caggcaagga ggctgaggag aaatcccttt ttatggcctt taaattgagg 840
ttccatatct atccctcaga gaagtgtgtc tgtgtccctg tttttgtccc tctccctcac 900
caccccccac aacattccag cctggggcag ggggaggcca gtggacacaa agccctctgt 960
gtatggggtg gtatgtgtcc ccccacccct ccacccagac tatacaatgc cccttctgct 1020
ccctgcactc tgccccccctc cccaccacct ctcaactgca catgccaggc tgcaattggt 1080
tactggctga ggacagcccc ctcatgctgg ggccctaggg gattttaagc aggttccagg 1140 aacccccccgt tcagttcctg gtcccccact ttctcaaccc cacagatgct ccgggcccct 1200
gcccctgccc cagcaccggt cgcggatcct gaggcaggat gaactggaca ggtttgtaca 1260
ccttgctcag tggcgtgaac cggcattcta ctgccattgg ccgagtatgg ctctcggtca 1320
tcttcatctt cagaatcatg gtgctggtgg tggctgcaga gagtgtgtgg ggtgatgaga 1380
aatcttcctt catctgcaac acactccagc ctggctgcaa cagcgtttgc tatgaccaat 1440
tcttccccat ctcccatgtg cggctgtggt ccctgcagct catcctagtt tccaccccag 1500
ctctcctcgt ggccatgcac gtggctcacc agcaacacat agagaagaaa atgctacggc 1560
ttgagggcca tggggacccc ctacacctgg aggaggtgaa gaggcacaag gtccacatct 1620
cagggacact gtggtggacc tatgtcatca gcgtggtgtt ccggctgttg tttgaggccg 1680
tcttcatgta tgtcttttat ctgctctacc ctggctatgc catggtgcgg ctggtcaagt 1740
gcgacgtcta cccctgcccc aacacagtgg actgcttcgt gtcccgcccc accgagaaaa 1800
ccgtcttcac cgtcttcatg ctagctgcct ctggcatctg catcatcctc aatgtggccg 1860
aggtggtgta cctcatcatc cgggcctgtg cccgccgagc ccagcgccgc tccaatccac 1920
cttcccgcaa gggctcgggc ttcggccacc gcctctcacc tgaatacaag cagaatgaga 1980

-continued

```
tcaacaagct gctgagtgag caggatggct ccctgaaaga catactgcgc cgcagccctg   2040
gcaccggggc tgggctggct gaaaagagcg accgctgctc ggcctgctga ctcgagatcg   2100
atatccatca cactggcggc cgcaagctta tcgataatca acctctggat tacaaaattt   2160
gtgaaagatt gactggtatt cttaactatg ttgctccttt tacgctatgt ggatacgctg   2220
ctttaatgcc tttgtatcat gctattgctt cccgtatggc tttcattttc tcctccttgt   2280
ataaatcctg gttgctgtct ctttatgagg agttgtggcc cgttgtcagg caacgtggcg   2340
tggtgtgcac tgtgtttgct gacgcaaccc ccactggttg gggcattgcc accacctgtc   2400
agctcctttc cgggactttc gctttccccc tccctattgc cacggcggaa ctcatcgccg   2460
cctgccttgc ccgctgctgg acaggggctc ggctgttggg cactgacaat tccgtggtgt   2520
tgtcggggaa atcatcgtcc tttccttggc tgctcgcctg tgttgccacc tggattctgc   2580
gcgggacgtc cttctgctac gtcccttcgg ccctcaatcc agcggacctt ccttcccgcg   2640
gcctgctgcc ggctctgcgg cctcttccgc gtcttcgcct tcgccctcag acgagtcgga   2700
tctccctttg ggccgcctcc ccgcatcgat accgtcgact cgctgatcag cctcgactgt   2760
gccttctagt tgccagccat ctgttgtttg cccctccccc gtgccttcct tgaccctgga   2820
aggtgccact cccactgtcc tttcctaata aaatgaggaa attgcatcgc attgtctgag   2880
taggtgtcat tctattctgg ggggtggggt ggggcaggac agcaaggggg aggattggga   2940
agacaatagc aggcatgctg gggatgcggt gggctctatg gcttctgagg cggaaagaac   3000
cagctggggc tcgactagag catggctacg tagataagta gcatggcggg ttaatcatta   3060
actacaagga acccctagtg atggagttgg ccactccctc tctgcgcgct cgctcgctca   3120
ctgaggccgg gcgaccaaag gtcgcccgac gcccgggctt tgcccgggcg gcctcagtga   3180
gcgagcgagc gcgcagagct ttttgcaaaa gcctaggcct ccaaaaaagc ctcctcacta   3240
cttctggaat agctcagagg ccgaggcggc ctcggcctct gcataaataa aaaaaattag   3300
tcagccatgg ggcggagaat gggcggaact gggcggagtt aggggcggga tgggcggagt   3360
taggggcggg actatggttg ctgactaatt gagatgcatg ctttgcatac ttctgcctgc   3420
tggggagcct ggggactttc cacacctggt tgctgactaa ttgagatgca tgctttgcat   3480
acttctgcct gctggggagc ctggggactt tccacaccct aactgacaca cattccacag   3540
ctgcattaat gaatcggcca acgcgcgggg agaggcggtt tgcgtattgg gcgctcttcc   3600
gcttcctcgc tcactgactc gctgcgctcg gtcgttcggc tgcggcgagc ggtatcagct   3660
cactcaaagg cggtaatacg gttatccaca gaatcagggg ataacgcagg aaagaacatg   3720
tgagcaaaag gccagcaaaa ggccaggaac cgtaaaaagg ccgcgttgct ggcgtttttc   3780
cataggctcc gcccccctga cgagcatcac aaaaatcgac gctcaagtca gaggtggcga   3840
aacccgacag gactataaag ataccaggcg tttccccctg gaagctccct cgtgcgctct   3900
cctgttccga ccctgccgct taccggatac ctgtccgcct ttctcccttc gggaagcgtg   3960
gcgctttctc atagctcacg ctgtaggtat ctcagttcgg tgtaggtcgt tcgctccaag   4020
ctgggctgtg tgcacgaacc ccccgttcag cccgaccgct gcgccttatc cggtaactat   4080
cgtcttgagt ccaacccggt aagacacgac ttatcgccac tggcagcagc cactggtaac   4140
aggattagca gagcgaggta tgtaggcggt gctacagagt tcttgaagtg gtggcctaac   4200
tacggctaca ctagaagaac agtatttggt atctgcgctc tgctgaagcc agttaccttc   4260
ggaaaaagag ttggtagctc ttgatccggc aaacaaacca ccgctggtag cggtggtttt   4320
tttgtttgca agcagcagat tacgcgcaga aaaaaaggat ctcaagaaga tcctttgatc   4380
```

```
ttttctacgg ggtctgacgc tcagtggaac gaaaactcac gttaagggat tttggtcatg   4440

agattatcaa aaaggatctt cacctagatc cttttaaatt aaaaatgaag ttttaaatca   4500

atctaaagta tatatgagta aacttggtct gacagttacc aatgcttaat cagtgaggca   4560

cctatctcag cgatctgtct atttcgttca tccatagttg cctgactccc cgtcgtgtag   4620

ataactacga tacgggaggg cttaccatct ggccccagtg ctgcaatgat accgcgagac   4680

ccacgctcac cggctccaga tttatcagca ataaaccagc cagccggaag ggccgagcgc   4740

agaagtggtc ctgcaacttt atccgcctcc atccagtcta ttaattgttg ccgggaagct   4800

agagtaagta gttcgccagt taatagtttg cgcaacgttg ttgccattgc tacaggcatc   4860

gtggtgtcac gctcgtcgtt tggtatggct tcattcagct ccggttccca acgatcaagg   4920

cgagttacat gatcccccat gttgtgcaaa aaagcggtta gctccttcgg tcctccgatc   4980

gttgtcagaa gtaagttggc cgcagtgtta tcactcatgg ttatggcagc actgcataat   5040

tctcttactg tcatgccatc cgtaagatgc ttttctgtga ctggtgagta ctcaaccaag   5100

tcattctgag aatagtgtat gcggcgaccg agttgctctt gcccggcgtc aatacgggat   5160

aataccgcgc cacatagcag aactttaaaa gtgctcatca ttggaaaacg ttcttcgggg   5220

cgaaaactct caaggatctt accgctgttg agatccagtt cgatgtaacc cactcgtgca   5280

cccaactgat cttcagcatc ttttactttc accagcgttt ctgggtgagc aaaaacagga   5340

aggcaaaatg ccgcaaaaaa gggaataagg gcgacacgga aatgttgaat actcatactc   5400

ttcctttttc aatattattg aagcatttat cagggttatt gtctcatgag cggatacata   5460

tttgaatgta tttagaaaaa taaacaaata ggggttccgc gcacatttcc ccgaaaagtg   5520

ccacctgacg tctaagaaac cattattatc atgacattaa cctataaaaa taggcgtatc   5580

acgaggccct ttcgtctcgc gcgtttcggt gatgacggtg aaaacctctg acacatgcag   5640

ctcccggaga cggtcacagc ttgtctgtaa gcggatgccg ggagcagaca agcccgtcag   5700

ggcgcgtcag cgggtgttgg cgggtgtcgg ggctggctta actatgcggc atcagagcag   5760

attgtactga gagtgcacca ttcgacgctc tcccttatgc gactcctgca ttaggaagca   5820

gcccagtagt aggttgaggc cgttgagcac cgccgccgca aggaatggtg catgcaagga   5880

gatggcgccc aacagtcccc cggccacggg gcctgccacc atacccacgc cgaaacaagc   5940

gctcatgagc ccgaagtggc gagcccgatc ttccccatcg gtgatgtcgg cgatataggc   6000

gccagcaacc gcacctgtgg cgccggtgat gccggccacg atgcgtccgg cgtagaggat   6060

ctggctagcg atgaccctgc tgattggttc gctgaccatt tccgggtgcg ggacggcgtt   6120

accagaaact cagaaggttc gtccaaccaa accgactctg acggcagttt acgagagaga   6180

tgatagggtc tgcttcagta agccagatgc tacacaatta ggcttgtaca tattgtcgtt   6240

agaacgcggc tacaattaat acataacctt atgtatcata cacatacgat ttaggtgaca   6300

ctatagaata cacggaatta attc                                          6324
```

```
<210> SEQ ID NO 18
<211> LENGTH: 1024
<212> TYPE: DNA
<213> ORGANISM: Homo sapiens
<220> FEATURE:
<223> OTHER INFORMATION: Human hP0 promoter

<400> SEQUENCE: 18

gcctggcata aacttcattt attaaagttt attttgtctt taatctctca tataacttag     60
```

-continued

```
tcttcctgat attgcagctg tgtgtgcccc tcttttgtac tcccagcatt ttgttcatta    120

ctaaaggaag tgtcatggct tattatactt gattgttgat gggtttgtcc tctgatcttc    180

ccatctccac ctccccaaac caaattttca actccttgct ggaaggactt aatttttatt    240

cctctctcta ttacctgcat tctcatactt tacatattgc tggcacttaa tacaattttg    300

tagccttgaa ataaattgaa atggacttaa acagcagcat gaagcactga aggacttctt    360

gacaaacgga aaggtcaggg gcttcttgcc tggaaatagt ccagtggaga aaaacttctg    420

tctgggaaga atcgcacagg atgaagggag gtgcggggaa aaaaactccc ataggacttg    480

gtcatctcaa gaagtctgta atgcagccca cattagagga gataacaggg gatatcctat    540

tttcagagtt ctctggggga aacctccctc tagttcctag ggctgtgagg cagcctctct    600

caggcaagga ggctgaggag aaatcccttt ttatggcctt taaattgagg ttccatatct    660

atccctcaga gaagtgtgtc tgtgtccctg tttttgtccc tctccctcac caccccccac    720

aacattccag cctggggcag ggggaggcca gtggacacaa agccctctgt gtatggggtg    780

gtatgtgtcc ccccacccct ccacccagac tatacaatgc cccttctgct ccctgcactc    840

tgccccccctc cccaccacct ctcaactgca catgccaggc tgcaattggt tactggctga    900

ggacagcccc ctcatgctgg ggccctaggg gattttaagc aggttccagg aaccccccgt    960

tcagttcctg gtcccccact ttctcaaccc cacagatgct ccgggcccct gcccctgccc   1020

cagc                                                                1024
```

<210> SEQ ID NO 19
<211> LENGTH: 6162
<212> TYPE: DNA
<213> ORGANISM: Artificial Sequence
<220> FEATURE:
<223> OTHER INFORMATION: AAV-human-Mpz-Egfp mock construct

<400> SEQUENCE: 19

```
tagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac gtagccatgc    180

tctaggtacc gcctggcata aacttcattt attaaagttt attttgtctt taatctctca    240

tataacttag tcttcctgat attgcagctg tgtgtgcccc tcttttgtac tcccagcatt    300

ttgttcatta ctaaaggaag tgtcatggct tattatactt gattgttgat gggtttgtcc    360

tctgatcttc ccatctccac ctccccaaac caaattttca actccttgct ggaaggactt    420

aatttttatt cctctctcta ttacctgcat tctcatactt tacatattgc tggcacttaa    480

tacaattttg tagccttgaa ataaattgaa atggacttaa acagcagcat gaagcactga    540

aggacttctt gacaaacgga aaggtcaggg gcttcttgcc tggaaatagt ccagtggaga    600

aaaacttctg tctgggaaga atcgcacagg atgaagggag gtgcggggaa aaaaactccc    660

ataggacttg gtcatctcaa gaagtctgta atgcagccca cattagagga gataacaggg    720

gatatcctat tttcagagtt ctctggggga aacctccctc tagttcctag ggctgtgagg    780

cagcctctct caggcaagga ggctgaggag aaatcccttt ttatggcctt taaattgagg    840

ttccatatct atccctcaga gaagtgtgtc tgtgtccctg tttttgtccc tctccctcac    900

caccccccac aacattccag cctggggcag ggggaggcca gtggacacaa agccctctgt    960

gtatggggtg gtatgtgtcc ccccacccct ccacccagac tatacaatgc cccttctgct   1020

ccctgcactc tgccccccctc cccaccacct ctcaactgca catgccaggc tgcaattggt   1080
```

-continued tactggctga ggacagcccc ctcatgctgg ggccctaggg gatttttaagc aggttccagg 1140 aacccccgt tcagttcctg gtccccact ttctcaaccc cacagatgct ccgggcccct 1200
gcccctgccc cagcaccggt cgccaccatg gtgagcaagg gcgaggagct gttcaccggg 1260
gtggtgccca tcctggtcga gctggacggc gacgtaaacg gccacaagtt cagcgtgtcc 1320
ggcgagggcg agggcgatgc cacctacggc aagctgaccc tgaagttcat ctgcaccacc 1380
ggcaagctgc ccgtgccctg gcccaccctc gtgaccaccc tgacctacgg cgtgcagtgc 1440
ttcagccgct accccgacca catgaagcag cacgacttct tcaagtccgc catgcccgaa 1500
ggctacgtcc aggagcgcac catcttcttc aaggacgacg gcaactacaa gacccgcgcc 1560
gaggtgaagt tcgagggcga caccctggtg aaccgcatcg agctgaaggg catcgacttc 1620
aaggaggacg gcaacatcct ggggcacaag ctggagtaca actacaacag ccacaacgtc 1680
tatatcatgg ccgacaagca gaagaacggc atcaaggtga acttcaagat ccgccacaac 1740
atcgaggacg gcagcgtgca gctcgccgac cactaccagc agaacacccc catcggcgac 1800
ggccccgtgc tgctgcccga caaccactac ctgagcaccc agtccgccct gagcaaagac 1860
cccaacgaga agcgcgatca catggtcctg ctggagttcg tgaccgccgc cgggatcact 1920
ctcggcatgg acgagctgta caagtaaagc ggccctagat caagcttatc gataatcaac 1980
ctctggatta caaaatttgt gaaagattga ctggtattct taactatgtt gctcctttta 2040
cgctatgtgg atacgctgct ttaatgcctt tgtatcatgc tattgcttcc cgtatggctt 2100
tcattttctc ctccttgtat aaatcctggt tgctgtctct ttatgaggag ttgtggcccg 2160
ttgtcaggca acgtggcgtg gtgtgcactg tgtttgctga cgcaaccccc actggttggg 2220
gcattgccac cacctgtcag ctcctttccg ggactttcgc tttccccctc cctattgcca 2280
cggcggaact catcgccgcc tgccttgccc gctgctggac aggggctcgg ctgttgggca 2340
ctgacaattc cgtggtgttg tcggggaaat catcgtcctt tccttggctg ctcgcctgtg 2400
ttgccacctg gattctgcgc gggacgtcct tctgctacgt cccttcggcc ctcaatccag 2460
cggaccttcc ttcccgcggc ctgctgccgg ctctgcggcc tcttccgcgt cttcgccttc 2520
gccctcagac gagtcggatc tccctttggg ccgcctcccc gcatcgatac cgtcgactcg 2580
ctgatcagcc tcgactgtgc cttctagttg ccagccatct gttgtttgcc cctcccccgt 2640
gccttccttg accctggaag gtgccactcc cactgtcctt tcctaataaa atgaggaaat 2700
tgcatcgcat tgtctgagta ggtgtcattc tattctgggg ggtggggtgg ggcaggacag 2760
caagggggag gattgggaag acaatagcag gcatgctggg gatgcggtgg gctctatggc 2820
ttctgaggcg gaaagaacca gctggggctc gactagagca tggctacgta gataagtagc 2880
atggcgggtt aatcattaac tacaaggaac ccctagtgat ggagttggcc actccctctc 2940
tgcgcgctcg ctcgctcact gaggccgggc gaccaaaggt cgcccgacgc ccgggctttg 3000
cccgggcggc ctcagtgagc gagcgagcgc gcagagcttt ttgcaaaagc ctaggcctcc 3060
aaaaaagcct cctcactact tctggaatag ctcagaggcc gaggcggcct cggcctctgc 3120
ataaataaaa aaaattagtc agccatgggg cggagaatgg gcggaactgg gcggagttag 3180
gggcgggatg ggcggagtta ggggcgggac tatggttgct gactaattga gatgcatgct 3240
ttgcatactt ctgcctgctg gggagcctgg ggactttcca cacctggttg ctgactaatt 3300
gagatgcatg ctttgcatac ttctgcctgc tggggagcct ggggactttc cacaccctaa 3360
ctgacacaca ttccacagct gcattaatga atcggccaac gcgcggggag aggcggtttg 3420

```
cgtattgggc gctcttccgc ttcctcgctc actgactcgc tgcgctcggt cgttcggctg   3480
cggcgagcgg tatcagctca ctcaaaggcg gtaatacggt tatccacaga atcaggggat   3540
aacgcaggaa agaacatgtg agcaaaaggc cagcaaaagg ccaggaaccg taaaaaggcc   3600
gcgttgctgg cgtttttcca taggctccgc ccccctgacg agcatcacaa aaatcgacgc   3660
tcaagtcaga ggtggcgaaa cccgacagga ctataaagat accaggcgtt tccccctgga   3720
agctccctcg tgcgctctcc tgttccgacc ctgccgctta ccggatacct gtccgccttt   3780
ctcccttcgg gaagcgtggc gctttctcat agctcacgct gtaggtatct cagttcggtg   3840
taggtcgttc gctccaagct gggctgtgtg cacgaacccc ccgttcagcc cgaccgctgc   3900
gccttatccg gtaactatcg tcttgagtcc aacccggtaa gacacgactt atcgccactg   3960
gcagcagcca ctggtaacag gattagcaga gcgaggtatg taggcggtgc tacagagttc   4020
ttgaagtggt ggcctaacta cggctacact agaagaacag tatttggtat ctgcgctctg   4080
ctgaagccag ttaccttcgg aaaaagagtt ggtagctctt gatccggcaa acaaaccacc   4140
gctggtagcg gtggtttttt tgtttgcaag cagcagatta cgcgcagaaa aaaaggatct   4200
caagaagatc ctttgatctt ttctacgggg tctgacgctc agtggaacga aaactcacgt   4260
taagggattt tggtcatgag attatcaaaa aggatcttca cctagatcct tttaaattaa   4320
aaatgaagtt ttaaatcaat ctaaagtata tatgagtaaa cttggtctga cagttaccaa   4380
tgcttaatca gtgaggcacc tatctcagcg atctgtctat ttcgttcatc catagttgcc   4440
tgactccccg tcgtgtagat aactacgata cgggagggct taccatctgg ccccagtgct   4500
gcaatgatac cgcgagaccc acgctcaccg gctccagatt tatcagcaat aaaccagcca   4560
gccggaaggg ccgagcgcag aagtggtcct gcaactttat ccgcctccat ccagtctatt   4620
aattgttgcc gggaagctag agtaagtagt tcgccagtta atagtttgcg caacgttgtt   4680
gccattgcta caggcatcgt ggtgtcacgc tcgtcgtttg gtatggcttc attcagctcc   4740
ggttcccaac gatcaaggcg agttacatga tcccccatgt tgtgcaaaaa agcggttagc   4800
tccttcggtc ctccgatcgt tgtcagaagt aagttggccg cagtgttatc actcatggtt   4860
atggcagcac tgcataattc tcttactgtc atgccatccg taagatgctt ttctgtgact   4920
ggtgagtact caaccaagtc attctgagaa tagtgtatgc ggcgaccgag ttgctcttgc   4980
ccggcgtcaa tacgggataa taccgcgcca catagcagaa ctttaaaagt gctcatcatt   5040
ggaaaacgtt cttcggggcg aaaactctca aggatcttac cgctgttgag atccagttcg   5100
atgtaaccca ctcgtgcacc caactgatct tcagcatctt ttactttcac cagcgtttct   5160
gggtgagcaa aaacaggaag gcaaaatgcc gcaaaaaagg gaataagggc gacacggaaa   5220
tgttgaatac tcatactctt cctttttcaa tattattgaa gcatttatca gggttattgt   5280
ctcatgagcg gatacatatt tgaatgtatt tagaaaaata aacaaatagg ggttccgcgc   5340
acatttcccc gaaaagtgcc acctgacgtc taagaaacca ttattatcat gacattaacc   5400
tataaaaata ggcgtatcac gaggcccttt cgtctcgcgc gtttcggtga tgacggtgaa   5460
aacctctgac acatgcagct cccggagacg gtcacagctt gtctgtaagc ggatgccggg   5520
agcagacaag cccgtcaggg cgcgtcagcg ggtgttggcg ggtgtcgggg ctggcttaac   5580
tatgcggcat cagagcagat tgtactgaga gtgcaccatt cgacgctctc ccttatgcga   5640
ctcctgcatt aggaagcagc ccagtagtag gttgaggccg ttgagcaccg ccgccgcaag   5700
gaatggtgca tgcaaggaga tggcgcccaa cagtcccccg gccacggggc ctgccaccat   5760
acccacgccg aaacaagcgc tcatgagccc gaagtggcga gcccgatctt ccccatcggt   5820
```

-continued

```
gatgtcggcg atataggcgc cagcaaccgc acctgtggcg ccggtgatgc cggccacgat   5880

gcgtccggcg tagaggatct ggctagcgat gaccctgctg attggttcgc tgaccatttc   5940

cgggtgcggg acggcgttac cagaaactca gaaggttcgt ccaaccaaac cgactctgac   6000

ggcagtttac gagagagatg atagggtctg cttcagtaag ccagatgcta cacaattagg   6060

cttgtacata ttgtcgttag aacgcggcta caattaatac ataaccttat gtatcataca   6120

catacgattt aggtgacact atagaataca cggaattaat tc                      6162
```

```
<210> SEQ ID NO 20
<211> LENGTH: 7916
<212> TYPE: DNA
<213> ORGANISM: Artificial Sequence
<220> FEATURE:
<223> OTHER INFORMATION: AAV-minMpz-SH3TC2.myc.ITR

<400> SEQUENCE: 20
```

```
tagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac gtagccatgc    180

tctaggtacc gctctcaggc aaggaggcta agaaggaatc ctttgctgta gccttttgga    240

tttaggtttc tcagcttatc tatccctcag agaagtgtgt ctatgtccct tttctgtccc    300

tctgcctcac cccaccccaa cattccaacc tagggtaggg ggaggtcagt atacacaaag    360

ccctctgtgt aaggggtggt atgtgtcccc ccaccccct acccagagta tacaatgccc     420

cttctgctcc atgcccctgc cacccctccc accacctctc aattgcacat gccaggctgc    480

aattggtcac tggctcagga cagccccctc atgctgggga tccaggggat tttaagcagg    540

ttccagaaaa caccactcag ttccttgtcc cccgctctct ccaccccaca gacgctctgc    600

caaccggtac catgggtggc tgcttctgca tccccaggga gcggagtctg acccggggcc    660

caggtaaaga aactccttcc aaggatccaa ctgtatcgag tgagtgtata gcctcatctg    720

aatacaagga aaaatgtttt ctgccacaga acattaatcc agacctgaca ctctccttct    780

gtgtaaagag ccgctccagg aggtgtgtaa atggacccct acaggaagct gctcggaggc    840

ggctctgggc actggagaat gaggaccagg aggtgcgcat gctgtttaag gacctctcag    900

caaggttggt cagtatccag tctcagaggg cccagtttct catcaccttc aagaccatgg    960

aggaaatctg gaagttctcc acctacctta atttaggcta cgtatccatg tgtctagaac   1020

atctcctctt tgaccacaag tactggctca actgcatatt ggtggaggat acagagatcc   1080

aagtgtctgt agatgataaa cacctggaaa caatatacct gggactcctg atacaggaag   1140

gccacttctt ctgcagagcc ctgtgctccg tgactccacc agccgagaag gaaggggaat   1200

gcttgacact ttgcaagaat gagttaatct cagtgaagat ggcagaagct ggctccgagt   1260

tggaaggcgt gtctttggtg acaggtcagc ggggcctggt actggtgtca gccttggagc   1320

ctctgcctct ccctttccac cagtggttcc taaagaatta tccaggaagc tgtggccttt   1380

ccaggaagag ggattggaca ggctcctatc agattggcag aggacgctgt aaggccttga   1440

cgggttatga gccaggagaa aaggatgaac tgaatttcta ccagggagaa agcattgaga   1500

tcatcggctt tgtcatacct gggcttcagt ggttcattgg aaagtcgaca agttcaggac   1560

aagtgggctt tgtccccacc aggaacatag atcctgattc ttattcccca atgagcagga   1620

actctgcctt tctcagtgat gaggagagat gctccctgtt ggccctggga agtgataagc   1680
```

-continued

```
agactgagtg ttccagcttc ctccacactc ttgctcgcac tgacatcaca tctgtctacc   1740
ggctcagtgg gtttgaatcc atccagaatc ctccaaatga tctgagtgca tcccagcctg   1800
aaggtttcaa ggaggtcagg cctggcagag cctgggagga gcatcaggcc gtggggtcca   1860
gacagtccag cagctctgag gactccagcc tggaggagga gctcctctcg gccacctcag   1920
acagctatcg cctgccggag cctgatgacc ttgatgaccc ggaactgctc atggacctaa   1980
gcactggtca ggaggaggag gctgagaact tcgcccccat attggctttt ctggatcatg   2040
agggttatgc tgaccacttt aagagtctct atgacttctc cttctctttc ctcacttctt   2100
ccttttatag cttctctgag gaggatgagt ttgtggccta cctggaggca tcaagaaagt   2160
gggccaagaa gagccacatg acctgggccc atgcccggct ctgcttcctc ctgggccggc   2220
tgagcatcag gaaggtcaaa ctctctcagg ccagggtgta cttcgaggag gccatccaca   2280
ttctcaatgg agcatttgag gacctatcct tggtggccac tctgtacatc aatttggctg   2340
ccatctacct gaaacagagg ctgagacata aaggctccgc cctgttggaa aaggcaggtg   2400
ccctgctggc ctgcctgcct gaccgtgagt ctagtgccaa gcatgaactc gacgtggtgg   2460
cctacgtgct gcgccagggg attgtggtgg gcagcagccc gctggaggcc agggcctgct   2520
ttctggccat ccgcttgctc ctgagcctag gccggcacga ggaggtcctg ccctttgccg   2580
agcgcctgca gctcctctct ggacaccctc ctgcctctga ggctgtggcc agtgttttga   2640
gttttctgta tgacaagaaa tatcttccac accttgcagt ggcctctgtc cagcaacatg   2700
gtatccagag tgcccaaggg atgtctcttc ctatttggca ggtccacctt gtcctccaga   2760
acacaaccaa gctccttggc tttccttccc caggctgggg tgaagtttct gccttggcct   2820
gcccaatgct cagacaggcc ctggctgcct gtgaggaact agcagaccgg agcacccaga   2880
gggccctgtg tctcatcctt tccaaagtgt acctcgagca caggtctcct gacggtgcca   2940
tccactacct gagccaggcc ttggtgctag ggcagctgct gggtgagcag gaatcctttg   3000
agtcttctct ctgcctggca tgggcctatc tcttagccag ccaggccaag aaggctttgg   3060
atgtgcttga gccactgcta tgctccctga aggagacaga gagtctcact caaaggggag   3120
tcatctataa cctcctggga cttgcactcc aaggtgaagg ccgggtgaac agggcagcca   3180
agagctatct tcgggccttg aacagagccc aggaggtggg agatgtgcat aaccaggcag   3240
tggctatggc caatcttggc cacctgagcc ttaagtcctg ggctcagcat ccagccagaa   3300
actatctcct gcaggctgta cgactctatt gtgaacttca ggccagtaag gagacagaca   3360
tggaattagt acaggtgttt ctctggttgg cccaagttct ggtgtctgga caccagctga   3420
cccatggcct tctttgttat gaaatggcat tgctgtttgg cttaaggcat cgacatctaa   3480
agagtcagct tcaggccacc aaatccctct gccatttcta cagctctgtg tccccaaacc   3540
ctgaggcatg catcacctac catgagcact ggctggccct ggctcagcaa ctcagggacc   3600
gggagatgga agggaggctg ctggagtccc tggggcagct ttatcggaac ctaaataccg   3660
ccaggtccct caggaggtca ctcacatgca tcaaggagag cctgcgtatc ttcattgacc   3720
tgggggagac agacaaggct gctgaggcct ggcttggggc ggggcgactc cactacctca   3780
tgcaggaaga cgagctggtg gagctgtgcc tgcaggcagc catccagaca gccctgaagt   3840
cagaggagcc tttgctggct ctcaaacttt atgaagaagc aggtgatgtg ttcttcaatg   3900
ggacccgcca caggcatcat gcagtggagt actaccgagc tggagctgtt cctttagcaa   3960
ggaggttgaa ggcggtgaga actgagctcc ggattttcaa taagctgaca gagctgcaga   4020
ttagcctcga aggctatgag aaggctttgg aatttgccac cctggccgcc aggctcagca   4080
```

```
cagtcacagg agatcagagg caagagctgg tggcctttca ccgcctggct acagtgtact   4140
actccctgca catgtatgag atggctgagg actgctacct gaagaccctg tccctctgtc   4200
caccatggct gcagagtccc aaggaggccc tgtactatgc caaggtgtat tatcgcctgg   4260
gcagactcac cttctgccag ctgaaggatg cccatgatgc cactgagtac ttccttctgg   4320
ccctggcagc agcggtcctg ctgggtgatg aggagcttca ggacaccatt aggagcaggc   4380
tggacaacat ctgccagagc cccctgtggc acagcaggcc ctccgggtgc tcctcagaga   4440
gggcgcggtg gctgagtggt ggtggcctgg ccctcgagca gaagctgatc agcgaggagg   4500
acctgtaaga tatccatcac actggcggcc gcggagctct cgagaggcct aataaagagc   4560
tcagatgcat cgatcagagt gtgttggttt tttgtgtgag atctaagctt agcatggcta   4620
cgtagataag tagcatggcg ggttaatcat taactacaag gaacccctag tgatggagtt   4680
ggccactccc tctctgcgcg ctcgctcgct cactgaggcc gggcgaccaa aggtcgcccg   4740
acgcccgggc tttgcccggg cggcctcagt gagcgagcga gcgcgcagag ctttttgcaa   4800
aagcctaggc ctccaaaaaa gcctcctcac tacttctgga atagctcaga ggccgaggcg   4860
gcctcggcct ctgcataaat aaaaaaaatt agtcagccat ggggcggaga atgggcggaa   4920
ctgggcggag ttaggggcgg gatgggcgga gttaggggcg ggactatggt tgctgactaa   4980
ttgagatgca tgctttgcat acttctgcct gctggggagc ctggggactt tccacacctg   5040
gttgctgact aattgagatg catgctttgc atacttctgc ctgctgggga gcctggggac   5100
tttccacacc ctaactgaca cacattccac agctgcatta atgaatcggc caacgcgcgg   5160
ggagaggcgg tttgcgtatt gggcgctctt ccgcttcctc gctcactgac tcgctgcgct   5220
cggtcgttcg gctgcggcga gcggtatcag ctcactcaaa ggcggtaata cggttatcca   5280
cagaatcagg ggataacgca ggaaagaaca tgtgagcaaa aggccagcaa aaggccagga   5340
accgtaaaaa ggccgcgttg ctggcgtttt tccataggct ccgcccccct gacgagcatc   5400
acaaaaatcg acgctcaagt cagaggtggc gaaacccgac aggactataa agataccagg   5460
cgtttccccc tggaagctcc ctcgtgcgct ctcctgttcc gaccctgccg cttaccggat   5520
acctgtccgc ctttctccct tcgggaagcg tggcgctttc tcatagctca cgctgtaggt   5580
atctcagttc ggtgtaggtc gttcgctcca agctgggctg tgtgcacgaa ccccccgttc   5640
agcccgaccg ctgcgcctta tccggtaact atcgtcttga gtccaacccg gtaagacacg   5700
acttatcgcc actggcagca gccactggta acaggattag cagagcgagg tatgtaggcg   5760
gtgctacaga gttcttgaag tggtggccta actacggcta cactagaaga acagtatttg   5820
gtatctgcgc tctgctgaag ccagttacct tcggaaaaag agttggtagc tcttgatccg   5880
gcaaacaaac caccgctggt agcggtggtt tttttgtttg caagcagcag attacgcgca   5940
gaaaaaaagg atctcaagaa gatcctttga tcttttctac ggggtctgac gctcagtgga   6000
acgaaaactc acgttaaggg attttggtca tgagattatc aaaaaggatc ttcacctaga   6060
tccttttaaa ttaaaaatga agttttaaat caatctaaag tatatatgag taaacttggt   6120
ctgacagtta ccaatgctta atcagtgagg cacctatctc agcgatctgt ctatttcgtt   6180
catccatagt tgcctgactc cccgtcgtgt agataactac gatacgggag ggcttaccat   6240
ctggccccag tgctgcaatg ataccgcgag acccacgctc accggctcca gatttatcag   6300
caataaacca gccagccgga agggccgagc gcagaagtgg tcctgcaact ttatccgcct   6360
ccatccagtc tattaattgt tgccgggaag ctagagtaag tagttcgcca gttaatagtt   6420
```

```
tgcgcaacgt tgttgccatt gctacaggca tcgtggtgtc acgctcgtcg tttggtatgg   6480
cttcattcag ctccggttcc caacgatcaa ggcgagttac atgatccccc atgttgtgca   6540
aaaaagcggt tagctccttc ggtcctccga tcgttgtcag aagtaagttg gccgcagtgt   6600
tatcactcat ggttatggca gcactgcata attctcttac tgtcatgcca tccgtaagat   6660
gcttttctgt gactggtgag tactcaacca agtcattctg agaatagtgt atgcggcgac   6720
cgagttgctc ttgcccggcg tcaatacggg ataataccgc gccacatagc agaactttaa   6780
aagtgctcat cattggaaaa cgttcttcgg ggcgaaaact ctcaaggatc ttaccgctgt   6840
tgagatccag ttcgatgtaa cccactcgtg cacccaactg atcttcagca tcttttactt   6900
tcaccagcgt ttctgggtga gcaaaaacag gaaggcaaaa tgccgcaaaa aagggaataa   6960
gggcgacacg gaaatgttga atactcatac tcttcctttt tcaatattat tgaagcattt   7020
atcagggtta ttgtctcatg agcggataca tatttgaatg tatttagaaa aataaacaaa   7080
taggggttcc gcgcacattt ccccgaaaag tgccacctga cgtctaagaa accattatta   7140
tcatgacatt aacctataaa aataggcgta tcacgaggcc ctttcgtctc gcgcgtttcg   7200
gtgatgacgg tgaaaacctc tgacacatgc agctcccgga gacggtcaca gcttgtctgt   7260
aagcggatgc cgggagcaga caagcccgtc agggcgcgtc agcgggtgtt ggcgggtgtc   7320
ggggctggct taactatgcg gcatcagagc agattgtact gagagtgcac cattcgacgc   7380
tctcccttat gcgactcctg cattaggaag cagcccagta gtaggttgag gccgttgagc   7440
accgccgccg caaggaatgg tgcatgcaag gagatggcgc ccaacagtcc cccggccacg   7500
gggcctgcca ccatacccac gccgaaacaa gcgctcatga gcccgaagtg gcgagcccga   7560
tcttccccat cggtgatgtc ggcgatatag gcgccagcaa ccgcacctgt ggcgccggtg   7620
atgccggcca cgatgcgtcc ggcgtagagg atctggctag cgatgaccct gctgattggt   7680
tcgctgacca tttccgggtg cgggacggcg ttaccagaaa ctcagaaggt tcgtccaacc   7740
aaaccgactc tgacggcagt ttacgagaga gatgataggg tctgcttcag taagccagat   7800
gctacacaat taggcttgta catattgtcg ttagaacgcg gctacaatta atacataacc   7860
ttatgtatca tacacatacg atttaggtga cactatagaa tacacggaat taattc       7916
```

<210> SEQ ID NO 21
<211> LENGTH: 7884
<212> TYPE: DNA
<213> ORGANISM: Artificial Sequence
<220> FEATURE:
<223> OTHER INFORMATION: AAV-human-miniMpz-SH3TC2

<400> SEQUENCE: 21

```
tagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctaggtacc tctctcaggc aaggaggctg aggagaaatc ccttttttatg gcctttaaat    240
tgaggttcca tatctatccc tcagagaagt gtgtctgtgt ccctgttttt gtccctctcc    300
ctcaccaccc cccacaacat tccagcctgg ggcaggggga ggccagtgga cacaaagccc    360
tctgtgtatg gggtggtatg tgtcccccca cccctccacc cagactatac aatgcccctt    420
ctgctccctg cactctgccc ccctccccac cacctctcaa ctgcacatgc caggctgcaa    480
ttggttactg gctgaggaca gccccctcat gctggggccc taggggattt taagcaggtt    540
ccaggaaccc cccgttcagt tcctggtccc ccactttctc aaccccacag atgctccggg    600
```

-continued

```
cccctgcccc tgccccagcg gtaccatggg tggctgcttc tgcatcccca gggagcggag    660
tctgacccgg ggcccaggta aagaaactcc ttccaaggat ccaactgtat cgagtgagtg    720
tatagcctca tctgaataca aggaaaaatg ttttctgcca cagaacatta atccagacct    780
gacactctcc ttctgtgtaa agagccgctc caggaggtgt gtaaatggac ccctacagga    840
agctgctcgg aggcggctct gggcactgga gaatgaggac caggaggtgc gcatgctgtt    900
taaggacctc tcagcaaggt tggtcagtat ccagtctcag agggcccagt ttctcatcac    960
cttcaagacc atggaggaaa tctggaagtt ctccacctac cttaatttag gctacgtatc   1020
catgtgtcta gaacatctcc tctttgacca caagtactgg ctcaactgca tattggtgga   1080
ggatacagag atccaagtgt ctgtagatga taaacacctg gaaacaatat acctgggact   1140
cctgatacag gaaggccact tcttctgcag agccctgtgc tccgtgactc caccagccga   1200
gaaggaaggg gaatgcttga cactttgcaa gaatgagtta atctcagtga agatggcaga   1260
agctggctcc gagttggaag gcgtgtcttt ggtgacaggt cagcggggcc tggtactggt   1320
gtcagccttg gagcctctgc ctctcccttt ccaccagtgg ttcctaaaga attatccagg   1380
aagctgtggc ctttccagga agagggattg gacaggctcc tatcagattg gcagaggacg   1440
ctgtaaggcc ttgacgggtt atgagccagg agaaaaggat gaactgaatt tctaccaggg   1500
agaaagcatt gagatcatcg gctttgtcat acctgggctt cagtggttca ttggaaagtc   1560
gacaagttca ggacaagtgg gctttgtccc caccaggaac atagatcctg attcttattc   1620
cccaatgagc aggaactctg cctttctcag tgatgaggag agatgctccc tgttggccct   1680
gggaagtgat aagcagactg agtgttccag cttcctccac actcttgctc gcactgacat   1740
cacatctgtc taccggctca gtgggtttga atccatccag aatcctccaa atgatctgag   1800
tgcatcccag cctgaaggtt tcaaggaggt caggcctggc agagcctggg aggagcatca   1860
ggccgtgggg tccagacagt ccagcagctc tgaggactcc agcctggagg aggagctcct   1920
ctcggccacc tcagacagct atcgcctgcc ggagcctgat gaccttgatg acccggaact   1980
gctcatggac ctaagcactg gtcaggagga ggaggctgag aacttcgccc ccatattggc   2040
ttttctggat catgagggtt atgctgacca ctttaagagt ctctatgact tctccttctc   2100
tttcctcact tcttcctttt atagcttctc tgaggaggat gagtttgtgg cctacctgga   2160
ggcatcaaga aagtgggcca agaagagcca catgacctgg gcccatgccc ggctctgctt   2220
cctcctgggc cggctgagca tcaggaaggt caaactctct caggccaggg tgtacttcga   2280
ggaggccatc cacattctca atggagcatt tgaggaccta tccttggtgg ccactctgta   2340
catcaatttg gctgccatct acctgaaaca gaggctgaga cataaaggct ccgccctgtt   2400
ggaaaaggca ggtgccctgc tggcctgcct gcctgaccgt gagtctagtg ccaagcatga   2460
actcgacgtg gtggcctacg tgctgcgcca ggggattgtg gtgggcagca gcccgctgga   2520
ggccagggcc tgctttctgg ccatccgctt gctcctgagc ctaggccggc acgaggaggt   2580
cctgcccttt gccgagcgcc tgcagctcct ctctggacac cctcctgcct ctgaggctgt   2640
ggccagtgtt ttgagttttc tgtatgacaa gaaatatctt ccacaccttg cagtggcctc   2700
tgtccagcaa catggtatcc agagtgccca agggatgtct cttcctattt ggcaggtcca   2760
ccttgtcctc cagaacacaa ccaagctcct tggctttcct tccccaggct ggggtgaagt   2820
ttctgccttg gcctgcccaa tgctcagaca ggccctggct gcctgtgagg aactagcaga   2880
ccggagcacc cagagggccc tgtgtctcat cctttccaaa gtgtacctcg agcacaggtc   2940
```

-continued

```
tcctgacggt gccatccact acctgagcca ggccttggtg ctagggcagc tgctgggtga   3000
gcaggaatcc tttgagtctt ctctctgcct ggcatgggcc tatctcttag ccagccaggc   3060
caagaaggct ttggatgtgc ttgagccact gctatgctcc ctgaaggaga cagagagtct   3120
cactcaaagg ggagtcatct ataacctcct gggacttgca ctccaaggtg aaggccgggt   3180
gaacagggca gccaagagct atcttcgggc cttgaacaga gcccaggagg tgggagatgt   3240
gcataaccag gcagtggcta tggccaatct tggccacctg agccttaagt cctgggctca   3300
gcatccagcc agaaactatc tcctgcaggc tgtacgactc tattgtgaac ttcaggccag   3360
taaggagaca gacatggaat tagtacaggt gtttctctgg ttggcccaag ttctggtgtc   3420
tggacaccag ctgacccatg gccttctttg ttatgaaatg gcattgctgt ttggcttaag   3480
gcatcgacat ctaaagagtc agcttcaggc caccaaatcc ctctgccatt tctacagctc   3540
tgtgtcccca aaccctgagg catgcatcac ctaccatgag cactggctgg ccctggctca   3600
gcaactcagg gaccgggaga tggaagggag gctgctggag tccctggggc agctttatcg   3660
gaacctaaat accgccaggt ccctcaggag gtcactcaca tgcatcaagg agagcctgcg   3720
tatcttcatt gacctggggg agacagacaa ggctgctgag gcctggcttg gggcggggcg   3780
actccactac ctcatgcagg aagacgagct ggtggagctg tgcctgcagg cagccatcca   3840
gacagccctg aagtcagagg agcctttgct ggctctcaaa ctttatgaag aagcaggtga   3900
tgtgttcttc aatgggaccc gccacaggca tcatgcagtg gagtactacc gagctggagc   3960
tgttccttta gcaaggaggt tgaaggcggt gagaactgag ctccggattt tcaataagct   4020
gacagagctg cagattagcc tcgaaggcta tgagaaggct ttggaatttg ccaccctggc   4080
cgccaggctc agcacagtca caggagatca gaggcaagag ctggtggcct ttcaccgcct   4140
ggctacagtg tactactccc tgcacatgta tgagatggct gaggactgct acctgaagac   4200
cctgtccctc tgtccaccat ggctgcagag tcccaaggag gccctgtact atgccaaggt   4260
gtattatcgc ctgggcagac tcaccttctg ccagctgaag gatgcccatg atgccactga   4320
gtacttcctt ctggccctgg cagcagcggt cctgctgggt gatgaggagc ttcaggacac   4380
cattaggagc aggctggaca acatctgcca gagccccctg tggcacagca ggccctccgg   4440
gtgctcctca gagagggcgc ggtggctgag tggtggtggc ctggccctct gagcggccgc   4500
ggagctctcg agaggcctaa taaagagctc agatgcatcg atcagagtgt gttggttttt   4560
tgtgtgagat ctaagcttag catggctacg tagataagta gcatggcggg ttaatcatta   4620
actacaagga acccctagtg atggagttgg ccactccctc tctgcgcgct cgctcgctca   4680
ctgaggccgg gcgaccaaag gtcgcccgac gcccgggctt tgcccgggcg gcctcagtga   4740
gcgagcgagc gcgcagagct ttttgcaaaa gcctaggcct ccaaaaaagc ctcctcacta   4800
cttctggaat agctcagagg ccgaggcggc ctcggcctct gcataaataa aaaaaattag   4860
tcagccatgg ggcggagaat gggcggaact gggcggagtt aggggcggga tgggcggagt   4920
taggggcggg actatggttg ctgactaatt gagatgcatg ctttgcatac ttctgcctgc   4980
tggggagcct ggggactttc cacacctggt tgctgactaa ttgagatgca tgctttgcat   5040
acttctgcct gctggggagc ctggggactt tccacaccct aactgacaca cattccacag   5100
ctgcattaat gaatcggcca acgcgcgggg agaggcggtt tgcgtattgg gcgctcttcc   5160
gcttcctcgc tcactgactc gctgcgctcg gtcgttcggc tgcggcgagc ggtatcagct   5220
cactcaaagg cggtaatacg gttatccaca gaatcagggg ataacgcagg aaagaacatg   5280
tgagcaaaag gccagcaaaa ggccaggaac cgtaaaaagg ccgcgttgct ggcgtttttc   5340
```

-continued

```
catatgctcc gcccccctga cgagcatcac aaaaatcgac gctcaagtca gaggtggcga   5400
aacccgacag gactataaag ataccaggcg tttccccctg gaagctccct cgtgcgctct   5460
cctgttccga ccctgccgct taccggatac ctgtccgcct ttctcccttc gggaagcgtg   5520
gcgctttctc atagctcacg ctgtaggtat ctcagttcgg tgtaggtcgt tcgctccaag   5580
ctgggctgtg tgcacgaacc ccccgttcag cccgaccgct gcgccttatc cggtaactat   5640
cgtcttgagt ccaacccggt aagacacgac ttatcgccac tggcagcagc cactggtaac   5700
aggattagca gagcgaggta tgtaggcggt gctacagagt tcttgaagtg gtggcctaac   5760
tacggctaca ctagaagaac agtatttggt atctgcgctc tgctgaagcc agttaccttc   5820
ggaaaaagag ttggtagctc ttgatccggc aaacaaacca ccgctggtag cggtggtttt   5880
tttgtttgca agcagcagat tacgcgcaga aaaaaaggat ctcaagaaga tcctttgatc   5940
ttttctacgg ggtctgacgc tcagtggaac gaaaactcac gttaagggat tttggtcatg   6000
agattatcaa aaaggatctt cacctagatc cttttaaatt aaaaatgaag ttttaaatca   6060
atctaaagta tatatgagta aacttggtct gacagttacc aatgcttaat cagtgaggca   6120
cctatctcag cgatctgtct atttcgttca tccatagttg cctgactccc cgtcgtgtag   6180
ataactacga tacgggaggg cttaccatct ggccccagtg ctgcaatgat accgcgagac   6240
ccacgctcac cggctccaga tttatcagca ataaaccagc cagccggaag ggccgagcgc   6300
agaagtggtc ctgcaacttt atccgcctcc atccagtcta ttaattgttg ccgggaagct   6360
agagtaagta gttcgccagt taatagtttg cgcaacgttg ttgccattgc tacaggcatc   6420
gtggtgtcac gctcgtcgtt tggtatggct tcattcagct ccggttccca acgatcaagg   6480
cgagttacat gatcccccat gttgtgcaaa aaagcggtta gctccttcgg tcctccgatc   6540
gttgtcagaa gtaagttggc cgcagtgtta tcactcatgg ttatggcagc actgcataat   6600
tctcttactg tcatgccatc cgtaagatgc ttttctgtga ctggtgagta ctcaaccaag   6660
tcattctgag aatagtgtat gcggcgaccg agttgctctt gcccggcgtc aatacgggat   6720
aataccgcgc cacatagcag aactttaaaa gtgctcatca ttggaaaacg ttcttcgggg   6780
cgaaaactct caaggatctt accgctgttg agatccagtt cgatgtaacc cactcgtgca   6840
cccaactgat cttcagcatc ttttactttc accagcgttt ctgggtgagc aaaaacagga   6900
aggcaaaatg ccgcaaaaaa gggaataagg gcgacacgga aatgttgaat actcatactc   6960
ttcctttttc aatattattg aagcatttat cagggttatt gtctcatgag cggatacata   7020
tttgaatgta tttagaaaaa taaacaaata ggggttccgc gcacatttcc ccgaaaagtg   7080
ccacctgacg tctaagaaac cattattatc atgacattaa cctataaaaa taggcgtatc   7140
acgaggccct ttcgtctcgc gcgtttcggt gatgacggtg aaaacctctg acacatgcag   7200
ctcccggaga cggtcacagc ttgtctgtaa gcggatgccg ggagcagaca agcccgtcag   7260
ggcgcgtcag cgggtgttgg cgggtgtcgg ggctggctta actatgcggc atcagagcag   7320
attgtactga gagtgcacca ttcgacgctc tcccttatgc gactcctgca ttaggaagca   7380
gcccagtagt aggttgaggc cgttgagcac cgccgccgca aggaatggtg catgcaagga   7440
gatggcgccc aacagtcccc cggccacggg gcctgccacc atacccacgc cgaaacaagc   7500
gctcatgagc ccgaagtggc gagcccgatc ttccccatcg gtgatgtcgg cgatataggc   7560
gccagcaacc gcacctgtgg cgccggtgat gccggccacg atgcgtccgg cgtagaggat   7620
ctggctagcg atgaccctgc tgattggttc gctgaccatt tccgggtgcg ggacggcgtt   7680
```

```
accagaaact cagaaggttc gtccaaccaa accgactctg acggcagttt acgagagaga   7740

tgatagggtc tgcttcagta agccagatgc tacacaatta ggcttgtaca tattgtcgtt   7800

agaacgcggc tacaattaat acataacctt atgtatcata cacatacgat ttaggtgaca   7860

ctatagaata cacggaatta attc                                          7884


<210> SEQ ID NO 22
<211> LENGTH: 429
<212> TYPE: DNA
<213> ORGANISM: Artificial Sequence
<220> FEATURE:
<223> OTHER INFORMATION: Mini-human hP0 promoter

<400> SEQUENCE: 22

tctctcaggc aaggaggctg aggagaaatc cctttttatg gcctttaaat tgaggttcca     60

tatctatccc tcagagaagt gtgtctgtgt ccctgttttt gtccctctcc ctcaccaccc    120

cccacaacat tccagcctgg ggcaggggga ggccagtgga cacaaagccc tctgtgtatg    180

gggtggtatg tgtcccccca cccctccacc cagactatac aatgcccctt ctgctccctg    240

cactctgccc ccctccccac cacctctcaa ctgcacatgc caggctgcaa ttggttactg    300

gctgaggaca gccccctcat gctggggccc taggggattt taagcaggtt ccaggaaccc    360

cccgttcagt tcctggtccc ccactttctc aaccccacag atgctccggg cccctgcccc    420

tgccccagc                                                            429


<210> SEQ ID NO 23
<211> LENGTH: 5567
<212> TYPE: DNA
<213> ORGANISM: Artificial Sequence
<220> FEATURE:
<223> OTHER INFORMATION: AAV-human-miniMpz-Egfp

<400> SEQUENCE: 23

tagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac gtagccatgc    180

tctaggtacc tctctcaggc aaggaggctg aggagaaatc cctttttatg gcctttaaat    240

tgaggttcca tatctatccc tcagagaagt gtgtctgtgt ccctgttttt gtccctctcc    300

ctcaccaccc cccacaacat tccagcctgg ggcaggggga ggccagtgga cacaaagccc    360

tctgtgtatg gggtggtatg tgtcccccca cccctccacc cagactatac aatgcccctt    420

ctgctccctg cactctgccc ccctccccac cacctctcaa ctgcacatgc caggctgcaa    480

ttggttactg gctgaggaca gccccctcat gctggggccc taggggattt taagcaggtt    540

ccaggaaccc cccgttcagt tcctggtccc ccactttctc aaccccacag atgctccggg    600

cccctgcccc tgccccagca ccggtcgcca ccatggtgag caagggcgag gagctgttca    660

ccggggtggt gcccatcctg gtcgagctgg acggcgacgt aaacggccac aagttcagcg    720

tgtccggcga gggcgagggc gatgccacct acggcaagct gaccctgaag ttcatctgca    780

ccaccggcaa gctgcccgtg ccctggccca ccctcgtgac caccctgacc tacggcgtgc    840

agtgcttcag ccgctacccc gaccacatga agcagcacga cttcttcaag tccgccatgc    900

ccgaaggcta cgtccaggag cgcaccatct tcttcaagga cgacggcaac tacaagaccc    960

gcgccgaggt gaagttcgag ggcgacaccc tggtgaaccg catcgagctg aagggcatcg   1020

acttcaagga ggacggcaac atcctggggc acaagctgga gtacaactac aacagccaca   1080
```

-continued acgtctatat catggccgac aagcagaaga acggcatcaa ggtgaacttc aagatccgcc 1140
acaacatcga ggacggcagc gtgcagctcg ccgaccacta ccagcagaac acccccatcg 1200
gcgacggccc cgtgctgctg cccgacaacc actacctgag cacccagtcc gccctgagca 1260
aagaccccaa cgagaagcgc gatcacatgg tcctgctgga gttcgtgacc gccgccggga 1320
tcactctcgg catggacgag ctgtacaagt aaagcggccc tagatcaagc ttatcgataa 1380
tcaacctctg gattacaaaa tttgtgaaag attgactggt attcttaact atgttgctcc 1440
ttttacgcta tgtggatacg ctgctttaat gcctttgtat catgctattg cttcccgtat 1500
ggctttcatt ttctcctcct tgtataaatc ctggttgctg tctctttatg aggagttgtg 1560
gcccgttgtc aggcaacgtg gcgtggtgtg cactgtgttt gctgacgcaa cccccactgg 1620
ttggggcatt gccaccacct gtcagctcct ttccgggact ttcgctttcc ccctccctat 1680
tgccacggcg gaactcatcg ccgcctgcct tgcccgctgc tggacagggg ctcggctgtt 1740
gggcactgac aattccgtgg tgttgtcggg gaaatcatcg tcctttcctt ggctgctcgc 1800
ctgtgttgcc acctggattc tgcgcgggac gtccttctgc tacgtccctt cggccctcaa 1860
tccagcggac cttccttccc gcggcctgct gccggctctg cggcctcttc cgcgtcttcg 1920
ccttcgccct cagacgagtc ggatctccct ttgggccgcc tccccgcatc gataccgtcg 1980
actcgctgat cagcctcgac tgtgccttct agttgccagc catctgttgt ttgcccctcc 2040
cccgtgcctt ccttgaccct ggaaggtgcc actcccactg tcctttccta ataaaatgag 2100
gaaattgcat cgcattgtct gagtaggtgt cattctattc tggggggtgg ggtggggcag 2160
gacagcaagg gggaggattg ggaagacaat agcaggcatg ctggggatgc ggtgggctct 2220
atggcttctg aggcggaaag aaccagctgg ggctcgacta gagcatggct acgtagataa 2280
gtagcatggc gggttaatca ttaactacaa ggaaccccta gtgatggagt tggccactcc 2340
ctctctgcgc gctcgctcgc tcactgaggc cgggcgacca aaggtcgccc gacgcccggg 2400
ctttgcccgg gcggcctcag tgagcgagcg agcgcgcaga gctttttgca aaagcctagg 2460
cctccaaaaa agcctcctca ctacttctgg aatagctcag aggccgaggc ggcctcggcc 2520
tctgcataaa taaaaaaaat tagtcagcca tggggcggag aatgggcgga actgggcgga 2580
gttaggggcg ggatgggcgg agttaggggc gggactatgg ttgctgacta attgagatgc 2640
atgctttgca tacttctgcc tgctggggag cctggggact ttccacacct ggttgctgac 2700
taattgagat gcatgctttg catacttctg cctgctgggg agcctgggga ctttccacac 2760
cctaactgac acacattcca cagctgcatt aatgaatcgg ccaacgcgcg gggagaggcg 2820
gtttgcgtat tgggcgctct tccgcttcct cgctcactga ctcgctgcgc tcggtcgttc 2880
ggctgcggcg agcggtatca gctcactcaa aggcggtaat acggttatcc acagaatcag 2940
gggataacgc aggaaagaac atgtgagcaa aaggccagca aaaggccagg aaccgtaaaa 3000
aggccgcgtt gctggcgttt ttccataggc tccgcccccc tgacgagcat cacaaaaatc 3060
gacgctcaag tcagaggtgg cgaaacccga caggactata aagataccag gcgtttcccc 3120
ctggaagctc cctcgtgcgc tctcctgttc cgaccctgcc gcttaccgga tacctgtccg 3180
cctttctccc ttcgggaagc gtggcgcttt ctcatagctc acgctgtagg tatctcagtt 3240
cggtgtaggt cgttcgctcc aagctgggct gtgtgcacga accccccgtt cagcccgacc 3300
gctgcgcctt atccggtaac tatcgtcttg agtccaaccc ggtaagacac gacttatcgc 3360
cactggcagc agccactggt aacaggatta gcagagcgag gtatgtaggc ggtgctacag 3420

-continued

```
agttcttgaa gtggtggcct aactacggct acactagaag aacagtattt ggtatctgcg   3480
ctctgctgaa gccagttacc ttcggaaaaa gagttggtag ctcttgatcc ggcaaacaaa   3540
ccaccgctgg tagcggtggt ttttttgttt gcaagcagca gattacgcgc agaaaaaaag   3600
gatctcaaga agatcctttg atcttttcta cggggtctga cgctcagtgg aacgaaaact   3660
cacgttaagg gattttggtc atgagattat caaaaaggat cttcacctag atccttttaa   3720
attaaaaatg aagttttaaa tcaatctaaa gtatatatga gtaaacttgg tctgacagtt   3780
accaatgctt aatcagtgag gcacctatct cagcgatctg tctatttcgt tcatccatag   3840
ttgcctgact ccccgtcgtg tagataacta cgatacggga gggcttacca tctggcccca   3900
gtgctgcaat gataccgcga gacccacgct caccggctcc agatttatca gcaataaacc   3960
agccagccgg aagggccgag cgcagaagtg gtcctgcaac tttatccgcc tccatccagt   4020
ctattaattg ttgccgggaa gctagagtaa gtagttcgcc agttaatagt ttgcgcaacg   4080
ttgttgccat tgctacaggc atcgtggtgt cacgctcgtc gtttggtatg gcttcattca   4140
gctccggttc ccaacgatca aggcgagtta catgatcccc catgttgtgc aaaaaagcgg   4200
ttagctcctt cggtcctccg atcgttgtca gaagtaagtt ggccgcagtg ttatcactca   4260
tggttatggc agcactgcat aattctctta ctgtcatgcc atccgtaaga tgcttttctg   4320
tgactggtga gtactcaacc aagtcattct gagaatagtg tatgcggcga ccgagttgct   4380
cttgcccggc gtcaatacgg gataataccg cgccacatag cagaacttta aaagtgctca   4440
tcattggaaa acgttcttcg gggcgaaaac tctcaaggat cttaccgctg ttgagatcca   4500
gttcgatgta acccactcgt gcacccaact gatcttcagc atcttttact ttcaccagcg   4560
tttctgggtg agcaaaaaca ggaaggcaaa atgccgcaaa aaagggaata agggcgacac   4620
ggaaatgttg aatactcata ctcttccttt ttcaatatta ttgaagcatt tatcagggtt   4680
attgtctcat gagcggatac atatttgaat gtatttagaa aaataaacaa ataggggttc   4740
cgcgcacatt tccccgaaaa gtgccacctg acgtctaaga aaccattatt atcatgacat   4800
taacctataa aaataggcgt atcacgaggc cctttcgtct cgcgcgtttc ggtgatgacg   4860
gtgaaaacct ctgacacatg cagctcccgg agacggtcac agcttgtctg taagcggatg   4920
ccgggagcag acaagcccgt cagggcgcgt cagcgggtgt tggcgggtgt cggggctggc   4980
ttaactatgc ggcatcagag cagattgtac tgagagtgca ccattcgacg ctctccctta   5040
tgcgactcct gcattaggaa gcagcccagt agtaggttga ggccgttgag caccgccgcc   5100
gcaaggaatg gtgcatgcaa ggagatggcg cccaacagtc cccggccac ggggcctgcc   5160
accataccca cgccgaaaca agcgctcatg agcccgaagt ggcgagcccg atcttcccca   5220
tcggtgatgt cggcgatata ggcgccagca accgcacctg tggcgccggt gatgccggcc   5280
acgatgcgtc cggcgtagag gatctggcta gcgatgaccc tgctgattgg ttcgctgacc   5340
atttccgggt gcgggacggc gttaccagaa actcagaagg ttcgtccaac caaaccgact   5400
ctgacggcag tttacgagag agatgatagg gtctgcttca gtaagccaga tgctacacaa   5460
ttaggcttgt acatattgtc gttagaacgc ggctacaatt aatacataac cttatgtatc   5520
atacacatac gatttaggtg acactataga atacacggaa ttaattc                 5567
```

<210> SEQ ID NO 24
<211> LENGTH: 72
<212> TYPE: DNA
<213> ORGANISM: Artificial Sequence
<220> FEATURE:
<223> OTHER INFORMATION: Minimal synthetic poly A sequence -continued

```
<400> SEQUENCE: 24

ggagctctcg agaggcctaa taaagagctc agatgcatcg atcagagtgt gttggttttt     60

tgtgtgagat ct                                                         72


<210> SEQ ID NO 25
<211> LENGTH: 22
<212> TYPE: DNA
<213> ORGANISM: Artificial Sequence
<220> FEATURE:
<223> OTHER INFORMATION: KpnhP0 forward primer

<400> SEQUENCE: 25

aggggtaccg cctggcataa ac                                              22


<210> SEQ ID NO 26
<211> LENGTH: 21
<212> TYPE: DNA
<213> ORGANISM: Artificial Sequence
<220> FEATURE:
<223> OTHER INFORMATION: AgehP0 reverse primer

<400> SEQUENCE: 26

aatttaccgg tgctggggca g                                               21
```